United States Patent
Major et al.

(10) Patent No.: US 10,479,777 B2
(45) Date of Patent: Nov. 19, 2019

(54) HERBICIDAL AZINES

(71) Applicant: BASF SE, Ludwigshafen (DE)

(72) Inventors: Julia Major, Freinsheim (DE); Florian Vogt, Mannheim (DE); Frederick Calo, Duesseldorf (DE); Matthias Witschel, Bad Duerkheim (DE); Doreen Schachtschabel, Mannheim (DE); Trevor William Newton, Neustadt (DE); Thomas Seitz, Viernheim (DE); Kristin Hanzlik, Bobenheim am Berg (DE)

(73) Assignee: BASF SE, Ludwigshafen (DE)

( * ) Notice: Subject to any disclaimer, the term of this patent is extended or adjusted under 35 U.S.C. 154(b) by 285 days.

(21) Appl. No.: 14/903,892

(22) PCT Filed: Jul. 15, 2014

(86) PCT No.: PCT/EP2014/065092
§ 371 (c)(1),
(2) Date: Jan. 8, 2016

(87) PCT Pub. No.: WO2015/007711
PCT Pub. Date: Jan. 22, 2015

(65) Prior Publication Data
US 2016/0159770 A1     Jun. 9, 2016

(30) Foreign Application Priority Data

Jul. 16, 2013  (EP) .................................... 13176634
Apr. 23, 2014  (EP) .................................... 14165546

(51) Int. Cl.
*A01N 43/68* (2006.01)
*C07D 401/12* (2006.01)

(52) U.S. Cl.
CPC ........... *C07D 401/12* (2013.01); *A01N 43/68* (2013.01)

(58) Field of Classification Search
CPC ... A01N 43/68; A01N 2300/00; C07D 401/12
See application file for complete search history.

(56) References Cited

U.S. PATENT DOCUMENTS

| | | | |
|---|---|---|---|
| 2,309,663 A | 2/1943 | Oldham | |
| 2,474,194 A | 6/1949 | Thurston | |
| 2,599,145 A | 6/1952 | Vogel | |
| 3,740,399 A | 6/1973 | Murai et al. | |
| 3,816,419 A | 6/1974 | Cross | |
| 3,828,002 A | 8/1974 | Westlinning | |
| 3,932,167 A * | 1/1976 | Cross | C07D 251/18 504/232 |
| 3,996,232 A | 12/1976 | Diamond et al. | |
| 4,816,064 A | 3/1989 | Konno et al. | |
| 5,922,648 A | 7/1999 | Lorenz | |
| 6,239,071 B1 | 5/2001 | Giencke et al. | |
| 6,346,574 B1 | 2/2002 | Nishihara | |
| 7,002,011 B1 | 2/2006 | Zindel et al. | |
| 2001/0006011 A1 | 7/2001 | Testa et al. | |
| 2004/0006011 A1 | 1/2004 | Gour | |
| 2010/0016158 A1 | 1/2010 | Kilian et al. | |

FOREIGN PATENT DOCUMENTS

| | | |
|---|---|---|
| CA | 2081413 | 5/1993 |
| CN | 102070649 | 5/2011 |
| DE | 195 22 137 | 1/1997 |
| DE | 195 31 084 | 2/1997 |
| DE | 19531084 | 2/1997 |
| DE | 197 44 711 | 4/1999 |
| DE | 19830902 | 1/2000 |
| EP | 0 171 708 | 10/1988 |
| EP | 0 336 494 | 10/1989 |
| EP | 0 545 149 | 9/1994 |
| EP | 1 479 397 | 11/2004 |
| EP | 2 147 600 | 1/2010 |
| EP | 12189762.3 | 10/2012 |
| EP | 13176634.7 | 7/2013 |

(Continued)

OTHER PUBLICATIONS

Thornber, C.W., Isostearism and Molecular Modification, Chemical Society Reviews, vol. 8, No. 1, 1979.*
Zauhar, Randy, "Structure-Activity Relationship and Drug Design", Remington, The Science and Practice of Pharmacy, 21$^{st}$ Edition, Chapter 28, pp. 468-478, Lippincott Williams & Wilkins, Baltimore, MD, US.
Nelson, Wendel L., "Antihistamines and Related Antiallergic and Antiulcer Agents", Foye's, Principles of Medicinal Chemistry, 7$^{th}$ Edition, Wolters Kluwer, Lippincott Williams & Wilkins, Baltimore, MD, US.

(Continued)

*Primary Examiner* — Johann R Richter
*Assistant Examiner* — Danielle Sullivan
(74) *Attorney, Agent, or Firm* — Brinks Gilson & Lione

(57) ABSTRACT

The present invention relates to diaminotriazine compounds of the formula (I)

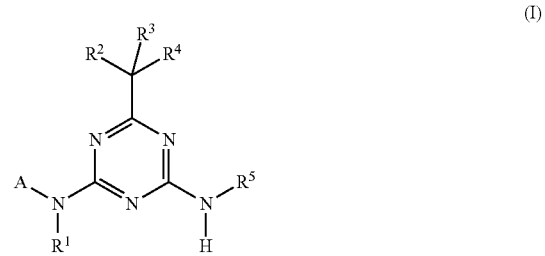

wherein A and $R^1$-$R^5$ are as defined herein, and their use as herbicides. The present invention also relates to agrochemical compositions for crop protection and to a method for controlling unwanted vegetation.

26 Claims, No Drawings

(56) References Cited

FOREIGN PATENT DOCUMENTS

| EP | 2912024 | * | 9/2015 |
|---|---|---|---|
| EP | 3022191 | | 5/2016 |
| WO | WO 91/13065 | | 9/1991 |
| WO | WO 99/18100 | | 4/1999 |
| WO | WO 02/10160 | | 2/2002 |
| WO | WO 2009/028891 | | 3/2009 |
| WO | WO 2011/140527 | | 11/2011 |
| WO | WO 2013/092244 | | 6/2013 |
| WO | WO 2014/064094 | | 5/2014 |
| WO | WO 2014/064094 | | 8/2014 |
| WO | WO 2015/003355 | | 1/2015 |
| WO | WO 2015/075174 | | 5/2015 |
| WO | WO 2015/144881 | | 10/2015 |
| WO | WO 2015/150541 | | 10/2015 |
| WO | WO 2015/155129 | | 10/2015 |
| WO | WO 2015/155271 | | 10/2015 |
| WO | WO 2015/155272 | | 10/2015 |
| WO | WO 2015/155273 | | 10/2015 |
| WO | WO 2015/162164 | | 10/2015 |
| WO | WO 2015/162166 | | 10/2015 |
| WO | WO 2015/162169 | | 10/2015 |

OTHER PUBLICATIONS

International Search Report dated Aug. 22, 2014, prepared in International Application No. PCT/EP2014/065092.
International Preliminary Report on Patentability dated Jul. 29, 2015, prepared in International Application No. PCT/EP2014/065092.
Goda, Fatma E. et al. "Synthesis , Biological Evaluation and molecular modeling investigation of some new benzimidazole analogs as antiviral agents" Saudi Pharmaceutical Journal, Apr. 2008, p. 103-111, vol. 16, No. 2.
Kostschelew, B. N. et.al, J. Org. Chemie, 1995, p. 291-294.
Chong, K. Myoung, "Synthesis of N2-phenyl-2,4-diamino-6-pyridyls-triazines and N2-(1,2,4-Triazoyl-3)s-triazines", 1985.
Samson, Daniel, et al. "Synthesis of Dihereroarylamine ligands by palladium-catalyzed mono- and diamination of Dichloroheteroarenamines", Helvetca Chimica Acta, 2011, p. 46-60, vo. 94.

Whitten, Jeffrey P., et al. "Rapid Microscale Synthesis a new method for lead optimization using robotics and solution phase chemistry application to the synthesis and optimization of corticotropin releasing factor 1 receptor antagonists" Journal of Medicinal Chemistry, 1996, p. 4354-4357, vol. 39. No. 22—Database CA [online] Chemical Abstracts Service Database Accession No. 1996:618910.
European Search Report dated Oct. 2, 2013, from corresponding European Application No. 13176634.
Koshelev, V. N. et.al, "Synthesis of 2,4-diamino-1,35-triazines containing pyridyl radicals", XP002713108, Database accession No. 1995:932941.
Kim, Myong Chon, "Synthesis of N2 phenyl-2,4-diamino-6-pyridyl-s-triazine s and N2 (1,24-triazoyl-3-s-trixines" , XP002713109, Database accession No. 1986-553039.
Shaikh, MS et al "Antifolate agents against wild and mutant strains of plasmodium falciparum", Indian J. Pharm sci., Mar. 2014, vol. 76, No. 2, p. 116-124.
Leroux, F.R. et al. "Trifluoromethyl ethers—synthesis and properties of an unusual substituent", Beilstein Journal of Organic Chemistry, 2008, vol. 4, No. 13., p. 1-5.
Office Action dated Sep. 21, 2017 in U.S. Appl. No. 15/300,354, filed Sep. 29, 2016.
Williams, David A., et al. Foye's Principles of Medicinal Chemistry, Fifth Edition, Copyright 2002, Lipponcott Eillliams & Wilkins, p. 37-67.
Office Action dated May 15, 2018 in U.S. Appl. No. 15/302,659, filed Oct. 7, 2016.
Office Action dated Jul. 9, 2018 in U.S. Appl. No. 15/300,354, filed Sep. 29, 2016.
Eisa et al. Pakistan journal of scientific and industrial Research (1998), 31 (7), 474-476, CA 113:17 171987, 1990 CAPLUS abstract provided.
Kreutzberger, Alfred, et al "Fluorinated 2-amino-4-arylamine-s-triazines", Liebigs Ann. Chem. 1977, p. 1625-1632.
Kaiser et al., "Cyanuric Chloride Derivatives. II. Substituted Melamines", Journal of the American Chemical Society, ACS Publications, Jul. 6, 1951, p. 2984/2986, vol. 73.
Mehta, K.L., et al. "Studies on thioureas/III. Preparation of 2/p/chlorophenylsulphophenylamino/4/arylamino s/triazine/6/yl/thioureas/phenylthioureas", Journal of the Indian Chemical Society, Apr. 1979, p. 383/385, vol. LVI.

* cited by examiner

HERBICIDAL AZINES

This application is a National Stage application of International Application No. PCT/EP2014/065092, filed Jul. 15, 2014. This application also claims priority under 35 U.S.C. § 119 to European Patent Application No. 13176634.7, filed Jul. 16, 2013, and European Patent Application No. 14165546.4, filed Apr. 23, 2014.

The present invention relates to azines of the general formula (I) defined below and to their use as herbicides. Moreover, the invention relates to agrochemical compositions for crop protection and to a method for controlling unwanted vegetation.

U.S. Pat. No. 3,816,419 describes structurally similar compounds for which herbicidal action is stated, which differ from the according to the present invention.

D. Samson et. al, Helvetica Chimica Acta, Vol. 94, 2011, S. 46-60, describes the synthesis of bidentate, bis-bidentate and oligo-bidentade di-heteroarylamine-based N,N-ligands, especially 2,4-diamine triazine compounds, which are substituted by phen-lylquinolin.

B. N. Kostschelew et. al, J. org. Chemie, 1995, S. 291-294 (Russia), describes the synthesis of N4-(2-pyridyl)-1,3,5-triazine-2,4-diamine derivatives, wherein the pyridyl ring is unsubstitued.

K. Myoung Chong, Synthesis of N2-phenyl-2,4-diamino-6-pyridyls-triazines and N2-(1,2,4-Triazoyl-3)s-triazines, 1985, describes the synthesis of 2,4-diamine triazine compounds.

G. Fatma et. al, Saudi Pharmaceutical Journal, Vol. 16, No. 2, 2008, S. 103-111, describes heterocyclic benzimidazole derivatives bearing 1,3,5-triazine group with different substituents at C-2 and C-5 of the benzimidazole ring. These derivatives have been evaluated for their antiviral activity against HSV-1.

U.S. Pat. No. 2,474,194 relates to N-heterocyclic guanaamines, which are capable of reacting with formaldehyde to yield resins.

US 2010/0016158 describes diamino-triazines, which are substituted by hydrogenated heterocycles.

DE 19744711 describes diamino-triazines, which are substituted by heteroarylalkyl radicals.

U.S. Pat. No. 3,932,167 describes diamino-triazines, which are substituted by arylalkyl radicals.

However, the herbicidal properties of these known compounds with regard to the harmful plants are not always entirely satisfactory.

It is therefore an object of the present invention to provide azines of formula (I) having improved herbicidal action. To be provided are in particular azines of formula (I) which have high herbicidal activity, in particular even at low application rates, and which are sufficiently compatible with crop plants for commercial utilization.

These and further objects are achieved by azines of formula (I), defined below, and by their agriculturally suitable salts.

Accordingly, the present invention provides azines of formula (I)

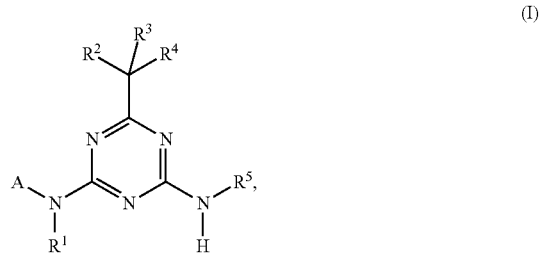

wherein
A is heteroaryl, which is substituted by 1, 2, 3, 4, 5 or 6 substituents $R^A$ selected from the group consisting of halogen, OH, CN, amino, $NO_2$, $C_1$-$C_6$-alkyl, $C_2$-$C_6$-alkenyl, $C_2$-$C_6$-alkynyl, $C_1$-$C_6$-alkoxy, $C_2$-$C_6$-alkenyloxy, $C_2$-$C_6$-alkynyloxy, ($C_1$-$C_6$-alkoxy)-$C_1$-$C_6$-alkyl, ($C_1$-$C_6$-alkoxy)-$C_1$-$C_6$-alkoxy, ($C_1$-$C_6$-alkoxy)-$C_2$-$C_6$-alkenyl, ($C_1$-$C_6$-alkoxy)-$C_2$-$C_6$-alkynyl, $C_1$-$C_6$-alkylthio, ($C_1$-$C_6$-alkyl)sulfinyl, ($C_1$-$C_6$-alkyl)sulfonyl, ($C_1$-$C_6$-alkyl)amino, di($C_1$-$C_6$-alkyl)amino, ($C_1$-$C_6$-alkyl)-carbonyl, ($C_1$-$C_6$-alkoxy)-carbonyl, ($C_1$-$C_6$-alkyl)-carbonyloxy, $C_3$-$C_6$-cycloalkyl, $C_3$-$C_6$-cycloalkoxy, ($C_3$-$C_6$-cycloalkyl)-$C_1$-$C_4$-alkyl, ($C_3$-$C_6$-cycloalkyl)-$C_1$-$C_4$-alkoxy, where the aliphatic and cycloaliphatic parts of the 22 aforementioned radicals are unsubstituted, partly or completely halogenated and where the cycloaliphatic parts of the last 4 mentioned radicals may carry 1, 2, 3, 4, 5 or 6 methyl groups;

$R^1$ is selected from the group consisting of H, OH, $S(O)_2NH_2$, CN, $C_1$-$C_6$-alkyl, $C_2$-$C_6$-alkenyl, $C_2$-$C_6$-alkynyl, ($C_3$-$C_6$-cycloalkyl)-$C_1$-$C_4$-alkyl, $C_1$-$C_6$-alkoxy, ($C_1$-$C_6$-alkoxy)-$C_1$-$C_6$-alkyl, ($C_1$-$C_6$-alkyl)-carbonyl, ($C_1$-$C_6$-alkoxy)carbonyl, ($C_1$-$C_6$-alkyl)sulfonyl, ($C_1$-$C_6$-alkylamino)carbonyl, di($C_1$-$C_6$-alkyl)aminocarbonyl, ($C_1$-$C_6$-alkylamino)sulfonyl, di($C_1$-$C_6$-alkyl)aminosulfonyl and ($C_1$-$C_6$-alkoxy)sulfonyl, where the aliphatic and cycloaliphatic parts of the 14 aforementioned radicals are unsubstituted, partly or completely halogenated,
phenyl, phenyl-$C_1$-$C_6$-alkyl, phenylsulfonyl, phenylaminosulfonyl, phenylcarbonyl and phenoxycarbonyl,
wherein phenyl in the last 6 mentioned radicals are unsubstituted or substituted by 1, 2, 3, 4 or 5 identical or different substituents selected from the group consisting of halogen, CN, $NO_2$, $C_1$-$C_6$-alkyl, $C_1$-$C_6$-haloalkyl, $C_1$-$C_6$-alkoxy and $C_1$-$C_6$-haloalkoxy;

$R^2$ is H, halogen, OH, CN, $C_1$-$C_6$-alkyl, $C_2$-$C_6$-alkenyl, $C_3$-$C_6$-alkynyl, ($C_1$-$C_6$-alkoxy)-$C_1$-$C_6$-alkyl, $C_3$-$C_6$-cycloalkyl, $C_3$-$C_6$-cycloalkenyl, ($C_3$-$C_6$-cycloalkyl)-$C_1$-$C_4$-alkyl, $C_1$-$C_6$-alkoxy, $C_2$-$C_6$-alkenyloxy, $C_2$-$C_6$-alkynyloxy, $C_3$-$C_6$-cycloalkoxy or ($C_3$-$C_6$-cycloalkyl)-$C_1$-$C_4$-alkoxy, where the aliphatic and cycloaliphatic parts of the 9 aforementioned radicals are unsubstituted, partly or completely halogenated, phenyl, phenyl-$C_1$-$C_6$-alkyl,
wherein phenyl in the last 2 mentioned radicals are unsubstituted or substituted by 1, 2, 3, 4 or 5 identical or different substituents selected from the group consisting of halogen, CN, $NO_2$, $C_1$-$C_6$-alkyl, $C_1$-$C_6$-haloalkyl, $C_1$-$C_6$-alkoxy and $C_1$-$C_6$-haloalkoxy;

$R^3$ is selected from the group consisting of H, halogen, CN, $C_1$-$C_6$-alkyl, $C_1$-$C_6$-haloalkyl, $C_1$-$C_6$-alkoxy and $C_1$-$C_6$-haloalkoxy;

$R^4$ is selected from the group consisting of H, halogen, CN, $C_1$-$C_6$-alkyl, $C_2$-$C_6$-alkenyl, $C_3$-$C_6$-alkynyl, $C_3$-$C_6$-cycloalkyl, ($C_3$-$C_6$-cycloalkyl)-$C_1$-$C_4$-alkyl, $C_3$-$C_6$-cycloalkenyl and $C_1$-$C_6$-alkoxy-$C_1$-$C_6$-alkyl, where the aliphatic and cycloaliphatic parts of the 7 aforementioned radicals are unsubstituted, partly or completely halogenated; or $R^3$ and $R^4$ together with the carbon atom to which they are attached form a moiety selected from the group consisting of carbonyl, $C_2$-$C_6$-alkenyl, $C_3$-$C_6$-cycloalkyl, $C_3$-$C_6$-cycloalkenyl and three- to six-membered heterocyclyl,
 wherein the $C_3$-$C_6$-cycloalkyl, $C_3$-$C_6$-cycloalkenyl, or three- to six-membered heterocyclyl is unsubstituted or substituted by one to three substituents selected from halogen, CN, $C_1$-$C_6$-alkyl and $C_1$-$C_6$-alkoxy; and $R^5$ is selected from the group consisting of H, OH, $S(O)_2NH_2$, CN, $C_1$-$C_6$-alkyl, $C_2$-$C_6$-alkenyl, $C_2$-$C_6$-alkynyl, ($C_3$-$C_6$-cycloalkyl)-$C_1$-$C_4$-alkyl, $C_1$-$C_6$-alkoxy, ($C_1$-$C_6$-alkoxy)-$C_1$-$C_6$-alkyl, ($C_1$-$C_6$-alkyl)-carbonyl, ($C_1$-$C_6$-alkoxy)carbonyl, ($C_1$-$C_6$-alkyl)sulfonyl, ($C_1$-$C_6$-alkylamino)carbonyl, di($C_1$-$C_6$-alkyl)aminocarbonyl, ($C_1$-$C_6$-alkylamino)sulfonyl, di($C_1$-$C_6$-alkyl)aminosulfonyl and ($C_1$-$C_6$-alkoxy)sulfonyl, where the aliphatic and cycloaliphatic parts of the 14 aforementioned radicals are unsubstituted, partly or completely halogenated,
 phenyl, phenyl-$C_1$-$C_6$-alkyl, phenylsulfonyl, phenylaminosulfonyl, phenylcarbonyl and phenoxycarbonyl,
  wherein phenyl in the last 6 mentioned radicals are unsubstituted or substituted by 1, 2, 3, 4 or 5 identical or different substituents selected from the group consisting of halogen, CN, $NO_2$, $C_1$-$C_6$-alkyl, $C_1$-$C_6$-haloalkyl, $C_1$-$C_6$-alkoxy and $C_1$-$C_6$-haloalkoxy;

and wherein the variables A, $R^1$, $R^2$, $R^3$, $R^4$ and $R^5$ are in particular:

A is heteroaryl, which is substituted by 1, 2, 3, 4, 5 or 6 substituents $R^A$ selected from the group consisting of halogen, OH, CN, amino, $NO_2$, $C_1$-$C_6$-alkyl, $C_2$-$C_6$-alkenyl, $C_2$-$C_6$-alkynyl, $C_1$-$C_6$-alkoxy, $C_2$-$C_6$-alkenyloxy, $C_2$-$C_6$-alkynyloxy, ($C_1$-$C_6$-alkoxy)-$C_1$-$C_6$-alkyl, ($C_1$-$C_6$-alkoxy)-$C_1$-$C_6$-alkoxy, ($C_1$-$C_6$-alkoxy)-$C_2$-$C_6$-alkenyl, ($C_1$-$C_6$-alkoxy)-$C_2$-$C_6$-alkynyl, $C_1$-$C_6$-alkylthio, ($C_1$-$C_6$-alkyl)sulfinyl, ($C_1$-$C_6$-alkyl)sulfonyl, ($C_1$-$C_6$-alkyl)amino, di($C_1$-$C_6$-alkyl)amino, ($C_1$-$C_6$-alkyl)-carbonyl, ($C_1$-$C_6$-alkoxy)-carbonyl, ($C_1$-$C_6$-alkyl)-carbonyloxy, $C_3$-$C_6$-cycloalkyl, $C_3$-$C_6$-cycloalkoxy, ($C_3$-$C_6$-cycloalkyl)-$C_1$-$C_4$-alkyl, ($C_3$-$C_6$-cycloalkyl)-$C_1$-$C_4$-alkoxy, where the aliphatic and cycloaliphatic parts of the 22 aforementioned radicals are unsubstituted, partly or completely halogenated and where the cycloaliphatic parts of the last 4 mentioned radicals may carry 1, 2, 3, 4, 5 or 6 methyl groups;

$R^1$ is selected from the group consisting of H, OH, $S(O)_2NH_2$, CN, $C_1$-$C_6$-alkyl, $C_2$-$C_6$-alkenyl, $C_2$-$C_6$-alkynyl, ($C_3$-$C_6$-cycloalkyl)-$C_1$-$C_4$-alkyl, $C_1$-$C_6$-alkoxy, ($C_1$-$C_6$-alkoxy)-$C_1$-$C_6$-alkyl, ($C_1$-$C_6$-alkyl)-carbonyl, ($C_1$-$C_6$-alkoxy)carbonyl, ($C_1$-$C_6$-alkyl)sulfonyl, ($C_1$-$C_6$-alkylamino)carbonyl, di($C_1$-$C_6$-alkyl)aminocarbonyl, ($C_1$-$C_6$-alkylamino)sulfonyl, di($C_1$-$C_6$-alkyl)aminosulfonyl and ($C_1$-$C_6$-alkoxy)sulfonyl, where the aliphatic and cycloaliphatic parts of the 14 aforementioned radicals are unsubstituted, partly or completely halogenated,
 phenyl, phenyl-$C_1$-$C_6$-alkyl, phenylsulfonyl, phenylaminosulfonyl, phenylcarbonyl and phenoxycarbonyl,
  wherein phenyl in the last 6 mentioned radicals are unsubstituted or substituted by 1, 2, 3, 4 or 5 identical or different substituents selected from the group consisting of halogen, CN, $NO_2$, $C_1$-$C_6$-alkyl, $C_1$-$C_6$-haloalkyl, $C_1$-$C_6$-alkoxy and $C_1$-$C_6$-haloalkoxy;

$R^2$ is H, halogen, OH, CN, $C_1$-$C_6$-alkyl, $C_2$-$C_6$-alkenyl, $C_3$-$C_6$-alkynyl, ($C_1$-$C_6$-alkoxy)-$C_1$-$C_6$-alkyl, $C_3$-$C_6$-cycloalkyl, $C_3$-$C_6$-cycloalkenyl, ($C_3$-$C_6$-cycloalkyl)-$C_1$-$C_4$-alkyl, $C_1$-$C_6$-alkoxy, $C_2$-$C_6$-alkenyloxy, $C_2$-$C_6$-alkynyloxy, $C_3$-$C_6$-cycloalkoxy or ($C_3$-$C_6$-cycloalkyl)-$C_1$-$C_4$-alkoxy, where the aliphatic and cycloaliphatic parts of the 9 aforementioned radicals are unsubstituted, partly or completely halogenated or phenyl, wherein phenyl is unsubstituted or substituted by 1, 2, 3, 4 or 5 identical or different substituents selected from the group consisting of halogen, CN, $NO_2$, $C_1$-$C_6$-alkyl, $C_1$-$C_6$-haloalkyl, $C_1$-$C_6$-alkoxy and $C_1$-$C_6$-haloalkoxy;

$R^3$ is selected from the group consisting of H, halogen, CN, $C_1$-$C_6$-alkyl, $C_1$-$C_6$-haloalkyl, $C_1$-$C_6$-alkoxy and $C_1$-$C_6$-haloalkoxy;

$R^4$ is selected from the group consisting of H, halogen, CN, $C_1$-$C_6$-alkyl, $C_2$-$C_6$-alkenyl, $C_3$-$C_6$-alkynyl, $C_3$-$C_6$-cycloalkyl, ($C_3$-$C_6$-cycloalkyl)-$C_1$-$C_4$-alkyl, $C_3$-$C_6$-cycloalkenyl and $C_1$-$C_6$-alkoxy-$C_1$-$C_6$-alkyl, where the aliphatic and cycloaliphatic parts of the 7 aforementioned radicals are unsubstituted, partly or completely halogenated; or $R^3$ and $R^4$ together with the carbon atom to which they are attached form a moiety selected from the group consisting of carbonyl, $C_2$-$C_6$-alkenyl, $C_3$-$C_6$-cycloalkyl, $C_3$-$C_6$-cycloalkenyl and three- to six-membered heterocyclyl,
 wherein the $C_3$-$C_6$-cycloalkyl, $C_3$-$C_6$-cycloalkenyl, or three- to six-membered heterocyclyl is unsubstituted or substituted by one to three substituents selected from halogen, CN, $C_1$-$C_6$-alkyl and $C_1$-$C_6$-alkoxy; and $R^5$ is selected from the group consisting of H, OH, $S(O)_2NH_2$, CN, $C_1$-$C_6$-alkyl, $C_2$-$C_6$-alkenyl, $C_2$-$C_6$-alkynyl, ($C_3$-$C_6$-cycloalkyl)-$C_1$-$C_4$-alkyl, $C_1$-$C_6$-alkoxy, ($C_1$-$C_6$-alkoxy)-$C_1$-$C_6$-alkyl, ($C_1$-$C_6$-alkyl)-carbonyl, ($C_1$-$C_6$-alkoxy)carbonyl, ($C_1$-$C_6$-alkyl)sulfonyl, ($C_1$-$C_6$-alkylamino)carbonyl, di($C_1$-$C_6$-alkyl)aminocarbonyl, ($C_1$-$C_6$-alkylamino)sulfonyl, di($C_1$-$C_6$-alkyl)aminosulfonyl and ($C_1$-$C_6$-alkoxy)sulfonyl, where the aliphatic and cycloaliphatic parts of the 14 aforementioned radicals are unsubstituted, partly or completely halogenated,
 phenyl, phenyl-$C_1$-$C_6$-alkyl, phenylsulfonyl, phenylaminosulfonyl, phenylcarbonyl and phenoxycarbonyl,
  wherein phenyl in the last 6 mentioned radicals are unsubstituted or substituted by 1, 2, 3, 4 or 5 identical or different substituents selected from the group consisting of halogen, CN, $NO_2$, $C_1$-$C_6$-alkyl, $C_1$-$C_6$-haloalkyl, $C_1$-$C_6$-alkoxy and $C_1$-$C_6$-haloalkoxy;

and wherein the variables A, $R^1$, $R^2$, $R^3$, $R^4$ and $R^5$ are in more particular:

A is heteroaryl, which is substituted by 1, 2, 3, 4, 5 or 6 substituents $R^A$ selected from the group consisting of halogen, OH, CN, amino, $NO_2$, $C_1$-$C_6$-alkyl, $C_2$-$C_6$-alkenyl, $C_2$-$C_6$-alkynyl, $C_1$-$C_6$-alkoxy, $C_2$-$C_6$-alkenyloxy, $C_2$-$C_6$-alkynyloxy, ($C_1$-$C_6$-alkoxy)-$C_1$-$C_6$-alkyl, ($C_1$-$C_6$-alkoxy)-$C_1$-$C_6$-alkoxy, ($C_1$-$C_6$-alkoxy)-$C_2$-$C_6$-alkenyl, ($C_1$-$C_6$-alkoxy)-$C_2$-$C_6$-alkynyl, $C_1$-$C_6$-alkylthio, ($C_1$-$C_6$-alkyl)sulfinyl, ($C_1$-$C_6$-alkyl)sulfonyl, ($C_1$-$C_6$-alkyl)amino, di($C_1$-$C_6$-alkyl)amino, ($C_1$-$C_6$-alkyl)-carbonyl, ($C_1$-$C_6$-alkoxy)-carbonyl, ($C_1$-$C_6$-alkyl)-carbonyloxy, $C_3$-$C_6$-cycloalkyl, $C_3$-$C_6$-cycloalkoxy, ($C_3$-$C_6$-cycloalkyl)-$C_1$-$C_4$-alkyl, ($C_3$-$C_6$-cycloalkyl)-$C_1$-$C_4$-alkoxy, where the aliphatic and cycloaliphatic parts of the 22 aforementioned radicals are unsubstituted, partly or completely halogenated and where the cycloaliphatic parts of the last 4 mentioned radicals may carry 1, 2, 3, 4, 5 or 6 methyl groups;

$R^1$ is selected from the group consisting of H, OH, $S(O)_2NH_2$, CN, $C_1$-$C_6$-alkyl, $C_2$-$C_6$-alkenyl, $C_2$-$C_6$-alkynyl, ($C_3$-$C_6$-cycloalkyl)-$C_1$-$C_4$-alkyl, $C_1$-$C_6$-alkoxy, ($C_1$-$C_6$-alkoxy)-$C_1$-$C_6$-alkyl, ($C_1$-$C_6$-alkyl)-carbonyl, ($C_1$-$C_6$-alkoxy)carbonyl, ($C_1$-$C_6$-alkyl)sulfonyl, ($C_1$-$C_6$-alkylamino)carbonyl, di($C_1$-$C_6$-alkyl)aminocarbonyl, ($C_1$-$C_6$-alkylamino)sulfonyl, di($C_1$-$C_6$-alkyl)aminosulfonyl and ($C_1$-$C_6$-alkoxy)sulfonyl, where the aliphatic and cycloaliphatic parts of the 14 aforementioned radicals are unsubstituted, partly or completely halogenated, phenyl, phenyl-$C_1$-$C_6$-alkyl, phenylsulfonyl, phenylaminosulfonyl, phenylcarbonyl and phenoxycarbonyl, wherein phenyl in the last 6 mentioned radicals are unsubstituted or substituted by 1, 2, 3, 4 or 5 identical or different substituents selected from the group consisting of halogen, CN, $NO_2$, $C_1$-$C_6$-alkyl, $C_1$-$C_6$-haloalkyl, $C_1$-$C_6$-alkoxy and $C_1$-$C_6$-haloalkoxy;

$R^2$ is H, halogen, OH, CN, $C_1$-$C_6$-alkyl, $C_2$-$C_6$-alkenyl, $C_3$-$C_6$-alkynyl, ($C_1$-$C_6$-alkoxy)-$C_1$-$C_6$-alkyl, $C_3$-$C_6$-cycloalkyl, $C_3$-$C_6$-cycloalkenyl, ($C_3$-$C_6$-cycloalkyl)-$C_1$-$C_4$-alkyl, $C_1$-$C_6$-alkoxy, $C_2$-$C_6$-alkenyloxy, $C_2$-$C_6$-alkynyloxy, $C_3$-$C_6$-cycloalkoxy or ($C_3$-$C_6$-cycloalkyl)-$C_1$-$C_4$-alkoxy, where the aliphatic and cycloaliphatic parts of the 9 aforementioned radicals are unsubstituted, partly or completely halogenated, $R^3$ is selected from the group consisting of H, halogen, CN, $C_1$-$C_6$-alkyl, $C_1$-$C_6$-haloalkyl, $C_1$-$C_6$-alkoxy and $C_1$-$C_6$-haloalkoxy;

$R^4$ is selected from the group consisting of H, halogen, CN, $C_1$-$C_6$-alkyl, $C_2$-$C_6$-alkenyl, $C_3$-$C_6$-alkynyl, $C_3$-$C_6$-cycloalkyl, ($C_3$-$C_6$-cycloalkyl)-$C_1$-$C_4$-alkyl, $C_3$-$C_6$-cycloalkenyl and $C_1$-$C_6$-alkoxy-$C_1$-$C_6$-alkyl, where the aliphatic and cycloaliphatic parts of the 7 aforementioned radicals are unsubstituted, partly or completely halogenated; or $R^3$ and $R^4$ together with the carbon atom to which they are attached form a moiety selected from the group consisting of carbonyl, $C_2$-$C_6$-alkenyl, $C_3$-$C_6$-cycloalkyl, $C_3$-$C_6$-cycloalkenyl and three- to six-membered heterocyclyl, wherein the $C_3$-$C_6$-cycloalkyl, $C_3$-$C_6$-cycloalkenyl, or three- to six-membered heterocyclyl is unsubstituted or substituted by one to three substituents selected from halogen, CN, $C_1$-$C_6$-alkyl and $C_1$-$C_6$-alkoxy; and $R^5$ is selected from the group consisting of H, OH, $S(O)_2NH_2$, CN, $C_1$-$C_6$-alkyl, $C_2$-$C_6$-alkenyl, $C_2$-$C_6$-alkynyl, ($C_3$-$C_6$-cycloalkyl)-$C_1$-$C_4$-alkyl, $C_1$-$C_6$-alkoxy, ($C_1$-$C_6$-alkoxy)-$C_1$-$C_6$-alkyl, ($C_1$-$C_6$-alkyl)-carbonyl, ($C_1$-$C_6$-alkoxy)carbonyl, ($C_1$-$C_6$-alkyl)sulfonyl, ($C_1$-$C_6$-alkylamino)carbonyl, di($C_1$-$C_6$-alkyl)aminocarbonyl, ($C_1$-$C_6$-alkylamino)sulfonyl, di($C_1$-$C_6$-alkyl)aminosulfonyl and ($C_1$-$C_6$-alkoxy)sulfonyl, where the aliphatic and cycloaliphatic parts of the 14 aforementioned radicals are unsubstituted, partly or completely halogenated, phenyl, phenyl-$C_1$-$C_6$-alkyl, phenylsulfonyl, phenylaminosulfonyl, phenylcarbonyl and phenoxycarbonyl, wherein phenyl in the last 6 mentioned radicals are unsubstituted or substituted by 1, 2, 3, 4 or 5 identical or different substituents selected from the group consisting of halogen, CN, $NO_2$, $C_1$-$C_6$-alkyl, $C_1$-$C_6$-haloalkyl, $C_1$-$C_6$-alkoxy and $C_1$-$C_6$-haloalkoxy;

and wherein the variables A, $R^1$, $R^2$, $R^3$, $R^4$ and $R^5$ are preferred:

A is heteroaryl, which is substituted by one to six substituents selected from the group consisting of halogen, CN, $NO_2$, $C_1$-$C_6$-alkyl, $C_1$-$C_6$-haloalkyl, OH, $C_1$-$C_6$-alkoxy, $C_1$-$C_6$-alkylthio, ($C_1$-$C_6$-alkyl)sulfinyl, ($C_1$-$C_6$-alkyl)sulfonyl, amino, ($C_1$-$C_6$-alkyl)amino, di($C_1$-$C_6$-alkyl)amino, ($C_1$-$C_6$-alkyl)carbonyl, ($C_1$-$C_6$-alkoxy)carbonyl;

$R^1$ is H, CN, $C_1$-$C_6$-alkyl, $C_1$-$C_6$-alkoxy-$C_1$-$C_6$-alkyl, $C_1$-$C_6$-alkoxy, ($C_1$-$C_6$-alkyl)-carbonyl, ($C_1$-$C_6$-alkoxy)carbonyl, ($C_1$-$C_6$-alkyl)sulfonyl or phenylsulfonyl, wherein the phenyl is unsubstituted or substituted by one to five substituents selected from the group consisting of halogen, CN, $NO_2$, $C_1$-$C_6$-alkyl, $C_1$-$C_6$-haloalkyl and $C_1$-$C_6$-alkoxy;

$R^2$ is is H, halogen, OH, CN, $C_1$-$C_6$-alkyl, $C_2$-$C_6$-alkenyl, $C_3$-$C_6$-alkynyl, ($C_1$-$C_6$-alkoxy)-$C_1$-$C_6$-alkyl, $C_3$-$C_6$-cycloalkyl, $C_3$-$C_6$-cycloalkenyl, ($C_3$-$C_6$-cycloalkyl)-$C_1$-$C_4$-alkyl, $C_1$-$C_6$-alkoxy, $C_2$-$C_6$-alkenyloxy, $C_2$-$C_6$-alkynyloxy, $C_3$-$C_6$-cycloalkoxy or ($C_3$-$C_6$-cycloalkyl)-$C_1$-$C_4$-alkoxy, where the aliphatic and cycloaliphatic parts of the 9 aforementioned radicals are unsubstituted, partly or completely halogenated $R^3$ is H, halogen, CN, $C_1$-$C_6$-alkyl, $C_1$-$C_6$-haloalkyl or $C_1$-$C_6$-alkoxy;

$R^4$ is H, halogen, CN, $C_1$-$C_6$-alkyl or $C_1$-$C_6$-haloalkyl; or $R^3$ and $R^4$ together with the carbon atom to which they are attached form a moiety selected from the group consisting of carbonyl, $C_2$-$C_6$-alkenyl, $C_3$-$C_6$-cycloalkyl, $C_3$-$C_6$-cycloalkenyl and three- to six-membered heterocyclyl, wherein the $C_3$-$C_6$-cycloalkyl, $C_3$-$C_6$-cycloalkenyl, or three- to six-membered heterocyclyl is unsubstituted or substituted by one to three substituents selected from halogen, CN, $C_1$-$C_6$-alkyl and $C_1$-$C_6$-alkoxy; and $R^5$ is H, CN, $C_1$-$C_6$-alkyl, $C_1$-$C_6$-alkoxy-$C_1$-$C_6$-alkyl, $C_1$-$C_6$-alkoxy, ($C_1$-$C_6$-alkyl)-carbonyl, ($C_1$-$C_6$-alkoxy)carbonyl, ($C_1$-$C_6$-alkyl)sulfonyl or phenylsulfonyl, wherein the phenyl is unsubstituted or substituted by one to five substituents selected from the group consisting of halogen, CN, $NO_2$, $C_1$-$C_6$-alkyl, $C_1$-$C_6$-haloalkyl and $C_1$-$C_6$-alkoxy;

including their agriculturally acceptable salts or N-oxides.

The present invention also provides agrochemical compositions comprising at least one azine of formula (I) and auxiliaries customary for formulating crop protection agents.

The present invention also provides the use of azines of formula (I) as herbicides, i.e. for controlling harmful plants.

The present invention furthermore provides a method for controlling unwanted vegetation where a herbicidal effective amount of at least one azine of the formula (I) is allowed to act on plants, their seeds and/or their habitat. Application can be done before (pre-emergence), during and/or after (post-emergence), preferably before, the emergence of the undesirable plants.

Moreover, the invention relates to processes for preparing azines of formula (I).

Further embodiments of the present invention are evident from the claims, the description and the examples. It is to be understood that the features mentioned above and still to be illustrated below of the subject matter of the invention can be applied not only in the combination given in each particular case but also in other combinations, without leaving the scope of the invention.

As used herein, the terms "controlling" and "combating" are synonyms.

As used herein, the terms "undesirable vegetation" and "harmful plants" are synonyms.

If the azines of formula (I) as described herein are capable of forming geometrical isomers, for example E/Z isomers, it is possible to use both, the pure isomers and mixtures thereof, in the compositions according to the invention.

If the azines of formula (I) as described herein have one or more centres of chirality and, as a consequence, are present as enantiomers or diastereomers, it is possible to use both, the pure enantiomers and diastereomers and their mixtures, in the compositions according to the invention.

If the azines of formula (I) as described herein have ionizable functional groups, they can also be employed in the form of their agriculturally acceptable salts. Suitable are, in general, the salts of those cations and the acid addition salts of those acids whose cations and anions, respectively, have no adverse effect on the activity of the active compounds.

Preferred cations are the ions of the alkali metals, preferably of lithium, sodium and potassium, of the alkaline earth metals, preferably of calcium and magnesium, and of the transition metals, preferably of manganese, copper, zinc and iron, further ammonium and substituted ammonium in which one to four hydrogen atoms are replaced by $C_1$-$C_4$-alkyl, hydroxy-$C_1$-$C_4$-alkyl, $C_1$-$C_4$-alkoxy-$C_1$-$C_4$-alkyl, hydroxy-$C_1$-$C_4$-alkoxy-$C_1$-$C_4$-alkyl, phenyl or benzyl, preferably ammonium, methylammonium, isopropylammonium, dimethylammonium, diisopropylammonium, trimethylammonium, heptylammonium, dodecylammonium, tetradecylammonium, tetramethylammonium, tetraethylammonium, tetrabutylammonium, 2-hydroxyethylammonium (olamine salt), 2-(2-hydroxyeth-1-oxy)eth-1-ylammonium (diglycolamine salt), di(2-hydroxyeth-1-yl)ammonium (diolamine salt), tris(2-hydroxyethyl)ammonium (trolamine salt), tris(2-hydroxypropyl)ammonium, benzyltrimethylammonium, benzyltriethylammonium, N,N,N-trimethylethanolammonium (choline salt), furthermore phosphonium ions, sulfonium ions, preferably tri($C_1$-$C_4$-alkyl)sulfonium, such as trimethylsulfonium, and sulfoxonium ions, preferably tri($C_1$-$C_4$-alkyl)sulfoxonium, and finally the salts of polybasic amines such as N,N-bis-(3-aminopropyl)methylamine and diethylenetriamine.

Anions of useful acid addition salts are primarily chloride, bromide, fluoride, iodide, hydrogensulfate, methylsulfate, sulfate, dihydrogenphosphate, hydrogenphosphate, nitrate, bicarbonate, carbonate, hexafluorosilicate, hexafluorophosphate, benzoate and also the anions of $C_1$-$C_4$-alkanoic acids, preferably formate, acetate, propionate and butyrate.

Further embodiments of the present invention are evident from the claims, the description and the examples. It is to be understood that the features mentioned above and still to be illustrated below of the subject matter of the invention can be applied not only in the combination given in each particular case but also in other combinations, without leaving the scope of the invention.

The organic moieties mentioned in the definition of the variables, e.g. A, $R^1$ to $R^5$ are—like the term halogen—collective terms for individual enumerations of the individual group members. The term halogen denotes in each case fluorine, chlorine, bromine or iodine. All hydrocarbon chains, i.e. all alkyl, haloalkyl, alkenyl, alkynyl, alkoxy, alkylthio, alkylsulfinyl, alkylsulfonyl, (alkyl)amino, di(alkyl)amino chains can be straight-chain or branched, the prefix $C_n$-$C_m$ denoting in each case the possible number of carbon atoms in the group.

Examples of such meanings are:

$C_1$-$C_4$-alkyl and also the $C_1$-$C_4$-alkyl moieties of $C_1$-$C_4$-alkoxy, $C_1$-$C_4$-alkylthio, $C_1$-$C_4$-alkylsulfonyl, ($C_1$-$C_4$-alkyl)carbonyl, ($C_1$-$C_4$-alkyl)carbonyl, ($C_1$-$C_4$-alkoxy)carbonyl, ($C_1$-$C_4$-alkyl)carbonyloxy, $C_1$-$C_4$-alkyloxy-$C_1$-$C_4$-alkyl, $C_3$-$C_6$-cycloalkyl-$C_1$-$C_4$-alkyl, ($C_1$-$C_4$-alkylamino)carbonyl, di($C_1$-$C_4$-alkyl)aminocarbonyl, ($C_1$-$C_4$-alkylamino)sulfonyl, di($C_1$-$C_4$-alkyl)aminosulfonyl or phenyl-$C_1$-$C_4$-alkyl: for example $CH_3$, $C_2H_5$, n-propyl, $CH(CH_3)_2$, n-butyl, $CH(CH_3)$—$C_2H_5$, $CH_2$—$CH(CH_3)_2$ and $C(CH_3)_3$;

$C_1$-$C_6$-alkyl and also the $C_1$-$C_6$-alkyl moieties of $C_1$-$C_6$-alkoxy, $C_1$-$C_6$-alkylthio, $C_1$-$C_6$-alkylsulfonyl, ($C_1$-$C_6$-alkyl)carbonyl, ($C_1$-$C_6$-alkyl)carbonyl, ($C_1$-$C_6$-alkoxy)carbonyl, ($C_1$-$C_6$-alkyl)carbonyloxy, $C_1$-$C_6$-alkyoxy-$C_1$-$C_6$-alkyl, $C_3$-$C_6$-cycloalkyl-$C_1$-$C_6$-alkyl, ($C_1$-$C_6$-alkylamino)carbonyl, di($C_1$-$C_6$-alkyl)aminocarbonyl, ($C_1$-$C_6$-alkylamino)sulfonyl, di($C_1$-$C_6$-alkyl)aminosulfonyl or phenyl-$C_1$-$C_6$-alkyl: $C_1$-$C_4$-alkyl as mentioned above, and also, for example, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl or 1-ethyl-2-methylpropyl, preferably methyl, ethyl, n-propyl, 1-methylethyl, n-butyl, 1,1-dimethylethyl, n-pentyl or n-hexyl;

$C_1$-$C_4$-haloalkyl: a $C_1$-$C_4$-alkyl radical as mentioned above which is partially or fully substituted by fluorine, chlorine, bromine and/or iodine, for example, chloromethyl, dichloromethyl, trichloromethyl, fluoromethyl, difluoromethyl, trifluoromethyl, chlorofluo-romethyl, dichlorofluoromethyl, chlorodifluoromethyl, bromomethyl, iodomethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, heptafluoropropyl, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl, nonafluorobutyl, 1,1,2,2,-tetrafluoroethyl and 1-trifluoromethyl-1,2,2,2-tetrafluoroethyl;

$C_1$-$C_6$-haloalkyl: $C_1$-$C_4$-haloalkyl as mentioned above, and also, for example, 5-fluoropentyl, 5-chloropentyl, 5-bromopentyl, 5-iodopentyl, undecafluoropentyl, 6-fluorohexyl, 6-chlorohexyl, 6-bromohexyl, 6-iodohexyl and dodecafluorohexyl;

$C_3$-$C_6$-cycloalkyl and also the $C_3$-$C_6$-cycloalkyl moieties of ($C_3$-$C_6$-cycloalkyl)-carbonyl, ($C_3$-$C_6$-cycloalkyl)-$C_1$-$C_6$-alkyl and ($C_3$-$C_6$-cycloalkyl)-$C_1$-$C_6$-alkoxy: monocyclic saturated hydrocarbons having 3 to 6 ring members, such as cyclopropyl, cyclobutyl, cyclopentyl and cyclohexyl;

$C_2$-$C_6$-alkenyl: for example ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl- 3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl;

$C_3$-$C_6$-cycloalkenyl: 1-cyclopropenyl, 2-cyclopropenyl, 1-cyclobutenyl, 2-cyclobutenyl, 1-cyclopentenyl, 2-cyclopentenyl, 1,3-cyclopentadienyl, 1,4-cyclopentadienyl, 2,4-cyclopentadienyl, 1-cyclohexenyl, 2-cyclohexenyl, 3-cyclohexenyl, 1,3-cyclohexadienyl, 1,4-cyclohexadienyl, 2,5-cyclohexadienyl;

$C_3$-$C_6$-alkynyl: for example 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl and 1-ethyl-1-methyl-2-propynyl;

$C_1$-$C_4$-alkoxy: for example methoxy, ethoxy, propoxy, 1-methylethoxy butoxy, 1-methylpropoxy, 2-methylpropoxy and 1,1-dimethylethoxy;

$C_1$-$C_6$-alkoxy and also the $C_1$-$C_6$-alkoxy moieties of ($C_1$-$C_6$-alkoxy)carbonyl, $C_1$-$C_6$-alkoxy-$C_1$-$C_6$-alkyl, ($C_1$-$C_6$-alkoxy)sulfonyl, ($C_1$-$C_6$-alkoxy)-$C_1$-$C_6$-alkoxy, ($C_1$-$C_6$-alkoxy)-$C_2$-$C_6$-alkenyl, ($C_1$-$C_6$-alkoxy)-$C_2$-$C_6$-alkynyl: $C_1$-$C_4$-alkoxy as mentioned above, and also, for example, pentoxy, 1-methylbutoxy, 2-methylbutoxy, 3-methoxylbutoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy and 1-ethyl-2-methylpropoxy.

$C_2$-$C_6$-alkenyloxy: $C_2$-$C_6$-alkenyl as defined above, which is bound via an oxygen atom, such as ethenyloxy (vinyloxy), 1-propenyloxy, 2-propenyloxy (allyloxy), 1-butenyloxy, 2-butenyloxy, 3-butenyloxy 1-methyl-2-propenyloxy and the like;

$C_2$-$C_6$-alkynyloxy: $C_2$-$C_6$-alkynyl as defined above, which is bound via an oxygen atom, such as ethynyloxy, 1-propynyl, 2-propynyloxy (propargyloxy), 1-butynyloxy, 2-butynyloxy, 3-butynyloxy 1-methyl-2-propynyloxy and the like;

$C_1$-$C_4$-alkylthio: for example methylthio, ethylthio, propylthio, 1-methylethylthio, butylthio, 1-methylpropylthio, 2-methylpropylthio and 1,1-dimethylethylthio;

$C_1$-$C_6$-alkylthio: $C_1$-$C_4$-alkylthio as mentioned above, and also, for example, pen-tylthio, 1-methylbutylthio, 2-methylbutylthio, 3-methylbutylthio, 2,2-dimethylpropylthio, 1-ethylpropylthio, hexylthio, 1,1-dimethylpropylthio, 1,2-dimethylpropylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropylthio and 1-ethyl-2-methylpropylthio;

$C_1$-$C_6$-alkylsulfinyl ($C_1$-$C_6$-alkyl-S(=O)—): z.B. methylsulfinyl, ethylsulfinyl, propylsulfinyl, 1-methylethylsulfinyl, butylsulfinyl, 1-methylpropylsulfinyl, 2-methylpropylsulfinyl, 1,1-dimethylethylsulfinyl, pentylsulfinyl, 1-methylbutylsulfinyl, 2-methylbutylsulfinyl, 3-methylbutylsulfinyl, 2,2-dimethylpropylsulfinyl, 1-ethylpropylsulfinyl, 1,1-dimethylpropylsulfinyl, 1,2-dimethylpropylsulfinyl, hexylsulfinyl, 1-methylpentyl-sulfinyl, 2-methylpentyl-sulfinyl, 3-methylpentyl-sulfinyl, 4-methylpentyl-sulfinyl, 1,1-dimethylbutyl-sulfinyl, 1,2-dimethylbutyl-sulfinyl, 1,3-dimethylbutyl-sulfinyl, 2,2-dimethylbutyl-sulfinyl, 2,3-dimethylbutyl-sulfinyl, 3,3-dimethylbutyl-sulfinyl, 1-ethylbutylsulfinyl, 2-ethylbutylsulfinyl, 1,1,2-trimethylpropylsulfinyl, 1,2,2-trimethylpropylsulfinyl, 1-ethyl-1-methylpropylsulfinyl and 1-ethyl-2-methylpropylsulfinyl;

$C_1$-$C_6$-alkylsulfonyl ($C_1$-$C_6$-alkyl-S(O)$_2$—): for example methylsulfonyl, ethylsulfonyl, propylsulfonyl, 1-methylethylsulfonyl, butylsulfonyl, 1-methylpropylsulfonyl, 2-methylpropylsulfonyl, 1,1-dimethylethylsulfonyl, pentylsulfonyl, 1-methylbutylsulfonyl, 2-methylbutylsulfonyl, 3-methylbutylsulfonyl, 1,1-dimethylpropylsulfonyl, 1,2-dimethylpropylsulfonyl, 2,2-dimethylpropylsulfonyl, 1-ethylpropylsulfonyl, hexylsulfonyl, 1-methylpentylsulfonyl, 2-methylpentylsulfonyl, 3-methylpentylsulfonyl, 4-methylpentylsulfonyl, 1,1-dimethylbutylsulfonyl, 1,2-dimethylbutylsulfonyl, 1,3-dimethylbutylsulfonyl, 2,2-dimethylbutylsulfonyl, 2,3-dimethylbutylsulfonyl, 3,3-dimethylbutylsulfonyl, 1-ethylbutylsulfonyl, 2-ethylbutylsulfonyl, 1,1,2-trimethylpropylsulfonyl, 1,2,2-trimethylpropylsulfonyl, 1-ethyl-1-methylpropylsulfonyl and 1-ethyl-2-methylpropylsulfonyl;

($C_1$-$C_4$-alkyl)amino and also the ($C_1$-$C_4$-alkylamino) moieties of ($C_1$-$C_4$-alkylamino)carbonyl or ($C_1$-$C_4$-alkylamino)sulfonyl: for example methylamino, ethylamino, propylamino, 1-methylethylamino, butylamino, 1-methylpropylamino, 2-methylpropylamino or 1,1-dimethylethylamino;

($C_1$-$C_6$-alkyl)amino and also the ($C_1$-$C_6$-alkylamino) moieties of ($C_1$-$C_6$-alkylamino)carbonyl or ($C_1$-$C_4$-alkylamino)sulfonyl: ($C_1$-$C_4$-alkylamino) as mentioned above, and also, for example, pentylamino, 1-methylbutylamino, 2-methylbutylamino, 3-methylbutylamino, 2,2-dimethylpropylamino, 1-ethylpropylamino, hexylamino, 1,1-dimethylpropylamino, 1,2-dimethylpropylamino, 1-methylpentylamino, 2-methylpentylamino, 3-methylpentylamino, 4-methylpentylamino, 1,1-dimethylbutyl-amino, 1,2-dimethylbutylamino, 1,3-dimethylbutylamino, 2,2-dimethylbutylamino, 2,3-dimethylbutyl-amino 3,3-dimethylbutylamino, 1-ethylbutylamino, 2-ethylbutylamino, 1,1,2-trimethylpropylamino, 1,2,2- trimethyl-propylamino, 1-ethyl-1-methylpropylamino or 1-ethyl-2-methylpropylamino;

di($C_1$-$C_4$-alkyl)amino and also the di($C_1$-$C_4$-alkylamino) moieties of di($C_1$-$C_4$-alkylamino)carbonyl or di($C_1$-$C_4$-alkylamino)sulfonyl: for example N,N-dimethylamino, N,N-diethylamino, N,N-di(1-methylethyl)amino, N,N-dipropylamino, N,N-dibutylamino, N,N-di(1-methylpropyl)amino, N,N-di(2-methylpropyl)amino, N,N-di(1,1-dimethylethyl)amino, N-ethyl-N-methylamino, N-methyl-N-propylamino, N-methyl-N-(1-methylethyl)amino, N-butyl-N-methylamino, N-methyl-N-(1-methylpropyl)amino, N-methyl-N-(2-methylpropyl)amino, N-(1,1-dimethylethyl)-N-methylamino, N-ethyl-N-propylamino, N-ethyl-N-(1-methylethyl)amino, N-butyl-N-ethylamino, N-ethyl-N-(1-methylpropyl)amino, N-ethyl-N-(2-methylpropyl)amino, N-ethyl-N-(1,1-dimethylethyl)amino, N-(1-methylethyl)-N-propylamino, N-butyl-N-propylamino, N-(1-methylpropyl)-N-propylamino, N-(2-methylpropyl)-N-propylamino, N-(1,1-dimethylethyl)-N-propylamino, N-butyl-N-(1-methylethyl)amino, N-(1-methylethyl)-N-(1-methylpropyl)amino, N-(1-methylethyl)-N-(2-methylpropyl)amino, N-(1,1-dimethylethyl)-N-(1-methylethyl)amino, N-butyl-N-(1-methylpropyl)amino, N-butyl-N-(2-methylpropyl)amino, N-butyl-N-(1,1-dimethylethyl)amino, N-(1-methylpropyl)-N-(2-methylpropyl)amino, N-(1,1-dimethylethyl)-N-(1-methylpropyl)amino or N-(1,1-dimethyl-ethyl)-N-(2-methylpropyl)amino;

di($C_1$-$C_6$-alkyl)amino and also the di($C_1$-$C_6$-alkylamino) moieties of di($C_1$-$C_6$-alkylamino)carbonyl or di($C_1$-$C_6$-alkylamino)sulfonyl: di($C_1$-$C_4$-alkyl)amino as mentioned above, and also, for example, N-methyl-N-pentylamino, N-methyl-N-(1-methylbutyl)-amino, N-methyl-N-(2-methylbutyl)amino, N-methyl-N-(3-methylbutyl)amino, N-methyl-N-(2,2-dimethylpropyl)amino, N-methyl-N-(1-ethylpropyl)amino, N-methyl-N-hexylamino, N-methyl-N-(1,1-dimethylpropyl)amino, N-methyl-N-(1,2-dimethylpropyl)amino, N-methyl-N-(1-methylpentyl)amino, N-methyl-N-(2-methylpentyl)amino, N-methyl-N-(3-methylpentyl)amino, N-methyl-N-(4-methylpentyl)amino, N-methyl-N-(1,1-dimethylbutyl)amino, N-methyl-N-(1,2-dimethylbutyl)amino, N-methyl-N-(1,3-dimethylbutyl)amino, N-methyl-N-(2,2-dimethylbutyl)amino, N-methyl-N-(2,3-dimethylbutyl)amino, N-methyl-N-(3,3-dimethyl-butyl)amino, N-methyl-N-(1-ethylbutyl)amino, N-methyl-N-(2-ethylbutyl)amino, N-methyl-N-(1,1,2-trimethylpropyl)amino, N-methyl-N-(1,2,2-trimethylpropyl)amino, N-methyl-N-(1-ethyl-1-methylpropyl)amino, N-methyl-N-(1-ethyl-2-methylpropyl)amino, N-ethyl-N-pentylamino, N-ethyl-N-(1-methylbutyl)amino, N-ethyl-N-(2-methylbutyl)-amino, N-ethyl-N-(3-methylbutyl)amino, N-ethyl-N-(2,2-dimethylpropyl)amino, N-ethyl-N-(1-ethylpropyl)amino, N-ethyl-N-hexylamino, N-ethyl-N-(1,1-dimethylpropyl)amino, N-ethyl-N-(1,2-dimethylpropyl)amino, N-ethyl-N-(1-methylpentyl)amino, N-ethyl-N-(2-methylpentyl)amino, N-ethyl-N-(3-methylpentyl)amino, N-ethyl-N-(4-methylpentyl)-amino, N-ethyl-N-(1,1-dimethylbutyl)amino, N-ethyl-N-(1,2-dimethylbutyl)amino, N-ethyl-N-(1,3-dimethylbutyl)amino, N-ethyl-N-(2,2-dimethylbutyl)amino, N-ethyl-N-(2,3-dimethylbutyl)amino, N-ethyl-N-(3,3-dimethylbutyl)amino, N-ethyl-N-(1-ethylbutyl)-amino, N-ethyl-N-(2-ethylbutyl)amino, N-ethyl-N-(1,1,2-trimethylpropyl)amino, N-ethyl-N-(1,2,2-trimethylpropyl)amino, N-ethyl-N-(1-ethyl-1-methylpropyl)amino, N-ethyl-N-(1-ethyl-2-methylpropyl)amino, N-propyl-N-pentylamino, N-butyl-N-pentylamino, N,N-di-pentylamino, N-propyl-N-hexylamino, N-butyl-N-hexylamino, N-pentyl-N-hexylamino or N,N-dihexylamino;

$C_3$-$C_6$-cycloalkoxy: a cycloaliphatic radical having 3 to 6 carbon atoms and bound via an oxygen atom, such as cyclopropyloxy, cyclobutyloxy, cyclopentyloxy and cyclo-hexyloxy;

($C_3$-$C_6$-cycloalkyl)-$C_1$-$C_6$-alkyl: $C_1$-$C_6$-alkyl, in particular $C_1$-$C_4$-alkyl as defined above, such as methyl or ethyl, wherein 1 hydrogen atom is replaced by $C_3$-$C_6$-cycloalkyl as defined above, examples including cyclopropylmethyl ($CH_2$-cyclopropyl), cyclobutylmethyl, cyclopentylmethyl, cycloexylmethyl, 1-cyclopropylethyl ($CH(CH_3)$-cyclopropyl), 1-cyclobutylethyl, 1-cyclopentylethyl, 1-cycloexylethyl, 2-cyclopropylethyl ($CH_2CH_2$-cyclopropyl), 2-cyclobutylethyl, 2-cyclopentylethyl or 2-cycloexylethyl;

($C_3$-$C_6$-cycloalkyl)-$C_1$-$C_6$-alkoxy: $C_1$-$C_6$-alkoxy, in particular $C_1$-$C_4$-alkoxy as defined above, such as methoxy or ethoxy, wherein 1 hydrogen atom is replaced by $C_3$-$C_6$-cycloalkyl as defined above, examples including cyclopropylmethoxy ($OCH_2$-cyclopropyl), cyclobutylmethoxy, cyclopentylmethoxy, cycloexylmethoxy, 1-cyclopropylethoxy (O—CH($CH_3$)-cyclopropyl), 1-cyclobutylethoxy, 1-cyclopentylethoxy, 1-cycloexylethoxy, 2-cyclopropylethoxy ($OCH_2CH_2$)-cyclopropyl), 2-cyclobutylethoxy, 2-cyclopentylethoxy and 2-cycloexylethoxy;

($C_1$-$C_6$-alkoxy)-$C_1$-$C_6$-alkyl: $C_1$-$C_6$-alkyl, in particular $C_1$-$C_4$-alkyl as defined above, such as methyl, ethyl or isopropyl, wherein 1 hydrogen atom is replaced by $C_1$-$C_6$-alkoxy as defined above, examples including methoxymethyl, ethoxymethyl, n-propoxymethyl, butoxymethyl, 1-methoxyethyl, 1-ethoxyethyl, 1-(n-propoxy)ethyl, 1-butoxyethyl, 2-methoxyethyl, 2-ethoxyethyl, 2-(n-propoxy)ethyl, 2-butoxyethyl, 2-methoxypropyl, 2-ethoxypropyl, 2-(n-propoxy)propyl, 2-butoxypropyl;

($C_1$-$C_6$-alkoxy)-$C_1$-$C_6$-alkoxy: $C_1$-$C_6$-alkoxy, in particular $C_1$-$C_4$-alkoxy as defined above, such as methoxy or ethoxy, wherein 1 hydrogen atom is replaced by $C_1$-$C_6$-alkoxy as defined above, examples including methoxymethoxy, ethoxymethoxy, n-propoxymethoxy, butoxymethoxy, 2-methoxyethoxy, 2-ethoxyethoxy, 2-(n-propoxy)ethoxy and 2-butoxyethoxy;

($C_1$-$C_6$-alkoxy)-$C_2$-$C_6$-alkenyl: $C_2$-$C_6$-alkenyl, in particular $C_2$-$C_4$-alkenyl as defined above, such as ethenyl, propenyl, 1-butenyl or 2-butenyl, wherein 1 hydrogen atom is replaced by $C_1$-$C_6$-alkoxy as defined above;

($C_1$-$C_6$-alkoxy)-$C_2$-$C_6$-alkynyl: $C_2$-$C_6$-alkynyl, in particular $C_2$-$C_4$-alkynyl as defined above, such as ethynyl, propynyl or 2-butynyl, wherein 1 hydrogen atom is replaced by $C_1$-$C_6$-alkoxy as defined above;

($C_1$-$C_6$-alkyl)carbonyl: $C_1$-$C_6$-alkyl as mentioned above, which is bound to the remainder of the molecule by a carbonyl group;

($C_1$-$C_6$-alkoxy)carbonyl: $C_1$-$C_6$-alkyloxy as mentioned above, which is bound to the remainder of the molecule by a carbonyl group;

($C_1$-$C_6$-alkylamino)carbonyl: ($C_1$-$C_6$-alkyl)amino as mentioned above, which is bound to the remainder of the molecule by a carbonyl group;

($C_1$-$C_6$-alkylamino)sulfonyl: ($C_1$-$C_6$-alkyl)amino as mentioned above, which is bound to the remainder of the molecule by a sulfonyl group;

di($C_1$-$C_6$-alkylamino)carbonyl: di($C_1$-$C_6$-alkyl)amino as mentioned above, which is bound to the remainder of the molecule by a carbonyl group;

di($C_1$-$C_6$-alkylamino)sulfonyl: di($C_1$-$C_6$-alkyl)amino as mentioned above, which is bound to the remainder of the molecule by a sulfonyl group;

phenyl-$C_1$-$C_6$-alkyl: $C_1$-$C_6$-alkyl, in particular $C_1$-$C_4$-alkyl as defined above, such as methyl or ethyl, wherein 1 hydrogen atom is replaced by phenyl, examples including benzyl, 1-phenylethyl, 2-phenylethyl, 1-phenylpropyl, 2-phenylpropyl, 1-phenyl-1-methylethyl etc.;

Ipso-carbocyclic radicals include:
  $C_3$-$C_6$-cycloalkan-1,1-diyl, e.g. cyclopropan-1,1-diyl, cyclobutan-1,1-diyl, cyclo-pentan-1,1-diyl or cyclohexan-1,1-diyl; and
  ipso-$C_3$-$C_6$-cycloalkendiyl: ipso-connected bivalent unsaturated cycloaliphatic radical having 3 to 6-carbon atoms as ring members, e.g. cyclobuten-3,3-diyl, cyclobuten-4,4-diyl, cyclopenten-3,3-diyl, cyclopenten-4,4-diyl, cyclopenten-5,5-diyl, cyclohexen-3,3-diyl, cyclohexen-4,4-diyl, cyclohexen-5,5-diyl or cyclohexen-6,6-diyl;

three- to six-membered saturated or partially unsaturated ipso-heterocyclic radical is an ipso-connected bivalent heterocyclodiyl radical, which is saturated or unsaturated, which has 3 to 6 ring atoms, wherein at least 1 ring atom, e.g. 1, 2 or 3 ring atoms are a heteroatom, which is preferably selected from O, S and N. Examples of ipso-heterocyclodiyl radicals include oxiran-2,2-diyl, oxetan-2,2-diyl, oxetan-3,3-diyl, oxolan-2,2-diyl, oxolan-3,3-diyl, 1,3-dioxolan-2,2-diyl, oxan-2,2-diyl, oxan-3,3-diyl or oxan-4,4-diyl, 1,3-dioxan-2,2-diyl, thiolan-2,2-diyl, thiolan-3,3-diyl, pyrrolidin-2,2-diyl, pyrroldin-3,3-diyl, piperidin-2,2,-diyl, piperidin-3,3-diyl and piperidin-4,4-diyl, where the aforementioned radicals may also be partly or completely halogenated or carry 1 to 6 $C_1$-$C_6$-alkyl groups.

three- to six-membered heterocyclyl: monocyclic saturated or partially unsaturated hydrocarbon having three to six ring members as mentioned above which, in addition to carbon atoms, contains one or two heteroatoms selected from O, S and N;

for example 2-oxiranyl, 2-oxetanyl, 3-oxetanyl, 2-aziridinyl, 3-thietanyl, 1-azetidinyl, 2-azetidinyl;

for example 2-tetrahydrofuranyl, 3-tetrahydrofuranyl, 2-tetrahydrothienyl, 3-tetrahydrothienyl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl;

for example 2,3-dihydrofur-2-yl, 2,3-dihydrofur-3-yl, 2,4-dihydrofur-2-yl, 2,4-dihydrofur-3-yl, 2,3-dihydrothien-2-yl, 2,3-dihydrothien-3-yl, 2,4-dihydrothien-2-yl, 2,4-dihydrothien-3-yl, 4,5-dihydropyrrol-2-yl, 4,5-dihydropyrrol-3-yl, 2,5-dihydropyrrol-2-yl, 2,5-dihydropyrrol-3-yl, 4,5-dihydroisoxazol-3-yl, 2,5-dihydroisoxazol-3-yl, 2,3-dihydroisoxazol-3-yl, 4,5-dihydroisoxazol-4-yl, 2,5-dihydroisoxazol-4-yl, 2,3-dihydroisoxazol-4-yl, 4,5-dihydroisoxazol-5-yl, 2,5-dihydroisoxazol-5-yl, 2,3-dihydroisoxazol-5-yl, 4,5-dihydroisothiazol-3-yl, 2,5-dihydroisothiazol-3-yl, 2,3-dihydroisothiazol-3-yl, 4,5-dihydroisothiazol-4-yl, 2,5-dihydroisothiazol-4-yl, 2,3-dihydroisothiazol-4-yl, 4,5-dihydroisothiazol-5-yl, 2,5-dihydroisothiazol-5-yl, 2,3-dihydroisothiazol-5-yl, 2,3-dihydropyrazol-2-yl, 2,3-dihydropyrazol-3-yl, 2,3-dihydropyrazol-4-yl, 2,3-dihydropyrazol-5-yl, 3,4-dihydropyrazol-3-yl, 3,4-dihydropyrazol-4-yl, 3,4-dihydropyrazol-5-yl, 4,5-dihydropyrazol-3-yl, 4,5-dihydropyrazol-4-yl, 4,5-dihydropyrazol-5-yl, 2,3-dihydroimidazol-2-yl, 2,3-dihydroimidazol-3-yl, 2,3-dihydroimidazol-4-yl, 2,3-dihydroimidazol-5-yl, 4,5-dihydroimidazol-2-yl, 4,5-dihydroimidazol-4-yl, 4,5-dihydroimidazol-5-yl, 2,5-dihydroimidazol-2-yl, 2,5-dihydroimidazol-4-yl, 2,5-dihydroimidazol-5-yl, 2,3-dihydrooxazol-3-yl, 2,3-dihydrooxazol-4-yl, 2,3-dihydrooxazol-5-yl, 3,4-dihydrooxazol-3-yl, 3,4-dihydrooxazol-4-yl, 3,4-dihydrooxazol-5-yl, 2,3-dihydrothiazol-3-yl, 2,3-dihydrothiazol-4-yl, 2,3-dihydrothiazol-5-yl, 3,4-dihydrothiazol-3-yl, 3,4-dihydrothiazol-4-yl, 3,4-dihydrothiazol-5-yl, 3,4-dihydrothiazol-2-yl, 3,4-dihydrothiazol-3-yl, 3,4-dihydrothiazol-4-yl;

for example 2-piperidinyl, 3-piperidinyl, 4-piperidinyl, 1,3-dioxan-2-yl, 1,3-dioxan-4-yl, 1,3-dioxan-5-yl, 1,4-dioxan-2-yl, 1,3-dithian-2-yl, 1,3-dithian-4-yl, 1,4-dithian-2-yl, 1,3-dithian-5-yl, 2-tetrahydropyranyl, 3-tetrahydropyranyl, 4-tetrahydropyranyl, 2-tetrahydrothiopyranyl, 3-tetrahydrothiopyranyl, 4-tetrahydro-thiopyranyl, 3-hexahydropyridazinyl, 4-hexahydropyridazinyl, 2-hexahydropyrimidinyl, 4-hexahydropyrimidinyl, 5-hexahydropyrimidinyl, 2-piperazinyl, tetrahydro-1,3-oxazin-2-yl, tetrahydro-1,3-oxazin-6-yl, 2-morpholinyl, 3-morpholinyl;

for example 2H-pyran-2-yl, 2H-pyran-3-yl, 2H-pyran-4-yl, 2H-pyran-5-yl, 2H-pyran-6-yl, 3,6-dihydro-2H-pyran-2-yl, 3,6-dihydro-2H-pyran-3-yl, 3,6-dihydro-2H-pyran-4-yl, 3,6-dihydro-2H-pyran-5-yl, 3,6-dihydro-2H-pyran-6-yl, 3,4-dihydro-2H-pyran-3-yl, 3,4-dihydro-2H-pyran-4-yl, 3,4-dihydro-2H-pyran-6-yl, 2H-thiopyran-2-yl, 2H-thiopyran-3-yl, 2H-thiopyran-4-yl, 2H-thiopyran-5-yl, 2H-thiopyran-6-yl, 5,6-dihydro-4H-1,3-oxazin-2-yl;

heteroaryl: mono- or bicyclic aromatic heteroaryl having 5 to 10 ring members which, in addition to carbon atoms, contains 1 to 3 nitrogen atoms, or 1 to 3, preferably 1 or 2, nitrogen atoms and an oxygen or sulfur atom, or an oxygen or a sulfur atom, for example monocycles, such as furyl (for example 2-furyl, 3-furyl), thienyl (for example 2-thienyl, 3-thienyl), pyrrolyl (for example pyrrol-2-yl, pyrrol-3-yl), pyrazolyl (for example pyrazol-3-yl, pyrazol-4-yl), isoxazolyl (for example isoxazol-3-yl, isoxazol-4-yl, isoxazol-5-yl), isothiazolyl (for example isothiazol-3-yl, isothiazol-4-yl, isothiazol-5-yl), imidazolyl (for example imidazole-2-yl, imidazole-4-yl), oxazolyl (for example oxazol-2-yl, oxazol-4-yl, oxazol-5-yl), thiazolyl (for example thiazol-2-yl, thiazol-4-yl, thiazol-5-yl), oxadiazolyl (for example 1,2,3-oxadiazol-4-yl, 1,2,3-oxadiazol-5-yl, 1,2,4-oxadiazol-3-yl, 1,2,4-oxadiazol-5-yl, 1,3,4-oxadiazol-2-yl), thiadiazolyl (for example 1,2,3-thiadiazol-4-yl, 1,2,3-thiadiazol-5-yl, 1,2,4-thiadiazol-3-yl, 1,2,4-thiadiazol-5-yl, 1,3,4-thiadiazolyl-2-yl), triazolyl (for example 1,2,3-triazol-4-yl, 1,2,4-triazol-3-yl), pyridyl (for example pyridine-2-yl, pyridine-3-yl, pyridine-4-yl), pyrazinyl (for example pyridazin-3-yl, pyridazin-4-yl), pyrimidinyl (for example pyrimidin-2-yl, pyrimidin-4-yl, pyrimidin-5-yl), pyrazin-2-yl, triazinyl (for example 1,3,5-triazin-2-yl, 1,2,4-triazin-3-yl, 1,2,4-triazin-5-yl, 1,2,4-triazin-6-yl); and also bicycles such as the benzo-fused derivatives of the abovementioned monocycles, for example quinolinyl, isoquinolinyl, indolyl, benzothienyl, benzofuranyl, benzoxazolyl, benzothiazolyl, benzisothiazolyl, benzimidazolyl, benzopyrazolyl, benzo-thiadiazolyl, benzotriazolyl.

The preferred embodiments of the invention mentioned herein below have to be understood as being preferred either independently from each other or in combination with one another.

According to a preferred embodiment of the invention preference is also given to those azines of formula (I), wherein the variables, either independently of one another or in combination with one another, have the following meanings:

A preferably is mono- or bicyclic aromatic heteroaryl having 5 to 10 ring members (hereinafter mono- or bicyclic 5- to 10-membered hetaryl) which, in addition to carbon atoms, contains 1 to 3 nitrogen atoms, or 1 to 3 nitrogen atoms and an oxygen or sulfur atom, or an oxygen or a sulfur atom,
which is substituted by one to six, in particular by 1, 2, 3 or 4 substituents $R^A$ as defined above.

A is in particular aromatic monocyclic aromatic heteroaryl having 5 or 6 ring members (hereinafter 5- to 6-membered hetaryl) which, in addition to carbon atoms, contains 1 to 3 nitrogen atoms, or 1 to 3 nitrogen atoms and an oxygen or sulfur atom, or an oxygen or a sulfur atom, which is substituted by 1, 2, 3 or 4 substituents $R^A$ as defined above.

A is more particularly 6-membered heteroaryl which, in addition to carbon atoms, contains 1 to 3 nitrogen atoms, in particular 1 or 2 nitrogen atoms as ring members, which is substituted by 1, 2, 3 or 4 substituents $R^A$ as defined above.

A is especially pyridyl, in particular 2- or 4-pyridyl, which, in addition to carbon atoms, contain 1 to 3 nitrogen atoms, in particular 1 or 2 nitrogen atoms as ring members, which is substituted by 1, 2, 3 or 4 substituents $R^A$ as defined above.

Irrespectively of its occurrence, $R^A$ is preferably selected from the group consisting of halogen, CN, $NO_2$, $C_1$-$C_6$-alkyl, $C_1$-$C_6$-haloalkyl, OH, $C_1$-$C_6$-alkoxy, $C_3$-$C_6$-cycloalkyl, $C_3$-$C_6$-cycloalkoxy, ($C_3$-$C_6$-cycloalkyl)methoxy, $C_2$-$C_6$-alkynyl, $C_2$-$C_6$-alkenyl, $C_2$-$C_6$-alkynyloxy, $C_2$-$C_6$-alkenyloxy, $C_1$-$C_6$-alkylthio, ($C_1$-$C_6$-alkyl)sulfinyl, ($C_1$-$C_6$-alkyl)sulfonyl, amino, ($C_1$-$C_6$-alkyl)amino, di($C_1$-$C_6$-alkyl)amino, ($C_1$-$C_6$-alkyl)carbonyl, ($C_1$-$C_6$-alkoxy)carbonyl and $C_1$-$C_6$-haloalkoxy;

$R^A$ is in particular selected form the group consisting of halogen, CN, $NO_2$, $C_1$-$C_6$-alkyl, $C_1$-$C_6$-haloalkyl, OH, $C_1$-$C_6$-alkoxy, $C_1$-$C_4$-haloalkoxy, $C_1$-$C_6$-alkylthio, ($C_1$-$C_6$-alkyl)sulfinyl, ($C_1$-$C_6$-alkyl)sulfonyl, amino, ($C_1$-$C_6$-alkyl)amino, di($C_1$-$C_6$-alkyl)amino, ($C_1$-$C_6$-alkyl)carbonyl and ($C_1$-$C_6$-alkoxy)carbonyl.

$R^A$ is more particularly selected form the group consisting of halogen, $C_1$-$C_4$-haloalkyl, $C_1$-$C_4$-alkoxy, $C_1$-$C_4$-haloalkoxy and CN; even more preferred from the group consisting of halogen, CN, $C_1$-$C_6$-alkyl and $C_1$-$C_6$-alkoxy; especially preferred selected from halogen and CN; also especially preferred selected from the group consisting of F, Cl, CN and $CH_3$; most preferred selected from the group consisting of F, Cl and CN.

A in particular is mono- or bicyclic aromatic heteroaryl having 5 to 10 ring members which, in addition to carbon atoms, contains 1 to 3 nitrogen atoms, or 1 to 3 nitrogen atoms and an oxygen or sulfur atom, or an oxygen or a sulfur atom, which is substituted by one to six, in particular by 1, 2, 3 or 4 substituents $R^A$ selected from the group consisting of halogen, CN, $NO_2$, $C_1$-$C_6$-alkyl, $C_1$-$C_6$-haloalkyl, OH, $C_1$-$C_6$-alkoxy, $C_1$-$C_6$-alkylthio, ($C_1$-$C_6$-alkyl)sulfinyl, ($C_1$-$C_6$-alkyl)sulfonyl, amino, ($C_1$-$C_6$-alkyl)amino, di($C_1$-$C_6$-alkyl)amino, ($C_1$-$C_6$-alkyl)carbonyl, ($C_1$-$C_6$-alkoxy)carbonyl;

Particularly preferred A is a 5- or 6-membered heteroaryl having 1 to 3 nitrogen atoms, or 1 or 2 nitrogen atoms and an oxygen or sulfur atom, or an oxygen or a sulfur atom, which is
substituted by one to four substituents $R^A$ as defined above, which are in particular selected from the group consisting of halogen, CN, $NO_2$, $C_1$-$C_6$-alkyl, $C_1$-$C_6$-haloalkyl, OH, $C_1$-$C_6$-alkoxy, $C_1$-$C_6$-alkylthio, ($C_1$-$C_6$-alkyl)sulfinyl, ($C_1$-$C_6$-alkyl)sulfonyl, amino, ($C_1$-$C_6$-alkyl)amino, di($C_1$-$C_6$-alkyl)amino, ($C_1$-$C_6$-alkyl)carbonyl, ($C_1$-$C_6$-alkoxy)carbonyl;
particularly preferred selected from the group consisting of halogen, CN, $C_1$-$C_6$-alkyl and $C_1$-$C_6$-alkoxy;
especially preferred selected from halogen and CN;
also especially preferred selected from the group consisting of F, Cl, CN and $CH_3$;
more preferred selected from the group consisting of F, Cl and CN;
preferably substituted by one to three substituents $R^A$ selected from the group consisting of halogen, CN, $NO_2$, $C_1$-$C_6$-alkyl, $C_1$-$C_6$-haloalkyl, OH, $C_1$-$C_6$-alkoxy, $C_1$-$C_6$-alkylthio, ($C_1$-$C_6$-alkyl)sulfinyl, ($C_1$-$C_6$-alkyl)sulfonyl, amino, ($C_1$-$C_6$-alkyl)amino, di($C_1$-$C_6$-alkyl)amino, ($C_1$-$C_6$-alkyl)carbonyl, ($C_1$-$C_6$-alkoxy)carbonyl;
particularly preferred selected from the group consisting of halogen, CN, $C_1$-$C_6$-alkyl and $C_1$-$C_6$-alkoxy;
especially preferred selected from halogen and CN;
also especially preferred selected from the group consisting of F, Cl, CN and $CH_3$;
more preferred selected from the group consisting of F, Cl and CN;
particularly preferred substituted by one or two substituents $R^A$ as defined above and in particular selected from the group consisting of halogen, CN, $NO_2$, $C_1$-$C_6$-alkyl, $C_1$-$C_6$-haloalkyl, OH, $C_1$-$C_6$-alkoxy, $C_1$-$C_6$-alkylthio, ($C_1$-$C_6$-alkyl)sulfinyl, ($C_1$-$C_6$-alkyl)sulfonyl, amino, ($C_1$-$C_6$-alkyl)amino, di($C_1$-$C_6$-alkyl)amino, ($C_1$-$C_6$-alkyl)carbonyl, ($C_1$-$C_6$-alkoxy)carbonyl;
particularly preferred selected from the group consisting of halogen, CN, $C_1$-$C_6$-alkyl and $C_1$-$C_6$-alkoxy;
especially preferred selected from halogen and CN;
also especially preferred selected from the group consisting of F, Cl, CN and $CH_3$;
more preferred selected from the group consisting of F, Cl and CN;
especially preferred substituted by one substituent $R^A$ as defined above and in particular selected from the group consisting of halogen, CN, $NO_2$, $C_1$-$C_6$-alkyl, $C_1$-$C_6$-haloalkyl, OH, $C_1$-$C_6$-alkoxy, $C_1$-$C_6$-alkylthio, ($C_1$-$C_6$-alkyl)sulfinyl, ($C_1$-$C_6$-alkyl)sulfonyl, amino, ($C_1$-$C_6$-alkyl)amino, di($C_1$-$C_6$-alkyl)amino, ($C_1$-$C_6$-alkyl)carbonyl, ($C_1$-$C_6$-alkoxy)carbonyl;
particularly preferred selected from the group consisting of halogen, CN, $C_1$-$C_6$-alkyl and $C_1$-$C_6$-alkoxy;
especially preferred selected from halogen and CN;
also especially preferred selected from the group consisting of F, Cl, CN and $CH_3$;
more preferred selected from the group consisting of F, Cl and CN;

also especially preferred substituted by two substituents $R^A$ as defined above and in particular selected from the group consisting of halogen, CN, $NO_2$, $C_1$-$C_6$-alkyl, $C_1$-$C_6$-haloalkyl, OH, $C_1$-$C_6$-alkoxy, $C_1$-$C_6$-alkylthio, ($C_1$-$C_6$-alkyl)sulfinyl, ($C_1$-$C_6$-alkyl)sulfonyl, amino, ($C_1$-$C_6$-alkyl)amino, di($C_1$-$C_6$-alkyl)amino, ($C_1$-$C_6$-alkyl)carbonyl, ($C_1$-$C_6$-alkoxy)carbonyl;

particularly preferred selected from the group consisting of halogen, CN, $C_1$-$C_6$-alkyl and $C_1$-$C_6$-alkoxy;

especially preferred selected from halogen and CN;

also especially preferred selected from the group consisting of F, Cl, CN and $CH_3$;

more preferred selected from the group consisting of F, Cl and CN;

also preferably substituted by two, three or four substituents $R^A$ as defined above and in particular selected from the group consisting of halogen, CN, $NO_2$, $C_1$-$C_6$-alkyl, $C_1$-$C_6$-haloalkyl, OH, $C_1$-$C_6$-alkoxy, $C_1$-$C_6$-alkylthio, ($C_1$-$C_6$-alkyl)sulfinyl, ($C_1$-$C_6$-alkyl)sulfonyl, amino, ($C_1$-$C_6$-alkyl)amino, di($C_1$-$C_6$-alkyl)amino, ($C_1$-$C_6$-alkyl)carbonyl, ($C_1$-$C_6$-alkoxy)carbonyl;

particularly preferred selected from the group consisting of halogen, CN, $C_1$-$C_6$-alkyl and $C_1$-$C_6$-alkoxy;

especially preferred selected from halogen and CN;

also especially preferred selected from the group consisting of F, Cl, CN and $CH_3$;

more preferred selected from the group consisting of F, Cl and CN;

particularly preferred substituted by two or three substituents $R^A$ as defined above and in particular selected from the group consisting of halogen, CN, $NO_2$, $C_1$-$C_6$-alkyl, $C_1$-$C_6$-haloalkyl, OH, $C_1$-$C_6$-alkoxy, $C_1$-$C_6$-alkylthio, ($C_1$-$C_6$-alkyl)sulfinyl, ($C_1$-$C_6$-alkyl)sulfonyl, amino, ($C_1$-$C_6$-alkyl)amino, di($C_1$-$C_6$-alkyl)amino, ($C_1$-$C_6$-alkyl)carbonyl, ($C_1$-$C_6$-alkoxy)carbonyl;

particularly preferred selected from the group consisting of halogen, CN, $C_1$-$C_6$-alkyl and $C_1$-$C_6$-alkoxy;

especially preferred selected from halogen and CN;

also especially preferred selected from the group consisting of F, Cl, CN and $CH_3$;

more preferred selected from the group consisting of F, Cl and CN;

also preferably substituted by three or four substituents $R^A$ as defined above and in particular selected from the group consisting of halogen, CN, $NO_2$, $C_1$-$C_6$-alkyl, $C_1$-$C_6$-haloalkyl, OH, $C_1$-$C_6$-alkoxy, $C_1$-$C_6$-alkylthio, ($C_1$-$C_6$-alkyl)sulfinyl, ($C_1$-$C_6$-alkyl)sulfonyl, amino, ($C_1$-$C_6$-alkyl)amino, di($C_1$-$C_6$-alkyl)amino, ($C_1$-$C_6$-alkyl)carbonyl, ($C_1$-$C_6$-alkoxy)carbonyl;

particularly preferred selected from the group consisting of halogen, CN, $C_1$-$C_6$-alkyl and $C_1$-$C_6$-alkoxy;

especially preferred selected from halogen and CN;

also especially preferred selected from the group consisting of F, Cl, CN and $CH_3$;

more preferred selected from the group consisting of F, Cl and CN;

particularly preferred substituted by three substituents $R^A$ as defined above and in particular selected from the group consisting of halogen, CN, $NO_2$, $C_1$-$C_6$-alkyl, $C_1$-$C_6$-haloalkyl, OH, $C_1$-$C_6$-alkoxy, $C_1$-$C_6$-alkylthio, ($C_1$-$C_6$-alkyl)sulfinyl, ($C_1$-$C_6$-alkyl)sulfonyl, amino, ($C_1$-$C_6$-alkyl)amino, di($C_1$-$C_6$-alkyl)amino, ($C_1$-$C_6$-alkyl)carbonyl, ($C_1$-$C_6$-alkoxy)carbonyl;

particularly preferred selected from the group consisting of halogen, CN, $C_1$-$C_6$-alkyl and $C_1$-$C_6$-alkoxy;

especially preferred selected from halogen and CN;

also especially preferred selected from the group consisting of F, Cl, CN and $CH_3$;

more preferred selected from the group consisting of F, Cl and CN;

also particularly preferred substituted by four substituents $R^A$ as defined above and in particular selected from the group consisting of halogen, CN, $NO_2$, $C_1$-$C_6$-alkyl, $C_1$-$C_6$-haloalkyl, OH, $C_1$-$C_6$-alkoxy, $C_1$-$C_6$-alkylthio, ($C_1$-$C_6$-alkyl)sulfinyl, ($C_1$-$C_6$-alkyl)sulfonyl, amino, ($C_1$-$C_6$-alkyl)amino, di($C_1$-$C_6$-alkyl)amino, ($C_1$-$C_6$-alkyl)carbonyl, ($C_1$-$C_6$-alkoxy)carbonyl;

particularly preferred selected from the group consisting of halogen, CN, $C_1$-$C_6$-alkyl and $C_1$-$C_6$-alkoxy;

especially preferred selected from halogen and CN;

also especially preferred selected from the group consisting of F, Cl, CN and $CH_3$;

more preferred selected from the group consisting of F, Cl and CN;

In particular groups of embodiments A is a 5-membered heteroaryl having 1 to 3 nitrogen atoms, or 1 or 2 nitrogen atoms and an oxygen or sulfur atom, or an oxygen or a sulfur atom, as ring members which 5-membered heteroaryl is substituted by one to three substituents $R^A$ as defined above and in particular selected from the group consisting of halogen, CN, $NO_2$, $C_1$-$C_6$-alkyl, $C_1$-$C_6$-haloalkyl, OH, $C_1$-$C_6$-alkoxy, $C_1$-$C_6$-alkylthio, ($C_1$-$C_6$-alkyl)sulfinyl, ($C_1$-$C_6$-alkyl)sulfonyl, amino, ($C_1$-$C_6$-alkyl)amino, di($C_1$-$C_6$-alkyl)amino, ($C_1$-$C_6$-alkyl)carbonyl, ($C_1$-$C_6$-alkoxy)carbonyl;

particularly preferred selected from the group consisting of halogen, CN, $C_1$-$C_6$-alkyl and $C_1$-$C_6$-alkoxy;

especially preferred selected from halogen and CN;

also especially preferred selected from the group consisting of F, Cl, CN and $CH_3$;

more preferred selected from the group consisting of F, Cl and CN;

preferably substituted by one or two substituents $R^A$ as defined above and in particular selected from the group consisting of halogen, CN, $NO_2$, $C_1$-$C_6$-alkyl, $C_1$-$C_6$-haloalkyl, OH, $C_1$-$C_6$-alkoxy, $C_1$-$C_6$-alkylthio, ($C_1$-$C_6$-alkyl)sulfinyl, ($C_1$-$C_6$-alkyl)sulfonyl, amino, ($C_1$-$C_6$-alkyl)amino, di($C_1$-$C_6$-alkyl)amino, ($C_1$-$C_6$-alkyl)carbonyl, ($C_1$-$C_6$-alkoxy)carbonyl;

particularly preferred selected from the group consisting of halogen, CN, $C_1$-$C_6$-alkyl and $C_1$-$C_6$-alkoxy;

especially preferred selected from halogen and CN;

also especially preferred selected from the group consisting of F, Cl, CN and $CH_3$;

more preferred selected from the group consisting of F, Cl and CN;

particularly preferred substituted by one substituent $R^A$ as defined above and in particular selected from the group consisting of halogen, CN, $NO_2$, $C_1$-$C_6$-alkyl, $C_1$-$C_6$-haloalkyl, OH, $C_1$-$C_6$-alkoxy, $C_1$-$C_6$-alkylthio, ($C_1$-$C_6$-alkyl)sulfinyl, ($C_1$-$C_6$-alkyl)sulfonyl, amino, ($C_1$-$C_6$-alkyl)amino, di($C_1$-$C_6$-alkyl)amino, ($C_1$-$C_6$-alkyl)carbonyl, ($C_1$-$C_6$-alkoxy)carbonyl;

particularly preferred selected from the group consisting of halogen, CN, $C_1$-$C_6$-alkyl and $C_1$-$C_6$-alkoxy;

especially preferred selected from halogen and CN;

also especially preferred selected from the group consisting of F, Cl, CN and $CH_3$;

more preferred selected from the group consisting of F, Cl and CN;

also particularly preferred substituted by two substituents $R^A$ as defined above and in particular selected from the group consisting of halogen, CN, $NO_2$, $C_1$-$C_6$-alkyl, $C_1$-$C_6$-haloalkyl, OH, $C_1$-$C_6$-alkoxy, $C_1$-$C_6$-alkylthio, ($C_1$-$C_6$-alkyl)sulfinyl, ($C_1$-$C_6$-alkyl)sulfonyl, amino, ($C_1$-$C_6$-alkyl)amino, di($C_1$-$C_6$-alkyl)amino, ($C_1$-$C_6$-alkyl)carbonyl, ($C_1$-$C_6$-alkoxy)carbonyl;

particularly preferred selected from the group consisting of halogen, CN, $C_1$-$C_6$-alkyl and $C_1$-$C_6$-alkoxy;

especially preferred selected from halogen and CN;

also especially preferred selected from the group consisting of F, Cl, CN and $CH_3$;

more preferred selected from the group consisting of F, Cl and CN;

also preferably substituted by two or three substituents $R^A$ as defined above and in particular selected from the group consisting of halogen, CN, $NO_2$, $C_1$-$C_6$-alkyl, $C_1$-$C_6$-haloalkyl, OH, $C_1$-$C_6$-alkoxy, $C_1$-$C_6$-alkylthio, ($C_1$-$C_6$-alkyl)sulfinyl, ($C_1$-$C_6$-alkyl)sulfonyl, amino, ($C_1$-$C_6$-alkyl)amino, di($C_1$-$C_6$-alkyl)amino, ($C_1$-$C_6$-alkyl)carbonyl, ($C_1$-$C_6$-alkoxy)carbonyl;

particularly preferred selected from the group consisting of halogen, CN, $C_1$-$C_6$-alkyl and $C_1$-$C_6$-alkoxy;

especially preferred selected from halogen and CN;

also especially preferred selected from the group consisting of F, Cl, CN and $CH_3$;

more preferred selected from the group consisting of F, Cl and CN;

particularly preferred substituted by three substituents $R^A$ as defined above and in particular selected from the group consisting of halogen, CN, $NO_2$, $C_1$-$C_6$-alkyl, $C_1$-$C_6$-haloalkyl, OH, $C_1$-$C_6$-alkoxy, $C_1$-$C_6$-alkylthio, ($C_1$-$C_6$-alkyl)sulfinyl, ($C_1$-$C_6$-alkyl)sulfonyl, amino, ($C_1$-$C_6$-alkyl)amino, di($C_1$-$C_6$-alkyl)amino, ($C_1$-$C_6$-alkyl)carbonyl, ($C_1$-$C_6$-alkoxy)carbonyl;

particularly preferred selected from the group consisting of halogen, CN, $C_1$-$C_6$-alkyl and $C_1$-$C_6$-alkoxy;

especially preferred selected from halogen and CN;

also especially preferred selected from the group consisting of F, Cl, CN and $CH_3$;

more preferred selected from the group consisting of F, Cl and CN;

In further particularly preferred groups of embodiments A is a 6-membered heteroaryl having 1 to 3 nitrogen atoms, preferably having 1 or 2 nitrogen atoms, particularly preferred A is pyridyl, especially preferred 2- or 4-pyridyl;

which is substituted by one to four substituents selected from the group consisting of halogen, CN, $NO_2$, $C_1$-$C_6$-alkyl, $C_1$-$C_6$-haloalkyl, OH, $C_1$-$C_6$-alkoxy, $C_1$-$C_6$-alkylthio, ($C_1$-$C_6$-alkyl)sulfinyl, ($C_1$-$C_6$-alkyl)sulfonyl, amino, ($C_1$-$C_6$-alkyl)amino, di($C_1$-$C_6$-alkyl)amino, ($C_1$-$C_6$-alkyl)carbonyl, ($C_1$-$C_6$-alkoxy)carbonyl;

particularly preferred selected from the group consisting of halogen, CN, $C_1$-$C_6$-alkyl and $C_1$-$C_6$-alkoxy;

especially preferred selected from halogen and CN;

also especially preferred selected from the group consisting of F, Cl, CN and $CH_3$;

more preferred selected from the group consisting of F, Cl and CN;

preferably substituted by one to three substituents $R^A$ as defined above and in particular selected from the group consisting of halogen, CN, $NO_2$, $C_1$-$C_6$-alkyl, $C_1$-$C_6$-haloalkyl, OH, $C_1$-$C_6$-alkoxy, $C_1$-$C_6$-alkylthio, ($C_1$-$C_6$-alkyl)sulfinyl, ($C_1$-$C_6$-alkyl)sulfonyl, amino, ($C_1$-$C_6$-alkyl)amino, di($C_1$-$C_6$-alkyl)amino, ($C_1$-$C_6$-alkyl)carbonyl, ($C_1$-$C_6$-alkoxy)carbonyl;

particularly preferred selected from the group consisting of halogen, CN, $C_1$-$C_6$-alkyl and $C_1$-$C_6$-alkoxy;

especially preferred selected from halogen and CN;

also especially preferred selected from the group consisting of F, Cl, CN and $CH_3$;

more preferred selected from the group consisting of F, Cl and CN;

particularly preferred substituted by one or two substituents $R^A$ as defined above and in particular selected from the group consisting of halogen, CN, $NO_2$, $C_1$-$C_6$-alkyl, $C_1$-$C_6$-haloalkyl, OH, $C_1$-$C_6$-alkoxy, $C_1$-$C_6$-alkylthio, ($C_1$-$C_6$-alkyl)sulfinyl, ($C_1$-$C_6$-alkyl)sulfonyl, amino, ($C_1$-$C_6$-alkyl)amino, di($C_1$-$C_6$-alkyl)amino, ($C_1$-$C_6$-alkyl)carbonyl, ($C_1$-$C_6$-alkoxy)carbonyl;

particularly preferred selected from the group consisting of halogen, CN, $C_1$-$C_6$-alkyl and $C_1$-$C_6$-alkoxy;

especially preferred selected from halogen and CN;

also especially preferred selected from the group consisting of F, Cl, CN and $CH_3$;

more preferred selected from the group consisting of F, Cl and CN;

especially preferred substituted by one substituent $R^A$ as defined above and in particular selected from the group consisting of halogen, CN, $NO_2$, $C_1$-$C_6$-alkyl, $C_1$-$C_6$-haloalkyl, OH, $C_1$-$C_6$-alkoxy, $C_1$-$C_6$-alkylthio, ($C_1$-$C_6$-alkyl)sulfinyl, ($C_1$-$C_6$-alkyl)sulfonyl, amino, ($C_1$-$C_6$-alkyl)amino, di($C_1$-$C_6$-alkyl)amino, ($C_1$-$C_6$-alkyl)carbonyl, ($C_1$-$C_6$-alkoxy)carbonyl;

particularly preferred selected from the group consisting of halogen, CN, $C_1$-$C_6$-alkyl and $C_1$-$C_6$-alkoxy;

especially preferred selected from halogen and CN;

also especially preferred selected from the group consisting of F, Cl, CN and $CH_3$;

more preferred selected from the group consisting of F, Cl and CN;

also especially preferred substituted by two substituents $R^A$ as defined above and in particular selected from the group consisting of halogen, CN, $NO_2$, $C_1$-$C_6$-alkyl, $C_1$-$C_6$-haloalkyl, OH, $C_1$-$C_6$-alkoxy, $C_1$-$C_6$-alkylthio, ($C_1$-$C_6$-alkyl)sulfinyl, ($C_1$-$C_6$-alkyl)sulfonyl, amino, ($C_1$-$C_6$-alkyl)amino, di($C_1$-$C_6$-alkyl)amino, ($C_1$-$C_6$-alkyl)carbonyl, ($C_1$-$C_6$-alkoxy)carbonyl;

particularly preferred selected from the group consisting of halogen, CN, $C_1$-$C_6$-alkyl and $C_1$-$C_6$-alkoxy;

especially preferred selected from halogen and CN;

also especially preferred selected from the group consisting of F, Cl, CN and $CH_3$;

more preferred selected from the group consisting of F, Cl and CN;

also preferably substituted by two to four substituents $R^A$ as defined above and in particular selected from the group consisting of halogen, CN, $NO_2$, $C_1$-$C_6$-alkyl, $C_1$-$C_6$-haloalkyl, OH, $C_1$-$C_6$-alkoxy, $C_1$-$C_6$-alkylthio, ($C_1$-$C_6$-alkyl)sulfinyl, ($C_1$-$C_6$-alkyl)sulfonyl, amino, ($C_1$-$C_6$-alkyl)amino, di($C_1$-$C_6$-alkyl)amino, ($C_1$-$C_6$-alkyl)carbonyl, ($C_1$-$C_6$-alkoxy)carbonyl;

particularly preferred selected from the group consisting of halogen, CN, $C_1$-$C_6$-alkyl and $C_1$-$C_6$-alkoxy;

especially preferred selected from halogen and CN;

also especially preferred selected from the group consisting of F, Cl, CN and $CH_3$;

more preferred selected from the group consisting of F, Cl and CN;

particularly preferred substituted by two or three $R^A$ as defined above and in particular substituents selected from the group consisting of halogen, CN, $NO_2$, $C_1$-$C_6$-alkyl, $C_1$-$C_6$-haloalkyl, OH, $C_1$-$C_6$-alkoxy, $C_1$-$C_6$-alkylthio, ($C_1$-$C_6$-alkyl)sulfinyl, ($C_1$-$C_6$-alkyl)sulfonyl, amino, ($C_1$-$C_6$-alkyl)amino, di($C_1$-$C_6$-alkyl)amino, ($C_1$-$C_6$-alkyl)carbonyl, ($C_1$-$C_6$-alkoxy)carbonyl;

particularly preferred selected from the group consisting of halogen, CN, $C_1$-$C_6$-alkyl and $C_1$-$C_6$-alkoxy;
especially preferred selected from halogen and CN;
also especially preferred selected from the group consisting of F, Cl, CN and $CH_3$;
more preferred selected from the group consisting of F, Cl and CN;
also preferably substituted by three or four substituents $R^A$ as defined above and in particular selected from the group consisting of halogen, CN, $NO_2$, $C_1$-$C_6$-alkyl, $C_1$-$C_6$-haloalkyl, OH, $C_1$-$C_6$-alkoxy, $C_1$-$C_6$-alkylthio, ($C_1$-$C_6$-alkyl)sulfinyl, ($C_1$-$C_6$-alkyl)sulfonyl, amino, ($C_1$-$C_6$-alkyl)amino, di($C_1$-$C_6$-alkyl)amino, ($C_1$-$C_6$-alkyl)carbonyl, ($C_1$-$C_6$-alkoxy)carbonyl;
particularly preferred selected from the group consisting of halogen, CN, $C_1$-$C_6$-alkyl and $C_1$-$C_6$-alkoxy;
especially preferred selected from halogen and CN;
also especially preferred selected from the group consisting of F, Cl, CN and $CH_3$;
more preferred selected from the group consisting of F, Cl and CN;
particularly preferred substituted by three substituents $R^A$ as defined above and in particular selected from the group consisting of halogen, CN, $NO_2$, $C_1$-$C_6$-alkyl, $C_1$-$C_6$-haloalkyl, OH, $C_1$-$C_6$-alkoxy, $C_1$-$C_6$-alkylthio, ($C_1$-$C_6$-alkyl)sulfinyl, ($C_1$-$C_6$-alkyl)sulfonyl, amino, ($C_1$-$C_6$-alkyl)amino, di($C_1$-$C_6$-alkyl)amino, ($C_1$-$C_6$-alkyl)carbonyl, ($C_1$-$C_6$-alkoxy)carbonyl;
particularly preferred selected from the group consisting of halogen, CN, $C_1$-$C_6$-alkyl and $C_1$-$C_6$-alkoxy;
especially preferred selected from halogen and CN;
also especially preferred selected from the group consisting of F, Cl, CN and $CH_3$;
more preferred selected from the group consisting of F, Cl and CN;
also particularly preferred substituted by four substituents $R^A$ as defined above and in particular selected from the group consisting of halogen, CN, $NO_2$, $C_1$-$C_6$-alkyl, $C_1$-$C_6$-haloalkyl, OH, $C_1$-$C_6$-alkoxy, $C_1$-$C_6$-alkylthio, ($C_1$-$C_6$-alkyl)sulfinyl, ($C_1$-$C_6$-alkyl)sulfonyl, amino, ($C_1$-$C_6$-alkyl)amino, di($C_1$-$C_6$-alkyl)amino, ($C_1$-$C_6$-alkyl)carbonyl, ($C_1$-$C_6$-alkoxy)carbonyl;
particularly preferred selected from the group consisting of halogen, CN, $C_1$-$C_6$-alkyl and $C_1$-$C_6$-alkoxy;
especially preferred selected from halogen and CN;
also especially preferred selected from the group consisting of F, Cl, CN and $CH_3$;
more preferred selected from the group consisting of F, Cl and CN;

In particularly preferred groups of embodiments A is selected from the group (A.1), (A.2) and (A.3)

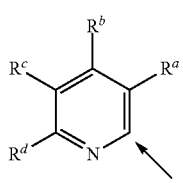

(A.1)

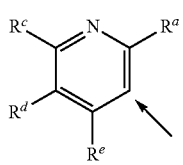

(A.2)

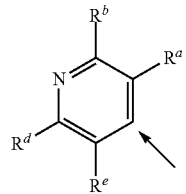

(A.3)

wherein $R^a$ and $R^e$ independently of one another are halogen, CN, $NO_2$, $C_1$-$C_6$-alkyl, $C_1$-$C_6$-haloalkyl, OH, $C_1$-$C_6$-alkoxy, $C_1$-$C_6$-alkylthio, ($C_1$-$C_6$-alkyl)sulfinyl, ($C_1$-$C_6$-alkyl)sulfonyl, amino, ($C_1$-$C_6$-alkyl)amino, di($C_1$-$C_6$-alkyl)amino, ($C_1$-$C_6$-alkyl)carbonyl, ($C_1$-$C_6$-alkoxy)carbonyl; and $R^b$, $R^c$ and $R^d$ independently of one another are hydrogen, halogen, CN, $NO_2$, $C_1$-$C_6$-alkyl, $C_1$-$C_6$-haloalkyl, OH, $C_1$-$C_6$-alkoxy, $C_1$-$C_6$-alkylthio, ($C_1$-$C_6$-alkyl)sulfinyl, ($C_1$-$C_6$-alkyl)sulfonyl, amino, ($C_1$-$C_6$-alkyl)amino, di($C_1$-$C_6$-alkyl)amino, ($C_1$-$C_6$-alkyl)carbonyl, ($C_1$-$C_6$-alkoxy)carbonyl;

particularly preferred $R^a$ and $R^e$ independently of one another are halogen, CN, $C_1$-$C_6$-alkyl or $C_1$-$C_6$-alkoxy; and $R^b$, $R^c$ and $R^d$ independently of one another are hydrogen, halogen, CN, $NO_2$, $C_1$-$C_6$-alkyl, $C_1$-$C_6$-haloalkyl or $C_1$-$C_6$-alkoxy;

especially preferred $R^a$ and $R^e$ independently of one another are halogen or CN; and $R^b$, $R^c$ and $R^d$ independently of one another are hydrogen, halogen, CN, $C_1$-$C_6$-alkyl or $C_1$-$C_6$-alkoxy;

more preferred $R^a$ and $R^e$ are halogen; and $R^b$, $R^c$ and $R^d$ independently of one another are hydrogen, halogen or CN;

most preferred $R^a$ and $R^e$ are halogen; and $R^b$, $R^c$ and $R^d$ are hydrogen;

also most preferred $R^a$, $R^b$, $R^d$ and $R^e$ are halogen; and $R^c$ is hydrogen;

also most preferred $R^a$, $R^b$, $R^c$, $R^d$ and $R^e$ are halogen;

In other particularly preferred groups of embodiments A is a radical of formula (A.4)

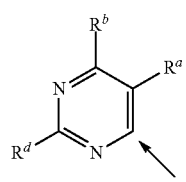

(A.4)

wherein $R^a$ is halogen, CN, $NO_2$, $C_1$-$C_6$-alkyl, $C_1$-$C_6$-haloalkyl, OH, $C_1$-$C_6$-alkoxy, $C_1$-$C_6$-alkylthio, ($C_1$-$C_6$-alkyl)sulfinyl, ($C_1$-$C_6$-alkyl)sulfonyl, amino, ($C_1$-$C_6$-alkyl)amino, di($C_1$-$C_6$-alkyl)amino, ($C_1$-$C_6$-alkyl)carbonyl, ($C_1$-$C_6$-alkoxy)carbonyl; and $R^b$ and $R^d$ independently of one another are hydrogen, halogen, CN, $NO_2$, $C_1$-$C_6$-alkyl, $C_1$-$C_6$-haloalkyl, OH, $C_1$-$C_6$-alkoxy, $C_1$-$C_6$-alkylthio, ($C_1$-$C_6$-alkyl)sulfinyl, ($C_1$-$C_6$-alkyl)sulfonyl, amino, ($C_1$-$C_6$-alkyl)amino, di($C_1$-$C_6$-alkyl)amino, ($C_1$-$C_6$-alkyl)carbonyl, ($C_1$-$C_6$-alkoxy)carbonyl;

particularly preferred $R^a$ is halogen, CN, $C_1$-$C_6$-alkyl or $C_1$-$C_6$-alkoxy; and
  $R^b$ and $R^d$ independently of one another are hydrogen, halogen, CN, $NO_2$, $C_1$-$C_6$-alkyl, $C_1$-$C_6$-haloalkyl or $C_1$-$C_6$-alkoxy;
especially preferred $R^a$ is halogen or CN; and
  $R^b$ and $R^d$ independently of one another are hydrogen, halogen, CN, $C_1$-$C_6$-alkyl or $C_1$-$C_6$-alkoxy;
more preferred $R^a$ and $R^e$ are halogen; and
  $R^b$, $R^c$ and $R^d$ independently of one another are hydrogen, halogen or CN;
most preferred $R^a$ is halogen; and
  $R^b$ and $R^d$ are hydrogen;
also most preferred $R^a$, $R^b$ and $R^d$ are halogen.

In especially preferred groups of embodiments A is selected from the group (A.1) and (A.3)

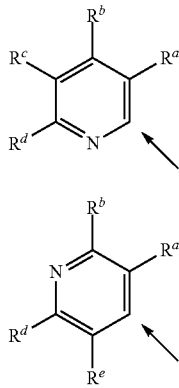

(A.1)

(A.3)

wherein
$R^a$ and $R^e$ independently of one another are halogen, CN, $NO_2$, $C_1$-$C_6$-alkyl, $C_1$-$C_6$-haloalkyl, OH, $C_1$-$C_6$-alkoxy, $C_1$-$C_6$-alkylthio, ($C_1$-$C_6$-alkyl)sulfinyl, ($C_1$-$C_6$-alkyl)sulfonyl, amino, ($C_1$-$C_6$-alkyl)amino, di($C_1$-$C_6$-alkyl)amino, ($C_1$-$C_6$-alkyl)carbonyl, ($C_1$-$C_6$-alkoxy)carbonyl; and
$R^b$, $R^c$ and $R^d$ independently of one another are hydrogen, halogen, CN, $NO_2$, $C_1$-$C_6$-alkyl, $C_1$-$C_6$-haloalkyl, OH, $C_1$-$C_6$-alkoxy, $C_1$-$C_6$-alkylthio, ($C_1$-$C_6$-alkyl)sulfinyl, ($C_1$-$C_6$-alkyl)sulfonyl, amino, ($C_1$-$C_6$-alkyl)amino, di($C_1$-$C_6$-alkyl)amino, ($C_1$-$C_6$-alkyl)carbonyl, ($C_1$-$C_6$-alkoxy)carbonyl;
particularly preferred $R^a$ and $R^e$ independently of one another are halogen, CN, $C_1$-$C_6$-alkyl or $C_1$-$C_6$-alkoxy; and
  $R^b$, $R^c$ and $R^d$ independently of one another are hydrogen, halogen, CN, $NO_2$, $C_1$-$C_6$-alkyl, $C_1$-$C_6$-haloalkyl or $C_1$-$C_6$-alkoxy;
especially preferred $R^a$ and $R^e$ independently of one another are halogen or CN; and
  $R^b$, $R^c$ and $R^d$ independently of one another are hydrogen, halogen, CN, $C_1$-$C_6$-alkyl or $C_1$-$C_6$-alkoxy;
more preferred $R^a$ and $R^e$ are halogen; and
  $R^b$, $R^c$ and $R^d$ independently of one another are hydrogen, halogen or CN;
most preferred $R^a$ and $R^e$ are halogen; and
  $R^b$, $R^c$ and $R^d$ are hydrogen;
also most preferred $R^a$, $R^b$, $R^d$ and $R^e$ are halogen; and
  $R^c$ is hydrogen;
also most preferred $R^a$, $R^b$, $R^c$, $R^d$ and $R^e$ are halogen.

In especially preferred groups of embodiments A is (A.1)

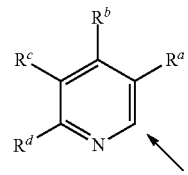

(A.1)

wherein $R^a$ is halogen or CN; and
  $R^b$, $R^c$ and $R^d$ are H, halogen or CN;
particularly preferred $R^a$ is halogen; and
  $R^b$, $R^c$ and $R^d$ are H or halogen;
especially preferred $R^a$, $R^b$ and $R^d$ are halogen; and
  $R^c$ is H or halogen;
more preferred $R^a$, $R^b$ and $R^d$ are F or Cl; and
  $R^c$ is H or F.

In other especially preferred groups of embodiments A is (A.2)

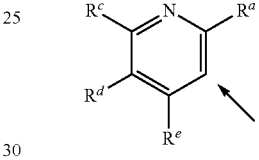

(A.2)

wherein $R^a$ and $R^e$ are halogen or CN; and
  $R^c$ and $R^d$ are H, halogen or CN;
particularly preferred $R^a$ and $R^e$ are halogen or CN; and
  $R^c$ and $R^d$ are H or halogen;
especially preferred $R^a$, $R^d$ and $R^e$ are halogen; and
  $R^c$ is H or halogen;
more preferred $R^a$, $R^d$ and $R^e$ are F or Cl; and
  $R^c$ is H or F.

In further especially preferred groups of embodiments A is (A.3)

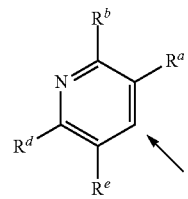

(A.3)

wherein $R^a$ and $R^e$ are halogen or CN; and
  $R^b$ and $R^d$ are H, halogen or CN;
particularly preferred $R^a$ is halogen;
  $R^b$ and $R^d$ are H or halogen; and
  $R^e$ is halogen or CN;
especially preferred $R^a$, $R^b$, $R^d$ and $R^e$ are halogen;
more preferred $R^a$, $R^b$, $R^d$ and $R^e$ are F or Cl.

Most preferred groups of embodiments relate to compounds of the formula (I), wherein A is 2,3,5,6-tetraflouro-4-pyridyl or 4-chloro-3,5,6-trifluoro-2-pyridyl.

Preference is given to compounds of formula (I), wherein $R^1$ is selected from the group consisting of H, CN, $C_1$-$C_6$-alkyl, $C_1$-$C_6$-haloalkyl, $C_1$-$C_6$-alkoxy-$C_1$-$C_6$-alkyl, $C_1$-$C_6$-alkoxy, ($C_1$-$C_6$-alkyl)carbonyl and ($C_1$-$C_6$-alkyl)sulfonyl;

in particular from the group consisting of H, CN, $C_1$-$C_6$-alkyl, $C_1$-$C_6$-alkoxy-$C_1$-$C_6$-alkyl, $C_1$-$C_6$-alkoxy, ($C_1$-$C_6$-alkyl)carbonyl and ($C_1$-$C_6$-alkyl)sulfonyl;

especially from the group consisting of H, CN, $CH_3$, $CH_2OCH_3$, $OCH_3$, $COCH_3$ and $SO_2CH_3$;

More preferred $R^1$ is hydrogen;

Further particular groups of embodiments relate to the diaminotriazine compounds of formula (I), wherein $R^2$ is selected from the group consisting of H, halogen, CN, $C_1$-$C_6$-alkyl, $C_1$-$C_6$-haloalkyl, $C_1$-$C_6$-alkoxy $C_1$-$C_6$-haloalkoxy and phenyl, in particular from the group consisting of H, halogen, CN, $C_1$-$C_6$-alkyl, $C_1$-$C_6$-haloalkyl, $C_1$-$C_6$-alkoxy $C_1$-$C_6$-haloalkoxy, more particular from the group consisting of hydrogen, fluorine, chlorine, $C_1$-$C_4$-alkyl, such as methyl, ethyl, n-propyl, 2-propyl, n-butyl, 2-butyl, isobutyl or tert.-butyl, $C_1$-$C_4$-haloalkyl, such as difluoromethyl, trifluoromethyl, 2,2,2-trifluoroethyl, 1,1-difluoroethyl, 1,1,2,2-tetrafluoroethyl or pentafluoroethyl, $C_1$-$C_4$-alkoxy, such as methoxy or ethoxy and $C_1$-$C_4$-haloalkoxy, such as difluoromethoxy or trifluoromethoxy.

Further particular groups (1) of embodiments relate to the diaminotriazine compounds of formula (I), wherein $R^3$ is selected from the group consisting of H, halogen, CN, $C_1$-$C_6$-alkyl, $C_1$-$C_6$-haloalkyl, $C_1$-$C_6$-alkoxy and $C_1$-$C_6$-haloalkoxy, in particular from the group consisting of hydrogen, fluorine and $C_1$-$C_4$-alkyl, more particularly from hydrogen, fluorine and methyl, especially from hydrogen and fluorine.

In groups (1) of embodiments, $R^4$ is as defined above and preferably selected from the group consisting of $C_1$-$C_6$-alkyl, $C_1$-$C_6$-haloalkyl, $C_2$-$C_6$-alkenyl, $C_3$-$C_6$-alkynyl, $C_3$-$C_6$-cycloalkyl, $C_3$-$C_6$-cycloalkenyl, $C_1$-$C_6$-alkoxy and $C_1$-$C_6$-alkoxy-$C_1$-$C_6$-alkyl or from $C_1$-$C_6$-alkyl, $C_1$-$C_6$-haloalkyl, $C_2$-$C_6$-alkenyl, $C_3$-$C_6$-alkynyl, $C_3$-$C_6$-cycloalkyl, $C_3$-$C_6$-cycloalkenyl, $C_1$-$C_6$-alkoxy and $C_1$-$C_6$-alkoxy-$C_1$-$C_6$-alkyl. In groups (1) of embodiments, $R^4$ is in particular selected from the group consisting of $C_1$-$C_4$-alkyl, such as ethyl, n-propyl, 2-propyl, n-butyl, 2-butyl, isobutyl or tert.-butyl, $C_1$-$C_4$-haloalkyl, such as difluoromethyl, trifluoromethyl, 2,2,2-trifluoroethyl, 1,1-difluoroethyl, 1,1,2,2-tetrafluoroethyl or pentafluoroethyl, $C_2$-$C_4$-alkenyl, such as vinyl or allyl, $C_3$-$C_4$-alkynyl, such as propargyl, $C_3$-$C_6$-cycloalkyl, such as cyclopropyl, cyclobutyl, cylopentyl or cyclohexyl, and $C_1$-$C_4$-alkoxy-$C_1$-$C_4$-alkyl, such as methoxymethyl, ethoxymethyl, 2-methoxyethyl or 2-ethoxyethyl.

Further particular groups (2) of embodiments relate to the diaminotriazine compounds of formula (I), wherein $R^3$ and $R^4$ together with the carbon atom to which they are attached form a moiety selected from the group consisting of carbonyl, $C_2$-$C_6$-alkenyl, $C_3$-$C_6$-cycloalkyl, $C_3$-$C_6$-cycloalkenyl and three- to six-membered heterocyclyl, wherein the $C_3$-$C_6$-cycloalkyl, $C_3$-$C_6$-cycloalkenyl, or three- to six-membered heterocyclyl is unsubstituted or substituted by one to six selected from halogen, CN, $C_1$-$C_6$-alkyl and $C_1$-$C_6$-alkoxy. A skilled person will readily appreciate that the cycloalkyl or cycloalkenyl radical and the heterocyclic radical are ipso-connected, i.e. the radical $R^2$ and the triazine ring of formula (I) are bound to the same carbon atom of the carboclic radical and the heterocyclic radical formed by $R^3$ and $R^4$ together with the carbon atom, to which $R^3$ and $R^4$ are attached. Therefore, the carbocyclic radical and the heterocyclic radical are also termed ipso-radicals. The carbocyclic radical and the heterocyclic radical are unsubstituted or substituted by one to six substituents selected from halogen, CN, $C_1$-$C_6$-alkyl and $C_1$-$C_6$-alkoxy.

Suitable ipso-carbocyclic radicals, which are formed by $R^3$ and $R^4$ together with the carbon atom to which they are attached, $C_3$-$C_6$-cycloalkan-1,1-diyl and ipso-$C_3$-$C_6$-cycloalkendiylas defined above. Suitable ipso-heterocyclic radicals, which are formed by $R^3$ and $R^4$ together with the carbon atom to which they are attached, may be saturated or unsaturated, and in particular saturated. Suitable ipso-heterocyclic radicals are 3- to 6-membered, i.e. they have 3, 4, 5 or 6 ring atoms, wherein at least 1 ring atom, e.g. 1, 2 or 3 ring atoms are a heteroatom, which is preferably selected from 0, S and N, while the other ring atoms are carbon atoms. Examples of ipso-heterocyclodiyl radicals include oxiran-2,2-diyl, oxetan-2,2-diyl, oxetan-3,3-diyl, oxolan-2,2-diyl, oxolan-3,3-diyl, 1,3-dioxolan-2,2-diyl, oxan-2,2-diyl, oxan-3,3-diyl or oxan-4,4-diyl, 1,3-dioxan-2,2-diyl, thiolan-2,2-diyl, thiolan-3,3-diyl, pyrrolidin-2,2-diyl, pyrroldin-3,3-diyl, piperidin-2,2,-diyl, piperidin-3,3-diyl and piperidin-4,4-diyl, where the aforementioned radicals may also be unsubstituted or substituted by one to six substituents selected from halogen, CN, $C_1$-$C_6$-alkyl and $C_1$-$C_6$-alkoxy.

In groups (2) of embodiments, $R^3$ and $R^4$ together with the carbon atom to which they are attached form in particular a moiety selected from the group consisting of $C_3$-$C_6$-cycloalkan-1,1-diyl, ipso-$C_3$-$C_6$-cycloalkendiyl, three- to six-membered saturated or partially unsaturated ipso-heterocyclodiyl, where the carbocycle and the heterocycle are unsubstituted or substituted by one to four substituents selected from halogen and $C_1$-$C_6$-alkyl groups and where the heterocycle preferably has 1 or 2 oxygen atoms as ring members. In groups (2) of embodiments, $R^3$ and $R^4$ together with the carbon atom to which they are attached more particularly form a moiety selected from the group consisting of $C_3$-$C_6$-cycloalkan-1,1-diylor three- to six-membered saturated ipso-heterocyclodiyl, where the carbocycle and the heterocycle are unsubstituted or substituted by one to four substituents selected from halogen and $C_1$-$C_6$-alkyl groups, and where heterocyclyl preferably has 1 or 2 oxygen atoms as ring members.

Preference is given to compounds of formula (I), wherein $R^2$ is selected from the group consisting of H, halogen, $C_1$-$C_6$-alkyl, $C_1$-$C_6$-haloalkyl, $C_1$-$C_6$-alkoxy $C_1$-$C_6$-haloalkoxy and phenyl;

in particular from the group consisting of H, halogen, $C_1$-$C_6$-alkyl, $C_1$-$C_6$-haloalkyl, $C_1$-$C_6$-alkoxy and $C_1$-$C_6$-haloalkoxy;

more particular from the group consisting of H, halogen, $C_1$-$C_4$-alkyl, $C_1$-$C_4$-alkoxy and $C_1$-$C_4$-haloalkyl or from the group consisting of H, halogen, $C_1$-$C_6$-alkyl and $C_1$-$C_6$-haloalkyl;

particularly preferred from the group consisting of halogen, $C_1$-$C_4$-alkyl, $C_1$-$C_4$-alkoxy and $C_1$-$C_4$-haloalkyl or from the group consisting of halogen, $C_1$-$C_6$-alkyl or $C_1$-$C_6$-haloalkyl;

also particularly preferred is H, F, Cl, $CH_3$ or $CF_3$ or $OCH_3$

Particular groups of embodiments relate to compounds of formula (I), wherein $R^3$ and $R^4$ independently of one another preferably are H, halogen, $C_1$-$C_6$-alkyl or $C_1$-$C_6$-haloalkyl; or together with the carbon atom to which they are attached form a moiety selected from the group consisting of $C_3$-$C_6$-cycloalkyl, $C_3$-$C_6$-cycloalkenyl and three- to six-membered heterocyclyl, wherein the $C_3$-$C_6$-cycloalkyl, $C_3$-$C_6$-cycloalkenyl or the three- to six-membered heterocyclyl is unsubstituted or substituted by one to three substituents selected from halogen, CN, $C_1$-$C_6$-alkyl and $C_1$-$C_6$-alkoxy.
particularly preferred are H, halogen, $C_1$-$C_6$-alkyl or $C_1$-$C_6$-haloalkyl; or
together with the carbon atom to which they are attached form a moiety selected from the group consisting of $C_3$-$C_6$-cycloalkyl and $C_3$-$C_6$-cycloalkenyl,
wherein the $C_3$-$C_6$-cycloalkyl or $C_3$-$C_6$-cycloalkenyl is unsubstituted or substituted by one to three substituents selected from halogen, CN, $C_1$-$C_6$-alkyl and $C_1$-$C_6$-alkoxy;
especially preferred are H, halogen, $C_1$-$C_6$-alkyl or $C_1$-$C_6$-haloalkyl; or together with the carbon atom to which they are attached form a moiety selected from the group consisting of $C_3$-$C_6$-cycloalkyl, wherein the $C_3$-$C_6$-cycloalkyl is unsubstituted or substituted by one to three substituents selected from halogen, CN, $C_1$-$C_6$-alkyl and $C_1$-$C_6$-alkoxy;
more preferred are H, halogen or $C_1$-$C_6$-alkyl;
Preference is given to compounds of formula (I), wherein
$R^2$ is as defined above and has in particular one of the preferred meanings and is especially selected from the group consisting of fluorine, $C_1$-$C_4$-alkyl, such as methyl, $C_1$-$C_4$-haloalkyl, such as trifluoromethyl, $C_1$-$C_4$-alkoxy, such as methoxy, and $C_1$-$C_6$-haloalkoxy such as trifluoromethoxy;
in particular from the group consisting of H, halogen, $C_1$-$C_4$-alkyl, $C_1$-$C_4$-alkoxy and $C_1$-$C_4$-haloalkyl or from the group consisting of H, halogen, $C_1$-$C_6$-alkyl and $C_1$-$C_6$-haloalkyl;
particularly preferred from the group consisting of halogen, $C_1$-$C_4$-alkyl, $C_1$-$C_4$-alkoxy and $C_1$-$C_4$-haloalkyl or from the group consisting of halogen, $C_1$-$C_6$-alkyl or $C_1$-$C_6$-haloalkyl;
also particularly preferred is H, F, Cl, $CH_3$ or $CF_3$ or $OCH_3$;
$R^3$ is selected from the group consisting of hydrogen, fluorine, $C_1$-$C_4$-alkyl, such as methyl, $C_1$-$C_4$-haloalkyl, such as trifluoromethyl, $C_1$-$C_4$-alkoxy, such as methoxy, and $C_1$-$C_6$-haloalkoxy such as trifluoromethoxy;
$R^4$ is selected from the group consisting of $C_1$-$C_6$-alkyl, $C_1$-$C_6$-haloalkyl, $C_2$-$C_6$-alkenyl, $C_3$-$C_6$-alkynyl, $C_3$-$C_6$-cycloalkyl, $C_3$-$C_6$-cycloalkenyl, and $C_1$-$C_6$-alkoxy-$C_1$-$C_6$-alkyl or
$R^3$ and $R^4$ together with the carbon atom to which they are attached form a moiety selected from the group consisting of $C_3$-$C_6$-cycloalkyl, wherein the $C_3$-$C_6$-cycloalkyl is unsubstituted or substituted by one to three substituents selected from halogen, CN, $C_1$-$C_6$-alkyl and $C_1$-$C_6$-alkoxy.
Particular preference is given to compounds of formula (I), wherein
$R^2$ is selected from the group consisting of halogen, $C_1$-$C_4$-alkyl, $C_1$-$C_4$-alkoxy and $C_1$-$C_4$-haloalkyl or from the group consisting of H, halogen, $C_1$-$C_6$-alkyl and $C_1$-$C_6$-haloalkyl;
particularly preferred from the group consisting of halogen, $C_1$-$C_4$-alkyl, $C_1$-$C_4$-alkoxy and $C_1$-$C_4$-haloalkyl or from the group consisting of halogen, $C_1$-$C_6$-alkyl or $C_1$-$C_6$-haloalkyl;
also particularly preferred is H, F, Cl, $CH_3$ or $CF_3$ or $OCH_3$;
$R^3$ is selected from the group consisting of hydrogen, fluorine, $C_1$-$C_4$-alkyl, such as methyl, $C_1$-$C_4$-haloalkyl, such as trifluoromethyl, $C_1$-$C_4$-alkoxy, such as methoxy, and $C_1$-$C_6$-haloalkoxy such as trifluoromethoxy;
$R^4$ is selected from the group consisting of $C_1$-$C_6$-alkyl, $C_1$-$C_6$-haloalkyl, $C_2$-$C_6$-alkenyl, $C_3$-$C_6$-alkynyl, $C_3$-$C_6$-cycloalkyl, $C_3$-$C_6$-cycloalkenyl, and $C_1$-$C_6$-alkoxy-$C_1$-$C_6$-alkyl or
$R^3$ and $R^4$ together with the carbon atom to which they are attached form a moiety selected from the group consisting of $C_3$-$C_6$-cycloalkyl, wherein the $C_3$-$C_6$-cycloalkyl is unsubstituted or substituted by one to three substituents selected from halogen, CN, $C_1$-$C_6$-alkyl and $C_1$-$C_6$-alkoxy.
Preference is also given to compounds of formula (I), wherein
$R^2$ is as defined above and has in particular one of the preferred meanings and is especially selected from the group consisting of H, fluorine, $C_1$-$C_4$-alkyl, such as methyl, $C_1$-$C_4$-haloalkyl, such as trifluoromethyl, $C_1$-$C_4$-alkoxy, such as methoxy, and $C_1$-$C_6$-haloalkoxy such as trifluoromethoxy;
in particular from the group consisting of H, halogen, $C_1$-$C_4$-alkyl, $C_1$-$C_4$-alkoxy and $C_1$-$C_4$-haloalkyl or from the group consisting of H, halogen, $C_1$-$C_6$-alkyl and $C_1$-$C_6$-haloalkyl;
particularly preferred from the group consisting of halogen, $C_1$-$C_4$-alkyl, $C_1$-$C_4$-alkoxy and $C_1$-$C_4$-haloalkyl or from the group consisting of halogen, $C_1$-$C_6$-alkyl or $C_1$-$C_6$-haloalkyl;
also particularly preferred is H, F, Cl, $CH_3$ or $CF_3$ or $OCH_3$;
$R^3$ and $R^4$ together with the carbon atom to which they are attached, form an ipso carbocyclic radical selected from $C_3$-$C_6$-cycloalkan-1,1-diyl and ipso-$C_3$-$C_6$-cycloalkendiyl where the ipso carbocyclic radical is unsubstituted or substituted by one to four substituents selected from halogen and $C_1$-$C_6$-alkyl groups.
Preference is also given to compounds of formula (I), wherein
$R^2$ is as defined above and has in particular one of the preferred meanings and is especially selected from the group consisting of H, fluorine, $C_1$-$C_4$-alkyl, such as methyl, $C_1$-$C_4$-haloalkyl, such as trifluoromethyl, $C_1$-$C_4$-alkoxy, such as methoxy, and $C_1$-$C_6$-haloalkoxy such as trifluoromethoxy;
in particular from the group consisting of H, halogen, $C_1$-$C_4$-alkyl, $C_1$-$C_4$-alkoxy and $C_1$-$C_4$-haloalkyl or from the group consisting of H, halogen, $C_1$-$C_6$-alkyl and $C_1$-$C_6$-haloalkyl;
particularly preferred from the group consisting of halogen, $C_1$-$C_4$-alkyl, $C_1$-$C_4$-alkoxy and $C_1$-$C_4$-haloalkyl or from the group consisting of halogen, $C_1$-$C_6$-alkyl or $C_1$-$C_6$-haloalkyl;
also particularly preferred is H, F, Cl, $CH_3$ or $CF_3$ or $OCH_3$;
$R^3$ and $R^4$ together with the carbon atom to which they are attached, form three- to six-membered saturated or partially unsaturated ipso-heterocyclodiyl, where ipso-heterocyclodiyl is unsubstituted or substituted by one to four substituents selected from halogen and $C_1$-$C_6$-alkyl groups and where the ipso-heterocyclodiyl preferably has 1 or 2 oxygen atoms as ring members.
Particular preference is given to compounds of formula (I), wherein
$R^2$ is selected from the group consisting of halogen, $C_1$-$C_4$-alkyl, $C_1$-$C_4$-alkoxy and $C_1$-$C_4$-haloalkyl or from the group consisting of H, halogen, $C_1$-$C_6$-alkyl and $C_1$-$C_6$-haloalkyl;

particularly preferred from the group consisting of halogen, $C_1$-$C_4$-alkyl, $C_1$-$C_4$-alkoxy and $C_1$-$C_4$-haloalkyl or from the group consisting of halogen, $C_1$-$C_6$-alkyl or $C_1$-$C_6$-haloalkyl;
also particularly preferred is H, F, Cl, $CH_3$ or $CF_3$ or $OCH_3$;
$R^3$ is selected from the group consisting of hydrogen, fluorine, $C_1$-$C_4$-alkyl, such as methyl, $C_1$-$C_4$-haloalkyl, such as trifluoromethyl, $C_1$-$C_4$-alkoxy, such as methoxy, and $C_1$-$C_6$-haloalkoxy such as trifluoromethoxy;
$R^4$ is selected from the group consisting of $C_1$-$C_6$-alkyl, $C_1$-$C_6$-haloalkyl, $C_2$-$C_6$-alkenyl, $C_3$-$C_6$-alkynyl, $C_3$-$C_6$-cycloalkyl, $C_3$-$C_6$-cycloalkenyl, and $C_1$-$C_6$-alkoxy-$C_1$-$C_6$-alkyl.

Particular preference is also given to compounds of formula (I), wherein
$R^2$ is selected from the group consisting of halogen, $C_1$-$C_4$-alkyl, $C_1$-$C_4$-alkoxy and $C_1$-$C_4$-haloalkyl or from the group consisting of H, halogen, $C_1$-$C_6$-alkyl and $C_1$-$C_6$-haloalkyl;
particularly preferred from the group consisting of halogen, $C_1$-$C_4$-alkyl, $C_1$-$C_4$-alkoxy and $C_1$-$C_4$-haloalkyl or from the group consisting of halogen, $C_1$-$C_6$-alkyl or $C_1$-$C_6$-haloalkyl;
also particularly preferred is H, F, Cl, $CH_3$ or $CF_3$ or $OCH_3$;
$R^3$ and $R^4$ together with the carbon atom to which they are attached more particularly form a moiety selected from the group consisting of $C_3$-$C_6$-cycloalkan-1,1-diyl or three- to six-membered saturated ipso-heterocyclodiyl, where the carbocycle and the heterocycle are unsubstituted or substituted by one to four substituents selected from halogen and $C_1$-$C_6$-alkyl groups, and where heterocyclyl preferably has 1 or 2 oxygen atoms as ring members.

$R^5$ preferably is H, CN, $C_1$-$C_6$-alkyl, $C_1$-$C_6$-haloalkyl, $C_1$-$C_6$-alkoxy-$C_1$-$C_6$-alkyl, $C_1$-$C_6$-alkoxy, ($C_1$-$C_6$-alkyl)carbonyl or ($C_1$-$C_6$-alkyl)sulfonyl;
particularly preferred is H, CN, $C_1$-$C_6$-alkyl, $C_1$-$C_6$-alkoxy-$C_1$-$C_6$-alkyl, $C_1$-$C_6$-alkoxy, ($C_1$-$C_6$-alkyl)carbonyl or ($C_1$-$C_6$-alkyl)sulfonyl;
especially preferred is H, CN, $CH_3$, $CH_2OCH_3$, $OCH_3$, $COCH_3$ or $SO_2CH_3$;
more preferred is hydrogen.

Also preferred are the azines of formula (I), wherein
$R^2$ is H, halogen, $C_1$-$C_6$-alkyl; and
$R^3$ and $R^4$ are independently of one another H, halogen, $C_1$-$C_6$-alkyl, or together with the carbon atom to which they are attached form a $C_3$-$C_6$-cycloalkyl;
particularly preferred $R^2$ is H, halogen or $C_1$-$C_6$-alkyl;
$R^3$ is $C_1$-$C_6$-alkyl;
$R^4$ is H, halogen or $C_1$-$C_6$-alkyl;
$R^3$ and $R^4$ together with the carbon atom to which they are attached form a $C_3$-$C_6$-cycloalkyl;
especially preferred $R^2$ is halogen or $C_1$-$C_6$-alkyl;
$R^3$ is $C_1$-$C_6$-alkyl;
$R^4$ is H or $C_1$-$C_6$-alkyl;
more preferred $R^2$ is halogen; and
$R^3$ and $R^4$ are $C_1$-$C_6$-alkyl.

Also preferred are the azines of formula (I), wherein
$R^2$ is H, halogen, $C_1$-$C_6$-alkyl; and
$R^3$ and $R^4$ together with the carbon atom to which they are attached form a saturated 3, 4, 5- or 6-membered heterocylcyl, in particular heterocyclyl, which comprises 1 or 2 oxygen atoms as ring members, especially an oxiran-2,2-diyl, oxetan-2,2-diyl, oxolan-2,2-diyl or oxan-2,2-diyl;
particularly preferred
$R^2$ is H, fluorine or $C_1$-$C_4$-alkyl;
$R^3$ and $R^4$ together with the carbon atom to which they are attached form a saturated 3, 4, 5- or 6-membered heterocylcyl, in particular heterocyclyl, which comprises 1 or 2 oxygen atoms as ring members, especially an oxiran-2,2-diyl, oxetan-2,2-diyl, oxolan-2,2-diyl or oxan-2,2-diyl.

Also preferred are the azines of formula (I), wherein
$R^2$ is H, halogen, $C_1$-$C_6$-alkyl or $C_1$-$C_6$-alkoxy; and
$R^3$ and $R^4$ together with the carbon atom to which they are attached form $C_3$-$C_6$-cycloalkan-1,1-diyl.

Examples of suitable combinations of $R^2$, $R^3$ and $R^4$ are given in the following table:

| # | $R^2$ | $R^3$ | $R^4$ |
|---|---|---|---|
| 1 | H | $CH_3$ | $CH_3$ |
| 2 | F | F | $CH_3$ |
| 3 | F | H | $CH_3$ |
| 4 | F | $CH_3$ | $CH_3$ |
| 5 | $CH_3$ | $CH_3$ | $CH_3$ |
| 6 | F | H | $C_2H_5$ |
| 7 | H | $CH_3$ | $C_2H_5$ |
| 8 | F | $CH_3$ | $C_2H_5$ |
| 9 | H | $OCH_3$ | $CH_3$ |
| 10 | H | $OCH_3$ | $C_2H_5$ |
| 11 | F | $C_2H_5$ | $C_2H_5$ |
| 12 | H | $OCH_3$ | $C_2H_5$ |
| 13 | H | H | $CH(CH_3)_2$ |
| 14 | H | F | $CH(CH_3)_2$ |
| 15 | F | F | $CH(CH_3)_2$ |
| 16 | H | $CH_3$ | $CH(CH_3)_2$ |
| 17 | H | $OCH_3$ | $CH(CH_3)_2$ |
| 18 | F | $CH_3$ | $CH(CH_3)_2$ |
| 19 | H | H | $CH_2CH_2CH_3$ |
| 20 | H | F | $CH_2CH_2CH_3$ |
| 21 | F | F | $CH_2CH_2CH_3$ |
| 22 | H | $CH_3$ | $CH_2CH_2CH_3$ |
| 23 | H | $OCH_3$ | $CH_2CH_2CH_3$ |
| 24 | F | $CH_3$ | $CH_2CH_2CH_3$ |
| 25 | H | H | $C(CH_3)_3$ |
| 26 | H | F | $C(CH_3)_3$ |
| 1 | H | $CH_3$ | $CH_3$ |
| 2 | F | F | $CH_3$ |
| 3 | F | H | $CH_3$ |
| 4 | F | $CH_3$ | $CH_3$ |
| 5 | $CH_3$ | $CH_3$ | $CH_3$ |
| 27 | F | F | $C(CH_3)_3$ |
| 28 | H | $CH_3$ | $C(CH_3)_3$ |
| 29 | H | $OCH_3$ | $C(CH_3)_3$ |
| 30 | F | $CH_3$ | $C(CH_3)_3$ |
| 31 | H | H | Cyclopropyl |
| 32 | H | F | Cyclopropyl |
| 33 | F | F | Cyclopropyl |
| 34 | H | $CH_3$ | Cyclopropyl |
| 35 | H | $OCH_3$ | Cyclopropyl |
| 36 | F | $CH_3$ | Cyclopropyl |
| 37 | H | $CH_3$ | $CF_3$ |
| 38 | F | $CH_3$ | $CF_3$ |
| 39 | H | $CH_2$—$CH_2$ | |
| 40 | $CH_3$ | $CH_2$—$CH_2$ | |
| 41 | $OCH_3$ | $CH_2$—$CH_2$ | |
| 42 | F | $CH_2$—$CH_2$ | |
| 43 | Cl | $CH_2$—$CH_2$ | |
| 44 | H | $CH_2$—$CH_2$—$CH_2$ | |
| 45 | $CH_3$ | $CH_2$—$CH_2$—$CH_2$ | |
| 46 | $OCH_3$ | $CH_2$—$CH_2$—$CH_2$ | |
| 47 | F | $CH_2$—$CH_2$—$CH_2$ | |
| 48 | Cl | $CH_2$—$CH_2$—$CH_2$ | |
| 49 | H | $CH_2$—$CH_2$—$CH_2$—$CH_2$ | |
| 50 | $CH_3$ | $CH_2$—$CH_2$—$CH_2$—$CH_2$ | |
| 51 | $OCH_3$ | $CH_2$—$CH_2$—$CH_2$—$CH_2$ | |

-continued

| # | $R^2$ | $R^3$ | $R^4$ |
|---|---|---|---|
| 52 | F | $CH_2-CH_2-CH_2-CH_2$ | |
| 53 | Cl | $CH_2-CH_2-CH_2-CH_2$ | |
| 54 | H | $CH_2-CH_2-CH_2-CH_2-CH_2$ | |
| 55 | $CH_3$ | $CH_2-CH_2-CH_2-CH_2-CH_2$ | |
| 56 | $OCH_3$ | $CH_2-CH_2-CH_2-CH_2-CH_2$ | |
| 57 | F | $CH_2-CH_2-CH_2-CH_2-CH_2$ | |
| 58 | Cl | $CH_2-CH_2-CH_2-CH_2-CH_2$ | |
| 59 | H | $O-CH_2-CH_2-CH_2$ | |
| 60 | $CH_3$ | $O-CH_2-CH_2-CH_2$ | |
| 1 | H | $CH_3$ | $CH_3$ |
| 2 | F | F | $CH_3$ |
| 3 | F | H | $CH_3$ |
| 4 | F | $CH_3$ | $CH_3$ |
| 5 | $CH_3$ | $CH_3$ | $CH_3$ |
| 61 | $OCF_3$ | $O-CH_2-CH_2-CH_2$ | |
| 62 | H | $O-CH_2-CH_2-CH_2-CH_2$ | |
| 63 | $CH_3$ | $O-CH_2-CH_2-CH_2-CH_2$ | |
| 64 | $OCF_3$ | $O-CH_2-CH_2-CH_2-CH_2$ | |

Also preferred are the azines of formula (I), wherein
A is a 6-membered heteroaryl having 1 to 3 nitrogen atoms,
  preferably having 1 or 2 nitrogen atoms,
  particularly preferred is pyridyl;
  which is substituted by one to four substituents,
    preferably substituted by one to three substituents,
      particularly preferred substituted by one or two substituents,
      especially preferred substituted by one substituent,
      also especially preferred substituted by two substituents,
    also preferably substituted by two to four substituents
      particularly preferred substituted by two or three substituents
    also preferably substituted by three or four substituents
      particularly preferred substituted by three substituents
      also particularly preferred substituted by four substituents
  selected from the group consisting of halogen, CN, $NO_2$, $C_1$-$C_6$-alkyl, $C_1$-$C_6$-haloalkyl, OH, $C_1$-$C_6$-alkoxy, $C_1$-$C_6$-alkylthio, ($C_1$-$C_6$-alkyl)sulfinyl, ($C_1$-$C_6$-alkyl)sulfonyl, amino, ($C_1$-$C_6$-alkyl)amino, di($C_1$-$C_6$-alkyl)amino, ($C_1$-$C_6$-alkyl)-carbonyl, ($C_1$-$C_6$-alkoxy)carbonyl;
  particularly preferred selected from the group consisting of halogen, CN, $C_1$-$C_6$-alkyl and $C_1$-$C_6$-alkoxy;
  especially preferred selected from halogen and CN;
  also especially preferred selected from the group consisting of F, Cl, CN and $CH_3$;
  more preferred selected from the group consisting of F, Cl and CN;
$R^1$ is H, CN, $C_1$-$C_6$-alkyl, $C_1$-$C_6$-haloalkyl, $C_1$-$C_6$-alkoxy-$C_1$-$C_6$-alkyl, $C_1$-$C_6$-alkoxy, ($C_1$-$C_6$-alkyl)carbonyl or ($C_1$-$C_6$-alkyl)sulfonyl;
  particularly preferred H, CN, $C_1$-$C_6$-alkyl, $C_1$-$C_6$-alkoxy-$C_1$-$C_6$-alkyl, $C_1$-$C_6$-alkoxy, ($C_1$-$C_6$-alkyl)carbonyl or ($C_1$-$C_6$-alkyl)sulfonyl;
  especially preferred H, CN, $CH_3$, $CH_2OCH_3$, $OCH_3$, $COCH_3$ or $SO_2CH_3$;
  more preferred hydrogen;
$R^2$ is H, halogen, $C_1$-$C_6$-alkyl or $C_1$-$C_6$-haloalkyl;
  particularly preferred halogen, $C_1$-$C_6$-alkyl or $C_1$-$C_6$-haloalkyl;
  also particularly preferred H, F, $CH_3$ or $CF_3$;
$R^3$ and $R^4$ are independently of one another H, halogen, $C_1$-$C_6$-alkyl or $C_1$-$C_6$-haloalkyl;
or
together with the carbon atom to which they are attached form a moiety selected from the group consisting of $C_3$-$C_6$-cycloalkyl, $C_3$-$C_6$-cycloalkenyl and three- to six-membered heterocyclyl,
  wherein the $C_3$-$C_6$-cycloalkyl, $C_3$-$C_6$-cycloalkenyl or the three- to six-membered heterocyclyl is unsubstituted or substituted by one to three substituents selected from halogen, CN, $C_1$-$C_6$-alkyl and $C_1$-$C_6$-alkoxy;
independently of one another particularly preferred H, halogen, $C_1$-$C_6$-alkyl or $C_1$-$C_6$-haloalkyl; or
together with the carbon atom to which they are attached form a moiety selected from the group consisting of $C_3$-$C_6$-cycloalkyl and $C_3$-$C_6$-cycloalkenyl,
  wherein the $C_3$-$C_6$-cycloalkyl or $C_3$-$C_6$-cycloalkenyl is unsubstituted or substituted by one to three substituents selected from halogen, CN, $C_1$-$C_6$-alkyl and $C_1$-$C_6$-alkoxy;
independently of one another especially preferred H, halogen, $C_1$-$C_6$-alkyl or $C_1$-$C_6$-haloalkyl;
independently of one another more preferred H, halogen or $C_1$-$C_6$-alkyl;
and
$R^5$ is H, CN, $C_1$-$C_6$-alkyl, $C_1$-$C_6$-haloalkyl, $C_1$-$C_6$-alkoxy-$C_1$-$C_6$-alkyl, $C_1$-$C_6$-alkoxy, ($C_1$-$C_6$-alkyl)carbonyl or ($C_1$-$C_6$-alkyl)sulfonyl;
  particularly preferred H, CN, $C_1$-$C_6$-alkyl, $C_1$-$C_6$-alkoxy-$C_1$-$C_6$-alkyl, $C_1$-$C_6$-alkoxy, ($C_1$-$C_6$-alkyl)carbonyl or ($C_1$-$C_6$-alkyl)sulfonyl;
  especially preferred H, CN, $CH_3$, $CH_2OCH_3$, $OCH_3$, $COCH_3$ or $SO_2CH_3$;
  more preferred hydrogen.

Particular preference is given to azines of formula (I.a), which correspond to azines of formula (I) wherein A is (A.1) with $R^b$ is F, $R^c$ is H, and $R^1$ and $R^5$ are H:

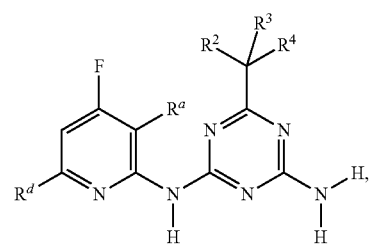

(I.a)

wherein the variables $R^a$, $R^d$, $R^2$, $R^3$ and $R^4$ have the meanings, in particular the preferred meanings, as defined above;
special preference is given to the azines of the formulae (I.a.1) to (I.a.546) of Table 1, where the definitions of the variables $R^a$, $R^e$, $R^2$, $R^3$ and $R^4$ are of particular importance for the compounds according to the invention not only in combination with one another but in each case also on their own:

TABLE 1

| No. | $R^a$ | $R^d$ | $R^2$ | $R^3$ | $R^4$ |
|---|---|---|---|---|---|
| I.a.1 | F | H | $CH_3$ | H | H |
| I.a.2 | F | H | $CH_3$ | $CH_3$ | H |
| I.a.3 | F | H | $CH_3$ | $CH_3$ | $CH_3$ |
| I.a.4 | F | H | F | F | F |

TABLE 1-continued

| No. | $R^a$ | $R^d$ | $R^2$ | $R^3$ | $R^4$ |
|---|---|---|---|---|---|
| I.a.5 | F | H | F | $CF_3$ | F |
| I.a.6 | F | H | F | $CH_3$ | F |
| I.a.7 | F | H | F | $CH_3$ | H |
| I.a.8 | F | H | F | $CH_3$ | $CH_3$ |
| I.a.9 | F | H | Cl | $CH_3$ | $CH_3$ |
| I.a.10 | F | H | F | $C_2H_5$ | $CH_3$ |
| I.a.11 | F | H | F | $C_2H_5$ | $C_2H_5$ |
| I.a.12 | F | H | H | | $-(CH_2)_2-$ |
| I.a.13 | F | H | H | | $-(CH_2)_3-$ |
| I.a.14 | F | H | H | | $-(CH_2)_4-$ |
| I.a.15 | F | H | H | | $-(CH_2)_5-$ |
| I.a.16 | F | H | $CH_3$ | | $-(CH_2)_2-$ |
| I.a.17 | F | H | $CH_3$ | | $-(CH_2)_3-$ |
| I.a.18 | F | H | $CH_3$ | | $-(CH_2)_4-$ |
| I.a.19 | F | H | $CH_3$ | | $-(CH_2)_5-$ |
| I.a.20 | F | H | F | | $-(CH_2)_2-$ |
| I.a.21 | F | H | F | | $-(CH_2)_3-$ |
| I.a.22 | F | H | F | | $-(CH_2)_4-$ |
| I.a.23 | F | H | F | | $-(CH_2)_5-$ |
| I.a.24 | F | H | Cl | | $-(CH_2)_2-$ |
| I.a.25 | F | H | Cl | | $-(CH_2)_3-$ |
| I.a.26 | F | H | Cl | | $-(CH_2)_4-$ |
| I.a.27 | F | H | Cl | | $-(CH_2)_5-$ |
| I.a.28 | F | F | $CH_3$ | H | H |
| I.a.29 | F | F | $CH_3$ | $CH_3$ | H |
| I.a.30 | F | F | $CH_3$ | $CH_3$ | $CH_3$ |
| I.a.31 | F | F | F | F | F |
| I.a.32 | F | F | F | $CF_3$ | F |
| I.a.33 | F | F | F | $CH_3$ | F |
| I.a.34 | F | F | F | $CH_3$ | H |
| I.a.35 | F | F | F | $CH_3$ | $CH_3$ |
| I.a.36 | F | F | Cl | $CH_3$ | $CH_3$ |
| I.a.37 | F | F | F | $C_2H_5$ | $CH_3$ |
| I.a.38 | F | F | F | $C_2H_5$ | $C_2H_5$ |
| I.a.39 | F | F | H | | $-(CH_2)_2-$ |
| I.a.40 | F | F | H | | $-(CH_2)_3-$ |
| I.a.41 | F | F | H | | $-(CH_2)_4-$ |
| I.a.42 | F | F | H | | $-(CH_2)_5-$ |
| I.a.43 | F | F | $CH_3$ | | $-(CH_2)_2-$ |
| I.a.44 | F | F | $CH_3$ | | $-(CH_2)_3-$ |
| I.a.45 | F | F | $CH_3$ | | $-(CH_2)_4-$ |
| I.a.46 | F | F | $CH_3$ | | $-(CH_2)_5-$ |
| I.a.47 | F | F | F | | $-(CH_2)_2-$ |
| I.a.48 | F | F | F | | $-(CH_2)_3-$ |
| I.a.49 | F | F | F | | $-(CH_2)_4-$ |
| I.a.50 | F | F | F | | $-(CH_2)_5-$ |
| I.a.51 | F | F | Cl | | $-(CH_2)_2-$ |
| I.a.52 | F | F | Cl | | $-(CH_2)_3-$ |
| I.a.53 | F | F | Cl | | $-(CH_2)_4-$ |
| I.a.54 | F | F | Cl | | $-(CH_2)_5-$ |
| I.a.55 | F | Cl | $CH_3$ | H | H |
| I.a.56 | F | Cl | $CH_3$ | $CH_3$ | H |
| I.a.57 | F | Cl | $CH_3$ | $CH_3$ | $CH_3$ |
| I.a.58 | F | Cl | F | F | F |
| I.a.59 | F | Cl | F | $CF_3$ | F |
| I.a.60 | F | Cl | F | $CH_3$ | F |
| I.a.61 | F | Cl | F | $CH_3$ | H |
| I.a.62 | F | Cl | F | $CH_3$ | $CH_3$ |
| I.a.63 | F | Cl | Cl | $CH_3$ | $CH_3$ |
| I.a.64 | F | Cl | F | $C_2H_5$ | $CH_3$ |
| I.a.65 | F | Cl | F | $C_2H_5$ | $C_2H_5$ |
| I.a.66 | F | Cl | H | | $-(CH_2)_2-$ |
| I.a.67 | F | Cl | H | | $-(CH_2)_3-$ |
| I.a.68 | F | Cl | H | | $-(CH_2)_4-$ |
| I.a.69 | F | Cl | H | | $-(CH_2)_5-$ |
| I.a.70 | F | Cl | $CH_3$ | | $-(CH_2)_2-$ |
| I.a.71 | F | Cl | $CH_3$ | | $-(CH_2)_3-$ |
| I.a.72 | F | Cl | $CH_3$ | | $-(CH_2)_4-$ |
| I.a.73 | F | Cl | $CH_3$ | | $-(CH_2)_5-$ |
| I.a.74 | F | Cl | F | | $-(CH_2)_2-$ |
| I.a.75 | F | Cl | F | | $-(CH_2)_3-$ |
| I.a.76 | F | Cl | F | | $-(CH_2)_4-$ |
| I.a.77 | F | Cl | F | | $-(CH_2)_5-$ |
| I.a.78 | F | Cl | Cl | | $-(CH_2)_2-$ |
| I.a.79 | F | Cl | Cl | | $-(CH_2)_3-$ |
| I.a.80 | F | Cl | Cl | | $-(CH_2)_4-$ |
| I.a.81 | F | Cl | Cl | | $-(CH_2)_5-$ |
| I.a.82 | F | CN | $CH_3$ | H | H |
| I.a.83 | F | CN | $CH_3$ | H | H |
| I.a.84 | F | CN | $CH_3$ | $CH_3$ | $CH_3$ |
| I.a.85 | F | CN | F | F | F |
| I.a.86 | F | CN | F | $CF_3$ | F |
| I.a.87 | F | CN | F | $CH_3$ | F |
| I.a.88 | F | CN | F | $CH_3$ | H |
| I.a.89 | F | CN | F | $CH_3$ | $CH_3$ |
| I.a.90 | F | CN | Cl | $CH_3$ | $CH_3$ |
| I.a.91 | F | CN | F | $C_2H_5$ | $CH_3$ |
| I.a.92 | F | CN | F | $C_2H_5$ | $C_2H_5$ |
| I.a.93 | F | CN | H | | $-(CH_2)_2-$ |
| I.a.94 | F | CN | H | | $-(CH_2)_3-$ |
| I.a.95 | F | CN | H | | $-(CH_2)_4-$ |
| I.a.96 | F | CN | H | | $-(CH_2)_5-$ |
| I.a.97 | F | CN | $CH_3$ | | $-(CH_2)_2-$ |
| I.a.98 | F | CN | $CH_3$ | | $-(CH_2)_3-$ |
| I.a.99 | F | CN | $CH_3$ | | $-(CH_2)_4-$ |
| I.a.100 | F | CN | $CH_3$ | | $-(CH_2)_5-$ |
| I.a.101 | F | CN | F | | $-(CH_2)_2-$ |
| I.a.102 | F | CN | F | | $-(CH_2)_3-$ |
| I.a.103 | F | CN | F | | $-(CH_2)_4-$ |
| I.a.104 | F | CN | F | | $-(CH_2)_5-$ |
| I.a.105 | F | CN | Cl | | $-(CH_2)_2-$ |
| I.a.106 | F | CN | Cl | | $-(CH_2)_3-$ |
| I.a.107 | F | CN | Cl | | $-(CH_2)_4-$ |
| I.a.108 | F | CN | Cl | | $-(CH_2)_5-$ |
| I.a.109 | Cl | H | $CH_3$ | H | H |
| I.a.110 | Cl | H | $CH_3$ | $CH_3$ | H |
| I.a.111 | Cl | H | $CH_3$ | $CH_3$ | $CH_3$ |
| I.a.112 | Cl | H | F | F | F |
| I.a.113 | Cl | H | F | $CF_3$ | F |
| I.a.114 | Cl | H | F | $CH_3$ | F |
| I.a.115 | Cl | H | F | $CH_3$ | H |
| I.a.116 | Cl | H | F | $CH_3$ | $CH_3$ |
| I.a.117 | Cl | H | Cl | $CH_3$ | $CH_3$ |
| I.a.118 | Cl | H | F | $C_2H_5$ | $CH_3$ |
| I.a.119 | Cl | H | F | $C_2H_5$ | $C_2H_5$ |
| I.a.120 | Cl | H | H | | $-(CH_2)_2-$ |
| I.a.121 | Cl | H | H | | $-(CH_2)_3-$ |
| I.a.122 | Cl | H | H | | $-(CH_2)_4-$ |
| I.a.123 | Cl | H | H | | $-(CH_2)_5-$ |
| I.a.124 | Cl | H | $CH_3$ | | $-(CH_2)_2-$ |
| I.a.125 | Cl | H | $CH_3$ | | $-(CH_2)_3-$ |
| I.a.126 | Cl | H | $CH_3$ | | $-(CH_2)_4-$ |
| I.a.127 | Cl | H | $CH_3$ | | $-(CH_2)_5-$ |
| I.a.128 | Cl | H | F | | $-(CH_2)_2-$ |
| I.a.129 | Cl | H | F | | $-(CH_2)_3-$ |
| I.a.130 | Cl | H | F | | $-(CH_2)_4-$ |
| I.a.131 | Cl | H | F | | $-(CH_2)_5-$ |
| I.a.132 | Cl | H | Cl | | $-(CH_2)_2-$ |
| I.a.133 | Cl | H | Cl | | $-(CH_2)_3-$ |
| I.a.134 | Cl | H | Cl | | $-(CH_2)_4-$ |
| I.a.135 | Cl | H | Cl | | $-(CH_2)_5-$ |
| I.a.136 | Cl | F | $CH_3$ | H | H |
| I.a.137 | Cl | F | $CH_3$ | $CH_3$ | H |
| I.a.138 | Cl | F | $CH_3$ | $CH_3$ | $CH_3$ |
| I.a.139 | Cl | F | F | F | F |
| I.a.140 | Cl | F | F | $CF_3$ | F |
| I.a.141 | Cl | F | F | $CH_3$ | F |
| I.a.142 | Cl | F | F | $CH_3$ | H |
| I.a.143 | Cl | F | F | $CH_3$ | $CH_3$ |
| I.a.144 | Cl | F | Cl | $CH_3$ | $CH_3$ |
| I.a.145 | Cl | F | F | $C_2H_5$ | $CH_3$ |
| I.a.146 | Cl | F | F | $C_2H_5$ | $C_2H_5$ |
| I.a.147 | Cl | F | H | | $-(CH_2)_2-$ |
| I.a.148 | Cl | F | H | | $-(CH_2)_3-$ |
| I.a.149 | Cl | F | H | | $-(CH_2)_4-$ |
| I.a.150 | Cl | F | H | | $-(CH_2)_5-$ |
| I.a.151 | Cl | F | $CH_3$ | | $-(CH_2)_2-$ |
| I.a.152 | Cl | F | $CH_3$ | | $-(CH_2)_3-$ |
| I.a.153 | Cl | F | $CH_3$ | | $-(CH_2)_4-$ |
| I.a.154 | Cl | F | $CH_3$ | | $-(CH_2)_5-$ |
| I.a.155 | Cl | F | F | | $-(CH_2)_2-$ |
| I.a.156 | Cl | F | F | | $-(CH_2)_3-$ |
| I.a.157 | Cl | F | F | | $-(CH_2)_4-$ |
| I.a.158 | Cl | F | F | | $-(CH_2)_5-$ |
| I.a.159 | Cl | F | Cl | | $-(CH_2)_2-$ |
| I.a.160 | Cl | F | Cl | | $-(CH_2)_3-$ |

TABLE 1-continued

| No. | $R^a$ | $R^d$ | $R^2$ | $R^3$ | $R^4$ |
|---|---|---|---|---|---|
| I.a.161 | Cl | F | Cl | | —(CH$_2$)$_4$— |
| I.a.162 | Cl | F | Cl | | —(CH$_2$)$_5$— |
| I.a.163 | CN | H | CH$_3$ | H | H |
| I.a.164 | CN | H | CH$_3$ | CH$_3$ | H |
| I.a.165 | CN | H | CH$_3$ | CH$_3$ | CH$_3$ |
| I.a.166 | CN | H | F | F | F |
| I.a.167 | CN | H | F | CF$_3$ | F |
| I.a.168 | CN | H | F | CH$_3$ | F |
| I.a.169 | CN | H | F | CH$_3$ | H |
| I.a.170 | CN | H | F | CH$_3$ | CH$_3$ |
| I.a.171 | CN | H | Cl | CH$_3$ | CH$_3$ |
| I.a.172 | CN | H | F | C$_2$H$_5$ | CH$_3$ |
| I.a.173 | CN | H | F | C$_2$H$_5$ | C$_2$H$_5$ |
| I.a.174 | CN | H | H | | —(CH$_2$)$_2$— |
| I.a.175 | CN | H | H | | —(CH$_2$)$_3$— |
| I.a.176 | CN | H | H | | —(CH$_2$)$_4$— |
| I.a.177 | CN | H | H | | —(CH$_2$)$_5$— |
| I.a.178 | CN | H | CH$_3$ | | —(CH$_2$)$_2$— |
| I.a.179 | CN | H | CH$_3$ | | —(CH$_2$)$_3$— |
| I.a.180 | CN | H | CH$_3$ | | —(CH$_2$)$_4$— |
| I.a.181 | CN | H | CH$_3$ | | —(CH$_2$)$_5$— |
| I.a.182 | CN | H | F | | —(CH$_2$)$_2$— |
| I.a.183 | CN | H | F | | —(CH$_2$)$_3$— |
| I.a.184 | CN | H | F | | —(CH$_2$)$_4$— |
| I.a.185 | CN | H | F | | —(CH$_2$)$_5$— |
| I.a.186 | CN | H | Cl | | —(CH$_2$)$_2$— |
| I.a.187 | CN | H | Cl | | —(CH$_2$)$_3$— |
| I.a.188 | CN | H | Cl | | —(CH$_2$)$_4$— |
| I.a.189 | CN | H | Cl | | —(CH$_2$)$_5$— |
| I.a.190 | CN | F | CH$_3$ | H | H |
| I.a.191 | CN | F | CH$_3$ | CH$_3$ | H |
| I.a.192 | CN | F | CH$_3$ | CH$_3$ | CH$_3$ |
| I.a.193 | CN | F | F | F | F |
| I.a.194 | CN | F | F | CF$_3$ | F |
| I.a.195 | CN | F | F | CH$_3$ | F |
| I.a.196 | CN | F | F | CH$_3$ | H |
| I.a.197 | CN | F | F | CH$_3$ | CH$_3$ |
| I.a.198 | CN | F | Cl | CH$_3$ | CH$_3$ |
| I.a.199 | CN | F | F | C$_2$H$_5$ | CH$_3$ |
| I.a.200 | CN | F | F | C$_2$H$_5$ | C$_2$H$_5$ |
| I.a.201 | CN | F | H | | —(CH$_2$)$_2$— |
| I.a.202 | CN | F | H | | —(CH$_2$)$_3$— |
| I.a.203 | CN | F | H | | —(CH$_2$)$_4$— |
| I.a.204 | CN | F | H | | —(CH$_2$)$_5$— |
| I.a.205 | CN | F | CH$_3$ | | —(CH$_2$)$_2$— |
| I.a.206 | CN | F | CH$_3$ | | —(CH$_2$)$_3$— |
| I.a.207 | CN | F | CH$_3$ | | —(CH$_2$)$_4$— |
| I.a.208 | CN | F | CH$_3$ | | —(CH$_2$)$_5$— |
| I.a.209 | CN | F | F | | —(CH$_2$)$_2$— |
| I.a.210 | CN | F | F | | —(CH$_2$)$_3$— |
| I.a.211 | CN | F | F | | —(CH$_2$)$_4$— |
| I.a.212 | CN | F | F | | —(CH$_2$)$_5$— |
| I.a.213 | CN | F | Cl | | —(CH$_2$)$_2$— |
| I.a.214 | CN | F | Cl | | —(CH$_2$)$_3$— |
| I.a.215 | CN | F | Cl | | —(CH$_2$)$_4$— |
| I.a.216 | CN | F | Cl | | —(CH$_2$)$_5$— |
| I.a.217 | F | H | F | H | C$_2$H$_5$ |
| I.a.218 | F | H | OCH$_3$ | H | C$_2$H$_5$ |
| I.a.219 | F | H | H | H | C(CH$_3$)$_3$ |
| I.a.220 | F | H | F | H | C(CH$_3$)$_3$ |
| I.a.221 | F | H | F | F | C(CH$_3$)$_3$ |
| I.a.222 | F | H | CH$_3$ | H | C(CH$_3$)$_3$ |
| I.a.223 | F | H | OCH$_3$ | H | C(CH$_3$)$_3$ |
| I.a.224 | F | H | CH$_3$ | F | CH(CH$_3$)$_3$ |
| I.a.225 | F | H | H | H | CH(CH$_3$)$_2$ |
| I.a.226 | F | H | F | H | CH(CH$_3$)$_2$ |
| I.a.227 | F | H | F | F | CH(CH$_3$)$_2$ |
| I.a.228 | F | H | CH$_3$ | H | CH(CH$_3$)$_2$ |
| I.a.229 | F | H | OCH$_3$ | H | CH(CH$_3$)$_2$ |
| I.a.230 | F | H | CH$_3$ | F | CH(CH$_3$)$_2$ |
| I.a.231 | F | H | H | H | c-C$_3$H$_5$ |
| I.a.232 | F | H | F | H | c-C$_3$H$_5$ |
| I.a.233 | F | H | F | F | c-C$_3$H$_5$ |
| I.a.234 | F | H | CH$_3$ | H | c-C$_3$H$_5$ |
| I.a.235 | F | H | OCH$_3$ | H | c-C$_3$H$_5$ |
| I.a.236 | F | H | CH$_3$ | F | c-C$_3$H$_5$ |
| I.a.237 | F | H | H | H | CH$_2$CH$_2$CH$_3$ |
| I.a.238 | F | H | F | H | CH$_2$CH$_2$CH$_3$ |
| I.a.239 | F | H | F | F | CH$_2$CH$_2$CH$_3$ |
| I.a.240 | F | H | CH$_3$ | H | CH$_2$CH$_2$CH$_3$ |
| I.a.241 | F | H | CH$_2$CH$_3$ | H | CH$_2$CH$_2$CH$_3$ |
| I.a.242 | F | H | OCH$_3$ | H | CH$_2$CH$_2$CH$_3$ |
| I.a.243 | F | H | CH$_3$ | F | CH$_2$CH$_2$CH$_3$ |
| I.a.244 | F | H | CH$_3$ | H | CF$_3$ |
| I.a.245 | F | H | CH$_3$ | F | CF$_3$ |
| I.a.246 | F | H | H | | —(CH$_2$)$_2$—CH(CH$_3$)—(CH$_2$)$_2$— |
| I.a.247 | F | H | H | | —O—(CH$_2$)$_2$— |
| I.a.248 | F | H | H | | —O—(CH$_2$)$_3$— |
| I.a.249 | F | H | H | | —O—(CH$_2$)$_4$— |
| I.a.250 | F | H | CH$_3$ | | —(CH$_2$)$_2$—CH(CH$_3$)—(CH$_2$)$_2$— |
| I.a.251 | F | H | CH$_3$ | | —O—(CH$_2$)$_2$— |
| I.a.252 | F | H | CH$_3$ | | —O—(CH$_2$)$_3$— |
| I.a.253 | F | H | CH$_3$ | | —O—(CH$_2$)$_4$— |
| I.a.254 | F | H | F | | —(CH$_2$)$_2$—CH(CH$_3$)—(CH$_2$)$_2$— |
| I.a.255 | F | H | F | | —O—(CH$_2$)$_2$— |
| I.a.256 | F | H | F | | —O—(CH$_2$)$_3$— |
| I.a.257 | F | H | F | | —O—(CH$_2$)$_4$— |
| I.a.258 | F | H | Cl | | —(CH$_2$)$_2$—CH(CH$_3$)—(CH$_2$)$_2$— |
| I.a.259 | F | H | Cl | | —O—(CH$_2$)$_2$— |
| I.a.260 | F | H | Cl | | —O—(CH$_2$)$_3$— |
| I.a.261 | F | H | Cl | | —O—(CH$_2$)$_4$— |
| I.a.262 | F | H | CH$_3$ | | —O—(CH$_2$)$_3$— |
| I.a.263 | F | H | CH$_3$ | | —O—(CH$_2$)$_4$— |
| I.a.264 | F | H | OCH$_3$ | | —O—(CH$_2$)$_3$— |
| I.a.265 | F | H | OCH$_3$ | | —O—(CH$_2$)$_4$— |
| I.a.266 | F | H | OCF$_3$ | | —O—(CH$_2$)$_3$— |
| I.a.267 | F | H | OCF$_3$ | | —O—(CH$_2$)$_4$— |
| I.a.268 | F | H | OCH$_3$ | | —(CH$_2$)$_2$— |
| I.a.269 | F | H | OCH$_3$ | | —(CH$_2$)$_3$— |
| I.a.270 | F | H | OCH$_3$ | | —(CH$_2$)$_4$— |
| I.a.271 | F | H | OCH$_3$ | | —(CH$_2$)$_5$— |
| I.a.272 | F | F | F | H | C$_2$H$_5$ |
| I.a.273 | F | F | OCH$_3$ | H | C$_2$H$_5$ |
| I.a.274 | F | F | H | H | C(CH$_3$)$_3$ |
| I.a.275 | F | F | F | H | C(CH$_3$)$_3$ |
| I.a.276 | F | F | F | F | C(CH$_3$)$_3$ |
| I.a.277 | F | F | CH$_3$ | H | C(CH$_3$)$_3$ |
| I.a.278 | F | F | OCH$_3$ | H | C(CH$_3$)$_3$ |
| I.a.279 | F | F | CH$_3$ | F | C(CH$_3$)$_3$ |
| I.a.280 | F | F | H | H | CH(CH$_3$)$_2$ |
| I.a.281 | F | F | F | H | CH(CH$_3$)$_2$ |
| I.a.282 | F | F | F | F | CH(CH$_3$)$_2$ |
| I.a.283 | F | F | CH$_3$ | H | CH(CH$_3$)$_2$ |
| I.a.284 | F | F | OCH$_3$ | H | CH(CH$_3$)$_2$ |
| I.a.285 | F | F | CH$_3$ | F | CH(CH$_3$)$_2$ |
| I.a.286 | F | F | H | H | c-C$_3$H$_5$ |
| I.a.287 | F | F | F | H | c-C$_3$H$_5$ |
| I.a.288 | F | F | F | F | c-C$_3$H$_5$ |
| I.a.289 | F | F | CH$_3$ | H | c-C$_3$H$_5$ |
| I.a.290 | F | F | OCH$_3$ | H | c-C$_3$H$_5$ |
| I.a.291 | F | F | CH$_3$ | F | c-C$_3$H$_5$ |
| I.a.292 | F | F | H | H | CH$_2$CH$_2$CH$_3$ |
| I.a.293 | F | F | F | H | CH$_2$CH$_2$CH$_3$ |
| I.a.294 | F | F | F | F | CH$_2$CH$_2$CH$_3$ |
| I.a.295 | F | F | CH$_3$ | H | CH$_2$CH$_2$CH$_3$ |
| I.a.296 | F | F | CH$_2$CH$_3$ | H | CH$_2$CH$_2$CH$_3$ |
| I.a.297 | F | F | OCH$_3$ | H | CH$_2$CH$_2$CH$_3$ |
| I.a.298 | F | F | CH$_3$ | F | CH$_2$CH$_2$CH$_3$ |
| I.a.299 | F | F | CH$_3$ | H | CF$_3$ |
| I.a.300 | F | F | CH$_3$ | F | CF$_3$ |
| I.a.301 | F | F | H | H | OH |
| I.a.302 | F | F | H | H | OCH$_3$ |
| I.a.303 | F | F | H | H | OCF$_3$ |
| I.a.304 | F | F | CH$_3$ | H | OH |
| I.a.305 | F | F | CH$_3$ | H | OCH$_3$ |
| I.a.306 | F | F | CH$_3$ | H | OCF$_3$ |
| I.a.307 | F | F | CH$_3$ | CH$_3$ | OH |
| I.a.308 | F | F | CH$_3$ | CH$_3$ | OCH$_3$ |
| I.a.309 | F | F | CH$_3$ | CH$_3$ | OCF$_3$ |
| I.a.310 | F | F | H | | —(CH$_2$)$_2$—CH(CH$_3$)—(CH$_2$)$_2$— |
| I.a.311 | F | F | H | | —O—(CH$_2$)$_2$— |
| I.a.312 | F | F | H | | —O—(CH$_2$)$_3$— |
| I.a.313 | F | F | H | | —O—(CH$_2$)$_4$— |
| I.a.314 | F | F | CH$_3$ | | —(CH$_2$)$_2$—CH(CH$_3$)—(CH$_2$)$_2$— |
| I.a.315 | F | F | CH$_3$ | | —O—(CH$_2$)$_2$— |
| I.a.316 | F | F | CH$_3$ | | —O—(CH$_2$)$_3$— |

TABLE 1-continued

| No. | $R^a$ | $R^d$ | $R^2$ | $R^3$ | $R^4$ |
|---|---|---|---|---|---|
| I.a.317 | F | F | CH$_3$ | | —O—(CH$_2$)$_4$— |
| I.a.318 | F | F | F | | —(CH$_2$)$_2$—CH(CH$_3$)—(CH$_2$)$_2$— |
| I.a.319 | F | F | F | | —O—(CH$_2$)$_2$— |
| I.a.320 | F | F | F | | —O—(CH$_2$)$_3$— |
| I.a.321 | F | F | F | | —O—(CH$_2$)$_4$— |
| I.a.322 | F | F | Cl | | —(CH$_2$)$_2$—CH(CH$_3$)—(CH$_2$)$_2$— |
| I.a.323 | F | F | Cl | | —O—(CH$_2$)$_2$— |
| I.a.324 | F | F | Cl | | —O—(CH$_2$)$_3$— |
| I.a.325 | F | F | Cl | | —O—(CH$_2$)$_4$— |
| I.a.326 | F | F | CH$_3$ | | —O—(CH$_2$)$_3$— |
| I.a.327 | F | F | CH$_3$ | | —O—(CH$_2$)$_4$— |
| I.a.328 | F | F | OCH$_3$ | | —O—(CH$_2$)$_3$— |
| I.a.329 | F | F | OCH$_3$ | | —O—(CH$_2$)$_4$— |
| I.a.330 | F | F | OCF$_3$ | | —O—(CH$_2$)$_3$— |
| I.a.331 | F | F | OCF$_3$ | | —O—(CH$_2$)$_4$— |
| I.a.332 | F | F | OCH$_3$ | | —(CH$_2$)$_2$— |
| I.a.333 | F | F | OCH$_3$ | | —(CH$_2$)$_3$— |
| I.a.334 | F | F | OCH$_3$ | | —(CH$_2$)$_4$— |
| I.a.335 | F | F | OCH$_3$ | | —(CH$_2$)$_5$— |
| I.a.336 | F | F | OH | | —(CH$_2$)$_2$— |
| I.a.337 | F | F | OH | | —(CH$_2$)$_3$— |
| I.a.338 | F | F | OH | | —(CH$_2$)$_4$— |
| I.a.339 | F | F | OH | | —(CH$_2$)$_5$— |
| I.a.340 | F | F | OCF$_3$ | | —(CH$_2$)$_2$— |
| I.a.341 | F | F | OCF$_3$ | | —(CH$_2$)$_3$— |
| I.a.342 | F | F | OCF$_3$ | | —(CH$_2$)$_4$— |
| I.a.343 | F | F | OCF$_3$ | | —(CH$_2$)$_5$— |
| I.a.344 | F | H | H | H | OH |
| I.a.345 | F | H | H | H | OCH$_3$ |
| I.a.346 | F | H | H | H | OCF$_3$ |
| I.a.347 | F | H | CH$_3$ | H | OH |
| I.a.348 | F | H | CH$_3$ | H | OCH$_3$ |
| I.a.349 | F | H | CH$_3$ | H | OCF$_3$ |
| I.a.350 | F | H | CH$_3$ | CH$_3$ | OH |
| I.a.351 | F | H | CH$_3$ | CH$_3$ | OCH$_3$ |
| I.a.352 | F | H | CH$_3$ | CH$_3$ | OCF$_3$ |
| I.a.353 | F | H | OH | | —(CH$_2$)$_2$— |
| I.a.354 | F | H | OH | | —(CH$_2$)$_3$— |
| I.a.355 | F | H | OH | | —(CH$_2$)$_4$— |
| I.a.356 | F | H | OH | | —(CH$_2$)$_5$— |
| I.a.357 | F | H | OCF$_3$ | | —(CH$_2$)$_2$— |
| I.a.358 | F | H | OCF$_3$ | | —(CH$_2$)$_3$— |
| I.a.359 | F | H | OCF$_3$ | | —(CH$_2$)$_4$— |
| I.a.360 | F | H | OCF$_3$ | | —(CH$_2$)$_5$— |
| I.a.361 | F | Cl | F | H | C$_2$H$_5$ |
| I.a.362 | F | Cl | OCH$_3$ | H | C$_2$H$_5$ |
| I.a.363 | F | Cl | H | H | C(CH$_3$)$_3$ |
| I.a.364 | F | Cl | F | H | C(CH$_3$)$_3$ |
| I.a.365 | F | Cl | F | F | C(CH$_3$)$_3$ |
| I.a.366 | F | Cl | CH$_3$ | H | C(CH$_3$)$_3$ |
| I.a.367 | F | Cl | OCH$_3$ | H | C(CH$_3$)$_3$ |
| I.a.368 | F | Cl | CH$_3$ | F | C(CH$_3$)$_3$ |
| I.a.369 | F | Cl | H | H | CH(CH$_3$)$_2$ |
| I.a.370 | F | Cl | F | H | CH(CH$_3$)$_2$ |
| I.a.371 | F | Cl | F | F | CH(CH$_3$)$_2$ |
| I.a.372 | F | Cl | CH$_3$ | H | CH(CH$_3$)$_2$ |
| I.a.373 | F | Cl | OCH$_3$ | H | CH(CH$_3$)$_2$ |
| I.a.374 | F | Cl | CH$_3$ | F | CH(CH$_3$)$_2$ |
| I.a.375 | F | Cl | H | H | c-C$_3$H$_5$ |
| I.a.376 | F | Cl | F | H | c-C$_3$H$_5$ |
| I.a.377 | F | Cl | F | F | c-C$_3$H$_5$ |
| I.a.378 | F | Cl | CH$_3$ | H | c-C$_3$H$_5$ |
| I.a.379 | F | Cl | OCH$_3$ | H | c-C$_3$H$_5$ |
| I.a.380 | F | Cl | CH$_3$ | F | c-C$_3$H$_5$ |
| I.a.381 | F | Cl | H | H | CH$_2$CH$_2$CH$_3$ |
| I.a.382 | F | Cl | F | H | CH$_2$CH$_2$CH$_3$ |
| I.a.383 | F | Cl | F | F | CH$_2$CH$_2$CH$_3$ |
| I.a.384 | F | Cl | CH$_3$ | H | CH$_2$CH$_2$CH$_3$ |
| I.a.385 | F | Cl | CH$_2$CH$_3$ | H | CH$_2$CH$_2$CH$_3$ |
| I.a.386 | F | Cl | OCH$_3$ | H | CH$_2$CH$_2$CH$_3$ |
| I.a.387 | F | Cl | CH$_3$ | F | CH$_2$CH$_2$CH$_3$ |
| I.a.388 | F | Cl | CH$_3$ | H | CF$_3$ |
| I.a.389 | F | Cl | CH$_3$ | F | CF$_3$ |
| I.a.390 | F | Cl | H | | —(CH$_2$)$_2$—CH(CH$_3$)—(CH$_2$)$_2$— |
| I.a.391 | F | Cl | H | | —O—(CH$_2$)$_2$— |
| I.a.392 | F | Cl | H | | —O—(CH$_2$)$_3$— |
| I.a.393 | F | Cl | H | | —O—(CH$_2$)$_4$— |
| I.a.394 | F | Cl | CH$_3$ | | —(CH$_2$)$_2$—CH(CH$_3$)—(CH$_2$)$_2$— |
| I.a.395 | F | Cl | CH$_3$ | | —O—(CH$_2$)$_2$— |
| I.a.396 | F | Cl | CH$_3$ | | —O—(CH$_2$)$_3$— |
| I.a.397 | F | Cl | CH$_3$ | | —O—(CH$_2$)$_4$— |
| I.a.398 | F | Cl | F | | —(CH$_2$)$_2$—CH(CH$_3$)—(CH$_2$)$_2$— |
| I.a.399 | F | Cl | F | | —O—(CH$_2$)$_2$— |
| I.a.400 | F | Cl | F | | —O—(CH$_2$)$_3$— |
| I.a.401 | F | Cl | F | | —O—(CH$_2$)$_4$— |
| I.a.402 | F | Cl | Cl | | —(CH$_2$)$_2$—CH(CH$_3$)—(CH$_2$)$_2$— |
| I.a.403 | F | Cl | Cl | | —O—(CH$_2$)$_2$— |
| I.a.404 | F | Cl | Cl | | —O—(CH$_2$)$_3$— |
| I.a.405 | F | Cl | Cl | | —O—(CH$_2$)$_4$— |
| I.a.406 | F | Cl | CH$_3$ | | —O—(CH$_2$)$_3$— |
| I.a.407 | F | Cl | CH$_3$ | | —O—(CH$_2$)$_4$— |
| I.a.408 | F | Cl | OCH$_3$ | | —O—(CH$_2$)$_3$— |
| I.a.409 | F | Cl | OCH$_3$ | | —O—(CH$_2$)$_4$— |
| I.a.410 | F | Cl | OCF$_3$ | | —O—(CH$_2$)$_3$— |
| I.a.411 | F | Cl | OCF$_3$ | | —O—(CH$_2$)$_4$— |
| I.a.412 | F | Cl | OCH$_3$ | | —(CH$_2$)$_2$— |
| I.a.413 | F | Cl | OCH$_3$ | | —(CH$_2$)$_3$— |
| I.a.414 | F | Cl | OCH$_3$ | | —(CH$_2$)$_4$— |
| I.a.415 | F | Cl | OCH$_3$ | | —(CH$_2$)$_5$— |
| I.a.416 | F | Cl | H | H | OH |
| I.a.417 | F | Cl | H | H | OCH$_3$ |
| I.a.418 | F | Cl | H | H | OCF$_3$ |
| I.a.419 | F | Cl | CH$_3$ | H | OH |
| I.a.420 | F | Cl | CH$_3$ | H | OCH$_3$ |
| I.a.421 | F | Cl | CH$_3$ | H | OCF$_3$ |
| I.a.422 | F | Cl | CH$_3$ | CH$_3$ | OH |
| I.a.423 | F | Cl | CH$_3$ | CH$_3$ | OCH$_3$ |
| I.a.424 | F | Cl | CH$_3$ | CH$_3$ | OCF$_3$ |
| I.a.425 | F | Cl | OH | | —(CH$_2$)$_2$— |
| I.a.426 | F | Cl | OH | | —(CH$_2$)$_3$— |
| I.a.427 | F | Cl | OH | | —(CH$_2$)$_4$— |
| I.a.428 | F | Cl | OH | | —(CH$_2$)$_5$— |
| I.a.429 | F | Cl | OCF$_3$ | | —(CH$_2$)$_2$— |
| I.a.430 | F | Cl | OCF$_3$ | | —(CH$_2$)$_3$— |
| I.a.431 | F | Cl | OCF$_3$ | | —(CH$_2$)$_4$— |
| I.a.432 | F | Cl | OCF$_3$ | | —(CH$_2$)$_5$— |
| I.a.433 | Cl | F | F | H | C$_2$H$_5$ |
| I.a.434 | Cl | F | OCH$_3$ | H | C$_2$H$_5$ |
| I.a.435 | Cl | F | H | H | C(CH$_3$)$_3$ |
| I.a.436 | Cl | F | F | H | C(CH$_3$)$_3$ |
| I.a.437 | Cl | F | F | F | C(CH$_3$)$_3$ |
| I.a.438 | Cl | F | CH$_3$ | H | C(CH$_3$)$_3$ |
| I.a.439 | Cl | F | OCH$_3$ | H | C(CH$_3$)$_3$ |
| I.a.440 | Cl | F | CH$_3$ | F | C(CH$_3$)$_3$ |
| I.a.441 | Cl | F | H | H | CH(CH$_3$)$_2$ |
| I.a.442 | Cl | F | F | H | CH(CH$_3$)$_2$ |
| I.a.443 | Cl | F | F | F | CH(CH$_3$)$_2$ |
| I.a.444 | Cl | F | CH$_3$ | H | CH(CH$_3$)$_2$ |
| I.a.445 | Cl | F | OCH$_3$ | H | CH(CH$_3$)$_2$ |
| I.a.446 | Cl | F | CH$_3$ | F | CH(CH$_3$)$_2$ |
| I.a.447 | Cl | F | H | H | c-C$_3$H$_5$ |
| I.a.448 | Cl | F | F | H | c-C$_3$H$_5$ |
| I.a.449 | Cl | F | F | F | c-C$_3$H$_5$ |
| I.a.450 | Cl | F | CH$_3$ | H | c-C$_3$H$_5$ |
| I.a.451 | Cl | F | OCH$_3$ | H | c-C$_3$H$_5$ |
| I.a.452 | Cl | F | CH$_3$ | F | c-C$_3$H$_5$ |
| I.a.453 | Cl | F | H | H | CH$_2$CH$_2$CH$_3$ |
| I.a.454 | Cl | F | F | H | CH$_2$CH$_2$CH$_3$ |
| I.a.455 | Cl | F | F | F | CH$_2$CH$_2$CH$_3$ |
| I.a.456 | Cl | F | CH$_3$ | H | CH$_2$CH$_2$CH$_3$ |
| I.a.457 | Cl | F | CH$_2$CH$_3$ | H | CH$_2$CH$_2$CH$_3$ |
| I.a.458 | Cl | F | OCH$_3$ | H | CH$_2$CH$_2$CH$_3$ |
| I.a.459 | Cl | F | CH$_3$ | F | CH$_2$CH$_2$CH$_3$ |
| I.a.460 | Cl | F | CH$_3$ | H | CF$_3$ |
| I.a.461 | Cl | F | CH$_3$ | F | CF$_3$ |
| I.a.462 | Cl | F | H | | —(CH$_2$)$_2$—CH(CH$_3$)—(CH$_2$)$_2$— |
| I.a.463 | Cl | F | H | | —O—(CH$_2$)$_2$— |
| I.a.464 | Cl | F | H | | —O—(CH$_2$)$_3$— |
| I.a.465 | Cl | F | H | | —O—(CH$_2$)$_4$— |
| I.a.466 | Cl | F | CH$_3$ | | —(CH$_2$)$_2$—CH(CH$_3$)—(CH$_2$)$_2$— |
| I.a.467 | Cl | F | CH$_3$ | | —O—(CH$_2$)$_2$— |
| I.a.468 | Cl | F | CH$_3$ | | —O—(CH$_2$)$_3$— |
| I.a.469 | Cl | F | CH$_3$ | | —O—(CH$_2$)$_4$— |
| I.a.470 | Cl | F | F | | —(CH$_2$)$_2$—CH(CH$_3$)—(CH$_2$)$_2$— |
| I.a.471 | Cl | F | F | | —O—(CH$_2$)$_2$— |
| I.a.472 | Cl | F | F | | —O—(CH$_2$)$_3$— |

TABLE 1-continued

| No. | $R^a$ | $R^d$ | $R^2$ | $R^3$ | $R^4$ |
|---|---|---|---|---|---|
| I.a.473 | Cl | F | F | | —O—(CH$_2$)$_4$— |
| I.a.474 | Cl | F | Cl | | —(CH$_2$)$_2$—CH(CH$_3$)—(CH$_2$)$_2$— |
| I.a.475 | Cl | F | Cl | | —O—(CH$_2$)$_2$— |
| I.a.476 | Cl | F | Cl | | —O—(CH$_2$)$_3$— |
| I.a.477 | Cl | F | Cl | | —O—(CH$_2$)$_4$— |
| I.a.478 | Cl | F | CH$_3$ | | —O—(CH$_2$)$_3$— |
| I.a.479 | Cl | F | CH$_3$ | | —O—(CH$_2$)$_4$— |
| I.a.480 | Cl | F | OCH$_3$ | | —O—(CH$_2$)$_3$— |
| I.a.481 | Cl | F | OCH$_3$ | | —O—(CH$_2$)$_4$— |
| I.a.482 | Cl | F | OCF$_3$ | | —O—(CH$_2$)$_3$— |
| I.a.483 | Cl | F | OCF$_3$ | | —O—(CH$_2$)$_4$— |
| I.a.484 | Cl | F | OCH$_3$ | | —(CH$_2$)$_2$— |
| I.a.485 | Cl | F | OCH$_3$ | | —(CH$_2$)$_3$— |
| I.a.486 | Cl | F | OCH$_3$ | | —(CH$_2$)$_4$— |
| I.a.487 | Cl | F | OCH$_3$ | | —(CH$_2$)$_5$— |
| I.a.488 | Cl | F | H | H | OH |
| I.a.489 | Cl | F | H | H | OCH$_3$ |
| I.a.490 | Cl | F | H | H | OCF$_3$ |
| I.a.491 | Cl | F | CH$_3$ | H | OH |
| I.a.492 | Cl | F | CHs | H | OCH$_3$ |
| I.a.493 | Cl | F | CH$_3$ | H | OCF$_3$ |
| I.a.494 | Cl | F | CH$_3$ | CH$_3$ | OH |
| I.a.495 | Cl | F | CH$_3$ | CH$_3$ | OCH$_3$ |
| I.a.496 | Cl | F | CH$_3$ | CH$_3$ | OCF$_3$ |
| I.a.497 | Cl | F | OH | | —(CH$_2$)$_2$— |
| I.a.498 | Cl | F | OH | | —(CH$_2$)$_3$— |
| I.a.499 | Cl | F | OH | | —(CH$_2$)$_4$— |
| I.a.500 | Cl | F | OH | | —(CH$_2$)$_5$— |
| I.a.501 | Cl | F | OCF$_3$ | | —(CH$_2$)$_2$— |
| I.a.502 | Cl | F | OCF$_3$ | | —(CH$_2$)$_3$— |
| I.a.503 | Cl | F | OCF$_3$ | | —(CH$_2$)$_4$— |
| I.a.504 | Cl | F | OCF$_3$ | | —(CH$_2$)$_5$— |
| I.a.505 | Cl | H | F | H | C$_2$H$_5$ |
| I.a.506 | Cl | H | OCH$_3$ | H | C$_2$H$_5$ |
| I.a.507 | Cl | H | H | H | C(CH$_3$)$_3$ |
| I.a.508 | Cl | H | F | H | C(CH$_3$)$_3$ |
| I.a.509 | Cl | H | F | F | C(CH$_3$)$_3$ |
| I.a.510 | Cl | H | CH$_3$ | H | C(CH$_3$)$_3$ |
| I.a.511 | Cl | H | OCH$_3$ | H | C(CH$_3$)$_3$ |
| I.a.512 | Cl | H | CH$_3$ | F | C(CH$_3$)$_3$ |
| I.a.513 | Cl | H | H | H | CH(CH$_3$)$_2$ |
| I.a.514 | Cl | H | F | H | CH(CH$_3$)$_2$ |
| I.a.515 | Cl | H | F | F | CH(CH$_3$)$_2$ |
| I.a.516 | Cl | H | CH$_3$ | H | CH(CH$_3$)$_2$ |
| I.a.517 | Cl | H | OCH$_3$ | H | CH(CH$_3$)$_2$ |
| I.a.518 | Cl | H | CH$_3$ | F | CH(CH$_3$)$_2$ |
| I.a.519 | Cl | H | H | H | c-C$_3$H$_5$ |
| I.a.520 | Cl | H | F | H | c-C$_3$H$_5$ |
| I.a.521 | Cl | H | F | F | c-C$_3$H$_5$ |
| I.a.522 | Cl | H | CH$_3$ | H | c-C$_3$H$_5$ |
| I.a.523 | Cl | H | OCH$_3$ | H | c-C$_3$H$_5$ |
| I.a.524 | Cl | H | CH$_3$ | F | c-C$_3$H$_5$ |
| I.a.525 | Cl | H | H | H | CH$_2$CH$_2$CH$_3$ |
| I.a.526 | Cl | H | F | H | CH$_2$CH$_2$CH$_3$ |
| I.a.527 | Cl | H | F | F | CH$_2$CH$_2$CH$_3$ |
| I.a.528 | Cl | H | CH$_3$ | H | CH$_2$CH$_2$CH$_3$ |
| I.a.529 | Cl | H | CH$_2$CH$_3$ | H | CH$_2$CH$_2$CH$_3$ |
| I.a.530 | Cl | H | OCH$_3$ | H | CH$_2$CH$_2$CH$_3$ |
| I.a.531 | Cl | H | CH$_3$ | F | CH$_2$CH$_2$CH$_3$ |
| I.a.532 | Cl | H | CH$_3$ | H | CF$_3$ |
| I.a.533 | Cl | H | CH$_3$ | F | CF$_3$ |
| I.a.534 | Cl | H | H | | —(CH$_2$)$_2$—CH(CH$_3$)—(CH$_2$)$_2$— |
| I.a.535 | Cl | H | H | | —O—(CH$_2$)$_2$— |
| I.a.536 | Cl | H | H | | —O—(CH$_2$)$_3$— |
| I.a.537 | Cl | H | H | | —O—(CH$_2$)$_4$— |
| I.a.538 | Cl | H | CH$_3$ | | —(CH$_2$)$_2$—CH(CH$_3$)—(CH$_2$)$_2$— |
| I.a.539 | Cl | H | CH$_3$ | | —O—(CH$_2$)$_2$— |
| I.a.540 | Cl | H | CH$_3$ | | —O—(CH$_2$)$_3$— |
| I.a.541 | Cl | H | CH$_3$ | | —O—(CH$_2$)$_4$— |
| I.a.542 | Cl | H | F | | —(CH$_2$)$_2$—CH(CH$_3$)—(CH$_2$)$_2$— |
| I.a.543 | Cl | H | F | | —O—(CH$_2$)$_2$— |
| I.a.544 | Cl | H | F | | —O—(CH$_2$)$_3$— |
| I.a.545 | Cl | H | F | | —O—(CH$_2$)$_4$— |
| I.a.546 | Cl | H | Cl | | —(CH$_2$)$_2$—CH(CH$_3$)—(CH$_2$)$_2$— |
| I.a.547 | Cl | H | Cl | | —O—(CH$_2$)$_2$— |
| I.a.548 | Cl | H | Cl | | —O—(CH$_2$)$_3$— |
| I.a.549 | Cl | H | Cl | | —O—(CH$_2$)$_4$— |
| I.a.550 | Cl | H | CH$_3$ | | —O—(CH$_2$)$_3$— |
| I.a.551 | Cl | H | CH$_3$ | | —O—(CH$_2$)$_4$— |
| I.a.552 | Cl | H | OCH$_3$ | | —O—(CH$_2$)$_3$— |
| I.a.553 | Cl | H | OCH$_3$ | | —O—(CH$_2$)$_4$— |
| I.a.554 | Cl | H | OCF$_3$ | | —O—(CH$_2$)$_3$— |
| I.a.555 | Cl | H | OCF$_3$ | | —O—(CH$_2$)$_4$— |
| I.a.556 | Cl | H | OCH$_3$ | | —(CH$_2$)$_2$— |
| I.a.557 | Cl | H | OCH$_3$ | | —(CH$_2$)$_3$— |
| I.a.558 | Cl | H | OCH$_3$ | | —(CH$_2$)$_4$— |
| I.a.559 | Cl | H | OCH$_3$ | | —(CH$_2$)$_5$— |
| I.a.560 | Cl | H | H | H | OH |
| I.a.561 | Cl | H | H | H | OCH$_3$ |
| I.a.562 | Cl | H | H | H | OCF$_3$ |
| I.a.563 | Cl | H | CH$_3$ | H | OH |
| I.a.564 | Cl | H | CH$_3$ | H | OCH$_3$ |
| I.a.565 | Cl | H | CH$_3$ | H | OCF$_3$ |
| I.a.566 | Cl | H | CHs | CH$_3$ | OH |
| I.a.567 | Cl | H | CH$_3$ | CH$_3$ | OCH$_3$ |
| I.a.568 | Cl | H | CH$_3$ | CH$_3$ | OCF$_3$ |
| I.a.569 | Cl | H | OH | | —(CH$_2$)$_2$— |
| I.a.570 | Cl | H | OH | | —(CH$_2$)$_3$— |
| I.a.571 | Cl | H | OH | | —(CH$_2$)$_4$— |
| I.a.572 | Cl | H | OH | | —(CH$_2$)$_5$— |
| I.a.573 | Cl | H | OCF$_3$ | | —(CH$_2$)$_2$— |
| I.a.574 | Cl | H | OCF$_3$ | | —(CH$_2$)$_3$— |
| I.a.575 | Cl | H | OCF$_3$ | | —(CH$_2$)$_4$— |
| I.a.576 | Cl | H | OCF$_3$ | | —(CH$_2$)$_5$— |
| I.a.577 | CN | F | F | H | C$_2$H$_5$ |
| I.a.578 | CN | F | OCH$_3$ | H | C$_2$H$_5$ |
| I.a.579 | CN | F | H | H | C(CH$_3$)$_3$ |
| I.a.580 | CN | F | F | H | C(CH$_3$)$_3$ |
| I.a.581 | CN | F | F | F | C(CH$_3$)$_3$ |
| I.a.582 | CN | F | CH$_3$ | H | C(CH$_3$)$_3$ |
| I.a.583 | CN | F | OCH$_3$ | H | C(CH$_3$)$_3$ |
| I.a.584 | CN | F | CH$_3$ | F | C(CH$_3$)$_3$ |
| I.a.585 | CN | F | H | H | CH(CH$_3$)$_2$ |
| I.a.586 | CN | F | F | H | CH(CH$_3$)$_2$ |
| I.a.587 | CN | F | F | F | CH(CH$_3$)$_2$ |
| I.a.588 | CN | F | CH$_3$ | H | CH(CH$_3$)$_2$ |
| I.a.589 | CN | F | OCH$_3$ | H | CH(CH$_3$)$_2$ |
| I.a.590 | CN | F | CH$_3$ | F | CH(CH$_3$)$_2$ |
| I.a.591 | CN | F | H | H | c-C$_3$H$_5$ |
| I.a.592 | CN | F | F | H | c-C$_3$H$_5$ |
| I.a.593 | CN | F | F | F | c-C$_3$H$_5$ |
| I.a.594 | CN | F | CH$_3$ | H | c-C$_3$H$_5$ |
| I.a.595 | CN | F | OCH$_3$ | H | c-C$_3$H$_5$ |
| I.a.596 | CN | F | CH$_3$ | F | c-C$_3$H$_5$ |
| I.a.597 | CN | F | H | H | CH$_2$CH$_2$CH$_3$ |
| I.a.599 | CN | F | F | F | CH$_2$CH$_2$CH$_3$ |
| I.a.600 | CN | F | CH$_3$ | H | CH$_2$CH$_2$CH$_3$ |
| I.a.601 | CN | F | CH$_2$CH$_3$ | H | CH$_2$CH$_2$CH$_3$ |
| I.a.602 | CN | F | OCH$_3$ | H | CH$_2$CH$_2$CH$_3$ |
| I.a.603 | CN | F | CH$_3$ | F | CH$_2$CH$_2$CH$_3$ |
| I.a.604 | CN | F | CH$_3$ | H | CF$_3$ |
| I.a.605 | CN | F | CH$_3$ | F | CF$_3$ |
| I.a.606 | CN | F | H | | —(CH$_2$)$_2$—CH(CH$_3$)—(CH$_2$)$_2$— |
| I.a.607 | CN | F | H | | —O—(CH$_2$)$_2$— |
| I.a.608 | CN | F | H | | —O—(CH$_2$)$_3$— |
| I.a.609 | CN | F | H | | —O—(CH$_2$)$_4$— |
| I.a.610 | CN | F | CH$_3$ | | —(CH$_2$)$_2$—CH(CH$_3$)—(CH$_2$)$_2$— |
| I.a.611 | CN | F | CH$_3$ | | —O—(CH$_2$)$_2$— |
| I.a.612 | CN | F | CH$_3$ | | —O—(CH$_2$)$_3$— |
| I.a.613 | CN | F | CH$_3$ | | —O—(CH$_2$)$_4$— |
| I.a.614 | CN | F | F | | —(CH$_2$)$_2$—CH(CH$_3$)—(CH$_2$)$_2$— |
| I.a.615 | CN | F | F | | —O—(CH$_2$)$_2$— |
| I.a.616 | CN | F | F | | —O—(CH$_2$)$_3$— |
| I.a.617 | CN | F | F | | —O—(CH$_2$)$_4$— |
| I.a.618 | CN | F | Cl | | —(CH$_2$)$_2$—CH(CH$_3$)—(CH$_2$)$_2$— |
| I.a.619 | CN | F | Cl | | —O—(CH$_2$)$_2$— |
| I.a.620 | CN | F | Cl | | —O—(CH$_2$)$_3$— |
| I.a.621 | CN | F | Cl | | —O—(CH$_2$)$_4$— |
| I.a.622 | CN | F | CH$_3$ | | —O—(CH$_2$)$_3$— |
| I.a.623 | CN | F | CH$_3$ | | —O—(CH$_2$)$_4$— |
| I.a.624 | CN | F | OCH$_3$ | | —O—(CH$_2$)$_3$— |
| I.a.625 | CN | F | OCH$_3$ | | —O—(CH$_2$)$_4$— |
| I.a.626 | CN | F | OCF$_3$ | | —O—(CH$_2$)$_3$— |
| I.a.627 | CN | F | OCF$_3$ | | —O—(CH$_2$)$_4$— |
| I.a.628 | CN | F | OCH$_3$ | | —(CH$_2$)$_2$— |
| I.a.629 | CN | F | OCH$_3$ | | —(CH$_2$)$_3$— |

TABLE 1-continued

| No. | $R^a$ | $R^d$ | $R^2$ | $R^3$ | $R^4$ |
|---|---|---|---|---|---|
| I.a.630 | CN | F | OCH$_3$ | | —(CH$_2$)$_4$— |
| I.a.631 | CN | F | OCH$_3$ | | —(CH$_2$)$_5$— |
| I.a.632 | CN | H | F | H | C$_2$H$_5$ |
| I.a.633 | CN | H | OCH$_3$ | H | C$_2$H$_5$ |
| I.a.634 | CN | H | H | H | C(CH$_3$)$_3$ |
| I.a.635 | CN | H | F | H | C(CH$_3$)$_3$ |
| I.a.636 | CN | H | F | F | C(CH$_3$)$_3$ |
| I.a.637 | CN | H | CH$_3$ | H | C(CH$_3$)$_3$ |
| I.a.638 | CN | H | OCH$_3$ | H | C(CH$_3$)$_3$ |
| I.a.639 | CN | H | CH$_3$ | F | C(CH$_3$)$_3$ |
| I.a.640 | CN | H | H | H | CH(CH$_3$)$_2$ |
| I.a.641 | CN | H | F | H | CH(CH$_3$)$_2$ |
| I.a.642 | CN | H | F | F | CH(CH$_3$)$_2$ |
| I.a.643 | CN | H | CH$_3$ | H | CH(CH$_3$)$_2$ |
| I.a.644 | CN | H | OCH$_3$ | H | CH(CH$_3$)$_2$ |
| I.a.645 | CN | H | CH$_3$ | F | CH(CH$_3$)$_2$ |
| I.a.646 | CN | H | H | H | c-C$_3$H$_5$ |
| I.a.647 | CN | H | F | H | c-C$_3$H$_5$ |
| I.a.648 | CN | H | F | F | c-C$_3$H$_5$ |
| I.a.649 | CN | H | CH$_3$ | H | c-C$_3$H$_5$ |
| I.a.650 | CN | H | OCH$_3$ | H | c-C$_3$H$_5$ |
| I.a.651 | CN | H | CH$_3$ | F | c-C$_3$H$_5$ |
| I.a.652 | CN | H | H | H | CH$_2$CH$_2$CH$_3$ |
| I.a.653 | CN | H | F | H | CH$_2$CH$_2$CH$_3$ |
| I.a.654 | CN | H | F | F | CH$_2$CH$_2$CH$_3$ |
| I.a.655 | CN | H | CH$_3$ | H | CH$_2$CH$_2$CH$_3$ |
| I.a.656 | CN | H | CH$_2$CH$_3$ | H | CH$_2$CH$_2$CH$_3$ |
| I.a.657 | CN | H | OCH$_3$ | H | CH$_2$CH$_2$CH$_3$ |
| I.a.658 | CN | H | CH$_3$ | F | CH$_2$CH$_2$CH$_3$ |
| I.a.659 | CN | H | CH$_3$ | H | CF$_3$ |
| I.a.660 | CN | H | CH$_3$ | F | CF$_3$ |
| I.a.661 | CN | H | H | | —(CH$_2$)$_2$—CH(CH$_3$)—(CH$_2$)$_2$— |
| I.a.662 | CN | H | H | | —O—(CH$_2$)$_2$— |
| I.a.663 | CN | H | H | | —O—(CH$_2$)$_3$— |
| I.a.664 | CN | H | H | | —O—(CH$_2$)$_4$— |
| I.a.665 | CN | H | CH$_3$ | | —(CH$_2$)$_2$—CH(CH$_3$)—(CH$_2$)$_2$— |
| I.a.666 | CN | H | CH$_3$ | | —O—(CH$_2$)$_2$— |
| I.a.667 | CN | H | CH$_3$ | | —O—(CH$_2$)$_3$— |
| I.a.668 | CN | H | CH$_3$ | | —O—(CH$_2$)$_4$— |
| I.a.669 | CN | H | F | | —(CH$_2$)$_2$—CH(CH$_3$)—(CH$_2$)$_2$— |
| I.a.670 | CN | H | F | | —O—(CH$_2$)$_2$— |
| I.a.671 | CN | H | F | | —O—(CH$_2$)$_3$— |
| I.a.672 | CN | H | F | | —O—(CH$_2$)$_4$— |
| I.a.673 | CN | H | Cl | | —(CH$_2$)$_2$—CH(CH$_3$)—(CH$_2$)$_2$— |
| I.a.674 | CN | H | Cl | | —O—(CH$_2$)$_2$— |
| I.a.675 | CN | H | Cl | | —O—(CH$_2$)$_3$— |
| I.a.676 | CN | H | Cl | | —O—(CH$_2$)$_4$— |
| I.a.677 | CN | H | CH$_3$ | | —O—(CH$_2$)$_3$— |
| I.a.678 | CN | H | CH$_3$ | | —O—(CH$_2$)$_4$— |
| I.a.679 | CN | H | OCH$_3$ | | —O—(CH$_2$)$_3$— |
| I.a.680 | CN | H | OCH$_3$ | | —O—(CH$_2$)$_4$— |
| I.a.681 | CN | H | OCF$_3$ | | —O—(CH$_2$)$_3$— |
| I.a.682 | CN | H | OCF$_3$ | | —O—(CH$_2$)$_4$— |
| I.a.683 | CN | H | OCH$_3$ | | —(CH$_2$)$_2$— |
| I.a.684 | CN | H | OCH$_3$ | | —(CH$_2$)$_3$— |
| I.a.685 | CN | H | OCH$_3$ | | —(CH$_2$)$_4$— |
| I.a.686 | CN | H | OCH$_3$ | | —(CH$_2$)$_5$— |
| I.a.687 | F | CN | F | H | C$_2$H$_5$ |
| I.a.688 | F | CN | OCH$_3$ | H | C$_2$H$_5$ |
| I.a.689 | F | CN | H | H | C(CH$_3$)$_3$ |
| I.a.690 | F | CN | F | H | C(CH$_3$)$_3$ |
| I.a.691 | F | CN | F | F | C(CH$_3$)$_3$ |
| I.a.692 | F | CN | CH$_3$ | H | C(CH$_3$)$_3$ |
| I.a.693 | F | CN | OCH$_3$ | H | C(CH$_3$)$_3$ |
| I.a.694 | F | CN | CH$_3$ | F | C(CH$_3$)$_3$ |
| I.a.695 | F | CN | H | H | CH(CH$_3$)$_2$ |
| I.a.696 | F | CN | F | H | CH(CH$_3$)$_2$ |
| I.a.697 | F | CN | F | F | CH(CH$_3$)$_2$ |
| I.a.698 | F | CN | CH$_3$ | H | CH(CH$_3$)$_2$ |
| I.a.699 | F | CN | OCH$_3$ | H | CH(CH$_3$)$_2$ |
| I.a.700 | F | CN | CH$_3$ | F | CH(CH$_3$)$_2$ |
| I.a.701 | F | CN | H | H | c-C$_3$H$_5$ |
| I.a.702 | F | CN | F | H | c-C$_3$H$_5$ |
| I.a.703 | F | CN | F | F | c-C$_3$H$_5$ |
| I.a.704 | F | CN | CH$_3$ | H | c-C$_3$H$_5$ |
| I.a.705 | F | CN | OCH$_3$ | H | c-C$_3$H$_5$ |
| I.a.706 | F | CN | CH$_3$ | F | c-C$_3$H$_5$ |
| I.a.707 | F | CN | H | H | CH$_2$CH$_2$CH$_3$ |
| I.a.708 | F | CN | F | H | CH$_2$CH$_2$CH$_3$ |
| I.a.709 | F | CN | F | F | CH$_2$CH$_2$CH$_3$ |
| I.a.710 | F | CN | CH$_3$ | H | CH$_2$CH$_2$CH$_3$ |
| I.a.711 | F | CN | CH$_2$CH$_3$ | H | CH$_2$CH$_2$CH$_3$ |
| I.a.712 | F | CN | OCH$_3$ | H | CH$_2$CH$_2$CH$_3$ |
| I.a.713 | F | CN | CH$_3$ | F | CH$_2$CH$_2$CH$_3$ |
| I.a.714 | F | CN | CH$_3$ | H | CF$_3$ |
| I.a.715 | F | CN | CH$_3$ | F | CF$_3$ |
| I.a.716 | F | CN | H | | —(CH$_2$)$_2$—CH(CH$_3$)—(CH$_2$)$_2$— |
| I.a.717 | F | CN | H | | —O—(CH$_2$)$_2$— |
| I.a.718 | F | CN | H | | —O—(CH$_2$)$_3$— |
| I.a.719 | F | CN | H | | —O—(CH$_2$)$_4$— |
| I.a.720 | F | CN | CH$_3$ | | —(CH$_2$)$_2$—CH(CH$_3$)—(CH$_2$)$_2$— |
| I.a.721 | F | CN | CH$_3$ | | —O—(CH$_2$)$_2$— |
| I.a.722 | F | CN | CH$_3$ | | —O—(CH$_2$)$_3$— |
| I.a.723 | F | CN | CH$_3$ | | —O—(CH$_2$)$_4$— |
| I.a.724 | F | CN | F | | —(CH$_2$)$_2$—CH(CH$_3$)—(CH$_2$)$_2$— |
| I.a.725 | F | CN | F | | —O—(CH$_2$)$_2$— |
| I.a.726 | F | CN | F | | —O—(CH$_2$)$_3$— |
| I.a.727 | F | CN | F | | —O—(CH$_2$)$_4$— |
| I.a.728 | F | CN | Cl | | —(CH$_2$)$_2$—CH(CH$_3$)—(CH$_2$)$_2$— |
| I.a.729 | F | CN | Cl | | —O—(CH$_2$)$_2$— |
| I.a.730 | F | CN | Cl | | —O—(CH$_2$)$_3$— |
| I.a.731 | F | CN | Cl | | —O—(CH$_2$)$_4$— |
| I.a.732 | F | CN | CH$_3$ | | —O—(CH$_2$)$_3$— |
| I.a.733 | F | CN | CH$_3$ | | —O—(CH$_2$)$_4$— |
| I.a.734 | F | CN | OCH$_3$ | | —O—(CH$_2$)$_3$— |
| I.a.735 | F | CN | OCH$_3$ | | —O—(CH$_2$)$_4$— |
| I.a.736 | F | CN | OCF$_3$ | | —O—(CH$_2$)$_3$— |
| I.a.737 | F | CN | OCF$_3$ | | —O—(CH$_2$)$_4$— |
| I.a.738 | F | CN | OCH$_3$ | | —(CH$_2$)$_2$— |
| I.a.739 | F | CN | OCH$_3$ | | —(CH$_2$)$_3$— |
| I.a.740 | F | CN | OCH$_3$ | | —(CH$_2$)$_4$— |
| I.a.741 | F | CN | OCH$_3$ | | —(CH$_2$)$_5$— |

Also preferred are the azines of formula (I.b), particularly preferred the azines of formulae (I.b.1) to (I.b.741) which differ from the corresponding azines of formulae (I.a.1) to (I.a.741) only in that $R^b$ is Cl:

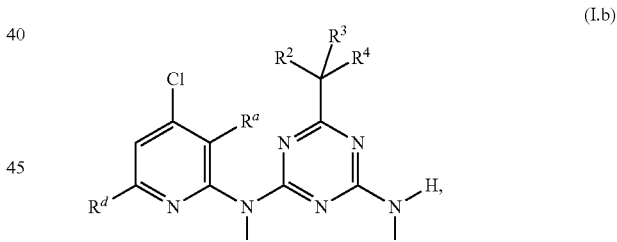

(I.b)

Also preferred are the azines of formula (I.c), particularly preferred the azines of formulae (I.c.1) to (I.c.741) which differ from the corresponding azines of formulae (I.a.1) to (I.a.741) only in that $R^b$ is Br:

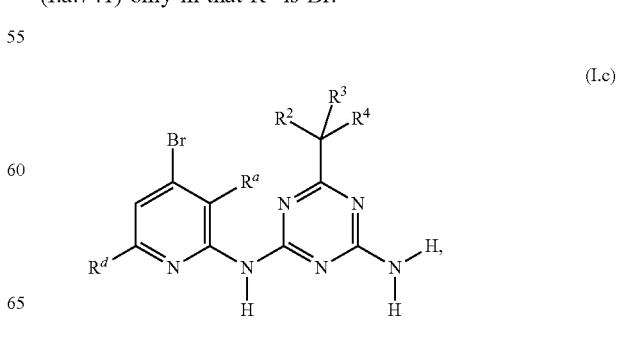

(I.c)

Also preferred are the azines of formula (I.d), particularly preferred the azines of formulae (I.d.1) to (I.d.741) which differ from the corresponding azines of formulae (I.a.1) to (I.a.741) only in that $R^c$ is F:

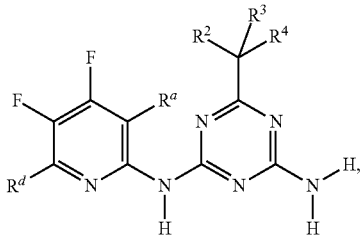
(I.d)

Also preferred are the azines of formula (I.e), particularly preferred the azines of formulae (I.e.1) to (I.e.741) which differ from the corresponding azines of formulae (I.a.1) to (I.a.741) only in that $R^c$ is Cl:

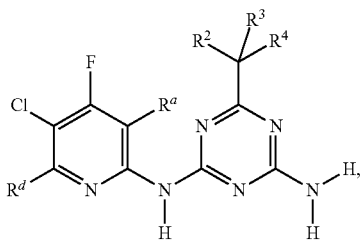
(I.e)

Also preferred are the azines of formula (I.f), particularly preferred the azines of formulae (I.f.1) to (I.f.741) which differ from the corresponding azines of formulae (I.a.1) to (I.a.741) only in that $R^c$ is Br:

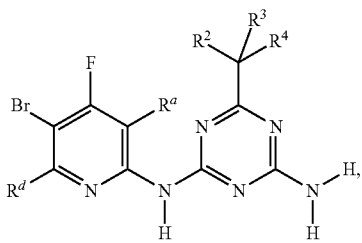
(I.f)

Also preferred are the azines of formula (I.g), particularly preferred the azines of formulae (I.g.1) to (I.g.741) which differ from the corresponding azines of formulae (I.a.1) to (I.a.741) only in that A is (A.2) with $R^c$ is H and $R^e$ is F:

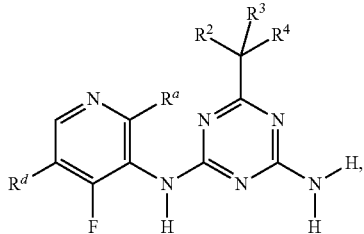
(I.g)

Also preferred are the azines of formula (I.h), particularly preferred the azines of formulae (I.h.1) to (I.h.741) which differ from the corresponding azines of formulae (I.a.1) to (I.a.741) only in that A is (A.2) with $R^c$ and $R^e$ are F:

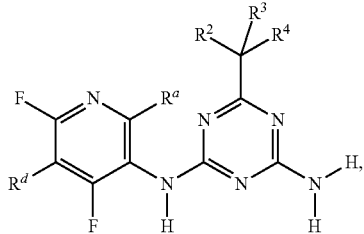
(I.h)

Also preferred are the azines of formula (I.i), particularly preferred the azines of formulae (I.i.1) to (I.i.741) which differ from the corresponding azines of formulae (I.a.1) to (I.a.741) only in that A is (A.3) with $R^b$ is H and $R^e$ is F:

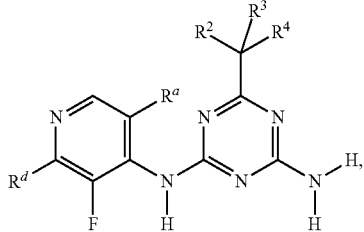
(I.i)

Also preferred are the azines of formula (I.k), particularly preferred the azines of formulae (I.k.1) to (I.k.741) which differ from the corresponding azines of formulae (I.a.1) to (I.a.741) only in that A is (A.3) with $R^b$ and $R^e$ are F:

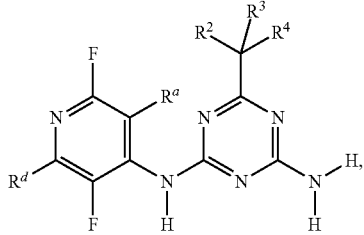
(I.k)

Also preferred are the azines of formula (I.l), particularly preferred the azines of formulae (I.l.1) to (I.l.741) which differ from the corresponding azines of formulae (I.a.1) to (I.a.741) only in that A is (A.3) with $R^b$ is F and $R^e$ is Cl:

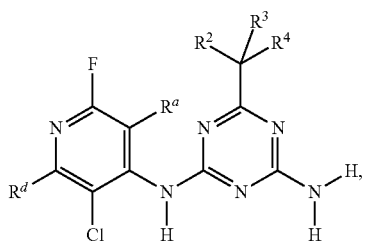

(I.l)

Also preferred are the azines of formula (I.m), particularly preferred the azines of formulae (I.m.1) to (I.m.741) which differ from the corresponding azines of formulae (I.a.1) to (I.a.741) only in that $R^b$ is Cl and $R^c$ is F:

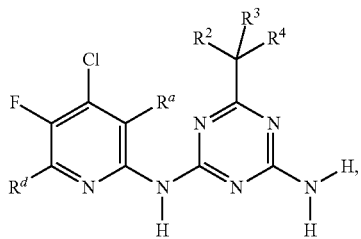

(I.m)

Also preferred are the azines of formula (I.n), particularly preferred the azines of formulae (I.n.1) to (I.n.741) which differ from the corresponding azines of formulae (I.a.1) to (I.a.741) only in that $R^b$ is Br and $R^c$ is F:

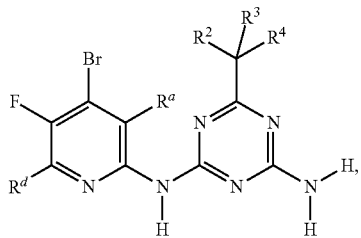

(I.n)

Also preferred are the azines of formula (I.o), particularly preferred the azines of formulae (I.o.1) to (I.o.741) which differ from the corresponding azines of formulae (I.a.1) to (I.a.741) only in that $R^b$ and $R^c$ is Cl:

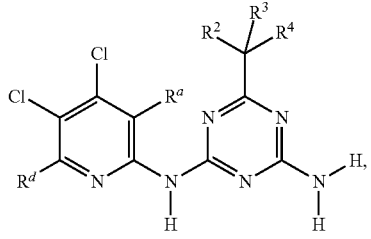

(I.o)

The azines of formula (I) according to the invention can be prepared by standard processes of organic chemistry, for example by the following processes:

Process A)

The azines of formula (I), wherein $R^1$ and $R^5$ are independently of one another H, $C_1$-$C_6$-alkyl, $C_1$-$C_6$-alkoxy-$C_1$-$C_6$-alkyl or $C_1$-$C_6$-alkoxy, can be prepared by reacting halotriazines of formula (II) with amines of formula (III) in the presence of a base and a catalyst:

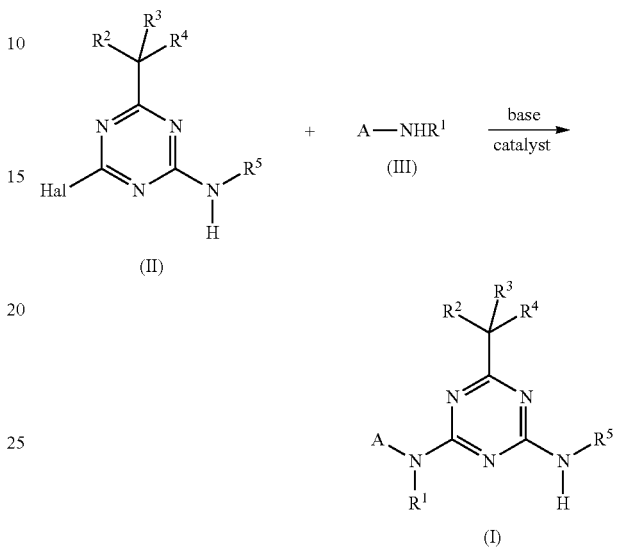

The variables A, $R^2$, $R^3$ and $R^4$ have the meanings, in particular the preferred meanings, as in formula (I) mentioned above;

Hal is halogen;
  preferably Cl or Br;
  particularly preferred Cl;

$R^1$ is H, $C_1$-$C_6$-alkyl, $C_1$-$C_6$-alkoxy-$C_1$-$C_6$-alkyl, $C_1$-$C_6$-alkoxy;
  particularly preferred H, $C_1$-$C_6$-alkoxy-$C_1$-$C_6$-alkyl or $C_1$-$C_6$-alkoxy;
  especially preferred H, $CH_2OCH_3$ or $OCH_3$;
  more preferred hydrogen; and $R^5$ is H, $C_1$-$C_6$-alkyl, $C_1$-$C_6$-alkoxy-$C_1$-$C_6$-alkyl, $C_1$-$C_6$-alkoxy;
  particularly preferred H, $C_1$-$C_6$-alkoxy-$C_1$-$C_6$-alkyl or $C_1$-$C_6$-alkoxy;
  especially preferred H, $CH_2OCH_3$ or $OCH_3$;
  more preferred hydrogen.

The reaction of the halotriazines of formula (II) with the amines of formula (III) is usually carried out from room temperature to the boiling point of the reaction mixture, preferably from 50° C. to 150° C., particularly preferably from 60° C. to 100° C., in an inert organic solvent (e.g. P. Dao et al., Tetrahedron 2012, 68, 3856-3860).

The reaction can be carried out at atmospheric pressure or under elevated pressure, if appropriate, under an inert gas, continuously or batchwise.

In one embodiment of the process according to the invention, the halotriazines of formula (II) and the amines of formula (III) are used in equimolar amounts.

In another embodiment of the process according to the invention, the amines of formula (III) are used in excess with regard to the halotriazines of formula (II).

Preferably the molar ratio of the amines of formula (III) to the halotriazines of formula (II) is in the range from 2:1 to 1:1, preferably 1.5:1 to 1:1, especially preferred 1.2:1.

The reaction of the halotriazines of formula (II) with the amines of formula (III) is carried out in an organic solvent.

Suitable in principle are all solvents which are capable of dissolving the halotriazines of formula (VI) and the amines of formula (III) at least partly and preferably fully under reaction conditions.

Examples of suitable solvents are aliphatic hydrocarbons such as pentane, hexane, cyclohexane, nitromethane and mixtures of $C_5$-$C_8$-alkanes, aromatic hydrocarbons such as benzene, chlorobenzene, toluene, cresols, o-, m- and p-xylene, halogenated hydrocarbons such as dichloromethane, 1,2-dichloroethane, chloroform, carbon tetrachloride and chlorobenzene, ethers such as diethyl ether, diisopropyl ether, tert.-butyl methylether (TBME), dioxane, anisole and tetrahydrofuran (THF), esters such as ethyl acetate and butyl acetate; nitriles such as acetonitrile and propionitrile, as well as dipolar aprotic solvents such as sulfolane, dimethylsulfoxide, N,N-dimethylformamide (DMF), N,N-dimethylacetamide (DMAC), 1,3-dimethyl-2-imidazolidinone (DMI), N,N'-dimethylpropylene urea (DMPU), dimethyl sulfoxide (DMSO) and 1-methyl-2 pyrrolidinone (NMP).

Preferred solvents are ethers as defined above.

The term solvent as used herein also includes mixtures of two or more of the above compounds.

The reaction of the halotriazines of formula (II) with the amines of formula (III) is carried out in the presence of a base.

Examples of suitable bases include metal-containing bases and nitrogen-containing bases.

Examples of suitable metal-containing bases are inorganic compounds such as alkali metal and alkaline earth metal hydroxides, and other metal hydroxides, such as lithium hydroxide, sodium hydroxide, potassium hydroxide, magnesium hydroxide, calcium hydroxide and aluminum hydroxide; alkali metal and alkaline earth metal oxide, and other metal oxides, such as lithium oxide, sodium oxide, potassium oxide, magnesium oxide, calcium oxide and magnesium oxide, iron oxide, silver oxide; alkali metal and alkaline earth metal hydrides such as lithium hydride, sodium hydride, potassium hydride and calcium hydride, alkali metal and alkaline earth metal formates, acetates and other metal salts of carboxylic acids, such as sodium formate, sodium benzoate, lithium acetate, sodium acetate, potassium acetate, magnesium acetate, and calcium acetate; alkali metal and alkaline earth metal carbonates such as lithium carbonate, sodium carbonate, potassium carbonate, magnesium carbonate, and calcium carbonate, as well as alkali metal hydrogen carbonates (bicarbonates) such as lithium hydrogen carbonate, sodium hydrogen carbonate, potassium hydrogen carbonate; alkali metal and alkaline earth metal phosphates such as sodium phosphate, potassium phosphate and calcium phosphate; alkali metal and alkaline earth metal alkoxides such as sodium methoxide, sodium ethoxide, potassium ethoxide, potassium tert-butoxide, potassium tert-pentoxide and dimethoxymagnesium; and furthermore organic bases, such as tertiary amines such as tri-$C_1$-$C_6$-alkylamines, for example triethylamine, trimethylamine, N-ethyldiisopropylamine, and N-methylpiperidine, pyridine, substituted pyridines such as collidine, lutidine, N-methylmorpholine and also bicyclic amines such as 1,8-diazabicyclo[5.4.0]undec-7-ene (DBU) or 1,5-diazabicyclo[4.3.0]non-5-ene (DBN).

Preferred bases are alkali metal and alkaline earth metal alkoxides as defined above.

The term base as used herein also includes mixtures of two or more, preferably two of the above compounds. Particular preference is given to the use of one base.

The bases can be used in excess, preferably from 1 to 10, especially preferred from 2 to 4 base equivalents based on the halotriazines of formula (II), and they may also be used as the solvent.

The reaction of the halotriazines of formula (II) with the amines of formula (III) is carried out in the presence of a catalyst.

Examples of suitable catalysts include for example, palladium based catalysts like, for example, Palladium(II) acetate, tetrakis(triphenylphosphine)palladium(O), bis(triphenyl-phosphine)palladium(II)chloride or (1,1,-bis(diphenylphosphino)ferrocene)-dichloro-palladium(II), and optionally suitable additives such as, for example, phosphines like, for example, P(o-tolyl)$_3$, triphenylphosphine or BINAP (2,2'-Bis(diphenylphospino)-1,1'-binaphthyl).

The amount of catalyst is usually 10 to 20 mol % (0.1 to 0.2 equivalents) based on the halotriazines of formula (II).

The end of the reaction can easily be determined by the skilled worker by means of routine methods.

The reaction mixtures are worked up in a customary manner, for example by mixing with water, separation of the phases and, if appropriate, chromatographic purification of the crude product.

The amines of formula (III) required for the preparation of azines of formula (I), wherein $R^1$ is H, $C_1$-$C_6$-alkyl, $C_1$-$C_6$-alkoxy-$C_1$-$C_6$-alkyl or $C_1$-$C_6$-alkoxy, are commercially available and/or can be prepared by analogy to known literature.

The halotriazines of formula (II) required for the preparation of azines of formula (I), wherein $R^5$ is H, $C_1$-$C_6$-alkyl, $C_1$-$C_6$-alkoxy-$C_1$-$C_6$-alkyl or $C_1$-$C_6$-alkoxy, are known from the literature, are commercially available and/or can be prepared by analogy (e.g. J. K. Chakrabarti et al., Tetrahedron 1975, 31, 1879-1882) by reacting thiotriazines of formula (IV) with a halogen:

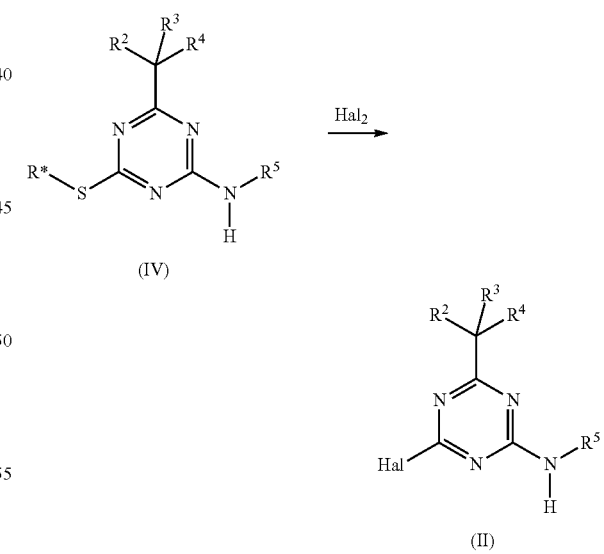

The variables $R^2$, $R^3$, and $R^4$ have the meanings, in particular the preferred meanings, as defined in formula (I) mentioned above;

Hal is halogen;
 preferably Cl or Br;
 particularly preferred Cl;
R* is $C_1$-$C_6$-alkyl, $C_2$-$C_6$-haloalkyl or phenyl;
 preferably $C_1$-$C_6$-alkyl or $C_2$-$C_6$-haloalkyl;

particularly preferred $C_1$-$C_6$-alkyl;
especially preferred $CH_3$; and
$R^5$ is H, $C_1$-$C_6$-alkyl, $C_1$-$C_6$-alkoxy-$C_1$-$C_6$-alkyl, $C_1$-$C_6$-alkoxy;
particularly preferred H, $C_1$-$C_6$-alkoxy-$C_1$-$C_6$-alkyl or $C_1$-$C_6$-alkoxy;
especially preferred H, $CH_2OCH_3$ or $OCH_3$;
more preferred hydrogen.

Preferably, the halotriazines of formula (II) required for the preparation of azines of formula (I), wherein the variables $R^3$ and $R^4$ have the meanings, in particular the preferred meanings, as defined in formula (I) mentioned above; $R^5$ and $R^*$ have the meanings, in particular the preferred meanings, as defined in formula (IV) mentioned above and $R^2$ in formula (IV) is hydrogen.

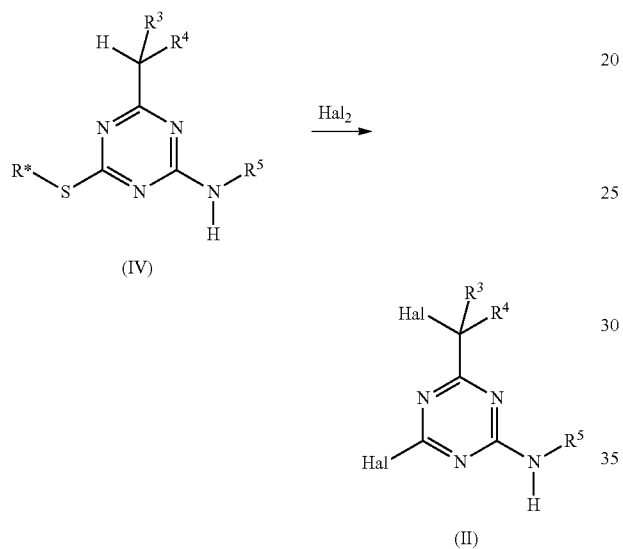

The reaction of the thiotriazines of formula (IV) with the halogen is usually carried out from 0° C. to the boiling point of the reaction mixture, preferably from 15° C. to the boiling point of the reaction mixture, particularly preferably from 15° C. to 40° C., in an inert organic solvent (e.g. J. K. Chakrabarti et al., Tetrahedron 1975, 31, 1879-1882).

The reaction can be carried out at atmospheric pressure or under elevated pressure, if appropriate under an inert gas, continuously or batchwise.

In the process according to the invention, the halogen is used in excess with regard to the thiotriazines of formula (IV).

The reaction of the thiotriazines of formula (IV) with the halogen is carried out in an organic solvent.

Suitable in principle are all solvents which are capable of dissolving the thiotriazines of formula (IV) and the halogen at least partly and preferably fully under reaction conditions.

Examples of suitable solvents are aliphatic hydrocarbons such as pentane, hexane, cyclohexane and mixtures of $C_5$-$C_8$-alkanes, halogenated hydrocarbons such as dichloromethane, 1,2-dichloroethane, chloroform and carbon tetrachloride; ethers such as diethyl ether, diisopropyl ether, tert.-butyl methylether (TBME), dioxane, anisole and tetrahydrofuran (THF), alcohols such as methanol, ethanol, n-propanol, isopropanol, n-butanol and tert.-butanol, as well as organic acids like formic acid, acetic acid, propionic acid, oxalic acid, citric acid, trifluoroacetic acid.

Preferred solvents are halogenated hydrocarbons and organic acids as defined above.

The term solvent as used herein also includes mixtures of two or more of the above compounds.

The end of the reaction can easily be determined by the skilled worker by means of routine methods.

The reaction mixtures are worked up in a customary manner, for example by mixing with water, separation of the phases and, if appropriate, chromatographic purification of the crude product.

The thiotriazines of formula (IV) required for the preparation of halotriazines of formula (II) can be prepared in accordance by reacting guanidine-salts of formula (V) with carbonyl compounds of formula (VI) in the presence of a base:

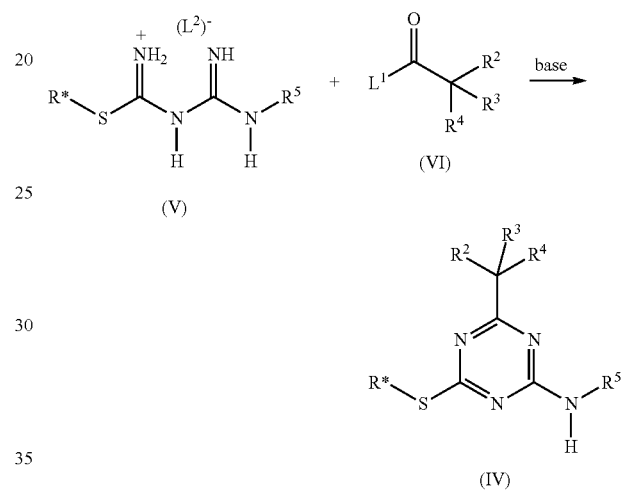

The variables $R^2$, $R^3$ and $R^4$ have the meanings, in particular the preferred meanings, as defined in formula (I) mentioned above;
$R^*$ is $C_1$-$C_6$-alkyl, $C_2$-$C_6$-haloalkyl or phenyl;
  preferably $C_1$-$C_6$-alkyl or $C_2$-$C_6$-haloalkyl;
  particularly preferred $C_1$-$C_6$-alkyl;
  especially preferred $CH_3$;
$L^1$ is a nucleophilically displaceable leaving group such as halogen, CN, $C_1$-$C_6$-alkoxy,
  $C_1$-$C_6$-alkoxycarbonyl, $C_1$-$C_6$-alkylcarbonyloxy or $C_1$-$C_6$-alkoxycarbonyloxy;
  preferably halogen or $C_1$-$C_6$-alkoxy;
  particularly preferred Cl or $C_1$-$C_6$-alkoxy,
  also particularly preferred halogen;
  especially preferred Cl and F; and
$L^2$ is a nucleophilically displaceable leaving group such as halogen, $C_1$-$C_6$-alkylsulfonyloxy, $C_1$-$C_6$-haloalkylsufonyloxy, $C_1$-$C_6$-alkoxysulfonyloxy or phenylsulfonyloxy;
  preferably halogen or $C_1$-$C_6$-haloalkylsufonyloxy;
  particularly preferred halogen;
  especially preferred I; and
$R^5$ is H, $C_1$-$C_6$-alkyl, $C_1$-$C_6$-alkoxy-$C_1$-$C_6$-alkyl, $C_1$-$C_6$-alkoxy;
  particularly preferred H, $C_1$-$C_6$-alkoxy-$C_1$-$C_6$-alkyl or $C_1$-$C_6$-alkoxy;
  especially preferred H, $CH_2OCH_3$ or $OCH_3$;
  more preferred hydrogen.

The reaction of the guanidine-salt of formula (V) with the carbonyl compound of formula (VI) is usually carried out at temperatures from 50° C. to the boiling point of the reaction mixture, preferably from 50° C. to 100° C.

The reaction can be carried out at atmospheric pressure or under elevated pressure, if appropriate under an inert gas, continuously or batchwise.

In one embodiment of the process according to the invention, the guanidine-salts of formula (V) and the carbonyl compound of formula (VI) are used in equimolar amounts.

In another embodiment of the process according to the invention, the carbonyl compound of formula (VI) is used in excess with regard to the guanidine-salts of formula (VIII).

Preferably the molar ratio of the carbonyl compound of formula (VI) to the guanidine-salt of formula (V) is in the range from 1.5:1 to 1:1, preferably 1.2:1 to 1:1, especially preferred 1.2:1, also especially preferred 1:1.

The reaction of the guanidine-salt of formula (V) with the carbonyl compound of formula (VI) is usually carried out in an organic solvent.

Suitable in principle are all solvents which are capable of dissolving the guanidine-salt of formula (V) and the carbonyl compound of formula (VI) at least partly and preferably fully under reaction conditions.

Examples of suitable solvents are halogenated hydrocarbons such as dichloromethane, 1,2-dichloroethane, chloroform, carbon tetrachloride and chlorobenzene, ethers such as diethyl ether, diisopropyl ether, tert.-butyl methylether (TBME), dioxane, anisole and tetrahydrofuran (THF), nitriles such as acetonitrile and propionitrile, as well as dipolar aprotic solvents such as sulfolane, dimethylsulfoxide, N,N-dimethylformamide (DMF), N,N-dimethylacetamide (DMAC), 1,3-dimethyl-2-imidazolidinone (DMI), N,N'-dimethylpropylene urea (DMPU), dimethyl sulfoxide (DMSO) and 1-methyl-2 pyrrolidinone (NMP).

Preferred solvents are ethers and dipolar aprotic solvents as defined above.

More preferred solvents are ethers as defined above.

The term solvent as used herein also includes mixtures of two or more of the above compounds.

The reaction of the guanidine-salts of formula (V) with the carbonyl compound of formula (VI) is carried out in the presence of a base.

Examples of suitable bases include metal-containing bases and nitrogen-containing bases.

Examples of suitable metal-containing bases are inorganic compounds such as alkali metal and alkaline earth metal oxide, and other metal oxides, such as lithium oxide, sodium oxide, potassium oxide, magnesium oxide, calcium oxide and magnesium oxide, iron oxide, silver oxide; alkali metal and alkaline earth metal hydrides such as lithium hydride, sodium hydride, potassium hydride and calcium hydride; alkali metal and alkaline earth metal carbonates such as lithium carbonate, sodium carbonate, potassium carbonate, magnesium carbonate, and calcium carbonate, as well as alkali metal hydrogen carbonates (bicarbonates) such as lithium hydrogen carbonate, sodium hydrogen carbonate, potassium hydrogen carbonate; alkali metal and alkaline earth metal phosphates such as sodium phosphate, potassium phosphate and calcium phosphate; and furthermore organic bases such as tertiary amines such as tri-$C_1$-$C_6$-alkylamines, for example triethylamine, trimethylamine, N-ethyldiisopropylamine, and N-methylpiperidine, pyridine, substituted pyridines such as collidine, lutidine, N-methylmorpholine, and also bicyclic amines such as 1,8-diazabicyclo[5.4.0]undec-7-ene (DBU) or 1,5-diazabicyclo[4.3.0]non-5-ene (DBN).

Preferred bases are tri-$C_1$-$C_6$-alkylamines as defined above.

The term base as used herein also includes mixtures of two or more, preferably two of the above compounds. Particular preference is given to the use of one base.

The bases are generally employed in excess; however they can also be employed in equimolar amounts, or, if appropriate, can be used as solvent.

Preferably from 1 to 5 base equivalents, particularly preferred 3 base equivalents of base are used, based on the guanidine-salts of formula (VIII).

The end of the reaction can easily be determined by the skilled worker by means of routine methods.

The reaction mixtures are worked up in a customary manner, for example by mixing with water, separation of the phases and, if appropriate, chromatographic purification of the crude product.

The carbonyl compounds of formula (VI) required for the preparation of azines of formula (I) are known from the literature. They can be prepared in accordance and/or are commercially available.

For example carbonyl compounds of formula (VI), wherein $L^1$ is F, $R^2$ is F, $R^3$ and $R^4$ have the meanings, in particular the preferred meanings, as defined in formula (I) mentioned above, can be prepared by reaction of compounds of formula (X), wherein $R^3$ and $R^4$ have the meanings, in particular the preferred meanings, as defined in formula (I) mentioned above, with diethylaminosulfur-trifluoride (DAST), sulfur tetrafluoride ($SR_4$), Deoxo-Fluor,Morph-DAST, Fluolead, 2,2-difluoro-1,3-dimethylimidazoline (DFI) or Fluorinox.

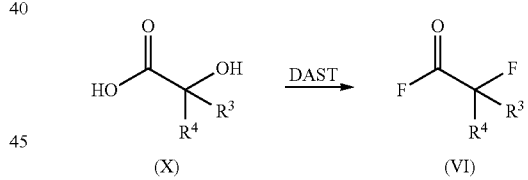

The guanidine-salt of formula (V), wherein $L^2$ is iodine, required for the preparation of thiotriazines of formula (IV) is known from the literature (e.g. M. Freund et al., Chem. Ber. 1901, 34, 3110-3122; H. Eilingsfeld et al., Chem. Ber. 1967, 100, 1874-1891). The guanidine-salts of formula (V) are commercially available and/or can be prepared in accordance with the literature cited.

Process B)

The azines of formula (I), wherein $R^5$ is CN, ($C_1$-$C_6$-alkyl)carbonyl, ($C_1$-$C_6$-alkoxy)carbonyl, ($C_1$-$C_6$-alkyl)sulfonyl or phenylsulfonyl, wherein the phenyl is unsubstituted or substituted by one to five substituents selected from the group consisting of halogen, CN, $NO_2$, $C_1$-$C_6$-alkyl, $C_1$-$C_6$-haloalkyl and $C_1$-$C_6$-alkoxy;

can be prepared by reacting azines of formula (I), wherein R⁵ is hydrogen with a compound of formula (VII):

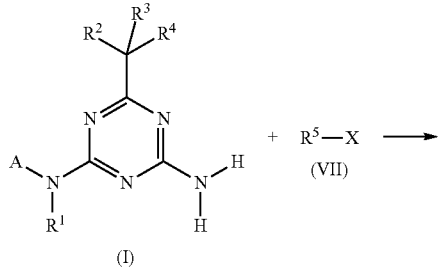

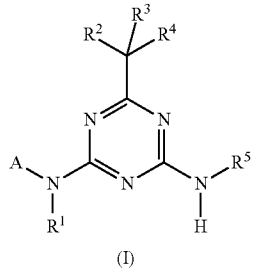

wherein R⁵ is hydrogen

The variables A, R¹, R², R³ and R⁴ have the meanings, in particular the preferred meanings, as in formula (I) mentioned above, R⁵ is CN, ($C_1$-$C_6$-alkyl)carbonyl, ($C_1$-$C_6$-alkoxy)carbonyl, ($C_1$-$C_6$-alkyl)sulfonyl or phenylsulfonyl,
  wherein the phenyl is unsubstituted or substituted by one to five substituents selected from the group consisting of halogen, CN, $NO_2$, $C_1$-$C_6$-alkyl, $C_1$-$C_6$-haloalkyl and $C_1$-$C_6$-alkoxy;
  particularly preferred CN, ($C_1$-$C_6$-alkyl)carbonyl, ($C_1$-$C_6$-alkoxy)carbonyl or ($C_1$-$C_6$-alkyl)sulfonyl;
  especially preferred CN, $COCH_3$, $COOCH_3$ or $SO_2CH_3$; and X is halogen or oxycarbonyl-$C_1$-$C_6$-alkyl;
  particularly preferred halogen;
  especially preferred Cl or Br.

Process D)

The azines of formula (I), wherein R¹ is CN, ($C_1$-$C_6$-alkyl)carbonyl, ($C_1$-$C_6$-alkoxy)carbonyl, ($C_1$-$C_6$-alkyl)sulfonyl or phenylsulfonyl,
  wherein the phenyl is unsubstituted or substituted by one to five substituents selected from the group consisting of halogen, CN, $NO_2$, $C_1$-$C_6$-alkyl, $C_1$-$C_6$-haloalkyl and $C_1$-$C_6$-alkoxy;
can be prepared by reacting azines of formula (I), wherein R¹ is hydrogen with a compound of formula (VIII):

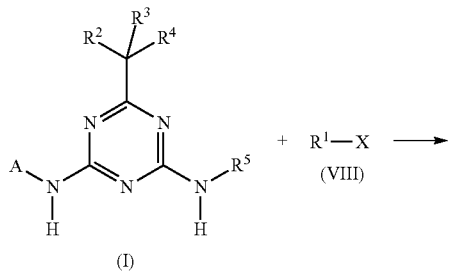

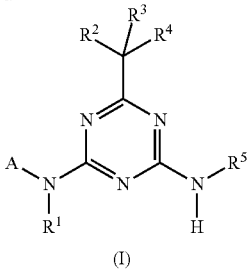

wherein R⁵ is hydrogen

The variables A, R², R³, R⁴ and R⁵ have the meanings, in particular the preferred meanings, as in formula (I) mentioned above, R¹ is CN, ($C_1$-$C_6$-alkyl)carbonyl, ($C_1$-$C_6$-alkoxy)carbonyl, ($C_1$-$C_6$-alkyl)sulfonyl or phenylsulfonyl,
  wherein the phenyl is unsubstituted or substituted by one to five substituents selected from the group consisting of halogen, CN, $NO_2$, $C_1$-$C_6$-alkyl, $C_1$-$C_6$-haloalkyl and $C_1$-$C_6$-alkoxy;
  particularly preferred CN, ($C_1$-$C_6$-alkyl)carbonyl, ($C_1$-$C_6$-alkoxy)carbonyl or ($C_1$-$C_6$-alkyl)sulfonyl;
  especially preferred CN, $COCH_3$, $COOCH_3$ or $SO_2CH_3$; and X is halogen or oxycarbonyl-$C_1$-$C_6$-alkyl;
  particularly preferred halogen;
  especially preferred Cl or Br.

Both processes C and D independently of one another usually carried out at from 0° C. to the boiling point of the reaction mixture, preferably from 23° C. to 130° C., particularly preferably from 23° C. to 100° C., (e.g. Y. Yuki et al., Polym. J. 1992, 24, 791-799).

Both processes C and D independently of one another can be carried out at atmospheric pressure or under elevated pressure, if appropriate under an inert gas, continuously or batchwise.

In one embodiment of processes C and D according to the invention independently of one another, the azines of formula (I), wherein R⁵, or R¹ respectively, is hydrogen are used in excess with regard to the compound of formula (VII), or (VIII) respectively.

In another embodiment of processes C and D according to the invention independently of one another, the azines of formula (I), wherein R⁵, or R¹ respectively, is hydrogen and the compound of formula (VII), or (VIII) respectively, are used in equimolar amounts.

Preferably the molar ratio of the azines of formula (I), wherein R⁵, or R¹ respectively, is hydrogen to the compound of formula (VII), or (VIII) respectively is in the range from 1:1.5 to 1:1, preferably 1:1.2 to 1:1, especially preferred 1:1.

Both processes C and D independently of one another are carried out in an organic solvent. Suitable in principle are all solvents which are capable of dissolving the azines of formula (I), wherein R⁵, or R¹ respectively, is hydrogen and the compound of formula (VII), or (VIII) respectively, at least partly and preferably fully under reaction conditions.

Examples of suitable solvents are halogenated hydrocarbons such as dichloromethane, 1,2-dichloroethane, chloroform, carbon tetrachloride and chlorobenzene; ethers such as diethyl ether, diisopropyl ether, tert.-butyl methylether (TBME), dioxane, anisole and tetrahydrofuran (THF); nitriles such as acetonitrile and propionitrile; alcohols such as methanol, ethanol, n-propanol, isopropanol, n-butanol and tert.-butanol; organic acids like formic acid, acetic acid, propionic acid, oxalic acid, methylbenzenesulfonic acid, benzenesulfonic acid, camphorsulfonic acid, citric acid, trifluoroacetic acid as well as dipolar aprotic solvents such as sulfolane, dimethylsulfoxide, N,N-dimethylformamide (DMF), N,N-dimethylacetamide (DMAC), 1,3-dimethyl-2-imidazolidinone (DMI), N,N'-dimethylpropylene urea (DMPU), dimethyl sulfoxide (DMSO) and 1-methyl-2 pyrrolidinone (NMP).

Preferred solvents are halogenated hydrocarbons, ethers and dipolar aprotic solvents as mentioned above.

More preferred solvents are dichloromethane or dioxane.

The term solvent as used herein also includes mixtures of two or more of the above solvents.

Both processes C and D independently of one another are optionally carried out in the presence of a base.

Examples of suitable bases include metal-containing bases and nitrogen-containing bases.

Examples of suitable metal-containing bases are inorganic compounds such as alkali metal and alkaline earth metal hydrides such as lithium hydride, sodium hydride, potassium hydride and calcium hydride, alkali metal and alkaline earth metal carbonates such as lithium carbonate, sodium carbonate, potassium carbonate, magnesium carbonate, and calcium carbonate, as well as alkali metal hydrogen carbonates (bicarbonates) such as lithium hydrogen carbonate, sodium hydrogen carbonate, potassium hydrogen carbonate; alkali metal and alkaline earth metal phosphates such as sodium phosphate, potassium phosphate and calcium phosphate; and furthermore organic bases such as tertiary amines such as tri-$C_1$-$C_6$-alkylamines, for example triethylamine, trimethylamine, N-ethyldiisopropylamine, and N-methylpiperidine, pyridine, substituted pyridines such as collidine, lutidine, N-methylmorpholine and 4-dimethylaminopyridine (DMAP), and also bicyclic amines such as 1,8-diazabicyclo[5.4.0]undec-7-ene (DBU) or 1,5-diazabicyclo[4.3.0]non-5-ene (DBN).

Preferred bases are organic bases and alkali metal carbonates as mentioned above. Especially preferred bases are organic bases as mentioned above.

The term base as used herein also includes mixtures of two or more, preferably two of the above compounds. Particular preference is given to the use of one base.

The bases are generally employed in excess; however they can also be employed in equimolar amounts, or, if appropriate, can be used as solvent.

Preferably from 1 to 5 base equivalents, particularly preferred 3 base equivalents of base are used, based on the azines of formula (I).

Work-up can be done in a known manner.

The compounds of formula (VII), or (VIII) respectively, are known compounds. They are commercially available or can be prepared in analogy to known methods.

To widen the spectrum of action and to achieve synergistic effects, the azines of formula (I) may be mixed with a large number of representatives of other herbicidal or growth-regulating active ingredient groups and then applied concomitantly. Suitable components for mixtures are, for example, herbicides from the classes of the acetamides, amides, aryloxyphenoxypropionates, benzamides, benzofuran, benzoic acids, benzothiadiazinones, bipyridylium, carbamates, chloroacetamides, chlorocarboxylic acids, cyclohexanediones, dinitroanilines, dinitrophenol, diphenyl ether, glycines, imidazolinones, isoxazoles, isoxazolidinones, nitriles, N-phenylphthalimides, oxadiazoles, oxazolidinediones, oxyacetamides, phenoxycarboxylic acids, phenylcarbamates, phenylpyrazoles, phenylpyrazolines, phenylpyridazines, phosphinic acids, phosphoroamidates, phosphorodithioates, phthalamates, pyrazoles, pyridazinones, pyridines, pyridinecarboxylic acids, pyridinecarboxamides, pyrimidinediones, pyrimidinyl(thio)benzoates, quinolinecarboxylic acids, semicarbazones, sulfonylaminocarbonyltriazolinones, sulfonylureas, tetrazolinones, thiadiazoles, thiocarbamates, triazines, triazinones, triazoles, triazolinones, triazolocarboxamides, triazolopyrimidines, triketones, uracils, ureas.

The invention also relates to combinations of diaminotriazine compounds of formula (I) with at least one further herbicide B and/or at least one safener C).

The further herbicidal compound B (component B) is in particular selected from the herbicides of class b1) to b15):
b1) lipid biosynthesis inhibitors;
b2) acetolactate synthase inhibitors (ALS inhibitors);
b3) photosynthesis inhibitors;
b4) protoporphyrinogen-IX oxidase inhibitors,
b5) bleacher herbicides;
b6) enolpyruvyl shikimate 3-phosphate synthase inhibitors (EPSP inhibitors);
b7) glutamine synthetase inhibitors;
b8) 7,8-dihydropteroate synthase inhibitors (DHP inhibitors);
b9) mitosis inhibitors;
b10) inhibitors of the synthesis of very long chain fatty acids (VLCFA inhibitors);
b11) cellulose biosynthesis inhibitors;
b12) decoupler herbicides;
b13) auxinic herbicides;
b14) auxin transport inhibitors; and
b15) other herbicides selected from the group consisting of bromobutide, chlorflurenol, chlorflurenol-methyl, cinmethylin, cumyluron, dalapon, dazomet, difenzoquat, difenzoquat-metilsulfate, dimethipin, DSMA, dymron, endothal and its salts, etobenzanid, flamprop, flamprop-isopropyl, flamprop-methyl, flamprop-M-isopropyl, flamprop-M-methyl, flurenol, flurenol-butyl, flurprimidol, fosamine, fosamine-ammonium, indanofan, indaziflam, maleic hydrazide, mefluidide, metam, methiozolin (CAS 403640-27-7), methyl azide, methyl bromide, methyl-dymron, methyl iodide, MSMA, oleic acid, oxaziclomefone, pelargonic acid, pyributicarb, quinoclamine, triaziflam, tridiphane and 6-chloro-3-(2-cyclopropyl-6-methylphenoxy)-4-pyridazinol (CAS 499223-49-3) and its salts and esters;
including their agriculturally acceptable salts or derivatives such as ethers, esters or amides.

Preference is given to those compositions according to the present invention comprising at least one herbicide B selected from herbicides of class b1, b6, b9, b10, b11 and b15.

Examples of herbicides B which can be used in combination with the compounds of formula (I) according to the present invention are:
b1) from the group of the lipid biosynthesis inhibitors: ACC-herbicides such as alloxydim, alloxydim-sodium, butroxydim, clethodim, clodinafop, clodinafop-propargyl, cycloxydim, cyhalofop, cyhalofop-butyl, diclofop, diclofop-methyl, fenoxaprop, fenoxaprop-ethyl, fenoxaprop-P, fenoxaprop-P-ethyl, fluazifop, fluazifop-butyl, fluazifop-P, fluazifop-P-butyl, haloxyfop, haloxyfop-methyl, haloxyfop-P, haloxyfop-P-methyl, metamifop, pinoxaden, profoxydim, propaquizafop, quizalofop, quizalofop-ethyl, quizalofop-tefuryl, quizalofop-P, quizalofop-P-ethyl, quizalofop-P-tefuryl, sethoxydim, tepraloxydim, tralkoxydim, 4-(4'-Chloro-4-cyclopropyl-2'-fluoro[1,1'-biphenyl]-3-yl)-5-hydroxy-2,2,6,6-tetramethyl-2H-pyran-3(6H)-one (CAS 1312337-72-6);

4-(2',4'-Dichloro-4-cyclopropyl[1,1'-biphenyl]-3-yl)-5-hydroxy-2,2,6,6-tetramethyl-2H-pyran-3(6H)-one (CAS 1312337-45-3); 4-(4'-Chloro-4-ethyl-2'-fluoro[1,1'-biphenyl]-3-yl)-5-hydroxy-2,2,6,6-tetramethyl-2H-pyran-3(6H)-one (CAS 1033757-93-5); 4-(2',4'-Dichloro-4-ethyl[1,1'-biphenyl]-3-yl)-2,2,6,6-tetramethyl-2H-pyran-3,5(4H,6H)-dione (CAS 1312340-84-3); 5-(Acetyloxy)-4-(4'-chloro-4-cyclopropyl-2'-fluoro[1,1'-biphenyl]-3-yl)-3,6-dihydro-2,2,6,6-tetramethyl-2H-pyran-3-one (CAS 1312337-48-6); 5-(Acetyloxy)-4-(2'',4'-dichloro-4-cyclopropyl-[1,1'-biphenyl]-3-yl)-3,6-dihydro-2,2,6,6-tetramethyl-2H-pyran-3-one; 5-(Acetyloxy)-4-(4'-chloro-4-ethyl-2'-fluoro[1,1'-biphenyl]-3-yl)-3,6-dihydro-2,2,6,6-tetramethyl-2H-pyran-3-one (CAS 1312340-82-1); 5-(Acetyloxy)-4-(2',4'-dichloro-4-ethyl[1,1'-biphenyl]-3-yl)-3,6-dihydro-2,2,6,6-tetramethyl-2H-pyran-3-one (CAS 1033760-55-2); 4-(4'-Chloro-4-cyclopropyl-2'-fluoro[1,1'-biphenyl]-3-yl)-5,6-dihydro-2,2,6,6-tetramethyl-5-oxo-2H-pyran-3-yl carbonic acid methyl ester (CAS 1312337-51-1); 4-(2',4'-Dichloro-4-cyclopropyl-[1,1'-biphenyl]-3-yl)-5,6-dihydro-2,2,6,6-tetramethyl-5-oxo-2H-pyran-3-yl carbonic acid methyl ester; 4-(4'-Chloro-4-ethyl-2'-fluoro[1,1'-biphenyl]-3-yl)-5,6-dihydro-2,2,6,6-tetramethyl-5-oxo-2H-pyran-3-yl carbonic acid methyl ester (CAS 1312340-83-2); 4-(2',4'-Dichloro-4-ethyl[1,1'-biphenyl]-3-yl)-5,6-dihydro-2,2,6,6-tetramethyl-5-oxo-2H-pyran-3-yl carbonic acid methyl ester (CAS 1033760-58-5); and non ACC herbicides such as benfuresate, butylate, cycloate, dalapon, dimepiperate, EPTC, esprocarb, ethofumesate, flupropanate, molinate, orbencarb, pebulate, prosulfocarb, TCA, thiobencarb, tiocarbazil, triallate and vernolate;

b2) from the group of the ALS inhibitors:

sulfonylureas such as amidosulfuron, azimsulfuron, bensulfuron, bensulfuron-methyl, chlorimuron, chlorimuron-ethyl, chlorsulfuron, cinosulfuron, cyclosulfamuron, ethametsulfuron, ethametsulfuron-methyl, ethoxysulfuron, flazasulfuron, flucetosulfuron, flupyrsulfuron, flupyrsulfuron-methyl-sodium, foramsulfuron, halosulfuron, halosulfuron-methyl, imazosulfuron, iodosulfuron, iodosulfuron-methyl-sodium, iofensulfuron, iofensulfuron-sodium, mesosulfuron, metazosulfuron, metsulfuron, metsulfuron-methyl, nicosulfuron, orthosulfamuron, oxasulfuron, primisulfuron, primisulfuron-methyl, propyrisulfuron, prosulfuron, pyrazosulfuron, pyrazosulfuron-ethyl, rimsulfuron, sulfometuron, sulfometuron-methyl, sulfosulfuron, thifensulfuron, thifensulfuron-methyl, triasulfuron, tribenuron, tribenuron-methyl, trifloxysulfuron, triflusulfuron, triflusulfuron-methyl and tritosulfuron, imidazolinones such as imazamethabenz, imazamethabenz-methyl, imazamox, imazapic, imazapyr, imazaquin and imazethapyr, triazolopyrimidine herbicides and sulfonanilides such as cloransulam, cloransulam-methyl, diclosulam, flumetsulam, florasulam, metosulam, penoxsulam, pyrimisulfan and pyroxsulam, pyrimidinylbenzoates such as bispyribac, bispyribac-sodium, pyribenzoxim, pyriftalid, pyriminobac, pyriminobac-methyl, pyrithiobac, pyrithiobac-sodium, 4-[[[2-[(4,6-dimethoxy-2-pyrimidinyl)oxy]phenyl]methyl]amino]-benzoic acid-1-methylethyl ester (CAS 420138-41-6), 4-[[[2-[(4,6-dimethoxy-2-pyrimidinyl)oxy]phenyl]methyl]amino]-benzoic acid propyl ester (CAS 420138-40-5), N-(4-bromophenyl)-2-[(4,6-dimethoxy-2-pyrimidinyl)oxy]benzenemethanamine (CAS 420138-01-8), sulfonylaminocarbonyl-triazolinone herbicides such as flucarbazone, flucarbazone-sodium, propoxycarbazone, propoxycarbazone-sodium, thiencarbazone and thien-carbazone-methyl; and triafamone;

among these, a preferred embodiment of the invention relates to those compositions comprising at least one imidazolinone herbicide;

b3) from the group of the photosynthesis inhibitors:

amicarbazone, inhibitors of the photosystem II, e.g. triazine herbicides, including of chlorotriazine, triazinones, triazindiones, methylthiotriazines and pyridazinones such as ametryn, atrazine, chloridazone, cyanazine, desmetryn, dimethametryn, hexazinone, metribuzin, prometon, prometryn, propazine, simazine, simetryn, terbumeton, terbuthylazin, terbutryn and trietazin, aryl urea such as chlorobromuron, chlorotoluron, chloroxuron, dimefuron, diuron, fluometuron, isoproturon, isouron, linuron, metamitron, methabenzthiazuron, metobenzuron, metoxuron, monolinuron, neburon, siduron, tebuthiuron and thiadiazuron, phenyl carbamates such as desmedipham, karbutilat, phenmedipham, phenmedipham-ethyl, nitrile herbicides such as bromofenoxim, bromoxynil and its salts and esters, ioxynil and its salts and esters, uraciles such as bromacil, lenacil and terbacil, and bentazon and bentazon-sodium, pyridate, pyridafol, pentanochlor and propanil and inhibitors of the photosystem I such as diquat, diquat-dibromide, paraquat, paraquat-dichloride and paraquat-dimetilsulfate. Among these, a preferred embodiment of the invention relates to those compositions comprising at least one aryl urea herbicide. Among these, likewise a preferred embodiment of the invention relates to those compositions comprising at least one triazine herbicide. Among these, likewise a preferred embodiment of the invention relates to those compositions comprising at least one nitrile herbicide;

b4) from the group of the protoporphyrinogen-IX oxidase inhibitors:

acifluorfen, acifluorfen-sodium, azafenidin, bencarbazone, benzfendizone, bifenox, butafenacil, carfentrazone, carfentrazone-ethyl, chlomethoxyfen, cinidon-ethyl, fluazolate, flufenpyr, flufenpyr-ethyl, flumiclorac, flumiclorac-pentyl, flumioxazin, fluoroglycofen, fluoroglycofen-ethyl, fluthiacet, fluthiacet-methyl, fomesafen, halosafen, lactofen, oxadiargyl, oxadiazon, oxyfluorfen, pentoxazone, profluazol, pyraclonil, pyraflufen, pyraflufen-ethyl, saflufenacil, sulfentrazone, thidiazimin, tiafenacil, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate (CAS 353292-31-6; S-3100), N-ethyl-3-(2,6-dichloro-4-trifluoromethylphenoxy)-5-methyl-1H-pyrazole-1-carboxamide (CAS 452098-92-9), N-tetrahydrofurfuryl-3-(2,6-dichloro-4-trifluoromethylphenoxy)-5-methyl-1H-pyrazole-1-carboxamide (CAS 915396-43-9), N-ethyl-3-(2-chloro-6-fluoro-4-trifluoromethylphenoxy)-5-methyl-1H-pyrazole-1-carboxamide (CAS 452099-05-7), N-tetrahydrofurfuryl-3-(2-chloro-6-fluoro-4-trifluoromethylphenoxy)-5-methyl-1H-pyrazole-1-carboxamide (CAS 452100-03-7), 3-[7-fluoro-3-oxo-4-(prop-2-ynyl)-3,4-dihydro-2H-benzo[1,4]oxazin-6-yl]-1,5-dimethyl-6-thioxo-[1,3,5]triazinan-2,4-dione, 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), 2-(2,2,7-Trifluoro-3-oxo-4-prop-2-ynyl-3,4-dihydro-2H-benzo[1,4]oxazin-6-yl)-4,5,6,7-tetrahydro-isoindole-1,3-dione, 1-Methyl-6-trifluoromethyl-3-(2,2,7-trifluoro-3-oxo-4-prop-2-ynyl-3,4-dihydro-2H-benzo[1,4]oxazin-6-yl)-1H-pyrimidine-2,4-dione, methyl (E)-4-[2-chloro-5-[4-chloro-5-(difluoromethoxy)-1H-methyl-pyrazol-3-yl]-4-fluoro-phenoxy]-3-methoxy-but-2-enoate [CAS 948893-00-3], and 3-[7-Chloro-5-fluoro-2-(trifluoromethyl)-1H- benzimidazol-4-yl]-1-methyl-6-(trifluoromethyl)-1H-pyrimidine-2,4-dione (CAS 212754-02-4);
b5) from the group of the bleacher herbicides:
PDS inhibitors: beflubutamid, diflufenican, fluridone, flurochloridone, flurtamone, norflurazon, picolinafen, and 4-(3-trifluoromethylphenoxy)-2-(4-trifluoromethylphenyl)pyrimidine (CAS 180608-33-7), HPPD inhibitors: benzobicyclon, benzofenap, donnazone, fenquintrione, isoxaflutole, mesotrione, pyrasulfotole, pyrazolynate, pyrazoxyfen, sulcotrione, tefuryltrione, tembotrione, topramezone and bicyclopyrone, bleacher, unknown target: aclonifen, amitrole and flumeturon;
b6) from the group of the EPSP synthase inhibitors:
glyphosate, glyphosate-isopropylammonium, glyposate-potassium and glyphosate-trimesium (sulfosate);
b7) from the group of the glutamine synthase inhibitors:
bilanaphos (bialaphos), bilanaphos-sodium, glufosinate, glufosinate-P and glufosinate-ammonium;
b8) from the group of the DHP synthase inhibitors:
asulam;
b9) from the group of the mitosis inhibitors:
compounds of group K1: dinitroanilines such as benfluralin, butralin, dinitramine, ethalfluralin, fluchloralin, oryzalin, pendimethalin, prodiamine and trifluralin, phosphoramidates such as amiprophos, amiprophos-methyl, and butamiphos, benzoic acid herbicides such as chlorthal, chlorthal-dimethyl, pyridines such as dithiopyr and thiazopyr, benzamides such as propyzamide and tebutam; compounds of group K2: chlorpropham, propham and carbetamide, among these, compounds of group K1, in particular dinitroanilines are preferred;
b10) from the group of the VLCFA inhibitors:
chloroacetamides such as acetochlor, alachlor, butachlor, dimethachlor, dimethenamid, dimethenamid-P, metazachlor, metolachlor, metolachlor-S, pethoxamid, pretilachlor, propachlor, propisochlor and thenylchlor, oxyacetanilides such as flufenacet and mefenacet, acetanilides such as diphenamid, naproanilide, napropamide and napropamide-M, tetrazolinones such fentrazamide, and other herbicides such as anilofos, cafenstrole, fenoxasulfone, ipfencarbazone, piperophos, pyroxasulfone and isoxazoline compounds of the formulae II.1, II.2, II.3, II.4, II.5, II.6, II.7, II.8 and II.9

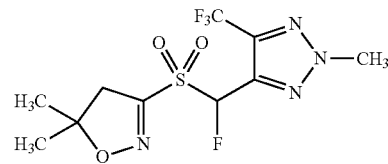
II.4

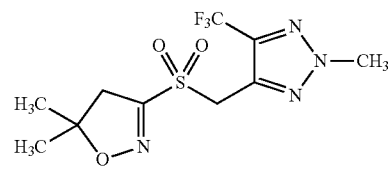
II.5

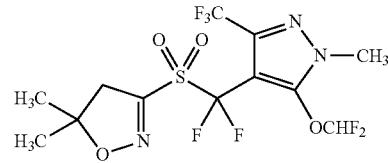
II.6

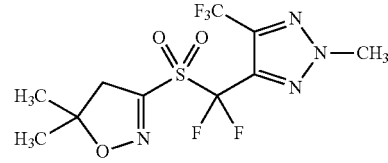
II.7

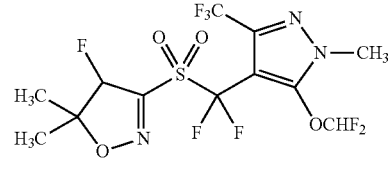
II.8

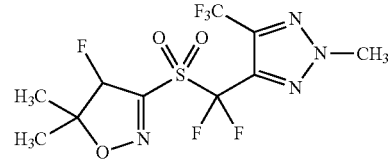
II.9

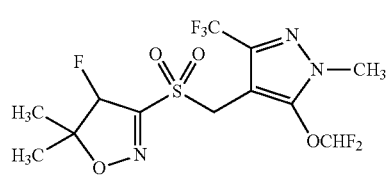
II.1

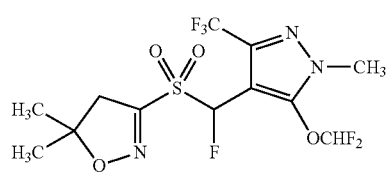
II.2

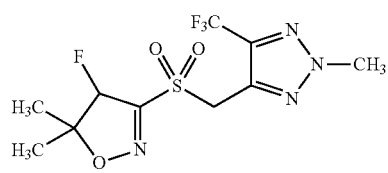
II.3 the isoxazoline compounds of the formula (I)I are known in the art, e.g. from WO 2006/024820, WO 2006/037945, WO 2007/071900 and WO 2007/096576;
among the VLCFA inhibitors, preference is given to chloroacetamides and oxyacetamides;
b11) from the group of the cellulose biosynthesis inhibitors:
chlorthiamid, dichlobenil, flupoxam, isoxaben and 1-Cyclohexyl-5-pentafluorphenyloxy-1$^4$-[1,2,4,6]thiatriazin-3-ylamine;
b12) from the group of the decoupler herbicides:
dinoseb, dinoterb and DNOC and its salts;
b13) from the group of the auxinic herbicides:
2,4-D and its salts and esters such as clacyfos, 2,4-DB and its salts and esters, aminocyclopyrachlor and its salts and esters, aminopyralid and its salts such as aminopyralid-dimethylammonium, aminopyralid-tris(2-hydroxypropyl) ammonium and its esters, benazolin, benazolin-ethyl, chloramben and its salts and esters, clomeprop, clopyralid and its salts and esters, dicamba and its salts and esters, dichlorprop and its salts and esters, dichlorprop-P and its salts and esters, fluroxypyr, fluroxypyr-butometyl, fluroxypyr-meptyl, halauxifen and its salts and esters (CAS 943832-60-8); MCPA and its salts and esters, MCPA-thioethyl, MCPB and its salts and esters, mecoprop and its salts and esters, mecoprop-P and its salts and esters, picloram and its salts and esters, quinclorac, quinmerac, TBA (2,3,6) and its salts and esters and triclopyr and its salts and esters;

b14) from the group of the auxin transport inhibitors: diflufenzopyr, diflufenzopyr-sodium, naptalam and naptalam-sodium;

b15) from the group of the other herbicides: bromobutide, chlorflurenol, chlorflurenol-methyl, cinmethylin, cumyluron, cyclopyrimorate (CAS 499223-49-3) and its salts and esters, dalapon, dazomet, difenzoquat, difenzoquat-metilsulfate, dimethipin, DSMA, dymron, endothal and its salts, etobenzanid, flamprop, flamprop-isopropyl, flamprop-methyl, flamprop-M-isopropyl, flamprop-M-methyl, flurenol, flurenol-butyl, flurprimidol, fosamine, fosamine-ammonium, indanofan, indaziflam, maleic hydrazide, mefluidide, metam, methiozolin (CAS 403640-27-7), methyl azide, methyl bromide, methyl-dymron, methyl iodide, MSMA, oleic acid, oxaziclomefone, pelargonic acid, pyributicarb, quinoclamine, triazifiam and tridiphane.

Preferred herbicides B that can be used in combination with the compounds of the formula (I) according to the present invention are:

b1) from the group of the lipid biosynthesis inhibitors:
clethodim, clodinafop-propargyl, cycloxydim, cyhalofop-butyl, diclofop-methyl, fenoxaprop-P-ethyl, fluazifop-P-butyl, haloxyfop-P-methyl, metamifop, pinoxaden, profoxydim, propaquizafop, quizalofop-P-ethyl, quizalofop-P-tefuryl, sethoxydim, tepraloxydim, tralkoxydim, 4-(4'-Chloro-4-cyclopropyl-2'-fluoro[1,1'-biphenyl]-3-yl)-5-hydroxy-2,2,6,6-tetramethyl-2H-pyran-3(6H)-one (CAS 1312337-72-6); 4-(2',4'-Dichloro-4-cyclopropyl[1,1'-biphenyl]-3-yl)-5-hydroxy-2,2,6,6-tetramethyl-2H-pyran-3(6H)-one (CAS 1312337-45-3); 4-(4'-Chloro-4-ethyl-2'-fluoro[1,1'-biphenyl]-3-yl)-5-hydroxy-2,2,6,6-tetramethyl-2H-pyran-3(6H)-one (CAS 1033757-93-5); 4-(2',4'-Dichloro-4-ethyl[1,1'-biphenyl]-3-yl)-2,2,6,6-tetramethyl-2H-pyran-3,5(4H,6H)-dione (CAS 1312340-84-3); 5-(Acetyloxy)-4-(4'-chloro-4-cyclopropyl-2'-fluoro[1,1'-biphenyl]-3-yl)-3,6-dihydro-2,2,6,6-tetramethyl-2H-pyran-3-one (CAS 1312337-48-6); 5-(Acetyloxy)-4-(2',4'-dichloro-4-cyclopropyl-[1,1'-biphenyl]-3-yl)-3,6-dihydro-2,2,6,6-tetramethyl-2H-pyran-3-one; 5-(Acetyloxy)-4-(4'-chloro-4-ethyl-2'-fluoro[1,1'-biphenyl]-3-yl)-3,6-dihydro-2,2,6,6-tetramethyl-2H-pyran-3-one (CAS 1312340-82-1); 5-(Acetyloxy)-4-(2',4'-dichloro-4-ethyl[1,1'-biphenyl]-3-yl)-3,6-dihydro-2,2,6,6-tetramethyl-2H-pyran-3-one (CAS 1033760-55-2); 4-(4'-Chloro-4-cyclopropyl-2'-fluoro[1,1'-biphenyl]-3-yl)-5,6-dihydro-2,2,6,6-tetramethyl-5-oxo-2H-pyran-3-yl carbonic acid methyl ester (CAS 1312337-51-1); 4-(2'',4'-Dichloro-4-cyclopropyl-[1,1'-biphenyl]-3-yl)-5,6-dihydro-2,2,6,6-tetramethyl-5-oxo-2H-pyran-3-yl carbonic acid methyl ester; 4-(4'-Chloro-4-ethyl-2'-fluoro[1,1'-biphenyl]-3-yl)-5,6-dihydro-2,2,6,6-tetramethyl-5-oxo-2H-pyran-3-yl carbonic acid methyl ester (CAS 1312340-83-2); 4-(2',4'-Dichloro-4-ethyl[1,1'-biphenyl]-3-yl)-5,6-dihydro-2,2,6,6-tetramethyl-5-oxo-2H-pyran-3-yl carbonic acid methyl ester (CAS 1033760-58-5); benfuresate, dimepiperate, EPTC, esprocarb, ethofumesate, molinate, orbencarb, prosulfocarb, thiobencarb and triallate;

b2) from the group of the ALS inhibitors:
amidosulfuron, azimsulfuron, bensulfuron-methyl, bispyribac-sodium, chlorimuron-ethyl, chlorsulfuron, cloransulam-methyl, cyclosulfamuron, diclosulam, ethametsulfuron-methyl, ethoxysulfuron, flazasulfuron, florasulam, flucarbazone-sodium, flucetosulfuron, flumetsulam, flupyrsulfuron-methyl-sodium, foramsulfuron, halosulfuron-methyl, imazamethabenz-methyl, imazamox, imazapic, imazapyr, imazaquin, imazethapyr, imazosulfuron, iodosulfuron, iodosulfuron-methyl-sodium, iofensulfuron, iofensulfuron-sodium, mesosulfuron, metazosulfuron, metosulam, metsulfuron-methyl, nicosulfuron, orthosulfamuron, oxasulfuron, penoxsulam, primisulfuron-methyl, propoxycarbazon-sodium, propyrisulfuron, prosulfuron, pyrazosulfuron-ethyl, pyribenzoxim, pyrimisulfan, pyriftalid, pyriminobac-methyl, pyrithiobac-sodium, pyroxsulam, rimsulfuron, sulfometuron-methyl, sulfosulfuron, thiencarbazone-methyl, thifensulfuron-methyl, triasulfuron, tribenuron-methyl, trifloxysulfuron, triflusulfuron-methyl, tritosulfuron and triafamone;

b3) from the group of the photosynthesis inhibitors:
ametryn, amicarbazone, atrazine, bentazone, bentazone-sodium, bromoxynil and its salts and esters, chloridazone, chlorotoluron, cyanazine, desmedipham, diquatdibromide, diuron, fluometuron, hexazinone, ioxynil and its salts and esters, isoproturon, lenacil, linuron, metamitron, methabenzthiazuron, metribuzin, paraquat, paraquat-dichloride, phenmedipham, propanil, pyridate, simazine, terbutryn, terbuthylazine and thidiazuron;

b4) from the group of the protoporphyrinogen-IX oxidase inhibitors:
acifluorfen-sodium, bencarbazone, benzfendizone, butafenacil, carfentrazone-ethyl, cinidon-ethyl, flufenpyr-ethyl, flumiclorac-pentyl, flumioxazin, fluoroglycofen-ethyl, fomesafen, lactofen, oxadiargyl, oxadiazon, oxyfluorfen, pentoxazone, pyraflufen-ethyl, saflufenacil, sulfentrazone, tiafenacil, ethyl[3-[2-chloro-4-fluoro-5-(1-methyl-6-trifluoromethyl-2,4-dioxo-1,2,3,4-tetrahydro-pyrimidin-3-yl)phenoxy]-2-pyridyloxy]acetate (CAS 353292-31-6; S-3100), N-ethyl-3-(2,6-dichloro-4-trifluoromethylphenoxy)-5-methyl-1H-pyrazole-1-carboxamide (CAS 452098-92-9), N-tetrahydrofurfuryl-3-(2,6-dichloro-4-trifluoromethylphenoxy)-5-methyl-1H-pyrazole-1-carboxamide (CAS 915396-43-9), N-ethyl-3-(2-chloro-6-fluoro-4-trifluoromethylphenoxy)-5-methyl-1H-pyrazole-1-carboxamide (CAS 452099-05-7), N-tetrahydrofurfuryl-3-(2-chloro-6-fluoro-4-trifluoromethylphenoxy)-5-methyl-1H-pyrazole-1-carboxamide (CAS 452100-03-7), 3-[7-fluoro-3-oxo-4-(prop-2-ynyl)-3,4-dihydro-2H-benzo[1,4]oxazin-6-yl]-1,5-dimethyl-6-thioxo-[1,3,5]triazinan-2,4-dione, 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), 2-(2,2,7-Trifluoro-3-oxo-4-prop-2-ynyl-3,4-dihydro-2H-benzo[1,4]oxazin-6-yl)-4,5,6,7-tetrahydro-isoindole-1,3-dione; 1-Methyl-6-trifluoromethyl-3-(2,2,7-trifluoro-3-oxo-4-prop-2-ynyl-3,4-dihydro-2H-benzo[1,4]oxazin-6-yl)-1H-pyrimidine-2,4-dione, and 3-[7-Chloro-5-fluoro-2-(trifluoromethyl)-1H-benzimidazol-4-yl]-1-methyl-6-(trifluoromethyl)-1H-pyrimidine-2,4-dione (CAS 212754-02-4);

b5) from the group of the bleacher herbicides:
aclonifen, amitrole, beflubutamid, benzobicyclon, bicyclopyrone, clomazone, diflufenican, fenquintrione, flumeturon, flurochloridone, flurtamone, isoxaflutole, mesotrione, norflurazon, picolinafen, pyrasulfotole, pyrazolynate, sulcotrione, tefuryltrione, tembotrione, topramezone and 4-(3-trifluoromethylphenoxy)-2-(4-trifluoromethylphenyl)-pyrimidine (CAS 180608-33-7);

b6) from the group of the EPSP synthase inhibitors: glyphosate, glyphosate-isopropylammonium, glyphosate-potassium and glyphosate-trimesium (sulfosate);

b7) from the group of the glutamine synthase inhibitors: glufosinate, glufosinate-P, glufosinate-ammonium;

b8) from the group of the DHP synthase inhibitors: asulam;

b9) from the group of the mitosis inhibitors: benfluralin, dithiopyr, ethalfluralin, oryzalin, pendimethalin, thiazopyr and trifluralin;

b10) from the group of the VLCFA inhibitors: acetochlor, alachlor, anilofos, butachlor, cafenstrole, dimethenamid, dimethenamid-P, fentrazamide, flufenacet, mefenacet, metazachlor, metolachlor, S-metolachlor, naproanilide, napropamide, napropamide-M, pretilachlor, fenoxasulfone, ipfencarbazone, pyroxasulfone thenylchlor and isoxazoline-compounds of the formulae II.1, II.2, II.3, II.4, II.5, II.6, II.7, II.8 and II.9 as mentioned above;

b11) from the group of the cellulose biosynthesis inhibitors: dichlobenil, flupoxam, isoxaben and 1-Cyclohexyl-5-pentafluorphenyloxy-1$^4$-[1,2,4,6]thiatriazin-3-ylamine;

b13) from the group of the auxinic herbicides: 2,4-D and its salts and esters, aminocyclopyrachlor and its salts and esters, aminopyralid and its salts such as aminopyralid-dimethylammonium, aminopyralid-tris(2-hydroxypropyl)ammonium and its esters, clopyralid and its salts and esters, dicamba and its salts and esters, dichlorprop-P and its salts and esters, fluroxypyr-meptyl, halauxifen and its salts and esters (CAS 943832-60-8), MCPA and its salts and esters, MCPB and its salts and esters, mecoprop-P and its salts and esters, picloram and its salts and esters, quinclorac, quinmerac and triclopyr and its salts and esters;

b14) from the group of the auxin transport inhibitors: diflufenzopyr and diflufen-zopyr-sodium;

b15) from the group of the other herbicides: bromobutide, cinmethylin, cumyluron, cyclopyrimorate (CAS 499223-49-3) and its salts and esters, dalapon, difenzoquat, difenzoquat-metilsulfate, DSMA, dymron (=daimuron), flamprop, flamprop-isopropyl, flamprop-methyl, flamprop-M-isopropyl, flamprop-M-methyl, indanofan, indaziflam, metam, methylbromide, MSMA, oxaziclomefone, pyributicarb, triaziflam and tridiphane.

Particularly preferred herbicides B that can be used in combination with the compounds A of the formula (I) according to the present invention are:

b1) from the group of the lipid biosynthesis inhibitors: clodinafop-propargyl, cycloxydim, cyhalofop-butyl, fenoxaprop-P-ethyl, pinoxaden, profoxydim, tepraloxydim, tralkoxydim, 4-(4'-Chloro-4-cyclopropyl-2'-fluoro[1,1'-biphenyl]-3-yl)-5-hydroxy-2,2,6,6-tetramethyl-2H-pyran-3(6H)-one (CAS 1312337-72-6); 4-(2',4'-Dichloro-4-cyclopropyl[1,1'-biphenyl]-3-yl)-5-hydroxy-2,2,6,6-tetramethyl-2H-pyran-3(6H)-one (CAS 1312337-45-3); 4-(4'-Chloro-4-ethyl-2'-fluoro[1,1'-biphenyl]-3-yl)-5-hydroxy-2,2,6,6-tetramethyl-2H-pyran-3(6H)-one (CAS 1033757-93-5); 4-(2',4'-Dichloro-4-ethyl[1,1'-biphenyl]-3-yl)-2,2,6,6-tetramethyl-2H-pyran-3,5(4H,6H)-dione (CAS 1312340-84-3); 5-(Acetyloxy)-4-(4'-chloro-4-cyclopropyl-2'-fluoro[1,1'-biphenyl]-3-yl)-3,6-dihydro-2,2,6,6-tetramethyl-2H-pyran-3-one (CAS 1312337-48-6); 5-(Acetyloxy)-4-(2',4'-dichloro-4-cyclopropyl-[1,1'-biphenyl]-3-yl)-3,6-dihydro-2,2,6,6-tetramethyl-2H-pyran-3-one; 5-(Acetyloxy)-4-(4'-chloro-4-ethyl-2'-fluoro[1,1'-biphenyl]-3-yl)-3,6-dihydro-2,2,6,6-tetramethyl-2H-pyran-3-one (CAS 1312340-82-1); 5-(Acetyloxy)-4-(2',4'-dichloro-4-ethyl[1,1'-biphenyl]-3-yl)-3,6-dihydro-2,2,6,6-tetramethyl-2H-pyran-3-one (CAS 1033760-55-2); 4-(4'-Chloro-4-cyclopropyl-2'-fluoro[1,1'-biphenyl]-3-yl)-5,6-dihydro-2,2,6,6-tetramethyl-5-oxo-2H-pyran-3-yl carbonic acid methyl ester (CAS 1312337-51-1); 4-(2'',4'-Dichloro-4-cyclopropyl-[1,1'-biphenyl]-3-yl)-5,6-dihydro-2,2,6,6-tetramethyl-5-oxo-2H-pyran-3-yl carbonic acid methyl ester; 4-(4'-Chloro-4-ethyl-2'-fluoro[1,1'-biphenyl]-3-yl)-5,6-dihydro-2,2,6,6-tetramethyl-5-oxo-2H-pyran-3-yl carbonic acid methyl ester (CAS 1312340-83-2); 4-(2',4'-Dichloro-4-ethyl[1,1'-biphenyl]-3-yl)-5,6-dihydro-2,2,6,6-tetramethyl-5-oxo-2H-pyran-3-yl carbonic acid methyl ester (CAS 1033760-58-5); esprocarb, prosulfocarb, thiobencarb and triallate;

b2) from the group of the ALS inhibitors: bensulfuron-methyl, bispyribac-sodium, cyclosulfamuron, diclosulam, flumetsulam, flupyrsulfuron-methyl-sodium, foramsulfuron, imazamox, imazapic, imazapyr, imazaquin, imazethapyr, imazosulfuron, iodosulfuron, iodosulfuron-methyl-sodium, iofensulfuron, iofensulfuron-sodium, mesosulfuron, metazosulfuron, nicosulfuron, penoxsulam, propoxycarbazon-sodium, propyrisulfuron, pyrazosulfuron-ethyl, pyroxsulam, rimsulfuron, sulfosulfuron, thiencarbazon-methyl, tritosulfuron and triafamone;

b3) from the group of the photosynthesis inhibitors: ametryn, atrazine, diuron, fluometuron, hexazinone, isoproturon, linuron, metribuzin, paraquat, paraquat-dichloride, propanil, terbutryn and terbuthylazine;

b4) from the group of the protoporphyrinogen-IX oxidase inhibitors: flumioxazin, oxyfluorfen, saflufenacil, sulfentrazone, ethyl[3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate (CAS 353292-31-6) 3-[7-fluoro-3-oxo-4-(prop-2-ynyl)-3,4-dihydro-2H-benzo[1,4]oxazin-6-yl]-1,5-dimethyl-6-thioxo-[1,3,5]triazinan-2,4-dione, 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), 2-(2,2,7-Trifluoro-3-oxo-4-prop-2-ynyl-3,4-dihydro-2H-benzo[1,4]oxazin-6-yl)-4,5,6,7-tetrahydro-isoindole-1,3-dione, and 1-Methyl-6-trifluoromethyl-3-(2,2,7-trifluoro-3-oxo-4-prop-2-ynyl-3,4-dihydro-2H-benzo[1,4]oxazin-6-yl)-1H-pyrimidine-2,4-dione;

b5) from the group of the bleacher herbicides: amitrole, bicyclopyrone, clomazone, diflufenican, fenquintrione, flumeturon, flurochloridone, isoxaflutole, mesotrione, picolinafen, sulcotrione, tefuryltrione, tembotrione and topramezone;

b6) from the group of the EPSP synthase inhibitors: glyphosate, glyphosate-isopropylammonium and glyphosate-trimesium (sulfosate);

b7) from the group of the glutamine synthase inhibitors: glufosinate, glufosinate-P and glufosinate-ammonium;

b9) from the group of the mitosis inhibitors: pendimethalin and trifluralin;

b10) from the group of the VLCFA inhibitors: acetochlor, cafenstrole, dimethenamid-P, fentrazamide, flufenacet, mefenacet, metazachlor, metolachlor, S-metolachlor, fenoxasulfone, ipfencarbazone and pyroxasulfone; likewise, preference is given to isoxazoline compounds of the formulae II.1, II.2, II.3, II.4, II.5, II.6, II.7, II.8 and II.9 as mentioned above;

b11) from the group of the cellulose biosynthesis inhibitors: isoxaben;

b13) from the group of the auxinic herbicides: 2,4-D and its salts and esters such as clacyfos, and aminocyclopyrachlor and its salts and esters, aminopyralid and its salts and its esters, clopyralid and its salts and esters, dicamba and its salts and esters, fluroxypyr-meptyl, quinclorac and quinmerac;

b14) from the group of the auxin transport inhibitors: diflufenzopyr and diflufenzopyr-sodium, b15) from the group of the other herbicides: dymron (=daimuron), indanofan, indaziflam, oxaziclomefone and triaziflam.

Active compounds B and C having a carboxyl group can be employed in the form of the acid, in the form of an agriculturally suitable salt as mentioned above or else in the form of an agriculturally acceptable derivative in the compositions according to the invention.

In the case of dicamba, suitable salts include those, where the counterion is an agriculturally acceptable cation. For example, suitable salts of dicamba are dicamba-sodium, dicamba-potassium, dicamba-methylammonium, dicamba-dimethylammonium, dicamba-isopropylammonium, dicamba-diglycolamine, dicamba-olamine, dicamba-diolamine, dicamba-trolamine, dicamba-N,N-bis-(3-aminopropyl)methylamine and dicamba-diethylenetriamine. Examples of a suitable ester are dicamba-methyl and dicamba-butotyl.

Suitable salts of 2,4-D are 2,4-D-ammonium, 2,4-D-dimethylammonium, 2,4-D-diethylammonium, 2,4-D-diethanolammonium (2,4-D-diolamine), 2,4-D-triethanol-ammonium, 2,4-D-isopropylammonium, 2,4-D-triisopropanolammonium, 2,4-D-heptylammonium, 2,4-D-dodecylammonium, 2,4-D-tetradecylammonium, 2,4-D-triethylammonium, 2,4-D-tris(2-hydroxypropyl)ammonium, 2,4-D-tris(isopropyl)-ammonium, 2,4-D-trolamine, 2,4-D-lithium, 2,4-D-sodium. Examples of suitable esters of 2,4-D are 2,4-D-butotyl, 2,4-D-2-butoxypropyl, 2,4-D-3-butoxypropyl, 2,4-D-butyl, 2,4-D-ethyl, 2,4-D-ethylhexyl, 2,4-D-isobutyl, 2,4-D-isooctyl, 2,4-D-isopropyl, 2,4-D-meptyl, 2,4-D-methyl, 2,4-D-octyl, 2,4-D-pentyl, 2,4-D-propyl, 2,4-D-tefuryl and clacyfos.

Suitable salts of 2,4-DB are for example 2,4-DB-sodium, 2,4-DB-potassium and 2,4-DB-dimethylammonium. Suitable esters of 2,4-DB are for example 2,4-DB-butyl and 2,4-DB-isoctyl.

Suitable salts of dichlorprop are for example dichlorprop-sodium, dichlorprop-potassium and dichlorprop-dimethylammonium. Examples of suitable esters of dichlorprop are dichlorprop-butotyl and dichlorprop-isoctyl.

Suitable salts and esters of MCPA include MCPA-butotyl, MCPA-butyl, MCPA-dimethylammonium, MCPA-diolamine, MCPA-ethyl, MCPA-thioethyl, MCPA-2-ethylhexyl, MCPA-isobutyl, MCPA-isoctyl, MCPA-isopropyl, MCPA-isopropylammonium, MCPA-methyl, MCPA-olamine, MCPA-potassium, MCPA-sodium and MCPA-trolamine.

A suitable salt of MCPB is MCPB sodium. A suitable ester of MCPB is MCPB-ethyl.

Suitable salts of clopyralid are clopyralid-potassium, clopyralid-olamine and clopyralid-tris-(2-hydroxypropyl) ammonium. Example of suitable esters of clopyralid is clopyralid-methyl.

Examples of a suitable ester of fluroxypyr are fluroxypyr-meptyl and fluroxypyr-2-butoxy-1-methylethyl, wherein fluroxypyr-meptyl is preferred.

Suitable salts of picloram are picloram-dimethylammonium, picloram-potassium, picloram-triisopropanolammonium, picloram-triisopropylammonium and picloram-trolamine. A suitable ester of picloram is picloram-isoctyl.

A suitable salt of triclopyr is triclopyr-triethylammonium. Suitable esters of triclopyr are for example triclopyr-ethyl and triclopyr-butotyl.

Suitable salts and esters of chloramben include chloramben-ammonium, chloramben-diolamine, chloramben-methyl, chloramben-methylammonium and chloramben-sodium. Suitable salts and esters of 2,3,6-TBA include 2,3,6-TBA-dimethylammonium, 2,3,6-TBA-lithium, 2,3,6-TBA-potassium and 2,3,6-TBA-sodium.

Suitable salts and esters of aminopyralid include aminopyralid-potassium, aminopyralid-dimethylammonium, and aminopyralid-tris(2-hydroxypropyl)ammonium.

Suitable salts of glyphosate are for example glyphosate-ammonium, glyphosate-diammonium, glyphoste-dimethylammonium, glyphosate-isopropylammonium, glyphosate-potassium, glyphosate-sodium, glyphosate-trimesium as well as the ethanolamine and diethanolamine salts, preferably glyphosate-diammonium, glyphosate-isopropylammonium and glyphosate-trimesium (sulfosate).

A suitable salt of glufosinate is for example glufosinate-ammonium.

A suitable salt of glufosinate-P is for example glufosinate-P-ammonium.

Suitable salts and esters of bromoxynil are for example bromoxynil-butyrate, bromoxynil-heptanoate, bromoxynil-octanoate, bromoxynil-potassium and bromoxynil-sodium.

Suitable salts and esters of ioxonil are for example ioxonil-octanoate, ioxonil-potassium and ioxonil-sodium.

Suitable salts and esters of mecoprop include mecoprop-butotyl, mecoprop-dimethylammonium, mecoprop-diolamine, mecoprop-ethadyl, mecoprop-2-ethylhexyl, mecoprop-isoctyl, mecoprop-methyl, mecoprop-potassium, mecoprop-sodium and mecoprop-trolamine.

Suitable salts of mecoprop-P are for example mecoprop-P-butotyl, mecoprop-P-dimethylammonium, mecoprop-P-2-ethylhexyl, mecoprop-P-isobutyl, mecoprop-P-potassium and mecoprop-P-sodium.

A suitable salt of diflufenzopyr is for example diflufenzopyr-sodium.

A suitable salt of naptalam is for example naptalam-sodium.

Suitable salts and esters of aminocyclopyrachlor are for example aminocyclopyrachlor-dimethylammonium, aminocyclopyrachlor-methyl, aminocyclopyrachlor-triisopropanolammonium, aminocyclopyrachlor-sodium and aminocyclopyrachlor-potassium.

A suitable salt of quinclorac is for example quinclorac-dimethylammonium.

A suitable salt of quinmerac is for example quinclorac-dimethylammonium.

A suitable salt of imazamox is for example imazamox-ammonium.

Suitable salts of imazapic are for example imazapic-ammonium and imazapic-isopropylammonium.

Suitable salts of imazapyr are for example imazapyr-ammonium and imazapyr-isopropylammonium.

A suitable salt of imazaquin is for example imazaquin-ammonium.

Suitable salts of imazethapyr are for example imazethapyr-ammonium and imazethapyr-isopropylammonium.

A suitable salt of topramezone is for example topramezone-sodium.

Particularly preferred herbicidal compounds B are the herbicides B as defined above; in particular the herbicides B.1-B.189 listed below in table B:

TABLE B

| | Herbicide B |
|---|---|
| B.1 | clethodim |
| B.2 | clodinafop-propargyl |
| B.3 | cycloxydim |
| B.4 | cyhalofop-butyl |
| B.5 | fenoxaprop-ethyl |
| B.6 | fenoxaprop-P-ethyl |
| B.7 | metamifop |
| B.8 | pinoxaden |
| B.9 | profoxydim |
| B.10 | sethoxydim |
| B.11 | tepraloxydim |
| B.12 | tralkoxydim |
| B.13 | esprocarb |
| B.14 | ethofumesate |
| B.15 | molinate |
| B.16 | prosulfocarb |
| B.17 | thiobencarb |
| B.18 | triallate |
| B.19 | bensulfuron-methyl |
| B.20 | bispyribac-sodium |
| B.21 | cloransulam-methyl |
| B.22 | chlorsulfuron |
| B.23 | clorimuron |
| B.24 | cyclosulfamuron |
| B.25 | diclosulam |
| B.26 | florasulam |
| B.27 | flumetsulam |
| B.28 | flupyrsulfuron-methyl-sodium |
| B.29 | foramsulfuron |
| B.30 | imazamox |
| B.31 | imazamox-ammonium |
| B.32 | imazapic |
| B.33 | imazapic-ammonium |
| B.34 | imazapic-isopropylammonium |
| B.35 | imazapyr |
| B.36 | imazapyr-ammonium |
| B.37 | imazapyr-isopropylammonium |
| B.38 | imazaquin |
| B.39 | imazaquin-ammonium |
| B.40 | imazethapyr |
| B.41 | imazethapyr-ammonium |
| B.42 | imazethapyr-isopropylammonium |
| B.43 | imazosulfuron |
| B.44 | iodosulfuron-methyl-sodium |
| B.45 | iofensulfuron |
| B.46 | iofensulfuron-sodium |
| B.47 | mesosulfuron-methyl |
| B.48 | metazosulfuron |
| B.49 | metsulfuron-methyl |
| B.50 | nnetosulam |
| B.51 | nicosulfuron |
| B.52 | penoxsulam |
| B.53 | propoxycarbazon-sodium |
| B.54 | pyrazosulfuron-ethyl |
| B.55 | pyribenzoxim |
| B.56 | pyriftalid |
| B.57 | pyroxsulam |
| B.58 | propyrisulfuron |
| B.59 | rimsulfuron |
| B.60 | sulfosulfuron |
| B.61 | thiencarbazone-methyl |
| B.62 | thifensulfuron-methyl |
| B.63 | tribenuron-methyl |
| B.64 | tritosulfuron |
| B.65 | triafamone |
| B.66 | ametryne |

TABLE B-continued

| | Herbicide B |
|---|---|
| B.67 | atrazine |
| B.68 | bentazon |
| B.69 | bromoxynil |
| B.70 | bromoxynil-octanoate |
| B.71 | bromoxynil-heptanoate |
| B.72 | bromoxynil-potassium |
| B.73 | diuron |
| B.74 | fluometuron |
| B.75 | hexazinone |
| B.76 | isoproturon |
| B.77 | linuron |
| B.78 | metamitron |
| B.79 | metribuzin |
| B.80 | propanil |
| B.81 | simazin |
| B.82 | terbuthylazine |
| B.83 | terbutryn |
| B.84 | paraquat-dichloride |
| B.85 | acifluorfen |
| B.86 | butafenacil |
| B.87 | carfentrazone-ethyl |
| B.88 | flumioxazin |
| B.89 | fomesafen |
| B.90 | oxadiargyl |
| B.91 | oxyfluorfen |
| B.92 | saflufenacil |
| B.93 | sulfentrazone |
| B.94 | ethyl [3-[2-chloro-4-fluoro-5-(1-methyl-6-trifluoromethyl-2,4-dioxo-1,2,3,4-tetrahydropyrimidin-3-yl)phenoxy]-2-pyridyl-oxy]acetate (CAS 353292-31-6) |
| B.95 | 1,5-dimethyl-6-thioxo-3-(2,2,7-trifluoro-3-oxo-4-(prop-2-ynyl)-3,4-dihydro-2H-benzo[b][1,4]-oxazin-6-yl)-1,3,5-triazinane-2,4-dione (CAS 1258836-72-4) |
| B.96 | benzobicyclon |
| B.97 | clomazone |
| B.98 | diflufenican |
| B.99 | flurochloridone |
| B.100 | isoxaflutole |
| B.101 | mesotrione |
| B.102 | norflurazon |
| B.103 | picolinafen |
| B.104 | sulcotrione |
| B.105 | tefuryltrione |
| B.106 | tembotrione |
| B.107 | topramezone |
| B.108 | topramezone-sodium |
| B.109 | bicyclopyrone |
| B.110 | amitrole |
| B.111 | fluometuron |
| B.112 | fenquintrione |
| B.113 | glyphosate |
| B.114 | glyphosate-ammonium |
| B.115 | glyphosate-dimethylammonium |
| B.116 | glyphosate-isopropylammonium |
| B.117 | glyphosate-trimesium (sulfosate) |
| B.118 | glyphosate-potassium |
| B.119 | glufosinate |
| B.120 | glufosinate-ammonium |
| B.121 | glufosinate-P |
| B.122 | glufosinate-P-ammonium |
| B.123 | pendimethalin |
| B.124 | trifluralin |
| B.125 | acetochlor |
| B.126 | butachlor |
| B.127 | cafenstrole |
| B.128 | dimethenamid-P |
| B.129 | fentrazamide |
| B.130 | flufenacet |
| B.131 | mefenacet |
| B.132 | metazachlor |
| B.133 | metolachlor |
| B.134 | S-metolachlor |
| B.135 | pretilachlor |

TABLE B-continued

| | Herbicide B |
|---|---|
| B.136 | fenoxasulfone |
| B.137 | isoxaben |
| B.138 | ipfencarbazone |
| B.139 | pyroxasulfone |
| B.140 | 2,4-D |
| B.141 | 2,4-D-isobutyl |
| B.142 | 2,4-D-dimethylammonium |
| B.143 | 2,4-D-N,N,N-trimethylethanolammonium |
| B.144 | aminopyralid |
| B.145 | aminopyralid-methyl |
| B.146 | aminopyralid-dimethyl-ammonium |
| B.147 | aminopyralid-tris(2-hydroxypropyl)ammonium |
| B.148 | clopyralid |
| B.149 | clopyralid-methyl |
| B.150 | clopyralid-olamine |
| B.151 | dicamba |
| B.152 | dicamba-butotyl |
| B.153 | dicamba-diglycolamine |
| B.154 | dicamba-dimethylammonium |
| B.155 | dicamba-diolamine |
| B.156 | dicamba-isopropylammonium |
| B.157 | dicamba-potassium |
| B.158 | dicamba-sodium |
| B.159 | dicamba-trolamine |
| B.160 | dicamba-N,N-bis-(3-aminopropyl)methylamine |
| B.161 | dicamba-diethylenetriamine |
| B.162 | fluroxypyr |
| B.163 | fluroxypyr-meptyl |
| B.164 | MCPA |
| B.165 | MCPA-2-ethylhexyl |
| B.166 | MCPA-dimethylammonium |
| B.167 | quinclorac |
| B.168 | quinclorac-dimethylammonium |
| B.169 | quinmerac |
| B.170 | quinmerac-dimethylammonium |
| B.171 | anninocyclopyrachlor |
| B.172 | anninocyclopyrachlor-potassium |
| B.173 | anninocyclopyrachlor-methyl |
| B.174 | diflufenzopyr |
| B.175 | diflufenzopyr-sodium |
| B.176 | dymron |
| B.177 | indanofan |
| B.178 | indaziflam |
| B.179 | oxaziclomefone |
| B.180 | triaziflam |
| B.181 | II.1 |
| B.182 | II.2 |
| B.183 | II.3 |
| B.184 | II.4 |
| B.185 | II.5 |
| B.186 | II.6 |
| B.187 | II.7 |
| B.188 | II.8 |
| B.189 | II.9 |

Moreover, it may be useful to apply the compounds of formula (I) in combination with safeners and optionally with one or more further heribicides. Safeners are chemical compounds which prevent or reduce damage on useful plants without having a major impact on the herbicidal action of the compounds of the formula (I) towards unwanted plants. They can be applied either before sowings (e.g. on seed treatments, shoots or seedlings) or in the pre-emergence application or post-emergence application of the useful plant. The safeners and the compounds of formula (I) and optionally the herbicides B can be applied simultaneously or in succession.

Suitable safeners are e.g. (quinolin-8-oxy)acetic acids, 1-phenyl-5-haloalkyl-1H-1,2,4-triazol-3-carboxylic acids, 1-phenyl-4,5-dihydro-5-alkyl-1H-pyrazol-3,5-dicarboxylic acids, 4,5-dihydro-5,5-diary)-3-isoxazol carboxylic acids, dichloroacetamides, alpha-oximinophenylacetonitriles, acetophenonoximes, 4,6-dihalo-2-phenylpyrimidines, N-[[4-(aminocarbonyl)phenyl]sulfonyl]-2-benzoic amides, 1,8-naphthalic anhydride, 2-halo-4-(haloalkyl)-5-thiazol carboxylic acids, phosphorthiolates and N-alkyl-O-phenyl-carbamates and their agriculturally acceptable salts and their agriculturally acceptable derivatives such amides, esters, and thioesters, provided they have an acid group.

Examples of preferred safeners C are benoxacor, cloquintocet, cyometrinil, cyprosulfamide, dichlormid, dicyclonon, dietholate, fenchlorazole, fenclorim, flurazole, fluxofenim, furilazole, isoxadifen, mefenpyr, mephenate, naphthalic anhydride, oxabetrinil, 4-(dichloroacetyl)-1-oxa-4-azaspiro[4.5]decane (MON4660, CAS 71526-07-3), 2,2,5-trimethyl-3-(dichloroacetyl)-1,3-oxazolidine (R-29148, CAS 52836-31-4) and N-(2-Methoxybenzoyl)-4-[(methylaminocarbonyl)amino]benzenesulfonamide (CAS 129531-12-0).

Particularly preferred safeners C are the following compounds C.1 to C.17

| C.1 | benoxacor |
|---|---|
| C.2 | cloquintocet |
| C.3 | cloquintocet-mexyl |
| C.4 | cyprosulfamide |
| C.5 | dichlormid |
| C.6 | fenchlorazole |
| C.7 | fenchlorazole-ethyl |
| C.8 | fenclorim |
| C.9 | furilazole |
| C.10 | isoxadifen |
| C.11 | isoxadifen-ethyl |
| C.12 | mefenpyr |
| C.13 | mefenpyr-diethyl |
| C.14 | naphtalic acid anhydride |
| C.15 | 4-(dichloroacetyl)-1-oxa-4-azaspiro[4.5]decane |
| C.16 | 2,2,5-trimethyl-3-(dichloro-acetyl)-1,3-oxazolidine |
| C.17 | N-(2-Methoxybenzoyl)-4-[(methylaminocarbon-yl)amino]benzenesulfonamide |

The active compounds B of groups b1) to b15) and the safener compounds C are known herbicides and safeners, see, for example, The Compendium of Pesticide Common Names (http://www.alanwood.net/pesticides/); Farm Chemicals Handbook 2000 volume 86, Meister Publishing Company, 2000; B. Hock, C. Fedtke, R. R. Schmidt, Herbizide [Herbicides], Georg Thieme Verlag, Stuttgart 1995; W. H. Ahrens, Herbicide Handbook, 7th edition, Weed Science Society of America, 1994; and K. K. Hatzios, Herbicide Handbook, Supplement for the 7th edition, Weed Science Society of America, 1998. 2,2,5-Trimethyl-3-(dichloroacetyl)-1,3-oxazolidine [CAS No. 52836-31-4] is also referred to as R-29148. 4-(Dichloroacetyl)-1-oxa-4-azaspiro[4.5]decane [CAS No. 71526-07-3] is also referred to as AD-67 and MON 4660.

The assignment of the active compounds to the respective mechanisms of action is based on current knowledge. If several mechanisms of action apply to one active compound, this substance was only assigned to one mechanism of action.

The following combinations indicated by the code I.x.Y.Z represent particular embodiments of the invention:

I.a.1.1 to I.a.741.3402
I.b.1.1 to I.b.741.3402
I.c.1.1 to I.c.741.3402

I.d.1.1 to I.d.741.3402
I.e.1.1 to I.e.741.3402
I.f.1.1 to I.f.741.3402
I.g.1.1 to I.g.741.3402
I.h.1.1 to I.h.741.3402
I.i.1.1 to I.i.741.3402
I.k.1.1 to I.k.741.3402
I.l.1.1 to I.l.741.3402
I.m.1.1 to I.m.741.3402
I.n.1.1 to I.n.741.3402

In the above codes I.x refers to the formulae I.a to I.n. The integer Y refers to the row of table A, while the integer Z refers to the row of table 2 below.

Hence, the code I.a.1.1 refers to the combination of the compound of formula I.a, wherein $R^a$, $R^d$, $R^2$, $R^3$ and $R^4$ are as defined in row 1 of table 1, with the combination of the herbicide B and and the safener C are as defined in combination no. 1.1 of table 2. The code I.k.2.35 refers to the combination of the compound of formula I.k, wherein $R^a$, $R^d$, $R^2$, $R^3$ and $R^4$ are as defined in row 2 of table 1, with the combination of the herbicide B and and the safener C are as defined in combination no. 1.35 of table 2.

The code I.m.228.1402 refers to the combination of the compound of formula I.m, wherein $R^a$, $R^d$, $R^2$, $R^3$ and $R^4$ are as defined in row 228 of table 1, with the combination of the herbicide B and and the safener C are as defined in combination no. 1.1402 of table 2.

Further particular examples are the following mixtures:

mixtures I.d.33.1 to I.d.33.3402, i.e. the mixtures of the compound formula I.d, where $R^a$, $R^d$, $R^2$, $R^3$ and $R^4$ are as defined in row 33 of table 1 and where the herbicide or herbicide safener combination is as defined in one of the rows 1.1 to 1.3402 of table 2;

mixtures I.d.34.1 to I.d.34.3402, i.e. the mixtures of the compound formula I.d, where $R^a$, $R^d$, $R^2$, $R^3$ and $R^4$ are as defined in row 34 of table 1 and where the herbicide or herbicide safener combination is as defined in one of the rows 1.1 to 1.3402 of table 2;

mixtures I.d.35.1 to I.d.35.3402, i.e. the mixtures of the compound formula I.d, where $R^a$, $R^d$, $R^2$, $R^3$ and $R^4$ are as defined in row 35 of table 1 and where the herbicide or herbicide safener combination is as defined in one of the rows 1.1 to 1.3402 of table 2;

mixtures I.d.36.1 to I.d.36.3402, i.e. the mixtures of the compound formula I.d, where $R^a$, $R^d$, $R^2$, $R^3$ and $R^4$ are as defined in row 36 of table 1 and where the herbicide or herbicide safener combination is as defined in one of the rows 1.1 to 1.3402 of table 2;

mixtures I.d.37.1 to I.d.37.3402, i.e. the mixtures of the compound formula I.d, where $R^a$, $R^d$, $R^2$, $R^3$ and $R^4$ are as defined in row 37 of table 1 and where the herbicide or herbicide safener combination is as defined in one of the rows 1.1 to 1.3402 of table 2;

mixtures I.d.38.1 to I.d.38.3402, i.e. the mixtures of the compound formula I.d, where $R^a$, $R^d$, $R^2$, $R^3$ and $R^4$ are as defined in row 38 of table 1 and where the herbicide or herbicide safener combination is as defined in one of the rows 1.1 to 1.3402 of table 2;

mixtures I.d.39.1 to I.d.39.3402, i.e. the mixtures of the compound formula I.d, where $R^a$, $R^d$, $R^2$, $R^3$ and $R^4$ are as defined in row 39 of table 1 and where the herbicide or herbicide safener combination is as defined in one of the rows 1.1 to 1.3402 of table 2;

mixtures I.d.40.1 to I.d.40.3402, i.e. the mixtures of the compound formula I.d, where $R^a$, $R^d$, $R^2$, $R^3$ and $R^4$ are as defined in row 40 of table 1 and where the herbicide or herbicide safener combination is as defined in one of the rows 1.1 to 1.3402 of table 2;

mixtures I.d.41.1 to I.d.41.3402, i.e. the mixtures of the compound formula I.d, where $R^a$, $R^d$, $R^2$, $R^3$ and $R^4$ are as defined in row 33 of table 1 and where the herbicide or herbicide safener combination is as defined in one of the rows 1.1 to 1.3402 of table 2;

mixtures I.d.42.1 to I.d.42.3402, i.e. the mixtures of the compound formula I.d, where $R^a$, $R^d$, $R^2$, $R^3$ and $R^4$ are as defined in row 42 of table 1 and where the herbicide or herbicide safener combination is as defined in one of the rows 1.1 to 1.3402 of table 2;

mixtures I.d.43.1 to I.d.43.3402, i.e. the mixtures of the compound formula I.d, where $R^a$, $R^d$, $R^2$, $R^3$ and $R^4$ are as defined in row 43 of table 1 and where the herbicide or herbicide safener combination is as defined in one of the rows 1.1 to 1.3402 of table 2;

mixtures I.d.44.1 to I.d.44.3402, i.e. the mixtures of the compound formula I.d, where $R^a$, $R^d$, $R^2$, $R^3$ and $R^4$ are as defined in row 44 of table 1 and where the herbicide or herbicide safener combination is as defined in one of the rows 1.1 to 1.3402 of table 2;

mixtures I.d.45.1 to I.d.45.3402, i.e. the mixtures of the compound formula I.d, where $R^a$, $R^d$, $R^2$, $R^3$ and $R^4$ are as defined in row 45 of table 1 and where the herbicide or herbicide safener combination is as defined in one of the rows 1.1 to 1.3402 of table 2;

mixtures I.d.46.1 to I.d.46.3402, i.e. the mixtures of the compound formula I.d, where $R^a$, $R^d$, $R^2$, $R^3$ and $R^4$ are as defined in row 46 of table 1 and where the herbicide or herbicide safener combination is as defined in one of the rows 1.1 to 1.3402 of table 2;

mixtures I.d.47.1 to I.d.47.3402, i.e. the mixtures of the compound formula I.d, where $R^a$, $R^d$, $R^2$, $R^3$ and $R^4$ are as defined in row 47 of table 1 and where the herbicide or herbicide safener combination is as defined in one of the rows 1.1 to 1.3402 of table 2;

mixtures I.d.48.1 to I.d.48.3402, i.e. the mixtures of the compound formula I.d, where $R^a$, $R^d$, $R^2$, $R^3$ and $R^4$ are as defined in row 48 of table 1 and where the herbicide or herbicide safener combination is as defined in one of the rows 1.1 to 1.3402 of table 2;

mixtures I.d.49.1 to I.d.49.3402, i.e. the mixtures of the compound formula I.d, where $R^a$, $R^d$, $R^2$, $R^3$ and $R^4$ are as defined in row 49 of table 1 and where the herbicide or herbicide safener combination is as defined in one of the rows 1.1 to 1.3402 of table 2;

mixtures I.d.50.1 to I.d.50.3402, i.e. the mixtures of the compound formula I.d, where $R^a$, $R^d$, $R^2$, $R^3$ and $R^4$ are as defined in row 50 of table 1 and where the herbicide or herbicide safener combination is as defined in one of the rows 1.1 to 1.3402 of table 2;

mixtures I.d.51.1 to I.d.51.3402, i.e. the mixtures of the compound formula I.d, where $R^a$, $R^d$, $R^2$, $R^3$ and $R^4$ are as defined in row 51 of table 1 and where the herbicide or herbicide safener combination is as defined in one of the rows 1.1 to 1.3402 of table 2;

mixtures I.d.52.1 to I.d.52.3402, i.e. the mixtures of the compound formula I.d, where $R^a$, $R^d$, $R^2$, $R^3$ and $R^4$ are as defined in row 52 of table 1 and where the herbicide or herbicide safener combination is as defined in one of the rows 1.1 to 1.3402 of table 2;

mixtures I.d.53.1 to I.d.53.3402, i.e. the mixtures of the compound formula I.d, where $R^a$, $R^d$, $R^2$, $R^3$ and $R^4$ are as defined in row 53 of table 1 and where the herbicide or herbicide safener combination is as defined in one of the rows 1.1 to 1.3402 of table 2;

mixtures I.d.54.1 to I.d.54.3402, i.e. the mixtures of the compound formula I.d, where $R^a$, $R^d$, $R^2$, $R^3$ and $R^4$ are as defined in row 54 of table 1 and where the herbicide or herbicide safener combination is as defined in one of the rows 1.1 to 1.3402 of table 2;

mixtures I.d.305.1 to I.d.305.3402, i.e. the mixtures of the compound formula I.d, where $R^a$, $R^d$, $R^2$, $R^3$ and $R^4$ are as defined in row 305 of table 1 and where the herbicide or herbicide safener combination is as defined in one of the rows 1.1 to 1.3402 of table 2;

mixtures I.d.306.1 to I.d.306.3402, i.e. the mixtures of the compound formula I.d, where $R^a$, $R^d$, $R^2$, $R^3$ and $R^4$ are as defined in row 306 of table 1 and where the herbicide or herbicide safener combination is as defined in one of the rows 1.1 to 1.3402 of table 2;

mixtures I.d.308.1 to I.d.308.3402, i.e. the mixtures of the compound formula I.d, where $R^a$, $R^d$, $R^2$, $R^3$ and $R^4$ are as defined in row 308 of table 1 and where the herbicide or herbicide safener combination is as defined in one of the rows 1.1 to 1.3402 of table 2;

mixtures I.d.309.1 to I.d.309.3402, i.e. the mixtures of the compound formula I.d, where $R^a$, $R^d$, $R^2$, $R^3$ and $R^4$ are as defined in row 309 of table 1 and where the herbicide or herbicide safener combination is as defined in one of the rows 1.1 to 1.3402 of table 2;

mixtures I.d.332.1 to I.d.332.3402, i.e. the mixtures of the compound formula I.d, where $R^a$, $R^d$, $R^2$, $R^3$ and $R^4$ are as defined in row 332 of table 1 and where the herbicide or herbicide safener combination is as defined in one of the rows 1.1 to 1.3402 of table 2;

mixtures I.d.333.1 to I.d.333.3402, i.e. the mixtures of the compound formula I.d, where $R^a$, $R^d$, $R^2$, $R^3$ and $R^4$ are as defined in row 333 of table 1 and where the herbicide or herbicide safener combination is as defined in one of the rows 1.1 to 1.3402 of table 2;

mixtures I.d.334.1 to I.d.334.3402, i.e. the mixtures of the compound formula I.d, where $R^a$, $R^d$, $R^2$, $R^3$ and $R^4$ are as defined in row 334 of table 1 and where the herbicide or herbicide safener combination is as defined in one of the rows 1.1 to 1.3402 of table 2;

mixtures I.d.335.1 to I.d.335.3402, i.e. the mixtures of the compound formula I.d, where $R^a$, $R^d$, $R^2$, $R^3$ and $R^4$ are as defined in row 335 of table 1 and where the herbicide or herbicide safener combination is as defined in one of the rows 1.1 to 1.3402 of table 2;

mixtures I.m.33.1 to I.m.33.3402, i.e. the mixtures of the compound formula I.m, where $R^a$, $R^d$, $R^2$, $R^3$ and $R^4$ are as defined in row 33 of table 1 and where the herbicide or herbicide safener combination is as defined in one of the rows 1.1 to 1.3402 of table 2;

mixtures I.m.34.1 to I.m.34.3402, i.e. the mixtures of the compound formula I.m, where $R^a$, $R^d$, $R^2$, $R^3$ and $R^4$ are as defined in row 34 of table 1 and where the herbicide or herbicide safener combination is as defined in one of the rows 1.1 to 1.3402 of table 2;

mixtures I.m.35.1 to I.m.35.3402, i.e. the mixtures of the compound formula I.m, where $R^a$, $R^d$, $R^2$, $R^3$ and $R^4$ are as defined in row 35 of table 1 and where the herbicide or herbicide safener combination is as defined in one of the rows 1.1 to 1.3402 of table 2;

mixtures I.m.36.1 to I.m.36.3402, i.e. the mixtures of the compound formula I.m, where $R^a$, $R^d$, $R^2$, $R^3$ and $R^4$ are as defined in row 36 of table 1 and where the herbicide or herbicide safener combination is as defined in one of the rows 1.1 to 1.3402 of table 2;

mixtures I.m.37.1 to I.m.37.3402, i.e. the mixtures of the compound formula I.m, where $R^a$, $R^d$, $R^2$, $R^3$ and $R^4$ are as defined in row 37 of table 1 and where the herbicide or herbicide safener combination is as defined in one of the rows 1.1 to 1.3402 of table 2;

mixtures I.m.38.1 to I.m.38.3402, i.e. the mixtures of the compound formula I.m, where $R^a$, $R^d$, $R^2$, $R^3$ and $R^4$ are as defined in row 38 of table 1 and where the herbicide or herbicide safener combination is as defined in one of the rows 1.1 to 1.3402 of table 2;

mixtures I.m.39.1 to I.m.39.3402, i.e. the mixtures of the compound formula I.m, where $R^a$, $R^d$, $R^2$, $R^3$ and $R^4$ are as defined in row 39 of table 1 and where the herbicide or herbicide safener combination is as defined in one of the rows 1.1 to 1.3402 of table 2;

mixtures I.m.40.1 to I.m.40.3402, i.e. the mixtures of the compound formula I.m, where $R^a$, $R^d$, $R^2$, $R^3$ and $R^4$ are as defined in row 40 of table 1 and where the herbicide or herbicide safener combination is as defined in one of the rows 1.1 to 1.3402 of table 2;

mixtures I.m.41.1 to I.m.41.3402, i.e. the mixtures of the compound formula I.m, where $R^a$, $R^d$, $R^2$, $R^3$ and $R^4$ are as defined in row 33 of table 1 and where the herbicide or herbicide safener combination is as defined in one of the rows 1.1 to 1.3402 of table 2;

mixtures I.m.42.1 to I.m.42.3402, i.e. the mixtures of the compound formula I.m, where $R^a$, $R^d$, $R^2$, $R^3$ and $R^4$ are as defined in row 42 of table 1 and where the herbicide or herbicide safener combination is as defined in one of the rows 1.1 to 1.3402 of table 2;

mixtures I.m.43.1 to I.m.43.3402, i.e. the mixtures of the compound formula I.m, where $R^a$, $R^d$, $R^2$, $R^3$ and $R^4$ are as defined in row 43 of table 1 and where the herbicide or herbicide safener combination is as defined in one of the rows 1.1 to 1.3402 of table 2;

mixtures I.m.44.1 to I.m.44.3402, i.e. the mixtures of the compound formula I.m, where $R^a$, $R^d$, $R^2$, $R^3$ and $R^4$ are as defined in row 44 of table 1 and where the herbicide or herbicide safener combination is as defined in one of the rows 1.1 to 1.3402 of table 2;

mixtures I.m.45.1 to I.m.45.3402, i.e. the mixtures of the compound formula I.m, where $R^a$, $R^d$, $R^2$, $R^3$ and $R^4$ are as defined in row 45 of table 1 and where the herbicide or herbicide safener combination is as defined in one of the rows 1.1 to 1.3402 of table 2;

mixtures I.m.46.1 to I.m.46.3402, i.e. the mixtures of the compound formula I.m, where $R^a$, $R^d$, $R^2$, $R^3$ and $R^4$ are as defined in row 46 of table 1 and where the herbicide or herbicide safener combination is as defined in one of the rows 1.1 to 1.3402 of table 2;

mixtures I.m.47.1 to I.m.47.3402, i.e. the mixtures of the compound formula I.m, where $R^a$, $R^d$, $R^2$, $R^3$ and $R^4$ are as defined in row 47 of table 1 and where the herbicide or herbicide safener combination is as defined in one of the rows 1.1 to 1.3402 of table 2;

mixtures I.m.48.1 to I.m.48.3402, i.e. the mixtures of the compound formula I.m, where $R^a$, $R^d$, $R^2$, $R^3$ and $R^4$ are as defined in row 48 of table 1 and where the herbicide or herbicide safener combination is as defined in one of the rows 1.1 to 1.3402 of table 2;

mixtures I.m.49.1 to I.m.49.3402, i.e. the mixtures of the compound formula I.m, where $R^a$, $R^d$, $R^2$, $R^3$ and $R^4$ are as defined in row 49 of table 1 and where the herbicide or herbicide safener combination is as defined in one of the rows 1.1 to 1.3402 of table 2;

mixtures I.m.50.1 to I.m.50.3402, i.e. the mixtures of the compound formula I.m, where $R^a$, $R^d$, $R^2$, $R^3$ and $R^4$ are as defined in row 50 of table 1 and where the herbicide or herbicide safener combination is as defined in one of the rows 1.1 to 1.3402 of table 2;

mixtures I.m.51.1 to I.m.51.3402, i.e. the mixtures of the compound formula I.m, where $R^a$, $R^d$, $R^2$, $R^3$ and $R^4$ are as defined in row 51 of table 1 and where the herbicide or herbicide safener combination is as defined in one of the rows 1.1 to 1.3402 of table 2;

mixtures I.m.52.1 to I.m.52.3402, i.e. the mixtures of the compound formula I.m, where $R^a$, $R^d$, $R^2$, $R^3$ and $R^4$ are as defined in row 52 of table 1 and where the herbicide or herbicide safener combination is as defined in one of the rows 1.1 to 1.3402 of table 2;

mixtures I.m.53.1 to I.m.53.3402, i.e. the mixtures of the compound formula I.m, where $R^a$, $R^d$, $R^2$, $R^3$ and $R^4$ are as defined in row 53 of table 1 and where the herbicide or herbicide safener combination is as defined in one of the rows 1.1 to 1.3402 of table 2;

mixtures I.m.54.1 to I.m.54.3402, i.e. the mixtures of the compound formula I.m, where $R^a$, $R^d$, $R^2$, $R^3$ and $R^4$ are as defined in row 54 of table 1 and where the herbicide or herbicide safener combination is as defined in one of the rows 1.1 to 1.3402 of table 2;

mixtures I.m.305.1 to I.m.305.3402, i.e. the mixtures of the compound formula I.m, where $R^a$, $R^d$, $R^2$, $R^3$ and $R^4$ are as defined in row 305 of table 1 and where the herbicide or herbicide safener combination is as defined in one of the rows 1.1 to 1.3402 of table 2;

mixtures I.m.306.1 to I.m.306.3402, i.e. the mixtures of the compound formula I.m, where $R^a$, $R^d$, $R^2$, $R^3$ and $R^4$ are as defined in row 306 of table 1 and where the herbicide or herbicide safener combination is as defined in one of the rows 1.1 to 1.3402 of table 2;

mixtures I.m.308.1 to I.m.308.3402, i.e. the mixtures of the compound formula I.m, where $R^a$, $R^d$, $R^2$, $R^3$ and $R^4$ are as defined in row 308 of table 1 and where the herbicide or herbicide safener combination is as defined in one of the rows 1.1 to 1.3402 of table 2;

mixtures I.m.309.1 to I.m.309.3402, i.e. the mixtures of the compound formula I.m, where $R^a$, $R^d$, $R^2$, $R^3$ and $R^4$ are as defined in row 309 of table 1 and where the herbicide or herbicide safener combination is as defined in one of the rows 1.1 to 1.3402 of table 2;

mixtures I.m.332.1 to I.m.332.3402, i.e. the mixtures of the compound formula I.m, where $R^a$, $R^d$, $R^2$, $R^3$ and $R^4$ are as defined in row 332 of table 1 and where the herbicide or herbicide safener combination is as defined in one of the rows 1.1 to 1.3402 of table 2;

mixtures I.m.333.1 to I.m.333.3402, i.e. the mixtures of the compound formula I.m, where $R^a$, $R^d$, $R^2$, $R^3$ and $R^4$ are as defined in row 333 of table 1 and where the herbicide or herbicide safener combination is as defined in one of the rows 1.1 to 1.3402 of table 2;

mixtures I.m.334.1 to I.m.334.3402, i.e. the mixtures of the compound formula I.m, where $R^a$, $R^d$, $R^2$, $R^3$ and $R^4$ are as defined in row 334 of table 1 and where the herbicide or herbicide safener combination is as defined in one of the rows 1.1 to 1.3402 of table 2;

mixtures I.m.335.1 to I.m.335.3402, i.e. the mixtures of the compound formula I.m, where $R^a$, $R^d$, $R^2$, $R^3$ and $R^4$ are as defined in row 335 of table 1 and where the herbicide or herbicide safener combination is as defined in one of the rows 1.1 to 1.3402 of table 2;

TABLE 2

| comb. no. | herbicide B | safener C |
|---|---|---|
| 1.1 | B.1 | — |
| 1.2 | B.2 | — |
| 1.3 | B.3 | — |
| 1.4 | B.4 | — |
| 1.5 | B.5 | — |
| 1.6 | B.6 | — |
| 1.7 | B.7 | — |
| 1.8 | B.8 | — |
| 1.9 | B.9 | — |
| 1.10 | B.10 | — |
| 1.11 | B.11 | — |
| 1.12 | B.12 | — |
| 1.13 | B.13 | — |
| 1.14 | B.14 | — |
| 1.15 | B.15 | — |
| 1.16 | B.16 | — |
| 1.17 | B.17 | — |
| 1.18 | B.18 | — |
| 1.19 | B.19 | — |
| 1.20 | B.20 | — |
| 1.21 | B.21 | — |
| 1.22 | B.22 | — |
| 1.23 | B.23 | — |
| 1.24 | B.24 | — |
| 1.25 | B.25 | — |
| 1.26 | B.26 | — |
| 1.27 | B.27 | — |
| 1.28 | B.28 | — |
| 1.29 | B.29 | — |
| 1.30 | B.30 | — |
| 1.31 | B.31 | — |
| 1.32 | B.32 | — |
| 1.33 | B.33 | — |
| 1.34 | B.34 | — |
| 1.35 | B.35 | — |
| 1.36 | B.36 | — |
| 1.37 | B.37 | — |
| 1.38 | B.38 | — |
| 1.39 | B.39 | — |
| 1.40 | B.40 | — |
| 1.41 | B.41 | — |
| 1.42 | B.42 | — |
| 1.43 | B.43 | — |
| 1.44 | B.44 | — |
| 1.45 | B.45 | — |
| 1.46 | B.46 | — |
| 1.47 | B.47 | — |
| 1.48 | B.48 | — |
| 1.49 | B.49 | — |
| 1.50 | B.50 | — |
| 1.51 | B.51 | — |
| 1.52 | B.52 | — |
| 1.53 | B.53 | — |
| 1.54 | B.54 | — |
| 1.55 | B.55 | — |
| 1.56 | B.56 | — |
| 1.57 | B.57 | — |
| 1.58 | B.58. | — |
| 1.59 | B.59 | — |
| 1.60 | B.60 | — |
| 1.61 | B.61 | — |
| 1.62 | B.62 | — |
| 1.63 | B.63 | — |
| 1.64 | B.64 | — |
| 1.65 | B.65 | — |
| 1.66 | B.66 | — |
| 1.67 | B.67 | — |
| 1.68 | B.68 | — |
| 1.69 | B.69 | — |
| 1.70 | B.70 | — |
| 1.71 | B.71 | — |
| 1.72 | B.72 | — |
| 1.73 | B.73 | — |
| 1.74 | B.74 | — |
| 1.75 | B.75 | — |
| 1.76 | B.76 | — |
| 1.77 | B.77 | — |
| 1.78 | B.78 | — |

TABLE 2-continued

| comb. no. | herbicide B | safener C |
|---|---|---|
| 1.79 | B.79 | — |
| 1.80 | B.80 | — |
| 1.81 | B.81 | — |
| 1.82 | B.82 | — |
| 1.83 | B.83 | — |
| 1.84 | B.84 | — |
| 1.85 | B.85 | — |
| 1.86 | B.86 | — |
| 1.87 | B.87 | — |
| 1.88 | B.88 | — |
| 1.89 | B.89 | — |
| 1.90 | B.90 | — |
| 1.91 | B.91 | — |
| 1.92 | B.92 | — |
| 1.93 | B.93 | — |
| 1.94 | B.94 | — |
| 1.95 | B.95 | — |
| 1.96 | B.96 | — |
| 1.97 | B.97 | — |
| 1.98 | B.98 | — |
| 1.99 | B.99 | — |
| 1.100 | B.100 | — |
| 1.101 | B.101 | — |
| 1.102 | B.102 | — |
| 1.103 | B.103 | — |
| 1.104 | B.104 | — |
| 1.105 | B.105 | — |
| 1.106 | B.106 | — |
| 1.107 | B.107 | — |
| 1.108 | B.108 | — |
| 1.109 | B.109 | — |
| 1.110 | B.110 | — |
| 1.111 | B.111 | — |
| 1.112 | B.112 | — |
| 1.113 | B.113 | — |
| 1.114 | B.114 | — |
| 1.115 | B.115 | — |
| 1.116 | B.116 | — |
| 1.117 | B.117 | — |
| 1.118 | B.118 | — |
| 1.119 | B.119 | — |
| 1.120 | B.120 | — |
| 1.121 | B.121 | — |
| 1.122 | B.122 | — |
| 1.123 | B.123 | — |
| 1.124 | B.124 | — |
| 1.125 | B.125 | — |
| 1.126 | B.126 | — |
| 1.127 | B.127 | — |
| 1.128 | B.128 | — |
| 1.129 | B.129 | — |
| 1.130 | B.130 | — |
| 1.131 | B.131 | — |
| 1.132 | B.132 | — |
| 1.133 | B.133 | — |
| 1.134 | B.134 | — |
| 1.135 | B.135 | — |
| 1.136 | B.136 | — |
| 1.137 | B.137 | — |
| 1.138 | B.138 | — |
| 1.139 | B.139 | — |
| 1.140 | B.140 | — |
| 1.141 | B.141 | — |
| 1.142 | B.142 | — |
| 1.143 | B.143 | — |
| 1.144 | B.144 | — |
| 1.145 | B.145 | — |
| 1.146 | B.146 | — |
| 1.147 | B.147 | — |
| 1.148 | B.148 | — |
| 1.149 | B.149 | — |
| 1.150 | B.150 | — |
| 1.151 | B.151 | — |
| 1.152 | B.152 | — |
| 1.153 | B.153 | — |
| 1.154 | B.154 | — |
| 1.155 | B.155 | — |
| 1.156 | B.156 | — |
| 1.157 | B.157 | — |
| 1.158 | B.158 | — |
| 1.159 | B.159 | — |
| 1.160 | B.160 | — |
| 1.161 | B.161 | — |
| 1.162 | B.162 | — |
| 1.163 | B.163 | — |
| 1.164 | B.164 | — |
| 1.165 | B.165 | — |
| 1.166 | B.166 | — |
| 1.167 | B.167 | — |
| 1.168 | B.168 | — |
| 1.169 | B.169 | — |
| 1.170 | B.170 | — |
| 1.171 | B.171 | — |
| 1.172 | B.172 | — |
| 1.173 | B.173 | — |
| 1.174 | B.174 | — |
| 1.175 | B.175 | — |
| 1.176 | B.176 | — |
| 1.177 | B.177 | — |
| 1.178 | B.178 | — |
| 1.179 | B.179 | — |
| 1.180 | B.180 | — |
| 1.181 | B.181 | — |
| 1.182 | B.182 | — |
| 1.183 | B.183 | — |
| 1.184 | B.184 | — |
| 1.185 | B.185 | — |
| 1.186 | B.186 | — |
| 1.187 | B.187 | — |
| 1.188 | B.188 | — |
| 1.189 | B.189 | — |
| 1.190 | B.1 | C.1 |
| 1.191 | B.2 | C.1 |
| 1.192 | B.3 | C.1 |
| 1.193 | B.4 | C.1 |
| 1.194 | B.5 | C.1 |
| 1.195 | B.6 | C.1 |
| 1.196 | B.7 | C.1 |
| 1.197 | B.8 | C.1 |
| 1.198 | B.9 | C.1 |
| 1.199 | B.10 | C.1 |
| 1.200 | B.11 | C.1 |
| 1.201 | B.12 | C.1 |
| 1.202 | B.13 | C.1 |
| 1.203 | B.14 | C.1 |
| 1.204 | B.15 | C.1 |
| 1.205 | B.16 | C.1 |
| 1.206 | B.17 | C.1 |
| 1.207 | B.18 | C.1 |
| 1.208 | B.19 | C.1 |
| 1.209 | B.20 | C.1 |
| 1.210 | B.21 | C.1 |
| 1.211 | B.22 | C.1 |
| 1.212 | B.23 | C.1 |
| 1.213 | B.24 | C.1 |
| 1.214 | B.25 | C.1 |
| 1.215 | B.26 | C.1 |
| 1.216 | B.27 | C.1 |
| 1.217 | B.28 | C.1 |
| 1.218 | B.29 | C.1 |
| 1.219 | B.30 | C.1 |
| 1.220 | B.31 | C.1 |
| 1.221 | B.32 | C.1 |
| 1.222 | B.33 | C.1 |
| 1.223 | B.34 | C.1 |
| 1.224 | B.35 | C.1 |
| 1.225 | B.36 | C.1 |
| 1.226 | B.37 | C.1 |
| 1.227 | B.38 | C.1 |
| 1.228 | B.39 | C.1 |
| 1.229 | B.40 | C.1 |
| 1.230 | B.41 | C.1 |
| 1.231 | B.42 | C.1 |
| 1.232 | B.43 | C.1 |
| 1.233 | B.44 | C.1 |
| 1.234 | B.45 | C.1 |

TABLE 2-continued

| comb. no. | herbicide B | safener C |
|---|---|---|
| 1.235 | B.46 | C.1 |
| 1.236 | B.47 | C.1 |
| 1.237 | B.48 | C.1 |
| 1.238 | B.49 | C.1 |
| 1.239 | B.50 | C.1 |
| 1.240 | B.51 | C.1 |
| 1.241 | B.52 | C.1 |
| 1.242 | B.53 | C.1 |
| 1.243 | B.54 | C.1 |
| 1.244 | B.55 | C.1 |
| 1.245 | B.56 | C.1 |
| 1.246 | B.57 | C.1 |
| 1.247 | B.58. | C.1 |
| 1.248 | B.59 | C.1 |
| 1.249 | B.60 | C.1 |
| 1.250 | B.61 | C.1 |
| 1.251 | B.62 | C.1 |
| 1.252 | B.63 | C.1 |
| 1.253 | B.64 | C.1 |
| 1.254 | B.65 | C.1 |
| 1.255 | B.66 | C.1 |
| 1.256 | B.67 | C.1 |
| 1.257 | B.68 | C.1 |
| 1.258 | B.69 | C.1 |
| 1.259 | B.70 | C.1 |
| 1.260 | B.71 | C.1 |
| 1.261 | B.72 | C.1 |
| 1.262 | B.73 | C.1 |
| 1.263 | B.74 | C.1 |
| 1.264 | B.75 | C.1 |
| 1.265 | B.76 | C.1 |
| 1.266 | B.77 | C.1 |
| 1.267 | B.78 | C.1 |
| 1.268 | B.79 | C.1 |
| 1.269 | B.80 | C.1 |
| 1.270 | B.81 | C.1 |
| 1.271 | B.82 | C.1 |
| 1.272 | B.83 | C.1 |
| 1.273 | B.84 | C.1 |
| 1.274 | B.85 | C.1 |
| 1.275 | B.86 | C.1 |
| 1.276 | B.87 | C.1 |
| 1.277 | B.88 | C.1 |
| 1.278 | B.89 | C.1 |
| 1.279 | B.90 | C.1 |
| 1.280 | B.91 | C.1 |
| 1.281 | B.92 | C.1 |
| 1.282 | B.93 | C.1 |
| 1.283 | B.94 | C.1 |
| 1.284 | B.95 | C.1 |
| 1.285 | B.96 | C.1 |
| 1.286 | B.97 | C.1 |
| 1.287 | B.98 | C.1 |
| 1.288 | B.99 | C.1 |
| 1.289 | B.100 | C.1 |
| 1.290 | B.101 | C.1 |
| 1.291 | B.102 | C.1 |
| 1.292 | B.103 | C.1 |
| 1.293 | B.104 | C.1 |
| 1.294 | B.105 | C.1 |
| 1.295 | B.106 | C.1 |
| 1.296 | B.107 | C.1 |
| 1.297 | B.108 | C.1 |
| 1.298 | B.109 | C.1 |
| 1.299 | B.110 | C.1 |
| 1.300 | B.111 | C.1 |
| 1.301 | B.112 | C.1 |
| 1.302 | B.113 | C.1 |
| 1.303 | B.114 | C.1 |
| 1.304 | B.115 | C.1 |
| 1.305 | B.116 | C.1 |
| 1.306 | B.117 | C.1 |
| 1.307 | B.118 | C.1 |
| 1.308 | B.119 | C.1 |
| 1.309 | B.120 | C.1 |
| 1.310 | B.121 | C.1 |
| 1.311 | B.122 | C.1 |
| 1.312 | B.123 | C.1 |
| 1.313 | B.124 | C.1 |
| 1.314 | B.125 | C.1 |
| 1.315 | B.126 | C.1 |
| 1.316 | B.127 | C.1 |
| 1.317 | B.128 | C.1 |
| 1.318 | B.129 | C.1 |
| 1.319 | B.130 | C.1 |
| 1.320 | B.131 | C.1 |
| 1.321 | B.132 | C.1 |
| 1.322 | B.133 | C.1 |
| 1.323 | B.134 | C.1 |
| 1.324 | B.135 | C.1 |
| 1.325 | B.136 | C.1 |
| 1.326 | B.137 | C.1 |
| 1.327 | B.138 | C.1 |
| 1.328 | B.139 | C.1 |
| 1.329 | B.140 | C.1 |
| 1.330 | B.141 | C.1 |
| 1.331 | B.142 | C.1 |
| 1.332 | B.143 | C.1 |
| 1.333 | B.144 | C.1 |
| 1.334 | B.145 | C.1 |
| 1.335 | B.146 | C.1 |
| 1.336 | B.147 | C.1 |
| 1.337 | B.148 | C.1 |
| 1.338 | B.149 | C.1 |
| 1.339 | B.150 | C.1 |
| 1.340 | B.151 | C.1 |
| 1.341 | B.152 | C.1 |
| 1.342 | B.153 | C.1 |
| 1.343 | B.154 | C.1 |
| 1.344 | B.155 | C.1 |
| 1.345 | B.156 | C.1 |
| 1.346 | B.157 | C.1 |
| 1.347 | B.158 | C.1 |
| 1.348 | B.159 | C.1 |
| 1.349 | B.160 | C.1 |
| 1.350 | B.161 | C.1 |
| 1.351 | B.162 | C.1 |
| 1.352 | B.163 | C.1 |
| 1.353 | B.164 | C.1 |
| 1.354 | B.165 | C.1 |
| 1.355 | B.166 | C.1 |
| 1.356 | B.167 | C.1 |
| 1.357 | B.168 | C.1 |
| 1.358 | B.169 | C.1 |
| 1.359 | B.170 | C.1 |
| 1.360 | B.171 | C.1 |
| 1.361 | B.172 | C.1 |
| 1.362 | B.173 | C.1 |
| 1.363 | B.174 | C.1 |
| 1.364 | B.175 | C.1 |
| 1.365 | B.176 | C.1 |
| 1.366 | B.177 | C.1 |
| 1.367 | B.178 | C.1 |
| 1.368 | B.179 | C.1 |
| 1.369 | B.180 | C.1 |
| 1.370 | B.181 | C.1 |
| 1.371 | B.182 | C.1 |
| 1.372 | B.183 | C.1 |
| 1.373 | B.184 | C.1 |
| 1.374 | B.185 | C.1 |
| 1.375 | B.186 | C.1 |
| 1.376 | B.187 | C.1 |
| 1.377 | B.188 | C.1 |
| 1.378 | B.189 | C.1 |
| 1.379 | B.1 | C.2 |
| 1.380 | B.2 | C.2 |
| 1.381 | B.3 | C.2 |
| 1.382 | B.4 | C.2 |
| 1.383 | B.5 | C.2 |
| 1.384 | B.6 | C.2 |
| 1.385 | B.7 | C.2 |
| 1.386 | B.8 | C.2 |
| 1.387 | B.9 | C.2 |
| 1.388 | B.10 | C.2 |
| 1.389 | B.11 | C.2 |
| 1.390 | B.12 | C.2 |

TABLE 2-continued

| comb. no. | herbicide B | safener C |
|---|---|---|
| 1.391 | B.13 | C.2 |
| 1.392 | B.14 | C.2 |
| 1.393 | B.15 | C.2 |
| 1.394 | B.16 | C.2 |
| 1.395 | B.17 | C.2 |
| 1.396 | B.18 | C.2 |
| 1.397 | B.19 | C.2 |
| 1.398 | B.20 | C.2 |
| 1.399 | B.21 | C.2 |
| 1.400 | B.22 | C.2 |
| 1.401 | B.23 | C.2 |
| 1.402 | B.24 | C.2 |
| 1.403 | B.25 | C.2 |
| 1.404 | B.26 | C.2 |
| 1.405 | B.27 | C.2 |
| 1.406 | B.28 | C.2 |
| 1.407 | B.29 | C.2 |
| 1.408 | B.30 | C.2 |
| 1.409 | B.31 | C.2 |
| 1.410 | B.32 | C.2 |
| 1.411 | B.33 | C.2 |
| 1.412 | B.34 | C.2 |
| 1.413 | B.35 | C.2 |
| 1.414 | B.36 | C.2 |
| 1.415 | B.37 | C.2 |
| 1.416 | B.38 | C.2 |
| 1.417 | B.39 | C.2 |
| 1.418 | B.40 | C.2 |
| 1.419 | B.41 | C.2 |
| 1.420 | B.42 | C.2 |
| 1.421 | B.43 | C.2 |
| 1.422 | B.44 | C.2 |
| 1.423 | B.45 | C.2 |
| 1.424 | B.46 | C.2 |
| 1.425 | B.47 | C.2 |
| 1.426 | B.48 | C.2 |
| 1.427 | B.49 | C.2 |
| 1.428 | B.50 | C.2 |
| 1.429 | B.51 | C.2 |
| 1.430 | B.52 | C.2 |
| 1.431 | B.53 | C.2 |
| 1.432 | B.54 | C.2 |
| 1.433 | B.55 | C.2 |
| 1.434 | B.56 | C.2 |
| 1.435 | B.57 | C.2 |
| 1.436 | B.58. | C.2 |
| 1.437 | B.59 | C.2 |
| 1.438 | B.60 | C.2 |
| 1.439 | B.61 | C.2 |
| 1.440 | B.62 | C.2 |
| 1.441 | B.63 | C.2 |
| 1.442 | B.64 | C.2 |
| 1.443 | B.65 | C.2 |
| 1.444 | B.66 | C.2 |
| 1.445 | B.67 | C.2 |
| 1.446 | B.68 | C.2 |
| 1.447 | B.69 | C.2 |
| 1.448 | B.70 | C.2 |
| 1.449 | B.71 | C.2 |
| 1.450 | B.72 | C.2 |
| 1.451 | B.73 | C.2 |
| 1.452 | B.74 | C.2 |
| 1.453 | B.75 | C.2 |
| 1.454 | B.76 | C.2 |
| 1.455 | B.77 | C.2 |
| 1.456 | B.78 | C.2 |
| 1.457 | B.79 | C.2 |
| 1.458 | B.80 | C.2 |
| 1.459 | B.81 | C.2 |
| 1.460 | B.82 | C.2 |
| 1.461 | B.83 | C.2 |
| 1.462 | B.84 | C.2 |
| 1.463 | B.85 | C.2 |
| 1.464 | B.86 | C.2 |
| 1.465 | B.87 | C.2 |
| 1.466 | B.88 | C.2 |
| 1.467 | B.89 | C.2 |
| 1.468 | B.90 | C.2 |
| 1.469 | B.91 | C.2 |
| 1.470 | B.92 | C.2 |
| 1.471 | B.93 | C.2 |
| 1.472 | B.94 | C.2 |
| 1.473 | B.95 | C.2 |
| 1.474 | B.96 | C.2 |
| 1.475 | B.97 | C.2 |
| 1.476 | B.98 | C.2 |
| 1.477 | B.99 | C.2 |
| 1.478 | B.100 | C.2 |
| 1.479 | B.101 | C.2 |
| 1.480 | B.102 | C.2 |
| 1.481 | B.103 | C.2 |
| 1.482 | B.104 | C.2 |
| 1.483 | B.105 | C.2 |
| 1.484 | B.106 | C.2 |
| 1.485 | B.107 | C.2 |
| 1.486 | B.108 | C.2 |
| 1.487 | B.109 | C.2 |
| 1.488 | B.110 | C.2 |
| 1.489 | B.111 | C.2 |
| 1.490 | B.112 | C.2 |
| 1.491 | B.113 | C.2 |
| 1.492 | B.114 | C.2 |
| 1.493 | B.115 | C.2 |
| 1.494 | B.116 | C.2 |
| 1.495 | B.117 | C.2 |
| 1.496 | B.118 | C.2 |
| 1.497 | B.119 | C.2 |
| 1.498 | B.120 | C.2 |
| 1.499 | B.121 | C.2 |
| 1.500 | B.122 | C.2 |
| 1.501 | B.123 | C.2 |
| 1.502 | B.124 | C.2 |
| 1.503 | B.125 | C.2 |
| 1.504 | B.126 | C.2 |
| 1.505 | B.127 | C.2 |
| 1.506 | B.128 | C.2 |
| 1.507 | B.129 | C.2 |
| 1.508 | B.130 | C.2 |
| 1.509 | B.131 | C.2 |
| 1.510 | B.132 | C.2 |
| 1.511 | B.133 | C.2 |
| 1.512 | B.134 | C.2 |
| 1.513 | B.135 | C.2 |
| 1.514 | B.136 | C.2 |
| 1.515 | B.137 | C.2 |
| 1.516 | B.138 | C.2 |
| 1.517 | B.139 | C.2 |
| 1.518 | B.140 | C.2 |
| 1.519 | B.141 | C.2 |
| 1.520 | B.142 | C.2 |
| 1.521 | B.143 | C.2 |
| 1.522 | B.144 | C.2 |
| 1.523 | B.145 | C.2 |
| 1.524 | B.146 | C.2 |
| 1.525 | B.147 | C.2 |
| 1.526 | B.148 | C.2 |
| 1.527 | B.149 | C.2 |
| 1.528 | B.150 | C.2 |
| 1.529 | B.151 | C.2 |
| 1.530 | B.152 | C.2 |
| 1.531 | B.153 | C.2 |
| 1.532 | B.154 | C.2 |
| 1.533 | B.155 | C.2 |
| 1.534 | B.156 | C.2 |
| 1.535 | B.157 | C.2 |
| 1.536 | B.158 | C.2 |
| 1.537 | B.159 | C.2 |
| 1.538 | B.160 | C.2 |
| 1.539 | B.161 | C.2 |
| 1.540 | B.162 | C.2 |
| 1.541 | B.163 | C.2 |
| 1.542 | B.164 | C.2 |
| 1.543 | B.165 | C.2 |
| 1.544 | B.166 | C.2 |
| 1.545 | B.167 | C.2 |
| 1.546 | B.168 | C.2 |

TABLE 2-continued

| comb. no. | herbicide B | safener C |
|---|---|---|
| 1.547 | B.169 | C.2 |
| 1.548 | B.170 | C.2 |
| 1.549 | B.171 | C.2 |
| 1.550 | B.172 | C.2 |
| 1.551 | B.173 | C.2 |
| 1.552 | B.174 | C.2 |
| 1.553 | B.175 | C.2 |
| 1.554 | B.176 | C.2 |
| 1.555 | B.177 | C.2 |
| 1.556 | B.178 | C.2 |
| 1.557 | B.179 | C.2 |
| 1.558 | B.180 | C.2 |
| 1.559 | B.181 | C.2 |
| 1.560 | B.182 | C.2 |
| 1.561 | B.183 | C.2 |
| 1.562 | B.184 | C.2 |
| 1.563 | B.185 | C.2 |
| 1.564 | B.186 | C.2 |
| 1.565 | B.187 | C.2 |
| 1.566 | B.188 | C.2 |
| 1.567 | B.189 | C.2 |
| 1.568 | B.1 | C.3 |
| 1.569 | B.2 | C.3 |
| 1.570 | B.3 | C.3 |
| 1.571 | B.4 | C.3 |
| 1.572 | B.5 | C.3 |
| 1.573 | B.6 | C.3 |
| 1.574 | B.7 | C.3 |
| 1.575 | B.8 | C.3 |
| 1.576 | B.9 | C.3 |
| 1.577 | B.10 | C.3 |
| 1.578 | B.11 | C.3 |
| 1.579 | B.12 | C.3 |
| 1.580 | B.13 | C.3 |
| 1.581 | B.14 | C.3 |
| 1.582 | B.15 | C.3 |
| 1.583 | B.16 | C.3 |
| 1.584 | B.17 | C.3 |
| 1.585 | B.18 | C.3 |
| 1.586 | B.19 | C.3 |
| 1.587 | B.20 | C.3 |
| 1.588 | B.21 | C.3 |
| 1.589 | B.22 | C.3 |
| 1.590 | B.23 | C.3 |
| 1.591 | B.24 | C.3 |
| 1.592 | B.25 | C.3 |
| 1.593 | B.26 | C.3 |
| 1.594 | B.27 | C.3 |
| 1.595 | B.28 | C.3 |
| 1.596 | B.29 | C.3 |
| 1.597 | B.30 | C.3 |
| 1.598 | B.31 | C.3 |
| 1.599 | B.32 | C.3 |
| 1.600 | B.33 | C.3 |
| 1.601 | B.34 | C.3 |
| 1.602 | B.35 | C.3 |
| 1.603 | B.36 | C.3 |
| 1.604 | B.37 | C.3 |
| 1.605 | B.38 | C.3 |
| 1.606 | B.39 | C.3 |
| 1.607 | B.40 | C.3 |
| 1.608 | B.41 | C.3 |
| 1.609 | B.42 | C.3 |
| 1.610 | B.43 | C.3 |
| 1.611 | B.44 | C.3 |
| 1.612 | B.45 | C.3 |
| 1.613 | B.46 | C.3 |
| 1.614 | B.47 | C.3 |
| 1.615 | B.48 | C.3 |
| 1.616 | B.49 | C.3 |
| 1.617 | B.50 | C.3 |
| 1.618 | B.51 | C.3 |
| 1.619 | B.52 | C.3 |
| 1.620 | B.53 | C.3 |
| 1.621 | B.54 | C.3 |
| 1.622 | B.55 | C.3 |
| 1.623 | B.56 | C.3 |
| 1.624 | B.57 | C.3 |
| 1.625 | B.58. | C.3 |
| 1.626 | B.59 | C.3 |
| 1.627 | B.60 | C.3 |
| 1.628 | B.61 | C.3 |
| 1.629 | B.62 | C.3 |
| 1.630 | B.63 | C.3 |
| 1.631 | B.64 | C.3 |
| 1.632 | B.65 | C.3 |
| 1.633 | B.66 | C.3 |
| 1.634 | B.67 | C.3 |
| 1.635 | B.68 | C.3 |
| 1.636 | B.69 | C.3 |
| 1.637 | B.70 | C.3 |
| 1.638 | B.71 | C.3 |
| 1.639 | B.72 | C.3 |
| 1.640 | B.73 | C.3 |
| 1.641 | B.74 | C.3 |
| 1.642 | B.75 | C.3 |
| 1.643 | B.76 | C.3 |
| 1.644 | B.77 | C.3 |
| 1.645 | B.78 | C.3 |
| 1.646 | B.79 | C.3 |
| 1.647 | B.80 | C.3 |
| 1.648 | B.81 | C.3 |
| 1.649 | B.82 | C.3 |
| 1.650 | B.83 | C.3 |
| 1.651 | B.84 | C.3 |
| 1.652 | B.85 | C.3 |
| 1.653 | B.86 | C.3 |
| 1.654 | B.87 | C.3 |
| 1.655 | B.88 | C.3 |
| 1.656 | B.89 | C.3 |
| 1.657 | B.90 | C.3 |
| 1.658 | B.91 | C.3 |
| 1.659 | B.92 | C.3 |
| 1.660 | B.93 | C.3 |
| 1.661 | B.94 | C.3 |
| 1.662 | B.95 | C.3 |
| 1.663 | B.96 | C.3 |
| 1.664 | B.97 | C.3 |
| 1.665 | B.98 | C.3 |
| 1.666 | B.99 | C.3 |
| 1.667 | B.100 | C.3 |
| 1.668 | B.101 | C.3 |
| 1.669 | B.102 | C.3 |
| 1.670 | B.103 | C.3 |
| 1.671 | B.104 | C.3 |
| 1.672 | B.105 | C.3 |
| 1.673 | B.106 | C.3 |
| 1.674 | B.107 | C.3 |
| 1.675 | B.108 | C.3 |
| 1.676 | B.109 | C.3 |
| 1.677 | B.110 | C.3 |
| 1.678 | B.111 | C.3 |
| 1.679 | B.112 | C.3 |
| 1.680 | B.113 | C.3 |
| 1.681 | B.114 | C.3 |
| 1.682 | B.115 | C.3 |
| 1.683 | B.116 | C.3 |
| 1.684 | B.117 | C.3 |
| 1.685 | B.118 | C.3 |
| 1.686 | B.119 | C.3 |
| 1.687 | B.120 | C.3 |
| 1.688 | B.121 | C.3 |
| 1.689 | B.122 | C.3 |
| 1.690 | B.123 | C.3 |
| 1.691 | B.124 | C.3 |
| 1.692 | B.125 | C.3 |
| 1.693 | B.126 | C.3 |
| 1.694 | B.127 | C.3 |
| 1.695 | B.128 | C.3 |
| 1.696 | B.129 | C.3 |
| 1.697 | B.130 | C.3 |
| 1.698 | B.131 | C.3 |
| 1.699 | B.132 | C.3 |
| 1.700 | B.133 | C.3 |
| 1.701 | B.134 | C.3 |
| 1.702 | B.135 | C.3 |

TABLE 2-continued

| comb. no. | herbicide B | safener C |
|---|---|---|
| 1.703 | B.136 | C.3 |
| 1.704 | B.137 | C.3 |
| 1.705 | B.138 | C.3 |
| 1.706 | B.139 | C.3 |
| 1.707 | B.140 | C.3 |
| 1.708 | B.141 | C.3 |
| 1.709 | B.142 | C.3 |
| 1.710 | B.143 | C.3 |
| 1.711 | B.144 | C.3 |
| 1.712 | B.145 | C.3 |
| 1.713 | B.146 | C.3 |
| 1.714 | B.147 | C.3 |
| 1.715 | B.148 | C.3 |
| 1.716 | B.149 | C.3 |
| 1.717 | B.150 | C.3 |
| 1.718 | B.151 | C.3 |
| 1.719 | B.152 | C.3 |
| 1.720 | B.153 | C.3 |
| 1.721 | B.154 | C.3 |
| 1.722 | B.155 | C.3 |
| 1.723 | B.156 | C.3 |
| 1.724 | B.157 | C.3 |
| 1.725 | B.158 | C.3 |
| 1.726 | B.159 | C.3 |
| 1.727 | B.160 | C.3 |
| 1.728 | B.161 | C.3 |
| 1.729 | B.162 | C.3 |
| 1.730 | B.163 | C.3 |
| 1.731 | B.164 | C.3 |
| 1.732 | B.165 | C.3 |
| 1.733 | B.166 | C.3 |
| 1.734 | B.167 | C.3 |
| 1.735 | B.168 | C.3 |
| 1.736 | B.169 | C.3 |
| 1.737 | B.170 | C.3 |
| 1.738 | B.171 | C.3 |
| 1.739 | B.172 | C.3 |
| 1.740 | B.173 | C.3 |
| 1.741 | B.174 | C.3 |
| 1.742 | B.175 | C.3 |
| 1.743 | B.176 | C.3 |
| 1.744 | B.177 | C.3 |
| 1.745 | B.178 | C.3 |
| 1.746 | B.179 | C.3 |
| 1.747 | B.180 | C.3 |
| 1.748 | B.181 | C.3 |
| 1.749 | B.182 | C.3 |
| 1.750 | B.183 | C.3 |
| 1.751 | B.184 | C.3 |
| 1.752 | B.185 | C.3 |
| 1.753 | B.186 | C.3 |
| 1.754 | B.187 | C.3 |
| 1.755 | B.188 | C.3 |
| 1.756 | B.189 | C.3 |
| 1.757 | B.1 | C.4 |
| 1.758 | B.2 | C.4 |
| 1.759 | B.3 | C.4 |
| 1.760 | B.4 | C.4 |
| 1.761 | B.5 | C.4 |
| 1.762 | B.6 | C.4 |
| 1.763 | B.7 | C.4 |
| 1.764 | B.8 | C.4 |
| 1.765 | B.9 | C.4 |
| 1.766 | B.10 | C.4 |
| 1.767 | B.11 | C.4 |
| 1.768 | B.12 | C.4 |
| 1.769 | B.13 | C.4 |
| 1.770 | B.14 | C.4 |
| 1.771 | B.15 | C.4 |
| 1.772 | B.16 | C.4 |
| 1.773 | B.17 | C.4 |
| 1.774 | B.18 | C.4 |
| 1.775 | B.19 | C.4 |
| 1.776 | B.20 | C.4 |
| 1.777 | B.21 | C.4 |
| 1.778 | B.22 | C.4 |
| 1.779 | B.23 | C.4 |
| 1.780 | B.24 | C.4 |
| 1.781 | B.25 | C.4 |
| 1.782 | B.26 | C.4 |
| 1.783 | B.27 | C.4 |
| 1.784 | B.28 | C.4 |
| 1.785 | B.29 | C.4 |
| 1.786 | B.30 | C.4 |
| 1.787 | B.31 | C.4 |
| 1.788 | B.32 | C.4 |
| 1.789 | B.33 | C.4 |
| 1.790 | B.34 | C.4 |
| 1.791 | B.35 | C.4 |
| 1.792 | B.36 | C.4 |
| 1.793 | B.37 | C.4 |
| 1.794 | B.38 | C.4 |
| 1.795 | B.39 | C.4 |
| 1.796 | B.40 | C.4 |
| 1.797 | B.41 | C.4 |
| 1.798 | B.42 | C.4 |
| 1.799 | B.43 | C.4 |
| 1.800 | B.44 | C.4 |
| 1.801 | B.45 | C.4 |
| 1.802 | B.46 | C.4 |
| 1.803 | B.47 | C.4 |
| 1.804 | B.48 | C.4 |
| 1.805 | B.49 | C.4 |
| 1.806 | B.50 | C.4 |
| 1.807 | B.51 | C.4 |
| 1.808 | B.52 | C.4 |
| 1.809 | B.53 | C.4 |
| 1.810 | B.54 | C.4 |
| 1.811 | B.55 | C.4 |
| 1.812 | B.56 | C.4 |
| 1.813 | B.57 | C.4 |
| 1.814 | B.58. | C.4 |
| 1.815 | B.59 | C.4 |
| 1.816 | B.60 | C.4 |
| 1.817 | B.61 | C.4 |
| 1.818 | B.62 | C.4 |
| 1.819 | B.63 | C.4 |
| 1.820 | B.64 | C.4 |
| 1.821 | B.65 | C.4 |
| 1.822 | B.66 | C.4 |
| 1.823 | B.67 | C.4 |
| 1.824 | B.68 | C.4 |
| 1.825 | B.69 | C.4 |
| 1.826 | B.70 | C.4 |
| 1.827 | B.71 | C.4 |
| 1.828 | B.72 | C.4 |
| 1.829 | B.73 | C.4 |
| 1.830 | B.74 | C.4 |
| 1.831 | B.75 | C.4 |
| 1.832 | B.76 | C.4 |
| 1.833 | B.77 | C.4 |
| 1.834 | B.78 | C.4 |
| 1.835 | B.79 | C.4 |
| 1.836 | B.80 | C.4 |
| 1.837 | B.81 | C.4 |
| 1.838 | B.82 | C.4 |
| 1.839 | B.83 | C.4 |
| 1.840 | B.84 | C.4 |
| 1.841 | B.85 | C.4 |
| 1.842 | B.86 | C.4 |
| 1.843 | B.87 | C.4 |
| 1.844 | B.88 | C.4 |
| 1.845 | B.89 | C.4 |
| 1.846 | B.90 | C.4 |
| 1.847 | B.91 | C.4 |
| 1.848 | B.92 | C.4 |
| 1.849 | B.93 | C.4 |
| 1.850 | B.94 | C.4 |
| 1.851 | B.95 | C.4 |
| 1.852 | B.96 | C.4 |
| 1.853 | B.97 | C.4 |
| 1.854 | B.98 | C.4 |
| 1.855 | B.99 | C.4 |
| 1.856 | B.100 | C.4 |
| 1.857 | B.101 | C.4 |
| 1.858 | B.102 | C.4 |

TABLE 2-continued

| comb. no. | herbicide B | safener C |
|---|---|---|
| 1.859 | B.103 | C.4 |
| 1.860 | B.104 | C.4 |
| 1.861 | B.105 | C.4 |
| 1.862 | B.106 | C.4 |
| 1.863 | B.107 | C.4 |
| 1.864 | B.108 | C.4 |
| 1.865 | B.109 | C.4 |
| 1.866 | B.110 | C.4 |
| 1.867 | B.111 | C.4 |
| 1.868 | B.112 | C.4 |
| 1.869 | B.113 | C.4 |
| 1.870 | B.114 | C.4 |
| 1.871 | B.115 | C.4 |
| 1.872 | B.116 | C.4 |
| 1.873 | B.117 | C.4 |
| 1.874 | B.118 | C.4 |
| 1.875 | B.119 | C.4 |
| 1.876 | B.120 | C.4 |
| 1.877 | B.121 | C.4 |
| 1.878 | B.122 | C.4 |
| 1.879 | B.123 | C.4 |
| 1.880 | B.124 | C.4 |
| 1.881 | B.125 | C.4 |
| 1.882 | B.126 | C.4 |
| 1.883 | B.127 | C.4 |
| 1.884 | B.128 | C.4 |
| 1.885 | B.129 | C.4 |
| 1.886 | B.130 | C.4 |
| 1.887 | B.131 | C.4 |
| 1.888 | B.132 | C.4 |
| 1.889 | B.133 | C.4 |
| 1.890 | B.134 | C.4 |
| 1.891 | B.135 | C.4 |
| 1.892 | B.136 | C.4 |
| 1.893 | B.137 | C.4 |
| 1.894 | B.138 | C.4 |
| 1.895 | B.139 | C.4 |
| 1.896 | B.140 | C.4 |
| 1.897 | B.141 | C.4 |
| 1.898 | B.142 | C.4 |
| 1.899 | B.143 | C.4 |
| 1.900 | B.144 | C.4 |
| 1.901 | B.145 | C.4 |
| 1.902 | B.146 | C.4 |
| 1.903 | B.147 | C.4 |
| 1.904 | B.148 | C.4 |
| 1.905 | B.149 | C.4 |
| 1.906 | B.150 | C.4 |
| 1.907 | B.151 | C.4 |
| 1.908 | B.152 | C.4 |
| 1.909 | B.153 | C.4 |
| 1.910 | B.154 | C.4 |
| 1.911 | B.155 | C.4 |
| 1.912 | B.156 | C.4 |
| 1.913 | B.157 | C.4 |
| 1.914 | B.158 | C.4 |
| 1.915 | B.159 | C.4 |
| 1.916 | B.160 | C.4 |
| 1.917 | B.161 | C.4 |
| 1.918 | B.162 | C.4 |
| 1.919 | B.163 | C.4 |
| 1.920 | B.164 | C.4 |
| 1.921 | B.165 | C.4 |
| 1.922 | B.166 | C.4 |
| 1.923 | B.167 | C.4 |
| 1.924 | B.168 | C.4 |
| 1.925 | B.169 | C.4 |
| 1.926 | B.170 | C.4 |
| 1.927 | B.171 | C.4 |
| 1.928 | B.172 | C.4 |
| 1.929 | B.173 | C.4 |
| 1.930 | B.174 | C.4 |
| 1.931 | B.175 | C.4 |
| 1.932 | B.176 | C.4 |
| 1.933 | B.177 | C.4 |
| 1.934 | B.178 | C.4 |
| 1.935 | B.179 | C.4 |
| 1.936 | B.180 | C.4 |
| 1.937 | B.181 | C.4 |
| 1.938 | B.182 | C.4 |
| 1.939 | B.183 | C.4 |
| 1.940 | B.184 | C.4 |
| 1.941 | B.185 | C.4 |
| 1.942 | B.186 | C.4 |
| 1.943 | B.187 | C.4 |
| 1.944 | B.188 | C.4 |
| 1.945 | B.189 | C.4 |
| 1.946 | B.1 | C.5 |
| 1.947 | B.2 | C.5 |
| 1.948 | B.3 | C.5 |
| 1.949 | B.4 | C.5 |
| 1.950 | B.5 | C.5 |
| 1.951 | B.6 | C.5 |
| 1.952 | B.7 | C.5 |
| 1.953 | B.8 | C.5 |
| 1.954 | B.9 | C.5 |
| 1.955 | B.10 | C.5 |
| 1.956 | B.11 | C.5 |
| 1.957 | B.12 | C.5 |
| 1.958 | B.13 | C.5 |
| 1.959 | B.14 | C.5 |
| 1.960 | B.15 | C.5 |
| 1.961 | B.16 | C.5 |
| 1.962 | B.17 | C.5 |
| 1.963 | B.18 | C.5 |
| 1.964 | B.19 | C.5 |
| 1.965 | B.20 | C.5 |
| 1.966 | B.21 | C.5 |
| 1.967 | B.22 | C.5 |
| 1.968 | B.23 | C.5 |
| 1.969 | B.24 | C.5 |
| 1.970 | B.25 | C.5 |
| 1.971 | B.26 | C.5 |
| 1.972 | B.27 | C.5 |
| 1.973 | B.28 | C.5 |
| 1.974 | B.29 | C.5 |
| 1.975 | B.30 | C.5 |
| 1.976 | B.31 | C.5 |
| 1.977 | B.32 | C.5 |
| 1.978 | B.33 | C.5 |
| 1.979 | B.34 | C.5 |
| 1.980 | B.35 | C.5 |
| 1.981 | B.36 | C.5 |
| 1.982 | B.37 | C.5 |
| 1.983 | B.38 | C.5 |
| 1.984 | B.39 | C.5 |
| 1.985 | B.40 | C.5 |
| 1.986 | B.41 | C.5 |
| 1.987 | B.42 | C.5 |
| 1.988 | B.43 | C.5 |
| 1.989 | B.44 | C.5 |
| 1.990 | B.45 | C.5 |
| 1.991 | B.46 | C.5 |
| 1.992 | B.47 | C.5 |
| 1.993 | B.48 | C.5 |
| 1.994 | B.49 | C.5 |
| 1.995 | B.50 | C.5 |
| 1.996 | B.51 | C.5 |
| 1.997 | B.52 | C.5 |
| 1.998 | B.53 | C.5 |
| 1.999 | B.54 | C.5 |
| 1.1000 | B.55 | C.5 |
| 1.1001 | B.56 | C.5 |
| 1.1002 | B.57 | C.5 |
| 1.1003 | B.58. | C.5 |
| 1.1004 | B.59 | C.5 |
| 1.1005 | B.60 | C.5 |
| 1.1006 | B.61 | C.5 |
| 1.1007 | B.62 | C.5 |
| 1.1008 | B.63 | C.5 |
| 1.1009 | B.64 | C.5 |
| 1.1010 | B.65 | C.5 |
| 1.1011 | B.66 | C.5 |
| 1.1012 | B.67 | C.5 |
| 1.1013 | B.68 | C.5 |
| 1.1014 | B.69 | C.5 |

TABLE 2-continued

| comb. no. | herbicide B | safener C |
|---|---|---|
| 1.1015 | B.70 | C.5 |
| 1.1016 | B.71 | C.5 |
| 1.1017 | B.72 | C.5 |
| 1.1018 | B.73 | C.5 |
| 1.1019 | B.74 | C.5 |
| 1.1020 | B.75 | C.5 |
| 1.1021 | B.76 | C.5 |
| 1.1022 | B.77 | C.5 |
| 1.1023 | B.78 | C.5 |
| 1.1024 | B.79 | C.5 |
| 1.1025 | B.80 | C.5 |
| 1.1026 | B.81 | C.5 |
| 1.1027 | B.82 | C.5 |
| 1.1028 | B.83 | C.5 |
| 1.1029 | B.84 | C.5 |
| 1.1030 | B.85 | C.5 |
| 1.1031 | B.86 | C.5 |
| 1.1032 | B.87 | C.5 |
| 1.1033 | B.88 | C.5 |
| 1.1034 | B.89 | C.5 |
| 1.1035 | B.90 | C.5 |
| 1.1036 | B.91 | C.5 |
| 1.1037 | B.92 | C.5 |
| 1.1038 | B.93 | C.5 |
| 1.1039 | B.94 | C.5 |
| 1.1040 | B.95 | C.5 |
| 1.1041 | B.96 | C.5 |
| 1.1042 | B.97 | C.5 |
| 1.1043 | B.98 | C.5 |
| 1.1044 | B.99 | C.5 |
| 1.1045 | B.100 | C.5 |
| 1.1046 | B.101 | C.5 |
| 1.1047 | B.102 | C.5 |
| 1.1048 | B.103 | C.5 |
| 1.1049 | B.104 | C.5 |
| 1.1050 | B.105 | C.5 |
| 1.1051 | B.106 | C.5 |
| 1.1052 | B.107 | C.5 |
| 1.1053 | B.108 | C.5 |
| 1.1054 | B.109 | C.5 |
| 1.1055 | B.110 | C.5 |
| 1.1056 | B.111 | C.5 |
| 1.1057 | B.112 | C.5 |
| 1.1058 | B.113 | C.5 |
| 1.1059 | B.114 | C.5 |
| 1.1060 | B.115 | C.5 |
| 1.1061 | B.116 | C.5 |
| 1.1062 | B.117 | C.5 |
| 1.1063 | B.118 | C.5 |
| 1.1064 | B.119 | C.5 |
| 1.1065 | B.120 | C.5 |
| 1.1066 | B.121 | C.5 |
| 1.1067 | B.122 | C.5 |
| 1.1068 | B.123 | C.5 |
| 1.1069 | B.124 | C.5 |
| 1.1070 | B.125 | C.5 |
| 1.1071 | B.126 | C.5 |
| 1.1072 | B.127 | C.5 |
| 1.1073 | B.128 | C.5 |
| 1.1074 | B.129 | C.5 |
| 1.1075 | B.130 | C.5 |
| 1.1076 | B.131 | C.5 |
| 1.1077 | B.132 | C.5 |
| 1.1078 | B.133 | C.5 |
| 1.1079 | B.134 | C.5 |
| 1.1080 | B.135 | C.5 |
| 1.1081 | B.136 | C.5 |
| 1.1082 | B.137 | C.5 |
| 1.1083 | B.138 | C.5 |
| 1.1084 | B.139 | C.5 |
| 1.1085 | B.140 | C.5 |
| 1.1086 | B.141 | C.5 |
| 1.1087 | B.142 | C.5 |
| 1.1088 | B.143 | C.5 |
| 1.1089 | B.144 | C.5 |
| 1.1090 | B.145 | C.5 |
| 1.1091 | B.146 | C.5 |
| 1.1092 | B.147 | C.5 |
| 1.1093 | B.148 | C.5 |
| 1.1094 | B.149 | C.5 |
| 1.1095 | B.150 | C.5 |
| 1.1096 | B.151 | C.5 |
| 1.1097 | B.152 | C.5 |
| 1.1098 | B.153 | C.5 |
| 1.1099 | B.154 | C.5 |
| 1.1100 | B.155 | C.5 |
| 1.1101 | B.156 | C.5 |
| 1.1102 | B.157 | C.5 |
| 1.1103 | B.158 | C.5 |
| 1.1104 | B.159 | C.5 |
| 1.1105 | B.160 | C.5 |
| 1.1106 | B.161 | C.5 |
| 1.1107 | B.162 | C.5 |
| 1.1108 | B.163 | C.5 |
| 1.1109 | B.164 | C.5 |
| 1.1110 | B.165 | C.5 |
| 1.1111 | B.166 | C.5 |
| 1.1112 | B.167 | C.5 |
| 1.1113 | B.168 | C.5 |
| 1.1114 | B.169 | C.5 |
| 1.1115 | B.170 | C.5 |
| 1.1116 | B.171 | C.5 |
| 1.1117 | B.172 | C.5 |
| 1.1118 | B.173 | C.5 |
| 1.1119 | B.174 | C.5 |
| 1.1120 | B.175 | C.5 |
| 1.1121 | B.176 | C.5 |
| 1.1122 | B.177 | C.5 |
| 1.1123 | B.178 | C.5 |
| 1.1124 | B.179 | C.5 |
| 1.1125 | B.180 | C.5 |
| 1.1126 | B.181 | C.5 |
| 1.1127 | B.182 | C.5 |
| 1.1128 | B.183 | C.5 |
| 1.1129 | B.184 | C.5 |
| 1.1130 | B.185 | C.5 |
| 1.1131 | B.186 | C.5 |
| 1.1132 | B.187 | C.5 |
| 1.1133 | B.188 | C.5 |
| 1.1134 | B.189 | C.5 |
| 1.1135 | B.1 | C.6 |
| 1.1136 | B.2 | C.6 |
| 1.1137 | B.3 | C.6 |
| 1.1138 | B.4 | C.6 |
| 1.1139 | B.5 | C.6 |
| 1.1140 | B.6 | C.6 |
| 1.1141 | B.7 | C.6 |
| 1.1142 | B.8 | C.6 |
| 1.1143 | B.9 | C.6 |
| 1.1144 | B.10 | C.6 |
| 1.1145 | B.11 | C.6 |
| 1.1146 | B.12 | C.6 |
| 1.1147 | B.13 | C.6 |
| 1.1148 | B.14 | C.6 |
| 1.1149 | B.15 | C.6 |
| 1.1150 | B.16 | C.6 |
| 1.1151 | B.17 | C.6 |
| 1.1152 | B.18 | C.6 |
| 1.1153 | B.19 | C.6 |
| 1.1154 | B.20 | C.6 |
| 1.1155 | B.21 | C.6 |
| 1.1156 | B.22 | C.6 |
| 1.1157 | B.23 | C.6 |
| 1.1158 | B.24 | C.6 |
| 1.1159 | B.25 | C.6 |
| 1.1160 | B.26 | C.6 |
| 1.1161 | B.27 | C.6 |
| 1.1162 | B.28 | C.6 |
| 1.1163 | B.29 | C.6 |
| 1.1164 | B.30 | C.6 |
| 1.1165 | B.31 | C.6 |
| 1.1166 | B.32 | C.6 |
| 1.1167 | B.33 | C.6 |
| 1.1168 | B.34 | C.6 |
| 1.1169 | B.35 | C.6 |
| 1.1170 | B.36 | C.6 |

TABLE 2-continued

| comb. no. | herbicide B | safener C |
|---|---|---|
| 1.1171 | B.37 | C.6 |
| 1.1172 | B.38 | C.6 |
| 1.1173 | B.39 | C.6 |
| 1.1174 | B.40 | C.6 |
| 1.1175 | B.41 | C.6 |
| 1.1176 | B.42 | C.6 |
| 1.1177 | B.43 | C.6 |
| 1.1178 | B.44 | C.6 |
| 1.1179 | B.45 | C.6 |
| 1.1180 | B.46 | C.6 |
| 1.1181 | B.47 | C.6 |
| 1.1182 | B.48 | C.6 |
| 1.1183 | B.49 | C.6 |
| 1.1184 | B.50 | C.6 |
| 1.1185 | B.51 | C.6 |
| 1.1186 | B.52 | C.6 |
| 1.1187 | B.53 | C.6 |
| 1.1188 | B.54 | C.6 |
| 1.1189 | B.55 | C.6 |
| 1.1190 | B.56 | C.6 |
| 1.1191 | B.57 | C.6 |
| 1.1192 | B.58. | C.6 |
| 1.1193 | B.59 | C.6 |
| 1.1194 | B.60 | C.6 |
| 1.1195 | B.61 | C.6 |
| 1.1196 | B.62 | C.6 |
| 1.1197 | B.63 | C.6 |
| 1.1198 | B.64 | C.6 |
| 1.1199 | B.65 | C.6 |
| 1.1200 | B.66 | C.6 |
| 1.1201 | B.67 | C.6 |
| 1.1202 | B.68 | C.6 |
| 1.1203 | B.69 | C.6 |
| 1.1204 | B.70 | C.6 |
| 1.1205 | B.71 | C.6 |
| 1.1206 | B.72 | C.6 |
| 1.1207 | B.73 | C.6 |
| 1.1208 | B.74 | C.6 |
| 1.1209 | B.75 | C.6 |
| 1.1210 | B.76 | C.6 |
| 1.1211 | B.77 | C.6 |
| 1.1212 | B.78 | C.6 |
| 1.1213 | B.79 | C.6 |
| 1.1214 | B.80 | C.6 |
| 1.1215 | B.81 | C.6 |
| 1.1216 | B.82 | C.6 |
| 1.1217 | B.83 | C.6 |
| 1.1218 | B.84 | C.6 |
| 1.1219 | B.85 | C.6 |
| 1.1220 | B.86 | C.6 |
| 1.1221 | B.87 | C.6 |
| 1.1222 | B.88 | C.6 |
| 1.1223 | B.89 | C.6 |
| 1.1224 | B.90 | C.6 |
| 1.1225 | B.91 | C.6 |
| 1.1226 | B.92 | C.6 |
| 1.1227 | B.93 | C.6 |
| 1.1228 | B.94 | C.6 |
| 1.1229 | B.95 | C.6 |
| 1.1230 | B.96 | C.6 |
| 1.1231 | B.97 | C.6 |
| 1.1232 | B.98 | C.6 |
| 1.1233 | B.99 | C.6 |
| 1.1234 | B.100 | C.6 |
| 1.1235 | B.101 | C.6 |
| 1.1236 | B.102 | C.6 |
| 1.1237 | B.103 | C.6 |
| 1.1238 | B.104 | C.6 |
| 1.1239 | B.105 | C.6 |
| 1.1240 | B.106 | C.6 |
| 1.1241 | B.107 | C.6 |
| 1.1242 | B.108 | C.6 |
| 1.1243 | B.109 | C.6 |
| 1.1244 | B.110 | C.6 |
| 1.1245 | B.111 | C.6 |
| 1.1246 | B.112 | C.6 |
| 1.1247 | B.113 | C.6 |
| 1.1248 | B.114 | C.6 |
| 1.1249 | B.115 | C.6 |
| 1.1250 | B.116 | C.6 |
| 1.1251 | B.117 | C.6 |
| 1.1252 | B.118 | C.6 |
| 1.1253 | B.119 | C.6 |
| 1.1254 | B.120 | C.6 |
| 1.1255 | B.121 | C.6 |
| 1.1256 | B.122 | C.6 |
| 1.1257 | B.123 | C.6 |
| 1.1258 | B.124 | C.6 |
| 1.1259 | B.125 | C.6 |
| 1.1260 | B.126 | C.6 |
| 1.1261 | B.127 | C.6 |
| 1.1262 | B.128 | C.6 |
| 1.1263 | B.129 | C.6 |
| 1.1264 | B.130 | C.6 |
| 1.1265 | B.131 | C.6 |
| 1.1266 | B.132 | C.6 |
| 1.1267 | B.133 | C.6 |
| 1.1268 | B.134 | C.6 |
| 1.1269 | B.135 | C.6 |
| 1.1270 | B.136 | C.6 |
| 1.1271 | B.137 | C.6 |
| 1.1272 | B.138 | C.6 |
| 1.1273 | B.139 | C.6 |
| 1.1274 | B.140 | C.6 |
| 1.1275 | B.141 | C.6 |
| 1.1276 | B.142 | C.6 |
| 1.1277 | B.143 | C.6 |
| 1.1278 | B.144 | C.6 |
| 1.1279 | B.145 | C.6 |
| 1.1280 | B.146 | C.6 |
| 1.1281 | B.147 | C.6 |
| 1.1282 | B.148 | C.6 |
| 1.1283 | B.149 | C.6 |
| 1.1284 | B.150 | C.6 |
| 1.1285 | B.151 | C.6 |
| 1.1286 | B.152 | C.6 |
| 1.1287 | B.153 | C.6 |
| 1.1288 | B.154 | C.6 |
| 1.1289 | B.155 | C.6 |
| 1.1290 | B.156 | C.6 |
| 1.1291 | B.157 | C.6 |
| 1.1292 | B.158 | C.6 |
| 1.1293 | B.159 | C.6 |
| 1.1294 | B.160 | C.6 |
| 1.1295 | B.161 | C.6 |
| 1.1296 | B.162 | C.6 |
| 1.1297 | B.163 | C.6 |
| 1.1298 | B.164 | C.6 |
| 1.1299 | B.165 | C.6 |
| 1.1300 | B.166 | C.6 |
| 1.1301 | B.167 | C.6 |
| 1.1302 | B.168 | C.6 |
| 1.1303 | B.169 | C.6 |
| 1.1304 | B.170 | C.6 |
| 1.1305 | B.171 | C.6 |
| 1.1306 | B.172 | C.6 |
| 1.1307 | B.173 | C.6 |
| 1.1308 | B.174 | C.6 |
| 1.1309 | B.175 | C.6 |
| 1.1310 | B.176 | C.6 |
| 1.1311 | B.177 | C.6 |
| 1.1312 | B.178 | C.6 |
| 1.1313 | B.179 | C.6 |
| 1.1314 | B.180 | C.6 |
| 1.1315 | B.181 | C.6 |
| 1.1316 | B.182 | C.6 |
| 1.1317 | B.183 | C.6 |
| 1.1318 | B.184 | C.6 |
| 1.1319 | B.185 | C.6 |
| 1.1320 | B.186 | C.6 |
| 1.1321 | B.187 | C.6 |
| 1.1322 | B.188 | C.6 |
| 1.1323 | B.189 | C.6 |
| 1.1324 | B.1 | C.7 |
| 1.1325 | B.2 | C.7 |
| 1.1326 | B.3 | C.7 |

TABLE 2-continued

| comb. no. | herbicide B | safener C |
|---|---|---|
| 1.1327 | B.4 | C.7 |
| 1.1328 | B.5 | C.7 |
| 1.1329 | B.6 | C.7 |
| 1.1330 | B.7 | C.7 |
| 1.1331 | B.8 | C.7 |
| 1.1332 | B.9 | C.7 |
| 1.1333 | B.10 | C.7 |
| 1.1334 | B.11 | C.7 |
| 1.1335 | B.12 | C.7 |
| 1.1336 | B.13 | C.7 |
| 1.1337 | B.14 | C.7 |
| 1.1338 | B.15 | C.7 |
| 1.1339 | B.16 | C.7 |
| 1.1340 | B.17 | C.7 |
| 1.1341 | B.18 | C.7 |
| 1.1342 | B.19 | C.7 |
| 1.1343 | B.20 | C.7 |
| 1.1344 | B.21 | C.7 |
| 1.1345 | B.22 | C.7 |
| 1.1346 | B.23 | C.7 |
| 1.1347 | B.24 | C.7 |
| 1.1348 | B.25 | C.7 |
| 1.1349 | B.26 | C.7 |
| 1.1350 | B.27 | C.7 |
| 1.1351 | B.28 | C.7 |
| 1.1352 | B.29 | C.7 |
| 1.1353 | B.30 | C.7 |
| 1.1354 | B.31 | C.7 |
| 1.1355 | B.32 | C.7 |
| 1.1356 | B.33 | C.7 |
| 1.1357 | B.34 | C.7 |
| 1.1358 | B.35 | C.7 |
| 1.1359 | B.36 | C.7 |
| 1.1360 | B.37 | C.7 |
| 1.1361 | B.38 | C.7 |
| 1.1362 | B.39 | C.7 |
| 1.1363 | B.40 | C.7 |
| 1.1364 | B.41 | C.7 |
| 1.1365 | B.42 | C.7 |
| 1.1366 | B.43 | C.7 |
| 1.1367 | B.44 | C.7 |
| 1.1368 | B.45 | C.7 |
| 1.1369 | B.46 | C.7 |
| 1.1370 | B.47 | C.7 |
| 1.1371 | B.48 | C.7 |
| 1.1372 | B.49 | C.7 |
| 1.1373 | B.50 | C.7 |
| 1.1374 | B.51 | C.7 |
| 1.1375 | B.52 | C.7 |
| 1.1376 | B.53 | C.7 |
| 1.1377 | B.54 | C.7 |
| 1.1378 | B.55 | C.7 |
| 1.1379 | B.56 | C.7 |
| 1.1380 | B.57 | C.7 |
| 1.1381 | B.58. | C.7 |
| 1.1382 | B.59 | C.7 |
| 1.1383 | B.60 | C.7 |
| 1.1384 | B.61 | C.7 |
| 1.1385 | B.62 | C.7 |
| 1.1386 | B.63 | C.7 |
| 1.1387 | B.64 | C.7 |
| 1.1388 | B.65 | C.7 |
| 1.1389 | B.66 | C.7 |
| 1.1390 | B.67 | C.7 |
| 1.1391 | B.68 | C.7 |
| 1.1392 | B.69 | C.7 |
| 1.1393 | B.70 | C.7 |
| 1.1394 | B.71 | C.7 |
| 1.1395 | B.72 | C.7 |
| 1.1396 | B.73 | C.7 |
| 1.1397 | B.74 | C.7 |
| 1.1398 | B.75 | C.7 |
| 1.1399 | B.76 | C.7 |
| 1.1400 | B.77 | C.7 |
| 1.1401 | B.78 | C.7 |
| 1.1402 | B.79 | C.7 |
| 1.1403 | B.80 | C.7 |
| 1.1404 | B.81 | C.7 |
| 1.1405 | B.82 | C.7 |
| 1.1406 | B.83 | C.7 |
| 1.1407 | B.84 | C.7 |
| 1.1408 | B.85 | C.7 |
| 1.1409 | B.86 | C.7 |
| 1.1410 | B.87 | C.7 |
| 1.1411 | B.88 | C.7 |
| 1.1412 | B.89 | C.7 |
| 1.1413 | B.90 | C.7 |
| 1.1414 | B.91 | C.7 |
| 1.1415 | B.92 | C.7 |
| 1.1416 | B.93 | C.7 |
| 1.1417 | B.94 | C.7 |
| 1.1418 | B.95 | C.7 |
| 1.1419 | B.96 | C.7 |
| 1.1420 | B.97 | C.7 |
| 1.1421 | B.98 | C.7 |
| 1.1422 | B.99 | C.7 |
| 1.1423 | B.100 | C.7 |
| 1.1424 | B.101 | C.7 |
| 1.1425 | B.102 | C.7 |
| 1.1426 | B.103 | C.7 |
| 1.1427 | B.104 | C.7 |
| 1.1428 | B.105 | C.7 |
| 1.1429 | B.106 | C.7 |
| 1.1430 | B.107 | C.7 |
| 1.1431 | B.108 | C.7 |
| 1.1432 | B.109 | C.7 |
| 1.1433 | B.110 | C.7 |
| 1.1434 | B.111 | C.7 |
| 1.1435 | B.112 | C.7 |
| 1.1436 | B.113 | C.7 |
| 1.1437 | B.114 | C.7 |
| 1.1438 | B.115 | C.7 |
| 1.1439 | B.116 | C.7 |
| 1.1440 | B.117 | C.7 |
| 1.1441 | B.118 | C.7 |
| 1.1442 | B.119 | C.7 |
| 1.1443 | B.120 | C.7 |
| 1.1444 | B.121 | C.7 |
| 1.1445 | B.122 | C.7 |
| 1.1446 | B.123 | C.7 |
| 1.1447 | B.124 | C.7 |
| 1.1448 | B.125 | C.7 |
| 1.1449 | B.126 | C.7 |
| 1.1450 | B.127 | C.7 |
| 1.1451 | B.128 | C.7 |
| 1.1452 | B.129 | C.7 |
| 1.1453 | B.130 | C.7 |
| 1.1454 | B.131 | C.7 |
| 1.1455 | B.132 | C.7 |
| 1.1456 | B.133 | C.7 |
| 1.1457 | B.134 | C.7 |
| 1.1458 | B.135 | C.7 |
| 1.1459 | B.136 | C.7 |
| 1.1460 | B.137 | C.7 |
| 1.1461 | B.138 | C.7 |
| 1.1462 | B.139 | C.7 |
| 1.1463 | B.140 | C.7 |
| 1.1464 | B.141 | C.7 |
| 1.1465 | B.142 | C.7 |
| 1.1466 | B.143 | C.7 |
| 1.1467 | B.144 | C.7 |
| 1.1468 | B.145 | C.7 |
| 1.1469 | B.146 | C.7 |
| 1.1470 | B.147 | C.7 |
| 1.1471 | B.148 | C.7 |
| 1.1472 | B.149 | C.7 |
| 1.1473 | B.150 | C.7 |
| 1.1474 | B.151 | C.7 |
| 1.1475 | B.152 | C.7 |
| 1.1476 | B.153 | C.7 |
| 1.1477 | B.154 | C.7 |
| 1.1478 | B.155 | C.7 |
| 1.1479 | B.156 | C.7 |
| 1.1480 | B.157 | C.7 |
| 1.1481 | B.158 | C.7 |
| 1.1482 | B.159 | C.7 |

TABLE 2-continued

| comb. no. | herbicide B | safener C |
|---|---|---|
| 1.1483 | B.160 | C.7 |
| 1.1484 | B.161 | C.7 |
| 1.1485 | B.162 | C.7 |
| 1.1486 | B.163 | C.7 |
| 1.1487 | B.164 | C.7 |
| 1.1488 | B.165 | C.7 |
| 1.1489 | B.166 | C.7 |
| 1.1490 | B.167 | C.7 |
| 1.1491 | B.168 | C.7 |
| 1.1492 | B.169 | C.7 |
| 1.1493 | B.170 | C.7 |
| 1.1494 | B.171 | C.7 |
| 1.1495 | B.172 | C.7 |
| 1.1496 | B.173 | C.7 |
| 1.1497 | B.174 | C.7 |
| 1.1498 | B.175 | C.7 |
| 1.1499 | B.176 | C.7 |
| 1.1500 | B.177 | C.7 |
| 1.1501 | B.178 | C.7 |
| 1.1502 | B.179 | C.7 |
| 1.1503 | B.180 | C.7 |
| 1.1504 | B.181 | C.7 |
| 1.1505 | B.182 | C.7 |
| 1.1506 | B.183 | C.7 |
| 1.1507 | B.184 | C.7 |
| 1.1508 | B.185 | C.7 |
| 1.1509 | B.186 | C.7 |
| 1.1510 | B.187 | C.7 |
| 1.1511 | B.188 | C.7 |
| 1.1512 | B.189 | C.7 |
| 1.1513 | B.1 | C.8 |
| 1.1514 | B.2 | C.8 |
| 1.1515 | B.3 | C.8 |
| 1.1516 | B.4 | C.8 |
| 1.1517 | B.5 | C.8 |
| 1.1518 | B.6 | C.8 |
| 1.1519 | B.7 | C.8 |
| 1.1520 | B.8 | C.8 |
| 1.1521 | B.9 | C.8 |
| 1.1522 | B.10 | C.8 |
| 1.1523 | B.11 | C.8 |
| 1.1524 | B.12 | C.8 |
| 1.1525 | B.13 | C.8 |
| 1.1526 | B.14 | C.8 |
| 1.1527 | B.15 | C.8 |
| 1.1528 | B.16 | C.8 |
| 1.1529 | B.17 | C.8 |
| 1.1530 | B.18 | C.8 |
| 1.1531 | B.19 | C.8 |
| 1.1532 | B.20 | C.8 |
| 1.1533 | B.21 | C.8 |
| 1.1534 | B.22 | C.8 |
| 1.1535 | B.23 | C.8 |
| 1.1536 | B.24 | C.8 |
| 1.1537 | B.25 | C.8 |
| 1.1538 | B.26 | C.8 |
| 1.1539 | B.27 | C.8 |
| 1.1540 | B.28 | C.8 |
| 1.1541 | B.29 | C.8 |
| 1.1542 | B.30 | C.8 |
| 1.1543 | B.31 | C.8 |
| 1.1544 | B.32 | C.8 |
| 1.1545 | B.33 | C.8 |
| 1.1546 | B.34 | C.8 |
| 1.1547 | B.35 | C.8 |
| 1.1548 | B.36 | C.8 |
| 1.1549 | B.37 | C.8 |
| 1.1550 | B.38 | C.8 |
| 1.1551 | B.39 | C.8 |
| 1.1552 | B.40 | C.8 |
| 1.1553 | B.41 | C.8 |
| 1.1554 | B.42 | C.8 |
| 1.1555 | B.43 | C.8 |
| 1.1556 | B.44 | C.8 |
| 1.1557 | B.45 | C.8 |
| 1.1558 | B.46 | C.8 |
| 1.1559 | B.47 | C.8 |
| 1.1560 | B.48 | C.8 |
| 1.1561 | B.49 | C.8 |
| 1.1562 | B.50 | C.8 |
| 1.1563 | B.51 | C.8 |
| 1.1564 | B.52 | C.8 |
| 1.1565 | B.53 | C.8 |
| 1.1566 | B.54 | C.8 |
| 1.1567 | B.55 | C.8 |
| 1.1568 | B.56 | C.8 |
| 1.1569 | B.57 | C.8 |
| 1.1570 | B.58. | C.8 |
| 1.1571 | B.59 | C.8 |
| 1.1572 | B.60 | C.8 |
| 1.1573 | B.61 | C.8 |
| 1.1574 | B.62 | C.8 |
| 1.1575 | B.63 | C.8 |
| 1.1576 | B.64 | C.8 |
| 1.1577 | B.65 | C.8 |
| 1.1578 | B.66 | C.8 |
| 1.1579 | B.67 | C.8 |
| 1.1580 | B.68 | C.8 |
| 1.1581 | B.69 | C.8 |
| 1.1582 | B.70 | C.8 |
| 1.1583 | B.71 | C.8 |
| 1.1584 | B.72 | C.8 |
| 1.1585 | B.73 | C.8 |
| 1.1586 | B.74 | C.8 |
| 1.1587 | B.75 | C.8 |
| 1.1588 | B.76 | C.8 |
| 1.1589 | B.77 | C.8 |
| 1.1590 | B.78 | C.8 |
| 1.1591 | B.79 | C.8 |
| 1.1592 | B.80 | C.8 |
| 1.1593 | B.81 | C.8 |
| 1.1594 | B.82 | C.8 |
| 1.1595 | B.83 | C.8 |
| 1.1596 | B.84 | C.8 |
| 1.1597 | B.85 | C.8 |
| 1.1598 | B.86 | C.8 |
| 1.1599 | B.87 | C.8 |
| 1.1600 | B.88 | C.8 |
| 1.1601 | B.89 | C.8 |
| 1.1602 | B.90 | C.8 |
| 1.1603 | B.91 | C.8 |
| 1.1604 | B.92 | C.8 |
| 1.1605 | B.93 | C.8 |
| 1.1606 | B.94 | C.8 |
| 1.1607 | B.95 | C.8 |
| 1.1608 | B.96 | C.8 |
| 1.1609 | B.97 | C.8 |
| 1.1610 | B.98 | C.8 |
| 1.1611 | B.99 | C.8 |
| 1.1612 | B.100 | C.8 |
| 1.1613 | B.101 | C.8 |
| 1.1614 | B.102 | C.8 |
| 1.1615 | B.103 | C.8 |
| 1.1616 | B.104 | C.8 |
| 1.1617 | B.105 | C.8 |
| 1.1618 | B.106 | C.8 |
| 1.1619 | B.107 | C.8 |
| 1.1620 | B.108 | C.8 |
| 1.1621 | B.109 | C.8 |
| 1.1622 | B.110 | C.8 |
| 1.1623 | B.111 | C.8 |
| 1.1624 | B.112 | C.8 |
| 1.1625 | B.113 | C.8 |
| 1.1626 | B.114 | C.8 |
| 1.1627 | B.115 | C.8 |
| 1.1628 | B.116 | C.8 |
| 1.1629 | B.117 | C.8 |
| 1.1630 | B.118 | C.8 |
| 1.1631 | B.119 | C.8 |
| 1.1632 | B.120 | C.8 |
| 1.1633 | B.121 | C.8 |
| 1.1634 | B.122 | C.8 |
| 1.1635 | B.123 | C.8 |
| 1.1636 | B.124 | C.8 |
| 1.1637 | B.125 | C.8 |
| 1.1638 | B.126 | C.8 |

TABLE 2-continued

| comb. no. | herbicide B | safener C |
|---|---|---|
| 1.1639 | B.127 | C.8 |
| 1.1640 | B.128 | C.8 |
| 1.1641 | B.129 | C.8 |
| 1.1642 | B.130 | C.8 |
| 1.1643 | B.131 | C.8 |
| 1.1644 | B.132 | C.8 |
| 1.1645 | B.133 | C.8 |
| 1.1646 | B.134 | C.8 |
| 1.1647 | B.135 | C.8 |
| 1.1648 | B.136 | C.8 |
| 1.1649 | B.137 | C.8 |
| 1.1650 | B.138 | C.8 |
| 1.1651 | B.139 | C.8 |
| 1.1652 | B.140 | C.8 |
| 1.1653 | B.141 | C.8 |
| 1.1654 | B.142 | C.8 |
| 1.1655 | B.143 | C.8 |
| 1.1656 | B.144 | C.8 |
| 1.1657 | B.145 | C.8 |
| 1.1658 | B.146 | C.8 |
| 1.1659 | B.147 | C.8 |
| 1.1660 | B.148 | C.8 |
| 1.1661 | B.149 | C.8 |
| 1.1662 | B.150 | C.8 |
| 1.1663 | B.151 | C.8 |
| 1.1664 | B.152 | C.8 |
| 1.1665 | B.153 | C.8 |
| 1.1666 | B.154 | C.8 |
| 1.1667 | B.155 | C.8 |
| 1.1668 | B.156 | C.8 |
| 1.1669 | B.157 | C.8 |
| 1.1670 | B.158 | C.8 |
| 1.1671 | B.159 | C.8 |
| 1.1672 | B.160 | C.8 |
| 1.1673 | B.161 | C.8 |
| 1.1674 | B.162 | C.8 |
| 1.1675 | B.163 | C.8 |
| 1.1676 | B.164 | C.8 |
| 1.1677 | B.165 | C.8 |
| 1.1678 | B.166 | C.8 |
| 1.1679 | B.167 | C.8 |
| 1.1680 | B.168 | C.8 |
| 1.1681 | B.169 | C.8 |
| 1.1682 | B.170 | C.8 |
| 1.1683 | B.171 | C.8 |
| 1.1684 | B.172 | C.8 |
| 1.1685 | B.173 | C.8 |
| 1.1686 | B.174 | C.8 |
| 1.1687 | B.175 | C.8 |
| 1.1688 | B.176 | C.8 |
| 1.1689 | B.177 | C.8 |
| 1.1690 | B.178 | C.8 |
| 1.1691 | B.179 | C.8 |
| 1.1692 | B.180 | C.8 |
| 1.1693 | B.181 | C.8 |
| 1.1694 | B.182 | C.8 |
| 1.1695 | B.183 | C.8 |
| 1.1696 | B.184 | C.8 |
| 1.1697 | B.185 | C.8 |
| 1.1698 | B.186 | C.8 |
| 1.1699 | B.187 | C.8 |
| 1.1700 | B.188 | C.8 |
| 1.1701 | B.189 | C.8 |
| 1.1702 | B.1 | C.9 |
| 1.1703 | B.2 | C.9 |
| 1.1704 | B.3 | C.9 |
| 1.1705 | B.4 | C.9 |
| 1.1706 | B.5 | C.9 |
| 1.1707 | B.6 | C.9 |
| 1.1708 | B.7 | C.9 |
| 1.1709 | B.8 | C.9 |
| 1.1710 | B.9 | C.9 |
| 1.1711 | B.10 | C.9 |
| 1.1712 | B.11 | C.9 |
| 1.1713 | B.12 | C.9 |
| 1.1714 | B.13 | C.9 |
| 1.1715 | B.14 | C.9 |
| 1.1716 | B.15 | C.9 |
| 1.1717 | B.16 | C.9 |
| 1.1718 | B.17 | C.9 |
| 1.1719 | B.18 | C.9 |
| 1.1720 | B.19 | C.9 |
| 1.1721 | B.20 | C.9 |
| 1.1722 | B.21 | C.9 |
| 1.1723 | B.22 | C.9 |
| 1.1724 | B.23 | C.9 |
| 1.1725 | B.24 | C.9 |
| 1.1726 | B.25 | C.9 |
| 1.1727 | B.26 | C.9 |
| 1.1728 | B.27 | C.9 |
| 1.1729 | B.28 | C.9 |
| 1.1730 | B.29 | C.9 |
| 1.1731 | B.30 | C.9 |
| 1.1732 | B.31 | C.9 |
| 1.1733 | B.32 | C.9 |
| 1.1734 | B.33 | C.9 |
| 1.1735 | B.34 | C.9 |
| 1.1736 | B.35 | C.9 |
| 1.1737 | B.36 | C.9 |
| 1.1738 | B.37 | C.9 |
| 1.1739 | B.38 | C.9 |
| 1.1740 | B.39 | C.9 |
| 1.1741 | B.40 | C.9 |
| 1.1742 | B.41 | C.9 |
| 1.1743 | B.42 | C.9 |
| 1.1744 | B.43 | C.9 |
| 1.1745 | B.44 | C.9 |
| 1.1746 | B.45 | C.9 |
| 1.1747 | B.46 | C.9 |
| 1.1748 | B.47 | C.9 |
| 1.1749 | B.48 | C.9 |
| 1.1750 | B.49 | C.9 |
| 1.1751 | B.50 | C.9 |
| 1.1752 | B.51 | C.9 |
| 1.1753 | B.52 | C.9 |
| 1.1754 | B.53 | C.9 |
| 1.1755 | B.54 | C.9 |
| 1.1756 | B.55 | C.9 |
| 1.1757 | B.56 | C.9 |
| 1.1758 | B.57 | C.9 |
| 1.1759 | B.58. | C.9 |
| 1.1760 | B.59 | C.9 |
| 1.1761 | B.60 | C.9 |
| 1.1762 | B.61 | C.9 |
| 1.1763 | B.62 | C.9 |
| 1.1764 | B.63 | C.9 |
| 1.1765 | B.64 | C.9 |
| 1.1766 | B.65 | C.9 |
| 1.1767 | B.66 | C.9 |
| 1.1768 | B.67 | C.9 |
| 1.1769 | B.68 | C.9 |
| 1.1770 | B.69 | C.9 |
| 1.1771 | B.70 | C.9 |
| 1.1772 | B.71 | C.9 |
| 1.1773 | B.72 | C.9 |
| 1.1774 | B.73 | C.9 |
| 1.1775 | B.74 | C.9 |
| 1.1776 | B.75 | C.9 |
| 1.1777 | B.76 | C.9 |
| 1.1778 | B.77 | C.9 |
| 1.1779 | B.78 | C.9 |
| 1.1780 | B.79 | C.9 |
| 1.1781 | B.80 | C.9 |
| 1.1782 | B.81 | C.9 |
| 1.1783 | B.82 | C.9 |
| 1.1784 | B.83 | C.9 |
| 1.1785 | B.84 | C.9 |
| 1.1786 | B.85 | C.9 |
| 1.1787 | B.86 | C.9 |
| 1.1788 | B.87 | C.9 |
| 1.1789 | B.88 | C.9 |
| 1.1790 | B.89 | C.9 |
| 1.1791 | B.90 | C.9 |
| 1.1792 | B.91 | C.9 |
| 1.1793 | B.92 | C.9 |
| 1.1794 | B.93 | C.9 |

TABLE 2-continued

| comb. no. | herbicide B | safener C |
|---|---|---|
| 1.1795 | B.94 | C.9 |
| 1.1796 | B.95 | C.9 |
| 1.1797 | B.96 | C.9 |
| 1.1798 | B.97 | C.9 |
| 1.1799 | B.98 | C.9 |
| 1.1800 | B.99 | C.9 |
| 1.1801 | B.100 | C.9 |
| 1.1802 | B.101 | C.9 |
| 1.1803 | B.102 | C.9 |
| 1.1804 | B.103 | C.9 |
| 1.1805 | B.104 | C.9 |
| 1.1806 | B.105 | C.9 |
| 1.1807 | B.106 | C.9 |
| 1.1808 | B.107 | C.9 |
| 1.1809 | B.108 | C.9 |
| 1.1810 | B.109 | C.9 |
| 1.1811 | B.110 | C.9 |
| 1.1812 | B.111 | C.9 |
| 1.1813 | B.112 | C.9 |
| 1.1814 | B.113 | C.9 |
| 1.1815 | B.114 | C.9 |
| 1.1816 | B.115 | C.9 |
| 1.1817 | B.116 | C.9 |
| 1.1818 | B.117 | C.9 |
| 1.1819 | B.118 | C.9 |
| 1.1820 | B.119 | C.9 |
| 1.1821 | B.120 | C.9 |
| 1.1822 | B.121 | C.9 |
| 1.1823 | B.122 | C.9 |
| 1.1824 | B.123 | C.9 |
| 1.1825 | B.124 | C.9 |
| 1.1826 | B.125 | C.9 |
| 1.1827 | B.126 | C.9 |
| 1.1828 | B.127 | C.9 |
| 1.1829 | B.128 | C.9 |
| 1.1830 | B.129 | C.9 |
| 1.1831 | B.130 | C.9 |
| 1.1832 | B.131 | C.9 |
| 1.1833 | B.132 | C.9 |
| 1.1834 | B.133 | C.9 |
| 1.1835 | B.134 | C.9 |
| 1.1836 | B.135 | C.9 |
| 1.1837 | B.136 | C.9 |
| 1.1838 | B.137 | C.9 |
| 1.1839 | B.138 | C.9 |
| 1.1840 | B.139 | C.9 |
| 1.1841 | B.140 | C.9 |
| 1.1842 | B.141 | C.9 |
| 1.1843 | B.142 | C.9 |
| 1.1844 | B.143 | C.9 |
| 1.1845 | B.144 | C.9 |
| 1.1846 | B.145 | C.9 |
| 1.1847 | B.146 | C.9 |
| 1.1848 | B.147 | C.9 |
| 1.1849 | B.148 | C.9 |
| 1.1850 | B.149 | C.9 |
| 1.1851 | B.150 | C.9 |
| 1.1852 | B.151 | C.9 |
| 1.1853 | B.152 | C.9 |
| 1.1854 | B.153 | C.9 |
| 1.1855 | B.154 | C.9 |
| 1.1856 | B.155 | C.9 |
| 1.1857 | B.156 | C.9 |
| 1.1858 | B.157 | C.9 |
| 1.1859 | B.158 | C.9 |
| 1.1860 | B.159 | C.9 |
| 1.1861 | B.160 | C.9 |
| 1.1862 | B.161 | C.9 |
| 1.1863 | B.162 | C.9 |
| 1.1864 | B.163 | C.9 |
| 1.1865 | B.164 | C.9 |
| 1.1866 | B.165 | C.9 |
| 1.1867 | B.166 | C.9 |
| 1.1868 | B.167 | C.9 |
| 1.1869 | B.168 | C.9 |
| 1.1870 | B.169 | C.9 |
| 1.1871 | B.170 | C.9 |
| 1.1872 | B.171 | C.9 |
| 1.1873 | B.172 | C.9 |
| 1.1874 | B.173 | C.9 |
| 1.1875 | B.174 | C.9 |
| 1.1876 | B.175 | C.9 |
| 1.1877 | B.176 | C.9 |
| 1.1878 | B.177 | C.9 |
| 1.1879 | B.178 | C.9 |
| 1.1880 | B.179 | C.9 |
| 1.1881 | B.180 | C.9 |
| 1.1882 | B.181 | C.9 |
| 1.1883 | B.182 | C.9 |
| 1.1884 | B.183 | C.9 |
| 1.1885 | B.184 | C.9 |
| 1.1886 | B.185 | C.9 |
| 1.1887 | B.186 | C.9 |
| 1.1888 | B.187 | C.9 |
| 1.1889 | B.188 | C.9 |
| 1.1890 | B.189 | C.9 |
| 1.1891 | B.1 | C.10 |
| 1.1892 | B.2 | C.10 |
| 1.1893 | B.3 | C.10 |
| 1.1894 | B.4 | C.10 |
| 1.1895 | B.5 | C.10 |
| 1.1896 | B.6 | C.10 |
| 1.1897 | B.7 | C.10 |
| 1.1898 | B.8 | C.10 |
| 1.1899 | B.9 | C.10 |
| 1.1900 | B.10 | C.10 |
| 1.1901 | B.11 | C.10 |
| 1.1902 | B.12 | C.10 |
| 1.1903 | B.13 | C.10 |
| 1.1904 | B.14 | C.10 |
| 1.1905 | B.15 | C.10 |
| 1.1906 | B.16 | C.10 |
| 1.1907 | B.17 | C.10 |
| 1.1908 | B.18 | C.10 |
| 1.1909 | B.19 | C.10 |
| 1.1910 | B.20 | C.10 |
| 1.1911 | B.21 | C.10 |
| 1.1912 | B.22 | C.10 |
| 1.1913 | B.23 | C.10 |
| 1.1914 | B.24 | C.10 |
| 1.1915 | B.25 | C.10 |
| 1.1916 | B.26 | C.10 |
| 1.1917 | B.27 | C.10 |
| 1.1918 | B.28 | C.10 |
| 1.1919 | B.29 | C.10 |
| 1.1920 | B.30 | C.10 |
| 1.1921 | B.31 | C.10 |
| 1.1922 | B.32 | C.10 |
| 1.1923 | B.33 | C.10 |
| 1.1924 | B.34 | C.10 |
| 1.1925 | B.35 | C.10 |
| 1.1926 | B.36 | C.10 |
| 1.1927 | B.37 | C.10 |
| 1.1928 | B.38 | C.10 |
| 1.1929 | B.39 | C.10 |
| 1.1930 | B.40 | C.10 |
| 1.1931 | B.41 | C.10 |
| 1.1932 | B.42 | C.10 |
| 1.1933 | B.43 | C.10 |
| 1.1934 | B.44 | C.10 |
| 1.1935 | B.45 | C.10 |
| 1.1936 | B.46 | C.10 |
| 1.1937 | B.47 | C.10 |
| 1.1938 | B.48 | C.10 |
| 1.1939 | B.49 | C.10 |
| 1.1940 | B.50 | C.10 |
| 1.1941 | B.51 | C.10 |
| 1.1942 | B.52 | C.10 |
| 1.1943 | B.53 | C.10 |
| 1.1944 | B.54 | C.10 |
| 1.1945 | B.55 | C.10 |
| 1.1946 | B.56 | C.10 |
| 1.1947 | B.57 | C.10 |
| 1.1948 | B.58. | C.10 |
| 1.1949 | B.59 | C.10 |
| 1.1950 | B.60 | C.10 |

TABLE 2-continued

| comb. no. | herbicide B | safener C |
|---|---|---|
| 1.1951 | B.61 | C.10 |
| 1.1952 | B.62 | C.10 |
| 1.1953 | B.63 | C.10 |
| 1.1954 | B.64 | C.10 |
| 1.1955 | B.65 | C.10 |
| 1.1956 | B.66 | C.10 |
| 1.1957 | B.67 | C.10 |
| 1.1958 | B.68 | C.10 |
| 1.1959 | B.69 | C.10 |
| 1.1960 | B.70 | C.10 |
| 1.1961 | B.71 | C.10 |
| 1.1962 | B.72 | C.10 |
| 1.1963 | B.73 | C.10 |
| 1.1964 | B.74 | C.10 |
| 1.1965 | B.75 | C.10 |
| 1.1966 | B.76 | C.10 |
| 1.1967 | B.77 | C.10 |
| 1.1968 | B.78 | C.10 |
| 1.1969 | B.79 | C.10 |
| 1.1970 | B.80 | C.10 |
| 1.1971 | B.81 | C.10 |
| 1.1972 | B.82 | C.10 |
| 1.1973 | B.83 | C.10 |
| 1.1974 | B.84 | C.10 |
| 1.1975 | B.85 | C.10 |
| 1.1976 | B.86 | C.10 |
| 1.1977 | B.87 | C.10 |
| 1.1978 | B.88 | C.10 |
| 1.1979 | B.89 | C.10 |
| 1.1980 | B.90 | C.10 |
| 1.1981 | B.91 | C.10 |
| 1.1982 | B.92 | C.10 |
| 1.1983 | B.93 | C.10 |
| 1.1984 | B.94 | C.10 |
| 1.1985 | B.95 | C.10 |
| 1.1986 | B.96 | C.10 |
| 1.1987 | B.97 | C.10 |
| 1.1988 | B.98 | C.10 |
| 1.1989 | B.99 | C.10 |
| 1.1990 | B.100 | C.10 |
| 1.1991 | B.101 | C.10 |
| 1.1992 | B.102 | C.10 |
| 1.1993 | B.103 | C.10 |
| 1.1994 | B.104 | C.10 |
| 1.1995 | B.105 | C.10 |
| 1.1996 | B.106 | C.10 |
| 1.1997 | B.107 | C.10 |
| 1.1998 | B.108 | C.10 |
| 1.1999 | B.109 | C.10 |
| 1.2000 | B.110 | C.10 |
| 1.2001 | B.111 | C.10 |
| 1.2002 | B.112 | C.10 |
| 1.2003 | B.113 | C.10 |
| 1.2004 | B.114 | C.10 |
| 1.2005 | B.115 | C.10 |
| 1.2006 | B.116 | C.10 |
| 1.2007 | B.117 | C.10 |
| 1.2008 | B.118 | C.10 |
| 1.2009 | B.119 | C.10 |
| 1.2010 | B.120 | C.10 |
| 1.2011 | B.121 | C.10 |
| 1.2012 | B.122 | C.10 |
| 1.2013 | B.123 | C.10 |
| 1.2014 | B.124 | C.10 |
| 1.2015 | B.125 | C.10 |
| 1.2016 | B.126 | C.10 |
| 1.2017 | B.127 | C.10 |
| 1.2018 | B.128 | C.10 |
| 1.2019 | B.129 | C.10 |
| 1.2020 | B.130 | C.10 |
| 1.2021 | B.131 | C.10 |
| 1.2022 | B.132 | C.10 |
| 1.2023 | B.133 | C.10 |
| 1.2024 | B.134 | C.10 |
| 1.2025 | B.135 | C.10 |
| 1.2026 | B.136 | C.10 |
| 1.2027 | B.137 | C.10 |
| 1.2028 | B.138 | C.10 |
| 1.2029 | B.139 | C.10 |
| 1.2030 | B.140 | C.10 |
| 1.2031 | B.141 | C.10 |
| 1.2032 | B.142 | C.10 |
| 1.2033 | B.143 | C.10 |
| 1.2034 | B.144 | C.10 |
| 1.2035 | B.145 | C.10 |
| 1.2036 | B.146 | C.10 |
| 1.2037 | B.147 | C.10 |
| 1.2038 | B.148 | C.10 |
| 1.2039 | B.149 | C.10 |
| 1.2040 | B.150 | C.10 |
| 1.2041 | B.151 | C.10 |
| 1.2042 | B.152 | C.10 |
| 1.2043 | B.153 | C.10 |
| 1.2044 | B.154 | C.10 |
| 1.2045 | B.155 | C.10 |
| 1.2046 | B.156 | C.10 |
| 1.2047 | B.157 | C.10 |
| 1.2048 | B.158 | C.10 |
| 1.2049 | B.159 | C.10 |
| 1.2050 | B.160 | C.10 |
| 1.2051 | B.161 | C.10 |
| 1.2052 | B.162 | C.10 |
| 1.2053 | B.163 | C.10 |
| 1.2054 | B.164 | C.10 |
| 1.2055 | B.165 | C.10 |
| 1.2056 | B.166 | C.10 |
| 1.2057 | B.167 | C.10 |
| 1.2058 | B.168 | C.10 |
| 1.2059 | B.169 | C.10 |
| 1.2060 | B.170 | C.10 |
| 1.2061 | B.171 | C.10 |
| 1.2062 | B.172 | C.10 |
| 1.2063 | B.173 | C.10 |
| 1.2064 | B.174 | C.10 |
| 1.2065 | B.175 | C.10 |
| 1.2066 | B.176 | C.10 |
| 1.2067 | B.177 | C.10 |
| 1.2068 | B.178 | C.10 |
| 1.2069 | B.179 | C.10 |
| 1.2070 | B.180 | C.10 |
| 1.2071 | B.181 | C.10 |
| 1.2072 | B.182 | C.10 |
| 1.2073 | B.183 | C.10 |
| 1.2074 | B.184 | C.10 |
| 1.2075 | B.185 | C.10 |
| 1.2076 | B.186 | C.10 |
| 1.2077 | B.187 | C.10 |
| 1.2078 | B.188 | C.10 |
| 1.2079 | B.189 | C.10 |
| 1.2080 | B.1 | C.11 |
| 1.2081 | B.2 | C.11 |
| 1.2082 | B.3 | C.11 |
| 1.2083 | B.4 | C.11 |
| 1.2084 | B.5 | C.11 |
| 1.2085 | B.6 | C.11 |
| 1.2086 | B.7 | C.11 |
| 1.2087 | B.8 | C.11 |
| 1.2088 | B.9 | C.11 |
| 1.2089 | B.10 | C.11 |
| 1.2090 | B.11 | C.11 |
| 1.2091 | B.12 | C.11 |
| 1.2092 | B.13 | C.11 |
| 1.2093 | B.14 | C.11 |
| 1.2094 | B.15 | C.11 |
| 1.2095 | B.16 | C.11 |
| 1.2096 | B.17 | C.11 |
| 1.2097 | B.18 | C.11 |
| 1.2098 | B.19 | C.11 |
| 1.2099 | B.20 | C.11 |
| 1.2100 | B.21 | C.11 |
| 1.2101 | B.22 | C.11 |
| 1.2102 | B.23 | C.11 |
| 1.2103 | B.24 | C.11 |
| 1.2104 | B.25 | C.11 |
| 1.2105 | B.26 | C.11 |
| 1.2106 | B.27 | C.11 |

TABLE 2-continued

| comb. no. | herbicide B | safener C |
|---|---|---|
| 1.2107 | B.28 | C.11 |
| 1.2108 | B.29 | C.11 |
| 1.2109 | B.30 | C.11 |
| 1.2110 | B.31 | C.11 |
| 1.2111 | B.32 | C.11 |
| 1.2112 | B.33 | C.11 |
| 1.2113 | B.34 | C.11 |
| 1.2114 | B.35 | C.11 |
| 1.2115 | B.36 | C.11 |
| 1.2116 | B.37 | C.11 |
| 1.2117 | B.38 | C.11 |
| 1.2118 | B.39 | C.11 |
| 1.2119 | B.40 | C.11 |
| 1.2120 | B.41 | C.11 |
| 1.2121 | B.42 | C.11 |
| 1.2122 | B.43 | C.11 |
| 1.2123 | B.44 | C.11 |
| 1.2124 | B.45 | C.11 |
| 1.2125 | B.46 | C.11 |
| 1.2126 | B.47 | C.11 |
| 1.2127 | B.48 | C.11 |
| 1.2128 | B.49 | C.11 |
| 1.2129 | B.50 | C.11 |
| 1.2130 | B.51 | C.11 |
| 1.2131 | B.52 | C.11 |
| 1.2132 | B.53 | C.11 |
| 1.2133 | B.54 | C.11 |
| 1.2134 | B.55 | C.11 |
| 1.2135 | B.56 | C.11 |
| 1.2136 | B.57 | C.11 |
| 1.2137 | B.58. | C.11 |
| 1.2138 | B.59 | C.11 |
| 1.2139 | B.60 | C.11 |
| 1.2140 | B.61 | C.11 |
| 1.2141 | B.62 | C.11 |
| 1.2142 | B.63 | C.11 |
| 1.2143 | B.64 | C.11 |
| 1.2144 | B.65 | C.11 |
| 1.2145 | B.66 | C.11 |
| 1.2146 | B.67 | C.11 |
| 1.2147 | B.68 | C.11 |
| 1.2148 | B.69 | C.11 |
| 1.2149 | B.70 | C.11 |
| 1.2150 | B.71 | C.11 |
| 1.2151 | B.72 | C.11 |
| 1.2152 | B.73 | C.11 |
| 1.2153 | B.74 | C.11 |
| 1.2154 | B.75 | C.11 |
| 1.2155 | B.76 | C.11 |
| 1.2156 | B.77 | C.11 |
| 1.2157 | B.78 | C.11 |
| 1.2158 | B.79 | C.11 |
| 1.2159 | B.80 | C.11 |
| 1.2160 | B.81 | C.11 |
| 1.2161 | B.82 | C.11 |
| 1.2162 | B.83 | C.11 |
| 1.2163 | B.84 | C.11 |
| 1.2164 | B.85 | C.11 |
| 1.2165 | B.86 | C.11 |
| 1.2166 | B.87 | C.11 |
| 1.2167 | B.88 | C.11 |
| 1.2168 | B.89 | C.11 |
| 1.2169 | B.90 | C.11 |
| 1.2170 | B.91 | C.11 |
| 1.2171 | B.92 | C.11 |
| 1.2172 | B.93 | C.11 |
| 1.2173 | B.94 | C.11 |
| 1.2174 | B.95 | C.11 |
| 1.2175 | B.96 | C.11 |
| 1.2176 | B.97 | C.11 |
| 1.2177 | B.98 | C.11 |
| 1.2178 | B.99 | C.11 |
| 1.2179 | B.100 | C.11 |
| 1.2180 | B.101 | C.11 |
| 1.2181 | B.102 | C.11 |
| 1.2182 | B.103 | C.11 |
| 1.2183 | B.104 | C.11 |
| 1.2184 | B.105 | C.11 |
| 1.2185 | B.106 | C.11 |
| 1.2186 | B.107 | C.11 |
| 1.2187 | B.108 | C.11 |
| 1.2188 | B.109 | C.11 |
| 1.2189 | B.110 | C.11 |
| 1.2190 | B.111 | C.11 |
| 1.2191 | B.112 | C.11 |
| 1.2192 | B.113 | C.11 |
| 1.2193 | B.114 | C.11 |
| 1.2194 | B.115 | C.11 |
| 1.2195 | B.116 | C.11 |
| 1.2196 | B.117 | C.11 |
| 1.2197 | B.118 | C.11 |
| 1.2198 | B.119 | C.11 |
| 1.2199 | B.120 | C.11 |
| 1.2200 | B.121 | C.11 |
| 1.2201 | B.122 | C.11 |
| 1.2202 | B.123 | C.11 |
| 1.2203 | B.124 | C.11 |
| 1.2204 | B.125 | C.11 |
| 1.2205 | B.126 | C.11 |
| 1.2206 | B.127 | C.11 |
| 1.2207 | B.128 | C.11 |
| 1.2208 | B.129 | C.11 |
| 1.2209 | B.130 | C.11 |
| 1.2210 | B.131 | C.11 |
| 1.2211 | B.132 | C.11 |
| 1.2212 | B.133 | C.11 |
| 1.2213 | B.134 | C.11 |
| 1.2214 | B.135 | C.11 |
| 1.2215 | B.136 | C.11 |
| 1.2216 | B.137 | C.11 |
| 1.2217 | B.138 | C.11 |
| 1.2218 | B.139 | C.11 |
| 1.2219 | B.140 | C.11 |
| 1.2220 | B.141 | C.11 |
| 1.2221 | B.142 | C.11 |
| 1.2222 | B.143 | C.11 |
| 1.2223 | B.144 | C.11 |
| 1.2224 | B.145 | C.11 |
| 1.2225 | B.146 | C.11 |
| 1.2226 | B.147 | C.11 |
| 1.2227 | B.148 | C.11 |
| 1.2228 | B.149 | C.11 |
| 1.2229 | B.150 | C.11 |
| 1.2230 | B.151 | C.11 |
| 1.2231 | B.152 | C.11 |
| 1.2232 | B.153 | C.11 |
| 1.2233 | B.154 | C.11 |
| 1.2234 | B.155 | C.11 |
| 1.2235 | B.156 | C.11 |
| 1.2236 | B.157 | C.11 |
| 1.2237 | B.158 | C.11 |
| 1.2238 | B.159 | C.11 |
| 1.2239 | B.160 | C.11 |
| 1.2240 | B.161 | C.11 |
| 1.2241 | B.162 | C.11 |
| 1.2242 | B.163 | C.11 |
| 1.2243 | B.164 | C.11 |
| 1.2244 | B.165 | C.11 |
| 1.2245 | B.166 | C.11 |
| 1.2246 | B.167 | C.11 |
| 1.2247 | B.168 | C.11 |
| 1.2248 | B.169 | C.11 |
| 1.2249 | B.170 | C.11 |
| 1.2250 | B.171 | C.11 |
| 1.2251 | B.172 | C.11 |
| 1.2252 | B.173 | C.11 |
| 1.2253 | B.174 | C.11 |
| 1.2254 | B.175 | C.11 |
| 1.2255 | B.176 | C.11 |
| 1.2256 | B.177 | C.11 |
| 1.2257 | B.178 | C.11 |
| 1.2258 | B.179 | C.11 |
| 1.2259 | B.180 | C.11 |
| 1.2260 | B.181 | C.11 |
| 1.2261 | B.182 | C.11 |
| 1.2262 | B.183 | C.11 |

TABLE 2-continued

| comb. no. | herbicide B | safener C |
| --- | --- | --- |
| 1.2263 | B.184 | C.11 |
| 1.2264 | B.185 | C.11 |
| 1.2265 | B.186 | C.11 |
| 1.2266 | B.187 | C.11 |
| 1.2267 | B.188 | C.11 |
| 1.2268 | B.189 | C.11 |
| 1.2269 | B.1 | C.12 |
| 1.2270 | B.2 | C.12 |
| 1.2271 | B.3 | C.12 |
| 1.2272 | B.4 | C.12 |
| 1.2273 | B.5 | C.12 |
| 1.2274 | B.6 | C.12 |
| 1.2275 | B.7 | C.12 |
| 1.2276 | B.8 | C.12 |
| 1.2277 | B.9 | C.12 |
| 1.2278 | B.10 | C.12 |
| 1.2279 | B.11 | C.12 |
| 1.2280 | B.12 | C.12 |
| 1.2281 | B.13 | C.12 |
| 1.2282 | B.14 | C.12 |
| 1.2283 | B.15 | C.12 |
| 1.2284 | B.16 | C.12 |
| 1.2285 | B.17 | C.12 |
| 1.2286 | B.18 | C.12 |
| 1.2287 | B.19 | C.12 |
| 1.2288 | B.20 | C.12 |
| 1.2289 | B.21 | C.12 |
| 1.2290 | B.22 | C.12 |
| 1.2291 | B.23 | C.12 |
| 1.2292 | B.24 | C.12 |
| 1.2293 | B.25 | C.12 |
| 1.2294 | B.26 | C.12 |
| 1.2295 | B.27 | C.12 |
| 1.2296 | B.28 | C.12 |
| 1.2297 | B.29 | C.12 |
| 1.2298 | B.30 | C.12 |
| 1.2299 | B.31 | C.12 |
| 1.2300 | B.32 | C.12 |
| 1.2301 | B.33 | C.12 |
| 1.2302 | B.34 | C.12 |
| 1.2303 | B.35 | C.12 |
| 1.2304 | B.36 | C.12 |
| 1.2305 | B.37 | C.12 |
| 1.2306 | B.38 | C.12 |
| 1.2307 | B.39 | C.12 |
| 1.2308 | B.40 | C.12 |
| 1.2309 | B.41 | C.12 |
| 1.2310 | B.42 | C.12 |
| 1.2311 | B.43 | C.12 |
| 1.2312 | B.44 | C.12 |
| 1.2313 | B.45 | C.12 |
| 1.2314 | B.46 | C.12 |
| 1.2315 | B.47 | C.12 |
| 1.2316 | B.48 | C.12 |
| 1.2317 | B.49 | C.12 |
| 1.2318 | B.50 | C.12 |
| 1.2319 | B.51 | C.12 |
| 1.2320 | B.52 | C.12 |
| 1.2321 | B.53 | C.12 |
| 1.2322 | B.54 | C.12 |
| 1.2323 | B.55 | C.12 |
| 1.2324 | B.56 | C.12 |
| 1.2325 | B.57 | C.12 |
| 1.2326 | B.58. | C.12 |
| 1.2327 | B.59 | C.12 |
| 1.2328 | B.60 | C.12 |
| 1.2329 | B.61 | C.12 |
| 1.2330 | B.62 | C.12 |
| 1.2331 | B.63 | C.12 |
| 1.2332 | B.64 | C.12 |
| 1.2333 | B.65 | C.12 |
| 1.2334 | B.66 | C.12 |
| 1.2335 | B.67 | C.12 |
| 1.2336 | B.68 | C.12 |
| 1.2337 | B.69 | C.12 |
| 1.2338 | B.70 | C.12 |
| 1.2339 | B.71 | C.12 |
| 1.2340 | B.72 | C.12 |
| 1.2341 | B.73 | C.12 |
| 1.2342 | B.74 | C.12 |
| 1.2343 | B.75 | C.12 |
| 1.2344 | B.76 | C.12 |
| 1.2345 | B.77 | C.12 |
| 1.2346 | B.78 | C.12 |
| 1.2347 | B.79 | C.12 |
| 1.2348 | B.80 | C.12 |
| 1.2349 | B.81 | C.12 |
| 1.2350 | B.82 | C.12 |
| 1.2351 | B.83 | C.12 |
| 1.2352 | B.84 | C.12 |
| 1.2353 | B.85 | C.12 |
| 1.2354 | B.86 | C.12 |
| 1.2355 | B.87 | C.12 |
| 1.2356 | B.88 | C.12 |
| 1.2357 | B.89 | C.12 |
| 1.2358 | B.90 | C.12 |
| 1.2359 | B.91 | C.12 |
| 1.2360 | B.92 | C.12 |
| 1.2361 | B.93 | C.12 |
| 1.2362 | B.94 | C.12 |
| 1.2363 | B.95 | C.12 |
| 1.2364 | B.96 | C.12 |
| 1.2365 | B.97 | C.12 |
| 1.2366 | B.98 | C.12 |
| 1.2367 | B.99 | C.12 |
| 1.2368 | B.100 | C.12 |
| 1.2369 | B.101 | C.12 |
| 1.2370 | B.102 | C.12 |
| 1.2371 | B.103 | C.12 |
| 1.2372 | B.104 | C.12 |
| 1.2373 | B.105 | C.12 |
| 1.2374 | B.106 | C.12 |
| 1.2375 | B.107 | C.12 |
| 1.2376 | B.108 | C.12 |
| 1.2377 | B.109 | C.12 |
| 1.2378 | B.110 | C.12 |
| 1.2379 | B.111 | C.12 |
| 1.2380 | B.112 | C.12 |
| 1.2381 | B.113 | C.12 |
| 1.2382 | B.114 | C.12 |
| 1.2383 | B.115 | C.12 |
| 1.2384 | B.116 | C.12 |
| 1.2385 | B.117 | C.12 |
| 1.2386 | B.118 | C.12 |
| 1.2387 | B.119 | C.12 |
| 1.2388 | B.120 | C.12 |
| 1.2389 | B.121 | C.12 |
| 1.2390 | B.122 | C.12 |
| 1.2391 | B.123 | C.12 |
| 1.2392 | B.124 | C.12 |
| 1.2393 | B.125 | C.12 |
| 1.2394 | B.126 | C.12 |
| 1.2395 | B.127 | C.12 |
| 1.2396 | B.128 | C.12 |
| 1.2397 | B.129 | C.12 |
| 1.2398 | B.130 | C.12 |
| 1.2399 | B.131 | C.12 |
| 1.2400 | B.132 | C.12 |
| 1.2401 | B.133 | C.12 |
| 1.2402 | B.134 | C.12 |
| 1.2403 | B.135 | C.12 |
| 1.2404 | B.136 | C.12 |
| 1.2405 | B.137 | C.12 |
| 1.2406 | B.138 | C.12 |
| 1.2407 | B.139 | C.12 |
| 1.2408 | B.140 | C.12 |
| 1.2409 | B.141 | C.12 |
| 1.2410 | B.142 | C.12 |
| 1.2411 | B.143 | C.12 |
| 1.2412 | B.144 | C.12 |
| 1.2413 | B.145 | C.12 |
| 1.2414 | B.146 | C.12 |
| 1.2415 | B.147 | C.12 |
| 1.2416 | B.148 | C.12 |
| 1.2417 | B.149 | C.12 |
| 1.2418 | B.150 | C.12 |

TABLE 2-continued

| comb. no. | herbicide B | safener C |
|---|---|---|
| 1.2419 | B.151 | C.12 |
| 1.2420 | B.152 | C.12 |
| 1.2421 | B.153 | C.12 |
| 1.2422 | B.154 | C.12 |
| 1.2423 | B.155 | C.12 |
| 1.2424 | B.156 | C.12 |
| 1.2425 | B.157 | C.12 |
| 1.2426 | B.158 | C.12 |
| 1.2427 | B.159 | C.12 |
| 1.2428 | B.160 | C.12 |
| 1.2429 | B.161 | C.12 |
| 1.2430 | B.162 | C.12 |
| 1.2431 | B.163 | C.12 |
| 1.2432 | B.164 | C.12 |
| 1.2433 | B.165 | C.12 |
| 1.2434 | B.166 | C.12 |
| 1.2435 | B.167 | C.12 |
| 1.2436 | B.168 | C.12 |
| 1.2437 | B.169 | C.12 |
| 1.2438 | B.170 | C.12 |
| 1.2439 | B.171 | C.12 |
| 1.2440 | B.172 | C.12 |
| 1.2441 | B.173 | C.12 |
| 1.2442 | B.174 | C.12 |
| 1.2443 | B.175 | C.12 |
| 1.2444 | B.176 | C.12 |
| 1.2445 | B.177 | C.12 |
| 1.2446 | B.178 | C.12 |
| 1.2447 | B.179 | C.12 |
| 1.2448 | B.180 | C.12 |
| 1.2449 | B.181 | C.12 |
| 1.2450 | B.182 | C.12 |
| 1.2451 | B.183 | C.12 |
| 1.2452 | B.184 | C.12 |
| 1.2453 | B.185 | C.12 |
| 1.2454 | B.186 | C.12 |
| 1.2455 | B.187 | C.12 |
| 1.2456 | B.188 | C.12 |
| 1.2457 | B.189 | C.12 |
| 1.2458 | B.1 | C.13 |
| 1.2459 | B.2 | C.13 |
| 1.2460 | B.3 | C.13 |
| 1.2461 | B.4 | C.13 |
| 1.2462 | B.5 | C.13 |
| 1.2463 | B.6 | C.13 |
| 1.2464 | B.7 | C.13 |
| 1.2465 | B.8 | C.13 |
| 1.2466 | B.9 | C.13 |
| 1.2467 | B.10 | C.13 |
| 1.2468 | B.11 | C.13 |
| 1.2469 | B.12 | C.13 |
| 1.2470 | B.13 | C.13 |
| 1.2471 | B.14 | C.13 |
| 1.2472 | B.15 | C.13 |
| 1.2473 | B.16 | C.13 |
| 1.2474 | B.17 | C.13 |
| 1.2475 | B.18 | C.13 |
| 1.2476 | B.19 | C.13 |
| 1.2477 | B.20 | C.13 |
| 1.2478 | B.21 | C.13 |
| 1.2479 | B.22 | C.13 |
| 1.2480 | B.23 | C.13 |
| 1.2481 | B.24 | C.13 |
| 1.2482 | B.25 | C.13 |
| 1.2483 | B.26 | C.13 |
| 1.2484 | B.27 | C.13 |
| 1.2485 | B.28 | C.13 |
| 1.2486 | B.29 | C.13 |
| 1.2487 | B.30 | C.13 |
| 1.2488 | B.31 | C.13 |
| 1.2489 | B.32 | C.13 |
| 1.2490 | B.33 | C.13 |
| 1.2491 | B.34 | C.13 |
| 1.2492 | B.35 | C.13 |
| 1.2493 | B.36 | C.13 |
| 1.2494 | B.37 | C.13 |
| 1.2495 | B.38 | C.13 |
| 1.2496 | B.39 | C.13 |
| 1.2497 | B.40 | C.13 |
| 1.2498 | B.41 | C.13 |
| 1.2499 | B.42 | C.13 |
| 1.2500 | B.43 | C.13 |
| 1.2501 | B.44 | C.13 |
| 1.2502 | B.45 | C.13 |
| 1.2503 | B.46 | C.13 |
| 1.2504 | B.47 | C.13 |
| 1.2505 | B.48 | C.13 |
| 1.2506 | B.49 | C.13 |
| 1.2507 | B.50 | C.13 |
| 1.2508 | B.51 | C.13 |
| 1.2509 | B.52 | C.13 |
| 1.2510 | B.53 | C.13 |
| 1.2511 | B.54 | C.13 |
| 1.2512 | B.55 | C.13 |
| 1.2513 | B.56 | C.13 |
| 1.2514 | B.57 | C.13 |
| 1.2515 | B.58. | C.13 |
| 1.2516 | B.59 | C.13 |
| 1.2517 | B.60 | C.13 |
| 1.2518 | B.61 | C.13 |
| 1.2519 | B.62 | C.13 |
| 1.2520 | B.63 | C.13 |
| 1.2521 | B.64 | C.13 |
| 1.2522 | B.65 | C.13 |
| 1.2523 | B.66 | C.13 |
| 1.2524 | B.67 | C.13 |
| 1.2525 | B.68 | C.13 |
| 1.2526 | B.69 | C.13 |
| 1.2527 | B.70 | C.13 |
| 1.2528 | B.71 | C.13 |
| 1.2529 | B.72 | C.13 |
| 1.2530 | B.73 | C.13 |
| 1.2531 | B.74 | C.13 |
| 1.2532 | B.75 | C.13 |
| 1.2533 | B.76 | C.13 |
| 1.2534 | B.77 | C.13 |
| 1.2535 | B.78 | C.13 |
| 1.2536 | B.79 | C.13 |
| 1.2537 | B.80 | C.13 |
| 1.2538 | B.81 | C.13 |
| 1.2539 | B.82 | C.13 |
| 1.2540 | B.83 | C.13 |
| 1.2541 | B.84 | C.13 |
| 1.2542 | B.85 | C.13 |
| 1.2543 | B.86 | C.13 |
| 1.2544 | B.87 | C.13 |
| 1.2545 | B.88 | C.13 |
| 1.2546 | B.89 | C.13 |
| 1.2547 | B.90 | C.13 |
| 1.2548 | B.91 | C.13 |
| 1.2549 | B.92 | C.13 |
| 1.2550 | B.93 | C.13 |
| 1.2551 | B.94 | C.13 |
| 1.2552 | B.95 | C.13 |
| 1.2553 | B.96 | C.13 |
| 1.2554 | B.97 | C.13 |
| 1.2555 | B.98 | C.13 |
| 1.2556 | B.99 | C.13 |
| 1.2557 | B.100 | C.13 |
| 1.2558 | B.101 | C.13 |
| 1.2559 | B.102 | C.13 |
| 1.2560 | B.103 | C.13 |
| 1.2561 | B.104 | C.13 |
| 1.2562 | B.105 | C.13 |
| 1.2563 | B.106 | C.13 |
| 1.2564 | B.107 | C.13 |
| 1.2565 | B.108 | C.13 |
| 1.2566 | B.109 | C.13 |
| 1.2567 | B.110 | C.13 |
| 1.2568 | B.111 | C.13 |
| 1.2569 | B.112 | C.13 |
| 1.2570 | B.113 | C.13 |
| 1.2571 | B.114 | C.13 |
| 1.2572 | B.115 | C.13 |
| 1.2573 | B.116 | C.13 |
| 1.2574 | B.117 | C.13 |

TABLE 2-continued

| comb. no. | herbicide B | safener C |
|---|---|---|
| 1.2575 | B.118 | C.13 |
| 1.2576 | B.119 | C.13 |
| 1.2577 | B.120 | C.13 |
| 1.2578 | B.121 | C.13 |
| 1.2579 | B.122 | C.13 |
| 1.2580 | B.123 | C.13 |
| 1.2581 | B.124 | C.13 |
| 1.2582 | B.125 | C.13 |
| 1.2583 | B.126 | C.13 |
| 1.2584 | B.127 | C.13 |
| 1.2585 | B.128 | C.13 |
| 1.2586 | B.129 | C.13 |
| 1.2587 | B.130 | C.13 |
| 1.2588 | B.131 | C.13 |
| 1.2589 | B.132 | C.13 |
| 1.2590 | B.133 | C.13 |
| 1.2591 | B.134 | C.13 |
| 1.2592 | B.135 | C.13 |
| 1.2593 | B.136 | C.13 |
| 1.2594 | B.137 | C.13 |
| 1.2595 | B.138 | C.13 |
| 1.2596 | B.139 | C.13 |
| 1.2597 | B.140 | C.13 |
| 1.2598 | B.141 | C.13 |
| 1.2599 | B.142 | C.13 |
| 1.2600 | B.143 | C.13 |
| 1.2601 | B.144 | C.13 |
| 1.2602 | B.145 | C.13 |
| 1.2603 | B.146 | C.13 |
| 1.2604 | B.147 | C.13 |
| 1.2605 | B.148 | C.13 |
| 1.2606 | B.149 | C.13 |
| 1.2607 | B.150 | C.13 |
| 1.2608 | B.151 | C.13 |
| 1.2609 | B.152 | C.13 |
| 1.2610 | B.153 | C.13 |
| 1.2611 | B.154 | C.13 |
| 1.2612 | B.155 | C.13 |
| 1.2613 | B.156 | C.13 |
| 1.2614 | B.157 | C.13 |
| 1.2615 | B.158 | C.13 |
| 1.2616 | B.159 | C.13 |
| 1.2617 | B.160 | C.13 |
| 1.2618 | B.161 | C.13 |
| 1.2619 | B.162 | C.13 |
| 1.2620 | B.163 | C.13 |
| 1.2621 | B.164 | C.13 |
| 1.2622 | B.165 | C.13 |
| 1.2623 | B.166 | C.13 |
| 1.2624 | B.167 | C.13 |
| 1.2625 | B.168 | C.13 |
| 1.2626 | B.169 | C.13 |
| 1.2627 | B.170 | C.13 |
| 1.2628 | B.171 | C.13 |
| 1.2629 | B.172 | C.13 |
| 1.2630 | B.173 | C.13 |
| 1.2631 | B.174 | C.13 |
| 1.2632 | B.175 | C.13 |
| 1.2633 | B.176 | C.13 |
| 1.2634 | B.177 | C.13 |
| 1.2635 | B.178 | C.13 |
| 1.2636 | B.179 | C.13 |
| 1.2637 | B.180 | C.13 |
| 1.2638 | B.181 | C.13 |
| 1.2639 | B.182 | C.13 |
| 1.2640 | B.183 | C.13 |
| 1.2641 | B.184 | C.13 |
| 1.2642 | B.185 | C.13 |
| 1.2643 | B.186 | C.13 |
| 1.2644 | B.187 | C.13 |
| 1.2645 | B.188 | C.13 |
| 1.2646 | B.189 | C.13 |
| 1.2647 | B.1 | C.14 |
| 1.2648 | B.2 | C.14 |
| 1.2649 | B.3 | C.14 |
| 1.2650 | B.4 | C.14 |
| 1.2651 | B.5 | C.14 |
| 1.2652 | B.6 | C.14 |
| 1.2653 | B.7 | C.14 |
| 1.2654 | B.8 | C.14 |
| 1.2655 | B.9 | C.14 |
| 1.2656 | B.10 | C.14 |
| 1.2657 | B.11 | C.14 |
| 1.2658 | B.12 | C.14 |
| 1.2659 | B.13 | C.14 |
| 1.2660 | B.14 | C.14 |
| 1.2661 | B.15 | C.14 |
| 1.2662 | B.16 | C.14 |
| 1.2663 | B.17 | C.14 |
| 1.2664 | B.18 | C.14 |
| 1.2665 | B.19 | C.14 |
| 1.2666 | B.20 | C.14 |
| 1.2667 | B.21 | C.14 |
| 1.2668 | B.22 | C.14 |
| 1.2669 | B.23 | C.14 |
| 1.2670 | B.24 | C.14 |
| 1.2671 | B.25 | C.14 |
| 1.2672 | B.26 | C.14 |
| 1.2673 | B.27 | C.14 |
| 1.2674 | B.28 | C.14 |
| 1.2675 | B.29 | C.14 |
| 1.2676 | B.30 | C.14 |
| 1.2677 | B.31 | C.14 |
| 1.2678 | B.32 | C.14 |
| 1.2679 | B.33 | C.14 |
| 1.2680 | B.34 | C.14 |
| 1.2681 | B.35 | C.14 |
| 1.2682 | B.36 | C.14 |
| 1.2683 | B.37 | C.14 |
| 1.2684 | B.38 | C.14 |
| 1.2685 | B.39 | C.14 |
| 1.2686 | B.40 | C.14 |
| 1.2687 | B.41 | C.14 |
| 1.2688 | B.42 | C.14 |
| 1.2689 | B.43 | C.14 |
| 1.2690 | B.44 | C.14 |
| 1.2691 | B.45 | C.14 |
| 1.2692 | B.46 | C.14 |
| 1.2693 | B.47 | C.14 |
| 1.2694 | B.48 | C.14 |
| 1.2695 | B.49 | C.14 |
| 1.2696 | B.50 | C.14 |
| 1.2697 | B.51 | C.14 |
| 1.2698 | B.52 | C.14 |
| 1.2699 | B.53 | C.14 |
| 1.2700 | B.54 | C.14 |
| 1.2701 | B.55 | C.14 |
| 1.2702 | B.56 | C.14 |
| 1.2703 | B.57 | C.14 |
| 1.2704 | B.58 | C.14 |
| 1.2705 | B.59 | C.14 |
| 1.2706 | B.60 | C.14 |
| 1.2707 | B.61 | C.14 |
| 1.2708 | B.62 | C.14 |
| 1.2709 | B.63 | C.14 |
| 1.2710 | B.64 | C.14 |
| 1.2711 | B.65 | C.14 |
| 1.2712 | B.66 | C.14 |
| 1.2713 | B.67 | C.14 |
| 1.2714 | B.68 | C.14 |
| 1.2715 | B.69 | C.14 |
| 1.2716 | B.70 | C.14 |
| 1.2717 | B.71 | C.14 |
| 1.2718 | B.72 | C.14 |
| 1.2719 | B.73 | C.14 |
| 1.2720 | B.74 | C.14 |
| 1.2721 | B.75 | C.14 |
| 1.2722 | B.76 | C.14 |
| 1.2723 | B.77 | C.14 |
| 1.2724 | B.78 | C.14 |
| 1.2725 | B.79 | C.14 |
| 1.2726 | B.80 | C.14 |
| 1.2727 | B.81 | C.14 |
| 1.2728 | B.82 | C.14 |
| 1.2729 | B.83 | C.14 |
| 1.2730 | B.84 | C.14 |

TABLE 2-continued

| comb. no. | herbicide B | safener C |
|---|---|---|
| 1.2731 | B.85 | C.14 |
| 1.2732 | B.86 | C.14 |
| 1.2733 | B.87 | C.14 |
| 1.2734 | B.88 | C.14 |
| 1.2735 | B.89 | C.14 |
| 1.2736 | B.90 | C.14 |
| 1.2737 | B.91 | C.14 |
| 1.2738 | B.92 | C.14 |
| 1.2739 | B.93 | C.14 |
| 1.2740 | B.94 | C.14 |
| 1.2741 | B.95 | C.14 |
| 1.2742 | B.96 | C.14 |
| 1.2743 | B.97 | C.14 |
| 1.2744 | B.98 | C.14 |
| 1.2745 | B.99 | C.14 |
| 1.2746 | B.100 | C.14 |
| 1.2747 | B.101 | C.14 |
| 1.2748 | B.102 | C.14 |
| 1.2749 | B.103 | C.14 |
| 1.2750 | B.104 | C.14 |
| 1.2751 | B.105 | C.14 |
| 1.2752 | B.106 | C.14 |
| 1.2753 | B.107 | C.14 |
| 1.2754 | B.108 | C.14 |
| 1.2755 | B.109 | C.14 |
| 1.2756 | B.110 | C.14 |
| 1.2757 | B.111 | C.14 |
| 1.2758 | B.112 | C.14 |
| 1.2759 | B.113 | C.14 |
| 1.2760 | B.114 | C.14 |
| 1.2761 | B.115 | C.14 |
| 1.2762 | B.116 | C.14 |
| 1.2763 | B.117 | C.14 |
| 1.2764 | B.118 | C.14 |
| 1.2765 | B.119 | C.14 |
| 1.2766 | B.120 | C.14 |
| 1.2767 | B.121 | C.14 |
| 1.2768 | B.122 | C.14 |
| 1.2769 | B.123 | C.14 |
| 1.2770 | B.124 | C.14 |
| 1.2771 | B.125 | C.14 |
| 1.2772 | B.126 | C.14 |
| 1.2773 | B.127 | C.14 |
| 1.2774 | B.128 | C.14 |
| 1.2775 | B.129 | C.14 |
| 1.2776 | B.130 | C.14 |
| 1.2777 | B.131 | C.14 |
| 1.2778 | B.132 | C.14 |
| 1.2779 | B.133 | C.14 |
| 1.2780 | B.134 | C.14 |
| 1.2781 | B.135 | C.14 |
| 1.2782 | B.136 | C.14 |
| 1.2783 | B.137 | C.14 |
| 1.2784 | B.138 | C.14 |
| 1.2785 | B.139 | C.14 |
| 1.2786 | B.140 | C.14 |
| 1.2787 | B.141 | C.14 |
| 1.2788 | B.142 | C.14 |
| 1.2789 | B.143 | C.14 |
| 1.2790 | B.144 | C.14 |
| 1.2791 | B.145 | C.14 |
| 1.2792 | B.146 | C.14 |
| 1.2793 | B.147 | C.14 |
| 1.2794 | B.148 | C.14 |
| 1.2795 | B.149 | C.14 |
| 1.2796 | B.150 | C.14 |
| 1.2797 | B.151 | C.14 |
| 1.2798 | B.152 | C.14 |
| 1.2799 | B.153 | C.14 |
| 1.2800 | B.154 | C.14 |
| 1.2801 | B.155 | C.14 |
| 1.2802 | B.156 | C.14 |
| 1.2803 | B.157 | C.14 |
| 1.2804 | B.158 | C.14 |
| 1.2805 | B.159 | C.14 |
| 1.2806 | B.160 | C.14 |
| 1.2807 | B.161 | C.14 |
| 1.2808 | B.162 | C.14 |
| 1.2809 | B.163 | C.14 |
| 1.2810 | B.164 | C.14 |
| 1.2811 | B.165 | C.14 |
| 1.2812 | B.166 | C.14 |
| 1.2813 | B.167 | C.14 |
| 1.2814 | B.168 | C.14 |
| 1.2815 | B.169 | C.14 |
| 1.2816 | B.170 | C.14 |
| 1.2817 | B.171 | C.14 |
| 1.2818 | B.172 | C.14 |
| 1.2819 | B.173 | C.14 |
| 1.2820 | B.174 | C.14 |
| 1.2821 | B.175 | C.14 |
| 1.2822 | B.176 | C.14 |
| 1.2823 | B.177 | C.14 |
| 1.2824 | B.178 | C.14 |
| 1.2825 | B.179 | C.14 |
| 1.2826 | B.180 | C.14 |
| 1.2827 | B.181 | C.14 |
| 1.2828 | B.182 | C.14 |
| 1.2829 | B.183 | C.14 |
| 1.2830 | B.184 | C.14 |
| 1.2831 | B.185 | C.14 |
| 1.2832 | B.186 | C.14 |
| 1.2833 | B.187 | C.14 |
| 1.2834 | B.188 | C.14 |
| 1.2835 | B.189 | C.14 |
| 1.2836 | B.1 | C.15 |
| 1.2837 | B.2 | C.15 |
| 1.2838 | B.3 | C.15 |
| 1.2839 | B.4 | C.15 |
| 1.2840 | B.5 | C.15 |
| 1.2841 | B.6 | C.15 |
| 1.2842 | B.7 | C.15 |
| 1.2843 | B.8 | C.15 |
| 1.2844 | B.9 | C.15 |
| 1.2845 | B.10 | C.15 |
| 1.2846 | B.11 | C.15 |
| 1.2847 | B.12 | C.15 |
| 1.2848 | B.13 | C.15 |
| 1.2849 | B.14 | C.15 |
| 1.2850 | B.15 | C.15 |
| 1.2851 | B.16 | C.15 |
| 1.2852 | B.17 | C.15 |
| 1.2853 | B.18 | C.15 |
| 1.2854 | B.19 | C.15 |
| 1.2855 | B.20 | C.15 |
| 1.2856 | B.21 | C.15 |
| 1.2857 | B.22 | C.15 |
| 1.2858 | B.23 | C.15 |
| 1.2859 | B.24 | C.15 |
| 1.2860 | B.25 | C.15 |
| 1.2861 | B.26 | C.15 |
| 1.2862 | B.27 | C.15 |
| 1.2863 | B.28 | C.15 |
| 1.2864 | B.29 | C.15 |
| 1.2865 | B.30 | C.15 |
| 1.2866 | B.31 | C.15 |
| 1.2867 | B.32 | C.15 |
| 1.2868 | B.33 | C.15 |
| 1.2869 | B.34 | C.15 |
| 1.2870 | B.35 | C.15 |
| 1.2871 | B.36 | C.15 |
| 1.2872 | B.37 | C.15 |
| 1.2873 | B.38 | C.15 |
| 1.2874 | B.39 | C.15 |
| 1.2875 | B.40 | C.15 |
| 1.2876 | B.41 | C.15 |
| 1.2877 | B.42 | C.15 |
| 1.2878 | B.43 | C.15 |
| 1.2879 | B.44 | C.15 |
| 1.2880 | B.45 | C.15 |
| 1.2881 | B.46 | C.15 |
| 1.2882 | B.47 | C.15 |
| 1.2883 | B.48 | C.15 |
| 1.2884 | B.49 | C.15 |
| 1.2885 | B.50 | C.15 |
| 1.2886 | B.51 | C.15 |

TABLE 2-continued

| comb. no. | herbicide B | safener C |
|---|---|---|
| 1.2887 | B.52 | C.15 |
| 1.2888 | B.53 | C.15 |
| 1.2889 | B.54 | C.15 |
| 1.2890 | B.55 | C.15 |
| 1.2891 | B.56 | C.15 |
| 1.2892 | B.57 | C.15 |
| 1.2893 | B.58. | C.15 |
| 1.2894 | B.59 | C.15 |
| 1.2895 | B.60 | C.15 |
| 1.2896 | B.61 | C.15 |
| 1.2897 | B.62 | C.15 |
| 1.2898 | B.63 | C.15 |
| 1.2899 | B.64 | C.15 |
| 1.2900 | B.65 | C.15 |
| 1.2901 | B.66 | C.15 |
| 1.2902 | B.67 | C.15 |
| 1.2903 | B.68 | C.15 |
| 1.2904 | B.69 | C.15 |
| 1.2905 | B.70 | C.15 |
| 1.2906 | B.71 | C.15 |
| 1.2907 | B.72 | C.15 |
| 1.2908 | B.73 | C.15 |
| 1.2909 | B.74 | C.15 |
| 1.2910 | B.75 | C.15 |
| 1.2911 | B.76 | C.15 |
| 1.2912 | B.77 | C.15 |
| 1.2913 | B.78 | C.15 |
| 1.2914 | B.79 | C.15 |
| 1.2915 | B.80 | C.15 |
| 1.2916 | B.81 | C.15 |
| 1.2917 | B.82 | C.15 |
| 1.2918 | B.83 | C.15 |
| 1.2919 | B.84 | C.15 |
| 1.2920 | B.85 | C.15 |
| 1.2921 | B.86 | C.15 |
| 1.2922 | B.87 | C.15 |
| 1.2923 | B.88 | C.15 |
| 1.2924 | B.89 | C.15 |
| 1.2925 | B.90 | C.15 |
| 1.2926 | B.91 | C.15 |
| 1.2927 | B.92 | C.15 |
| 1.2928 | B.93 | C.15 |
| 1.2929 | B.94 | C.15 |
| 1.2930 | B.95 | C.15 |
| 1.2931 | B.96 | C.15 |
| 1.2932 | B.97 | C.15 |
| 1.2933 | B.98 | C.15 |
| 1.2934 | B.99 | C.15 |
| 1.2935 | B.100 | C.15 |
| 1.2936 | B.101 | C.15 |
| 1.2937 | B.102 | C.15 |
| 1.2938 | B.103 | C.15 |
| 1.2939 | B.104 | C.15 |
| 1.2940 | B.105 | C.15 |
| 1.2941 | B.106 | C.15 |
| 1.2942 | B.107 | C.15 |
| 1.2943 | B.108 | C.15 |
| 1.2944 | B.109 | C.15 |
| 1.2945 | B.110 | C.15 |
| 1.2946 | B.111 | C.15 |
| 1.2947 | B.112 | C.15 |
| 1.2948 | B.113 | C.15 |
| 1.2949 | B.114 | C.15 |
| 1.2950 | B.115 | C.15 |
| 1.2951 | B.116 | C.15 |
| 1.2952 | B.117 | C.15 |
| 1.2953 | B.118 | C.15 |
| 1.2954 | B.119 | C.15 |
| 1.2955 | B.120 | C.15 |
| 1.2956 | B.121 | C.15 |
| 1.2957 | B.122 | C.15 |
| 1.2958 | B.123 | C.15 |
| 1.2959 | B.124 | C.15 |
| 1.2960 | B.125 | C.15 |
| 1.2961 | B.126 | C.15 |
| 1.2962 | B.127 | C.15 |
| 1.2963 | B.128 | C.15 |
| 1.2964 | B.129 | C.15 |
| 1.2965 | B.130 | C.15 |
| 1.2966 | B.131 | C.15 |
| 1.2967 | B.132 | C.15 |
| 1.2968 | B.133 | C.15 |
| 1.2969 | B.134 | C.15 |
| 1.2970 | B.135 | C.15 |
| 1.2971 | B.136 | C.15 |
| 1.2972 | B.137 | C.15 |
| 1.2973 | B.138 | C.15 |
| 1.2974 | B.139 | C.15 |
| 1.2975 | B.140 | C.15 |
| 1.2976 | B.141 | C.15 |
| 1.2977 | B.142 | C.15 |
| 1.2978 | B.143 | C.15 |
| 1.2979 | B.144 | C.15 |
| 1.2980 | B.145 | C.15 |
| 1.2981 | B.146 | C.15 |
| 1.2982 | B.147 | C.15 |
| 1.2983 | B.148 | C.15 |
| 1.2984 | B.149 | C.15 |
| 1.2985 | B.150 | C.15 |
| 1.2986 | B.151 | C.15 |
| 1.2987 | B.152 | C.15 |
| 1.2988 | B.153 | C.15 |
| 1.2989 | B.154 | C.15 |
| 1.2990 | B.155 | C.15 |
| 1.2991 | B.156 | C.15 |
| 1.2992 | B.157 | C.15 |
| 1.2993 | B.158 | C.15 |
| 1.2994 | B.159 | C.15 |
| 1.2995 | B.160 | C.15 |
| 1.2996 | B.161 | C.15 |
| 1.2997 | B.162 | C.15 |
| 1.2998 | B.163 | C.15 |
| 1.2999 | B.164 | C.15 |
| 1.3000 | B.165 | C.15 |
| 1.3001 | B.166 | C.15 |
| 1.3002 | B.167 | C.15 |
| 1.3003 | B.168 | C.15 |
| 1.3004 | B.169 | C.15 |
| 1.3005 | B.170 | C.15 |
| 1.3006 | B.171 | C.15 |
| 1.3007 | B.172 | C.15 |
| 1.3008 | B.173 | C.15 |
| 1.3009 | B.174 | C.15 |
| 1.3010 | B.175 | C.15 |
| 1.3011 | B.176 | C.15 |
| 1.3012 | B.177 | C.15 |
| 1.3013 | B.178 | C.15 |
| 1.3014 | B.179 | C.15 |
| 1.3015 | B.180 | C.15 |
| 1.3016 | B.181 | C.15 |
| 1.3017 | B.182 | C.15 |
| 1.3018 | B.183 | C.15 |
| 1.3019 | B.184 | C.15 |
| 1.3020 | B.185 | C.15 |
| 1.3021 | B.186 | C.15 |
| 1.3022 | B.187 | C.15 |
| 1.3023 | B.188 | C.15 |
| 1.3024 | B.189 | C.15 |
| 1.3025 | B.1 | C.16 |
| 1.3026 | B.2 | C.16 |
| 1.3027 | B.3 | C.16 |
| 1.3028 | B.4 | C.16 |
| 1.3029 | B.5 | C.16 |
| 1.3030 | B.6 | C.16 |
| 1.3031 | B.7 | C.16 |
| 1.3032 | B.8 | C.16 |
| 1.3033 | B.9 | C.16 |
| 1.3034 | B.10 | C.16 |
| 1.3035 | B.11 | C.16 |
| 1.3036 | B.12 | C.16 |
| 1.3037 | B.13 | C.16 |
| 1.3038 | B.14 | C.16 |
| 1.3039 | B.15 | C.16 |
| 1.3040 | B.16 | C.16 |
| 1.3041 | B.17 | C.16 |
| 1.3042 | B.18 | C.16 |

TABLE 2-continued

| comb. no. | herbicide B | safener C |
|---|---|---|
| 1.3043 | B.19 | C.16 |
| 1.3044 | B.20 | C.16 |
| 1.3045 | B.21 | C.16 |
| 1.3046 | B.22 | C.16 |
| 1.3047 | B.23 | C.16 |
| 1.3048 | B.24 | C.16 |
| 1.3049 | B.25 | C.16 |
| 1.3050 | B.26 | C.16 |
| 1.3051 | B.27 | C.16 |
| 1.3052 | B.28 | C.16 |
| 1.3053 | B.29 | C.16 |
| 1.3054 | B.30 | C.16 |
| 1.3055 | B.31 | C.16 |
| 1.3056 | B.32 | C.16 |
| 1.3057 | B.33 | C.16 |
| 1.3058 | B.34 | C.16 |
| 1.3059 | B.35 | C.16 |
| 1.3060 | B.36 | C.16 |
| 1.3061 | B.37 | C.16 |
| 1.3062 | B.38 | C.16 |
| 1.3063 | B.39 | C.16 |
| 1.3064 | B.40 | C.16 |
| 1.3065 | B.41 | C.16 |
| 1.3066 | B.42 | C.16 |
| 1.3067 | B.43 | C.16 |
| 1.3068 | B.44 | C.16 |
| 1.3069 | B.45 | C.16 |
| 1.3070 | B.46 | C.16 |
| 1.3071 | B.47 | C.16 |
| 1.3072 | B.48 | C.16 |
| 1.3073 | B.49 | C.16 |
| 1.3074 | B.50 | C.16 |
| 1.3075 | B.51 | C.16 |
| 1.3076 | B.52 | C.16 |
| 1.3077 | B.53 | C.16 |
| 1.3078 | B.54 | C.16 |
| 1.3079 | B.55 | C.16 |
| 1.3080 | B.56 | C.16 |
| 1.3081 | B.57 | C.16 |
| 1.3082 | B.58. | C.16 |
| 1.3083 | B.59 | C.16 |
| 1.3084 | B.60 | C.16 |
| 1.3085 | B.61 | C.16 |
| 1.3086 | B.62 | C.16 |
| 1.3087 | B.63 | C.16 |
| 1.3088 | B.64 | C.16 |
| 1.3089 | B.65 | C.16 |
| 1.3090 | B.66 | C.16 |
| 1.3091 | B.67 | C.16 |
| 1.3092 | B.68 | C.16 |
| 1.3093 | B.69 | C.16 |
| 1.3094 | B.70 | C.16 |
| 1.3095 | B.71 | C.16 |
| 1.3096 | B.72 | C.16 |
| 1.3097 | B.73 | C.16 |
| 1.3098 | B.74 | C.16 |
| 1.3099 | B.75 | C.16 |
| 1.3100 | B.76 | C.16 |
| 1.3101 | B.77 | C.16 |
| 1.3102 | B.78 | C.16 |
| 1.3103 | B.79 | C.16 |
| 1.3104 | B.80 | C.16 |
| 1.3105 | B.81 | C.16 |
| 1.3106 | B.82 | C.16 |
| 1.3107 | B.83 | C.16 |
| 1.3108 | B.84 | C.16 |
| 1.3109 | B.85 | C.16 |
| 1.3110 | B.86 | C.16 |
| 1.3111 | B.87 | C.16 |
| 1.3112 | B.88 | C.16 |
| 1.3113 | B.89 | C.16 |
| 1.3114 | B.90 | C.16 |
| 1.3115 | B.91 | C.16 |
| 1.3116 | B.92 | C.16 |
| 1.3117 | B.93 | C.16 |
| 1.3118 | B.94 | C.16 |
| 1.3119 | B.95 | C.16 |
| 1.3120 | B.96 | C.16 |
| 1.3121 | B.97 | C.16 |
| 1.3122 | B.98 | C.16 |
| 1.3123 | B.99 | C.16 |
| 1.3124 | B.100 | C.16 |
| 1.3125 | B.101 | C.16 |
| 1.3126 | B.102 | C.16 |
| 1.3127 | B.103 | C.16 |
| 1.3128 | B.104 | C.16 |
| 1.3129 | B.105 | C.16 |
| 1.3130 | B.106 | C.16 |
| 1.3131 | B.107 | C.16 |
| 1.3132 | B.108 | C.16 |
| 1.3133 | B.109 | C.16 |
| 1.3134 | B.110 | C.16 |
| 1.3135 | B.111 | C.16 |
| 1.3136 | B.112 | C.16 |
| 1.3137 | B.113 | C.16 |
| 1.3138 | B.114 | C.16 |
| 1.3139 | B.115 | C.16 |
| 1.3140 | B.116 | C.16 |
| 1.3141 | B.117 | C.16 |
| 1.3142 | B.118 | C.16 |
| 1.3143 | B.119 | C.16 |
| 1.3144 | B.120 | C.16 |
| 1.3145 | B.121 | C.16 |
| 1.3146 | B.122 | C.16 |
| 1.3147 | B.123 | C.16 |
| 1.3148 | B.124 | C.16 |
| 1.3149 | B.125 | C.16 |
| 1.3150 | B.126 | C.16 |
| 1.3151 | B.127 | C.16 |
| 1.3152 | B.128 | C.16 |
| 1.3153 | B.129 | C.16 |
| 1.3154 | B.130 | C.16 |
| 1.3155 | B.131 | C.16 |
| 1.3156 | B.132 | C.16 |
| 1.3157 | B.133 | C.16 |
| 1.3158 | B.134 | C.16 |
| 1.3159 | B.135 | C.16 |
| 1.3160 | B.136 | C.16 |
| 1.3161 | B.137 | C.16 |
| 1.3162 | B.138 | C.16 |
| 1.3163 | B.139 | C.16 |
| 1.3164 | B.140 | C.16 |
| 1.3165 | B.141 | C.16 |
| 1.3166 | B.142 | C.16 |
| 1.3167 | B.143 | C.16 |
| 1.3168 | B.144 | C.16 |
| 1.3169 | B.145 | C.16 |
| 1.3170 | B.146 | C.16 |
| 1.3171 | B.147 | C.16 |
| 1.3172 | B.148 | C.16 |
| 1.3173 | B.149 | C.16 |
| 1.3174 | B.150 | C.16 |
| 1.3175 | B.151 | C.16 |
| 1.3176 | B.152 | C.16 |
| 1.3177 | B.153 | C.16 |
| 1.3178 | B.154 | C.16 |
| 1.3179 | B.155 | C.16 |
| 1.3180 | B.156 | C.16 |
| 1.3181 | B.157 | C.16 |
| 1.3182 | B.158 | C.16 |
| 1.3183 | B.159 | C.16 |
| 1.3184 | B.160 | C.16 |
| 1.3185 | B.161 | C.16 |
| 1.3186 | B.162 | C.16 |
| 1.3187 | B.163 | C.16 |
| 1.3188 | B.164 | C.16 |
| 1.3189 | B.165 | C.16 |
| 1.3190 | B.166 | C.16 |
| 1.3191 | B.167 | C.16 |
| 1.3192 | B.168 | C.16 |
| 1.3193 | B.169 | C.16 |
| 1.3194 | B.170 | C.16 |
| 1.3195 | B.171 | C.16 |
| 1.3196 | B.172 | C.16 |
| 1.3197 | B.173 | C.16 |
| 1.3198 | B.174 | C.16 |

TABLE 2-continued

| comb. no. | herbicide B | safener C |
|---|---|---|
| 1.3199 | B.175 | C.16 |
| 1.3200 | B.176 | C.16 |
| 1.3201 | B.177 | C.16 |
| 1.3202 | B.178 | C.16 |
| 1.3203 | B.179 | C.16 |
| 1.3204 | B.180 | C.16 |
| 1.3205 | B.181 | C.16 |
| 1.3206 | B.182 | C.16 |
| 1.3207 | B.183 | C.16 |
| 1.3208 | B.184 | C.16 |
| 1.3209 | B.185 | C.16 |
| 1.3210 | B.186 | C.16 |
| 1.3211 | B.187 | C.16 |
| 1.3212 | B.188 | C.16 |
| 1.3213 | B.189 | C.16 |
| 1.3214 | B.1 | C.17 |
| 1.3215 | B.2 | C.17 |
| 1.3216 | B.3 | C.17 |
| 1.3217 | B.4 | C.17 |
| 1.3218 | B.5 | C.17 |
| 1.3219 | B.6 | C.17 |
| 1.3220 | B.7 | C.17 |
| 1.3221 | B.8 | C.17 |
| 1.3222 | B.9 | C.17 |
| 1.3223 | B.10 | C.17 |
| 1.3224 | B.11 | C.17 |
| 1.3225 | B.12 | C.17 |
| 1.3226 | B.13 | C.17 |
| 1.3227 | B.14 | C.17 |
| 1.3228 | B.15 | C.17 |
| 1.3229 | B.16 | C.17 |
| 1.3230 | B.17 | C.17 |
| 1.3231 | B.18 | C.17 |
| 1.3232 | B.19 | C.17 |
| 1.3233 | B.20 | C.17 |
| 1.3234 | B.21 | C.17 |
| 1.3235 | B.22 | C.17 |
| 1.3236 | B.23 | C.17 |
| 1.3237 | B.24 | C.17 |
| 1.3238 | B.25 | C.17 |
| 1.3239 | B.26 | C.17 |
| 1.3240 | B.27 | C.17 |
| 1.3241 | B.28 | C.17 |
| 1.3242 | B.29 | C.17 |
| 1.3243 | B.30 | C.17 |
| 1.3244 | B.31 | C.17 |
| 1.3245 | B.32 | C.17 |
| 1.3246 | B.33 | C.17 |
| 1.3247 | B.34 | C.17 |
| 1.3248 | B.35 | C.17 |
| 1.3249 | B.36 | C.17 |
| 1.3250 | B.37 | C.17 |
| 1.3251 | B.38 | C.17 |
| 1.3252 | B.39 | C.17 |
| 1.3253 | B.40 | C.17 |
| 1.3254 | B.41 | C.17 |
| 1.3255 | B.42 | C.17 |
| 1.3256 | B.43 | C.17 |
| 1.3257 | B.44 | C.17 |
| 1.3258 | B.45 | C.17 |
| 1.3259 | B.46 | C.17 |
| 1.3260 | B.47 | C.17 |
| 1.3261 | B.48 | C.17 |
| 1.3262 | B.49 | C.17 |
| 1.3263 | B.50 | C.17 |
| 1.3264 | B.51 | C.17 |
| 1.3265 | B.52 | C.17 |
| 1.3266 | B.53 | C.17 |
| 1.3267 | B.54 | C.17 |
| 1.3268 | B.55 | C.17 |
| 1.3269 | B.56 | C.17 |
| 1.3270 | B.57 | C.17 |
| 1.3271 | B.58. | C.17 |
| 1.3272 | B.59 | C.17 |
| 1.3273 | B.60 | C.17 |
| 1.3274 | B.61 | C.17 |
| 1.3275 | B.62 | C.17 |
| 1.3276 | B.63 | C.17 |
| 1.3277 | B.64 | C.17 |
| 1.3278 | B.65 | C.17 |
| 1.3279 | B.66 | C.17 |
| 1.3280 | B.67 | C.17 |
| 1.3281 | B.68 | C.17 |
| 1.3282 | B.69 | C.17 |
| 1.3283 | B.70 | C.17 |
| 1.3284 | B.71 | C.17 |
| 1.3285 | B.72 | C.17 |
| 1.3286 | B.73 | C.17 |
| 1.3287 | B.74 | C.17 |
| 1.3288 | B.75 | C.17 |
| 1.3289 | B.76 | C.17 |
| 1.3290 | B.77 | C.17 |
| 1.3291 | B.78 | C.17 |
| 1.3292 | B.79 | C.17 |
| 1.3293 | B.80 | C.17 |
| 1.3294 | B.81 | C.17 |
| 1.3295 | B.82 | C.17 |
| 1.3296 | B.83 | C.17 |
| 1.3297 | B.84 | C.17 |
| 1.3298 | B.85 | C.17 |
| 1.3299 | B.86 | C.17 |
| 1.3300 | B.87 | C.17 |
| 1.3301 | B.88 | C.17 |
| 1.3302 | B.89 | C.17 |
| 1.3303 | B.90 | C.17 |
| 1.3304 | B.91 | C.17 |
| 1.3305 | B.92 | C.17 |
| 1.3306 | B.93 | C.17 |
| 1.3307 | B.94 | C.17 |
| 1.3308 | B.95 | C.17 |
| 1.3309 | B.96 | C.17 |
| 1.3310 | B.97 | C.17 |
| 1.3311 | B.98 | C.17 |
| 1.3312 | B.99 | C.17 |
| 1.3313 | B.100 | C.17 |
| 1.3314 | B.101 | C.17 |
| 1.3315 | B.102 | C.17 |
| 1.3316 | B.103 | C.17 |
| 1.3317 | B.104 | C.17 |
| 1.3318 | B.105 | C.17 |
| 1.3319 | B.106 | C.17 |
| 1.3320 | B.107 | C.17 |
| 1.3321 | B.108 | C.17 |
| 1.3322 | B.109 | C.17 |
| 1.3323 | B.110 | C.17 |
| 1.3324 | B.111 | C.17 |
| 1.3325 | B.112 | C.17 |
| 1.3326 | B.113 | C.17 |
| 1.3327 | B.114 | C.17 |
| 1.3328 | B.115 | C.17 |
| 1.3329 | B.116 | C.17 |
| 1.3330 | B.117 | C.17 |
| 1.3331 | B.118 | C.17 |
| 1.3332 | B.119 | C.17 |
| 1.3333 | B.120 | C.17 |
| 1.3334 | B.121 | C.17 |
| 1.3335 | B.122 | C.17 |
| 1.3336 | B.123 | C.17 |
| 1.3337 | B.124 | C.17 |
| 1.3338 | B.125 | C.17 |
| 1.3339 | B.126 | C.17 |
| 1.3340 | B.127 | C.17 |
| 1.3341 | B.128 | C.17 |
| 1.3342 | B.129 | C.17 |
| 1.3343 | B.130 | C.17 |
| 1.3344 | B.131 | C.17 |
| 1.3345 | B.132 | C.17 |
| 1.3346 | B.133 | C.17 |
| 1.3347 | B.134 | C.17 |
| 1.3348 | B.135 | C.17 |
| 1.3349 | B.136 | C.17 |
| 1.3350 | B.137 | C.17 |
| 1.3351 | B.138 | C.17 |
| 1.3352 | B.139 | C.17 |
| 1.3353 | B.140 | C.17 |
| 1.3354 | B.141 | C.17 |

TABLE 2-continued

| comb. no. | herbicide B | safener C |
|---|---|---|
| 1.3355 | B.142 | C.17 |
| 1.3356 | B.143 | C.17 |
| 1.3357 | B.144 | C.17 |
| 1.3358 | B.145 | C.17 |
| 1.3359 | B.146 | C.17 |
| 1.3360 | B.147 | C.17 |
| 1.3361 | B.148 | C.17 |
| 1.3362 | B.149 | C.17 |
| 1.3363 | B.150 | C.17 |
| 1.3364 | B.151 | C.17 |
| 1.3365 | B.152 | C.17 |
| 1.3366 | B.153 | C.17 |
| 1.3367 | B.154 | C.17 |
| 1.3368 | B.155 | C.17 |
| 1.3369 | B.156 | C.17 |
| 1.3370 | B.157 | C.17 |
| 1.3371 | B.158 | C.17 |
| 1.3372 | B.159 | C.17 |
| 1.3373 | B.160 | C.17 |
| 1.3374 | B.161 | C.17 |
| 1.3375 | B.162 | C.17 |
| 1.3376 | B.163 | C.17 |
| 1.3377 | B.164 | C.17 |
| 1.3378 | B.165 | C.17 |
| 1.3379 | B.166 | C.17 |
| 1.3380 | B.167 | C.17 |
| 1.3381 | B.168 | C.17 |
| 1.3382 | B.169 | C.17 |
| 1.3383 | B.170 | C.17 |
| 1.3384 | B.171 | C.17 |
| 1.3385 | B.172 | C.17 |
| 1.3386 | B.173 | C.17 |
| 1.3387 | B.174 | C.17 |
| 1.3388 | B.175 | C.17 |
| 1.3389 | B.176 | C.17 |
| 1.3390 | B.177 | C.17 |
| 1.3391 | B.178 | C.17 |
| 1.3392 | B.179 | C.17 |
| 1.3393 | B.180 | C.17 |
| 1.3394 | B.181 | C.17 |
| 1.3395 | B.182 | C.17 |
| 1.3396 | B.183 | C.17 |
| 1.3397 | B.184 | C.17 |
| 1.3398 | B.185 | C.17 |
| 1.3399 | B.186 | C.17 |
| 1.3400 | B.187 | C.17 |
| 1.3401 | B.188 | C.17 |
| 1.3402 | B.189 | C.17 |

It may furthermore be beneficial to apply the azines of formula (I) alone or in combination with other herbicides, or else in the form of a mixture with other crop protection agents, for example together with agents for controlling pests or phytopathogenic fungi or bacteria. Also of interest is the miscibility with mineral salt solutions, which are employed for treating nutritional and trace element deficiencies. Other additives such as non-phytotoxic oils and oil concentrates may also be added.

The invention also relates to agrochemical compositions comprising at least an auxiliary and at least one azine of formula (I) according to the invention.

An agrochemical composition comprises a pesticidally effective amount of an azine of formula (I). The term "effective amount" denotes an amount of the composition or of the compounds I, which is sufficient for controlling unwanted plants, especially for controlling unwanted plants in cultivated plants and which does not result in a substantial damage to the treated plants. Such an amount can vary in a broad range and is dependent on various factors, such as the plants to be controlled, the treated cultivated plant or material, the climatic conditions and the specific azine of formula (I) used.

The azines of formula (I), their N-oxides or salts can be converted into customary types of agrochemical compositions, e.g. solutions, emulsions, suspensions, dusts, powders, pastes, granules, pressings, capsules, and mixtures thereof. Examples for agrochemical composition types are suspensions (e.g. SC, OD, FS), emulsifiable concentrates (e.g. EC), emulsions (e.g. EW, EO, ES, ME), capsules (e.g. CS, ZC), pastes, pastilles, wettable powders or dusts (e.g. WP, SP, WS, DP, DS), pressings (e.g. BR, TB, DT), granules (e.g. WG, SG, GR, FG, GG, MG), insecticidal articles (e.g. LN), as well as gel formulations for the treatment of plant propagation materials such as seeds (e.g. GF). These and further agrochemical compositions types are defined in the "Catalogue of pesticide formulation types and international coding system", Technical Monograph No. 2, $6^{th}$ Ed. May 2008, CropLife International.

The agrochemical compositions are prepared in a known manner, such as described by Mollet and Grubemann, Formulation technology, Wiley VCH, Weinheim, 2001; or Knowles, New developments in crop protection product formulation, Agrow Reports DS243, T&F Informa, London, 2005.

Suitable auxiliaries are solvents, liquid carriers, solid carriers or fillers, surfactants, dispersants, emulsifiers, wetters, adjuvants, solubilizers, penetration enhancers, protective colloids, adhesion agents, thickeners, humectants, repellents, attractants, feeding stimulants, compatibilizers, bactericides, anti-freezing agents, anti-foaming agents, colorants, tackifiers and binders.

Suitable solvents and liquid carriers are water and organic solvents, such as mineral oil fractions of medium to high boiling point, e.g. kerosene, diesel oil; oils of vegetable or animal origin; aliphatic, cyclic and aromatic hydrocarbons, e.g. toluene, paraffin, tetrahydronaphthalene, alkylated naphthalenes; alcohols, e.g. ethanol, propanol, butanol, benzylalcohol, cyclohexanol; glycols; DMSO; ketones, e.g. cyclohexanone; esters, e.g. lactates, carbonates, fatty acid esters, gamma-butyrolactone; fatty acids; phosphonates; amines; amides, e.g. N-methylpyrrolidone, fatty acid dimethylamides; and mixtures thereof.

Suitable solid carriers or fillers are mineral earths, e.g. silicates, silica gels, talc, kaolins, limestone, lime, chalk, clays, dolomite, diatomaceous earth, bentonite, calcium sulfate, magnesium sulfate, magnesium oxide; polysaccharides, e.g. cellulose, starch; fertilizers, e.g. ammonium sulfate, ammonium phosphate, ammonium nitrate,ureas; products of vegetable origin, e.g. cereal meal, tree bark meal, wood meal, nutshell meal, and mixtures thereof.

Suitable surfactants are surface-active compounds, such as anionic, cationic, nonionic and amphoteric surfactants, block polymers, polyelectrolytes, and mixtures thereof. Such surfactants can be used as emulsifier, dispersant, solubilizer, wetter, penetration enhancer, protective colloid, or adjuvant. Examples of surfactants are listed in McCutcheon's, Vol. 1: Emulsifiers & Detergents, McCutcheon's Directories, Glen Rock, USA, 2008 (International Ed. or North American Ed.).

Suitable anionic surfactants are alkali, alkaline earth or ammonium salts of sulfonates, sulfates, phosphates, carboxylates, and mixtures thereof. Examples of sulfonates are alkylarylsulfonates, diphenylsulfonates, alpha-olefin sulfonates, lignine sulfonates, sulfonates of fatty acids and oils, sulfonates of ethoxylated alkylphenols, sulfonates of alkoxylated arylphenols, sulfonates of condensed naphthalenes, sulfonates of dodecyl- and tridecylbenzenes, sulfonates of naphthalenes and alkylnaphthalenes, sulfosuccinates or sulfosuccinamates. Examples of sulfates are sulfates of fatty acids and oils, of ethoxylated alkylphenols, of alcohols, of ethoxylated alcohols, or of fatty acid esters. Examples of phosphates are phosphate esters. Examples of carboxylates are alkyl carboxylates, and carboxylated alcohol or alkylphenol ethoxylates.

Suitable nonionic surfactants are alkoxylates, N-substituted fatty acid amides, amine oxides, esters, sugar-based surfactants, polymeric surfactants, and mixtures thereof. Examples of alkoxylates are compounds such as alcohols, alkylphenols, amines, amides, arylphenols, fatty acids or fatty acid esters which have been alkoxylated with 1 to 50 equivalents. Ethylene oxide and/or propylene oxide may be employed for the alkoxylation, preferably ethylene oxide. Examples of N-substituted fatty acid amides are fatty acid glucamides or fatty acid alkanolamides.

Examples of esters are fatty acid esters, glycerol esters or monoglycerides. Examples of sugar-based surfactants are sorbitans, ethoxylated sorbitans, sucrose and glucose esters or alkylpolyglucosides. Examples of polymeric surfactants are home- or copolymers of vinylpyrrolidone, vinylalcohols, or vinylacetate.

Suitable cationic surfactants are quaternary surfactants, for example quaternary ammonium compounds with one or two hydrophobic groups, or salts of long-chain primary amines. Suitable amphoteric surfactants are alkylbetains and imidazolines. Suitable block polymers are block polymers of the A-B or A-B-A type comprising blocks of polyethylene oxide and polypropylene oxide, or of the A-B-C type comprising alkanol, polyethylene oxide and polypropylene oxide. Suitable polyelectrolytes are polyacids or polybases. Examples of polyacids are alkali salts of polyacrylic acid or polyacid comb polymers. Examples of polybases are polyvinylamines or polyethyleneamines.

Suitable adjuvants are compounds, which have a neglectable or even no pesticidally activity themselves, and which improve the biological performance of the compound I on the target. Examples are surfactants, mineral or vegetable oils, and other auxiliaries. Further examples are listed by Knowles, Adjuvants and additives, Agrow Reports DS256, T&F Informa UK, 2006, chapter 5.

Suitable thickeners are polysaccharides (e.g. xanthan gum, carboxymethylcellulose), inorganic clays (organically modified or unmodified), polycarboxylates, and silicates.

Suitable bactericides are bronopol and isothiazolinone derivatives such as alkylisothiazolinones and benzisothiazolinones.

Suitable anti-freezing agents are ethylene glycol, propylene glycol, urea and glycerin.

Suitable anti-foaming agents are silicones, long chain alcohols, and salts of fatty acids.

Suitable colorants (e.g. in red, blue, or green) are pigments of low water solubility and water-soluble dyes. Examples are inorganic colorants (e.g. iron oxide, titan oxide, iron hexacyanoferrate) and organic colorants (e.g. alizarin-, azo- and phthalocyanine colorants).

Suitable tackifiers or binders are polyvinylpyrrolidons, polyvinylacetates, polyvinyl alcohols, polyacrylates, biological or synthetic waxes, and cellulose ethers.

Examples for agrochemical composition types and their preparation are:

i) Water-soluble concentrates (SL, LS)

10-60 wt % of an azine of formula (I) according to the invention and 5-15 wt % wetting agent (e.g. alcohol alkoxylates) are dissolved in water and/or in a water-soluble solvent (e.g. alcohols) ad 100 wt %. The active substance dissolves upon dilution with water.

ii) Dispersible concentrates (DC)

5-25 wt % of an azine of formula (I) according to the invention and 1-10 wt % dispersant (e.g. polyvinylpyrrolidone) are dissolved in organic solvent (e.g. cyclohexanone) ad 100 wt %. Dilution with water gives a dispersion.

iii) Emulsifiable concentrates (EC)

15-70 wt % of an azine of formula (I) according to the invention and 5-10 wt % emulsifiers (e.g. calcium dodecylbenzenesulfonate and castor oil ethoxylate) are dissolved in water-insoluble organic solvent (e.g. aromatic hydrocarbon) ad 100 wt %. Dilution with water gives an emulsion.

iv) Emulsions (EW, EO, ES)

5-40 wt % of an azine of formula (I) according to the invention and 1-10 wt % emulsifiers (e.g. calcium dodecylbenzenesulfonate and castor oil ethoxylate) are dissolved in 20-40 wt % water-insoluble organic solvent (e.g. aromatic hydrocarbon). This mixture is introduced into water ad 100 wt % by means of an emulsifying machine and made into a homogeneous emulsion. Dilution with water gives an emulsion.

v) Suspensions (SC, OD, FS)

In an agitated ball mill, 20-60 wt % of an azine of formula (I) according to the invention are comminuted with addition of 2-10 wt % dispersants and wetting agents (e.g. sodium lignosulfonate and alcohol ethoxylate), 0.1-2 wt % thickener (e.g. xanthan gum) and water ad 100 wt % to give a fine active substance suspension. Dilution with water gives a stable suspension of the active substance. For FS type composition up to 40 wt % binder (e.g. polyvinylalcohol) is added.

vi) Water-dispersible granules and water-soluble granules (WG, SG)

50-80 wt % of an azine of formula (I) according to the invention are ground finely with addition of dispersants and wetting agents (e.g. sodium lignosulfonate and alcohol ethoxylate) ad 100 wt % and prepared as water-dispersible or water-soluble granules by means of technical appliances (e.g. extrusion, spray tower, fluidized bed). Dilution with water gives a stable dispersion or solution of the active substance.

vii) Water-dispersible powders and water-soluble powders (WP, SP, WS)

50-80 wt % of an azine of formula (I) according to the invention are ground in a rotor-stator mill with addition of 1-5 wt % dispersants (e.g. sodium lignosulfonate), 1-3 wt % wetting agents (e.g. alcohol ethoxylate) and solid carrier (e.g. silica gel) ad 100 wt %. Dilution with water gives a stable dispersion or solution of the active substance.

viii) Gel (GW, GF)

In an agitated ball mill, 5-25 wt % of an azine of formula (I) according to the invention are comminuted with addition of 3-10 wt % dispersants (e.g. sodium lignosulfonate), 1-5 wt % thickener (e.g. carboxymethylcellulose) and water ad 100 wt % to give a fine suspension of the active substance. Dilution with water gives a stable suspension of the active substance.

iv) Microemulsion (ME)

5-20 wt % of an azine of formula (I) according to the invention are added to 5-30 wt % organic solvent blend (e.g. fatty acid dimethylamide and cyclohexanone), 10-25 wt % surfactant blend (e.g. alcohol ethoxylate and arylphenol ethoxylate), and water ad 100%. This mixture is stirred for 1 h to produce spontaneously a thermodynamically stable microemulsion.

iv) Microcapsules (CS)

An oil phase comprising 5-50 wt % of an azine of formula (I) according to the invention, 0-40 wt % water insoluble organic solvent (e.g. aromatic hydrocarbon), 2-15 wt % acrylic monomers (e.g. methylmethacrylate, methacrylic acid and a di- or triacrylate) are dispersed into an aqueous solution of a protective colloid (e.g. polyvinyl alcohol). Radical polymerization initiated by a radical initiator results in the formation of poly(meth)acrylate microcapsules. Alternatively, an oil phase comprising 5-50 wt % of an azine of formula (I) according to the invention, 0-40 wt % water insoluble organic solvent (e.g. aromatic hydrocarbon), and an isocyanate monomer (e.g. diphenylmethene-4,4'-diisocyanate) are dispersed into an aqueous solution of a protective colloid (e.g. polyvinyl alcohol). The addition of a polyamine (e.g. hexamethylenediamine) results in the formation of polyurea microcapsules. The monomers amount to 1-10 wt %. The wt % relate to the total CS composition.

ix) Dustable powders (DP, DS)

1-10 wt % of an azine of formula (I) according to the invention are ground finely and mixed intimately with solid carrier (e.g. finely divided kaolin) ad 100 wt %.

x) Granules (GR, FG)

0.5-30 wt % of an azine of formula (I) according to the invention is ground finely and associated with solid carrier (e.g. silicate) ad 100 wt %. Granulation is achieved by extrusion, spray-drying or the fluidized bed.

xi) Ultra-low volume liquids (UL)

1-50 wt % of an azine of formula (I) according to the invention are dissolved in organic solvent (e.g. aromatic hydrocarbon) ad 100 wt %.

The agrochemical compositions types i) to xi) may optionally comprise further auxiliaries, such as 0.1-1 wt % bactericides, 5-15 wt % anti-freezing agents, 0.1-1 wt % anti-foaming agents, and 0.1-1 wt % colorants.

The agrochemical compositions generally comprise between 0.01 and 95%, preferably between 0.1 and 90%, and in particular between 0.5 and 75%, by weight of the azines of formula (I). The azines of formula (I) are employed in a purity of from 90% to 100%, preferably from 95% to 100% (according to NMR spectrum).

Solutions for seed treatment (LS), suspoemulsions (SE), flowable concentrates (FS), powders for dry treatment (DS), water-dispersible powders for slurry treatment (WS), water-soluble powders (SS), emulsions (ES), emulsifiable concentrates (EC) and gels (GF) are usually employed for the purposes of treatment of plant propagation materials, particularly seeds. The agrochemical compositions in question give, after two-to-tenfold dilution, active substance concentrations of from 0.01 to 60% by weight, preferably from 0.1 to 40% by weight, in the ready-to-use preparations. Application can be carried out before or during sowing.

Methods for applying azines of formula (I) or agrochemical compositions thereof, on to plant propagation material, especially seeds, include dressing, coating, pelleting, dusting, soaking and in-furrow application methods of the propagation material. Preferably, compound I or the compositions thereof, respectively, are applied on to the plant propagation material by a method such that germination is not induced, e.g. by seed dressing, pelleting, coating and dusting.

Various types of oils, wetters, adjuvants, fertilizer, or micronutrients, and further pesticides (e.g. herbicides, insecticides, fungicides, growth regulators, safeners) may be added to the azines of formula (I) or the agrochemical compositions comprising them as premix or, if appropriate not until immediately prior to use (tank mix). These agents can be admixed with the agrochemical compositions according to the invention in a weight ratio of 1:100 to 100:1, preferably 1:10 to 10:1.

The user applies the azines of formula (I) according to the invention or the agrochemical compositions comprising them usually from a pre-dosage device, a knapsack sprayer, a spray tank, a spray plane, or an irrigation system. Usually, the agrochemical composition is made up with water, buffer, and/or further auxiliaries to the desired application concentration and the ready-to-use spray liquor or the agrochemical composition according to the invention is thus obtained. Usually, 20 to 2000 liters, preferably 50 to 400 liters, of the ready-to-use spray liquor are applied per hectare of agricultural useful area.

According to one embodiment, either individual components of the agrochemical composition according to the invention or partially premixed components, e.g. components comprising azines of formula (I) may be mixed by the user in a spray tank and further auxiliaries and additives may be added, if appropriate.

In a further embodiment, individual components of the agrochemical composition according to the invention such as parts of a kit or parts of a binary or ternary mixture may be mixed by the user himself in a spray tank and further auxiliaries may be added, if appropriate.

In a further embodiment, either individual components of the agrochemical composition according to the invention or partially premixed components, e.g components comprising azines of formula (I), can be applied jointly (e.g. after tank mix) or consecutively.

The azines of formula (I), are suitable as herbicides. They are suitable as such or as an appropriately formulated composition (agrochemical composition).

The azines of formula (I), or the agrochemical compositions comprising the azines of formula (I), control vegetation on non-crop areas very efficiently, especially at high rates of application. They act against broad-leaved weeds and grass weeds in crops such as wheat, rice, maize, soya and cotton without causing any significant damage to the crop plants. This effect is mainly observed at low rates of application.

The azines of formula (I), or the agrochemical compositions comprising them, are applied to the plants mainly by spraying the leaves or are applied to the soil in which the plant seeds have been sown. Here, the application can be carried out using, for example, water as carrier by customary spraying techniques using spray liquor amounts of from about 100 to 1000 l/ha (for example from 300 to 400 l/ha). The azines of formula (I), or the agrochemical compositions comprising them, may also be applied by the low-volume or the ultra-low-volume method, or in the form of microgranules.

Application of the azines of formula (I), or the agrochemical compositions comprising them, can be done before, during and/or after the emergence of the undesirable plants.

The azines of formula (I), or the agrochemical compositions comprising them, can be applied pre-, post-emergence or pre-plant, or together with the seed of a crop plant. It is also possible to apply the azines of formula (I), or the agrochemical compositions comprising them, by applying seed, pretreated with the azines of formula (I), or the agrochemical compositions comprising them, of a crop plant. If the active ingredients are less well tolerated by certain crop plants, application techniques may be used in which the herbicidal compositions are sprayed, with the aid of the spraying equipment, in such a way that as far as possible they do not come into contact with the leaves of the sensitive crop plants, while the active ingredients reach the leaves of undesirable plants growing underneath, or the bare soil surface (post-directed, lay-by).

In a further embodiment, the azines of formula (I), or the agrochemical compositions comprising them, can be applied by treating seed. The treatment of seeds comprises essentially all procedures familiar to the person skilled in the art (seed dressing, seed coating, seed dusting, seed soaking, seed film coating, seed multilayer coating, seed encrusting, seed dripping and seed pelleting) based on the azines of formula (I), or the agrochemical compositions prepared therefrom. Here, the herbicidal compositions can be applied diluted or undiluted.

The term "seed" comprises seed of all types, such as, for example, corns, seeds, fruits, tubers, seedlings and similar forms. Here, preferably, the term seed describes corns and seeds. The seed used can be seed of the useful plants mentioned above, but also the seed of transgenic plants or plants obtained by customary breeding methods.

When employed in plant protection, the amounts of active substances applied, i.e. the azines of formula (I), without formulation auxiliaries, are, depending on the kind of effect desired, from 0.001 to 2 kg per ha, preferably from 0.005 to 2 kg per ha, more preferably from 0.005 to 0.9 kg per ha and in particular from 0.05 to 0.5 kg per ha.

In another embodiment of the invention, the application rate of the azines of formula (I) is from 0.001 to 3 kg/ha, preferably from 0.005 to 2.5 kg/ha, of active substance (a.s.).

In another preferred embodiment of the invention, the rates of application of the azines of formula (I) according to the present invention (total amount of azine of formula (I)) are from 0.1 g/ha to 3000 g/ha, preferably 10 g/ha to 1000 g/ha, depending on the control target, the season, the target plants and the growth stage.

In another preferred embodiment of the invention, the application rates of the azines of formula (I) are in the range from 0.1 g/ha to 5000 g/ha and preferably in the range from 1 g/ha to 2500 g/ha or from 5 g/ha to 2000 g/ha.

In another preferred embodiment of the invention, the application rate of the azines of formula (I) is 0.1 to 1000 g/ha, preferably 1 to 750 g/ha, more preferably 5 to 500 g/ha.

In treatment of plant propagation materials such as seeds, e.g. by dusting, coating or drenching seed, amounts of active substance of from 0.1 to 1000 g, preferably from 1 to 1000 g, more preferably from 1 to 100 g and most preferably from 5 to 100 g, per 100 kilogram of plant propagation material (preferably seeds) are generally required.

In another embodiment of the invention, to treat the seed, the amounts of active substances applied, i.e. the azines of formula (I) are generally employed in amounts of from 0.001 to 10 kg per 100 kg of seed.

When used in the protection of materials or stored products, the amount of active substance applied depends on the kind of application area and on the desired effect. Amounts customarily applied in the protection of materials are 0.001 g to 2 kg, preferably 0.005 g to 1 kg, of active substance per cubic meter of treated material.

Depending on the application method in question, the azines of formula (I), or the agrochemical compositions comprising them, can additionally be employed in a further number of crop plants for eliminating undesirable plants. Examples of suitable crops are the following: *Allium cepa, Ananas comosus, Arachis hypogaea, Asparagus officinalis, Avena sativa, Beta vulgaris* spec. *altissima, Beta vulgaris* spec. *rapa, Brassica napus* var. *napus, Brassica napus* var. *napobrassica, Brassica rapa* var. *silvestris, Brassica oleracea, Brassica nigra, Camellia sinensis, Carthamus tinctorius, Carya illinoinensis, Citrus limon, Citrus sinensis, Coffea arabica* (*Coffea canephora, Coffea liberica*), *Cucumis sativus, Cynodon dactylon, Daucus carota, Elaeis guineensis, Fragaria vesca, Glycine max, Gossypium hirsutum,* (*Gossypium arboreum, Gossypium herbaceum, Gossypium vitifolium*), *Helianthus annuus, Hevea brasiliensis, Hordeum vulgare, Humulus lupulus, Ipomoea batatas, Juglans regia, Lens culinaris, Linum usitatissimum, Lycopersicon lycopersicum, Malus* spec., *Manihot esculenta, Medicago sativa, Musa* spec., *Nicotiana tabacum* (*N. rustica*), *Olea europaea, Oryza sativa, Phaseolus lunatus, Phaseolus vulgaris, Picea abies, Pinus* spec., *Pistacia vera, Pisum sativum, Prunus avium, Prunus persica, Pyrus communis, Prunus armeniaca, Prunus cerasus, Prunus dulcis* and *Prunus domestica, Ribes sylvestre, Ricinus communis, Saccharum officinarum, Secale cereale, Sinapis alba, Solanum tuberosum, Sorghum bicolor* (s. *vulgare*), *Theobroma cacao, Trifolium pratense, Triticum aestivum, Triticale, Triticum durum, Vicia faba, Vitis vinifera* and *Zea mays*.

Preferred crops are *Arachis hypogaea, Beta vulgaris* spec. *altissima, Brassica napus* var. *napus, Brassica oleracea, Citrus limon, Citrus sinensis, Coffea arabica* (*Coffea canephora, Coffea liberica*), *Cynodon dactylon, Glycine max, Gossypium hirsutum,* (*Gossypium arboreum, Gossypium herbaceum, Gossypium vitifolium*), *Helianthus annuus, Hordeum vulgare, Juglans regia, Lens culinaris, Linum usitatissimum, Lycopersicon lycopersicum, Malus* spec., *Medicago sativa, Nicotiana tabacum* (*N. rustica*), *Olea europaea, Oryza sativa, Phaseolus lunatus, Phaseolus vulgaris, Pistacia vera, Pisum sativum, Prunus dulcis, Saccharum officinarum, Secale cereale, Solanum tuberosum, Sorghum bicolor* (s. *vulgare*), *Triticale, Triticum aestivum, Triticum durum, Vicia faba, Vitis vinifera* and *Zea mays*.

Especially preferred crops are crops of cereals, corn, soybeans, rice, oilseed rape, cotton, potatoes, peanuts or permanent crops.

The azines of formula (I) according to the invention, or the agrochemical compositions comprising them, can also be used in genetically modified plants. The term "genetically modified plants" is to be understood as plants whose genetic material has been modified by the use of recombinant DNA techniques to include an inserted sequence of DNA that is not native to that plant species' genome or to exhibit a deletion of DNA that was native to that species' genome, wherein the modification(s) cannot readily be obtained by cross breeding, mutagenesis or natural recombination alone. Often, a particular genetically modified plant will be one that has obtained its genetic modification(s) by inheritance through a natural breeding or propagation process from an ancestral plant whose genome was the one directly treated by use of a recombinant DNA technique. Typically, one or more genes have been integrated into the genetic material of a genetically modified plant in order to improve certain properties of the plant. Such genetic modifications also include but are not limited to targeted post-translational modification of protein(s), oligo- or polypeptides. e.g., by inclusion therein of amino acid mutation(s) that permit, decrease, or promote glycosylation or polymer additions such as prenylation, acetylation farnesylation, or PEG moiety attachment.

Plants that have been modified by breeding, mutagenesis or genetic engineering, e.g. have been rendered tolerant to applications of specific classes of herbicides, such as auxin herbicides such as dicamba or 2,4-D; bleacher herbicides such as hydroxyphenylpyruvate dioxygenase (HPPD) inhibitors or phytoene desaturase (PDS) inhibitors; acetolactate synthase (ALS) inhibitors such as sulfonyl ureas or imidazolinones; enolpyruvyl shikimate 3-phosphate synthase (EPSP) inhibitors such as glyphosate; glutamine synthetase (GS) inhibitors such as glufosinate; protoporphyrinogen-IX oxidase inhibitors; lipid biosynthesis inhibitors such as acetyl CoA carboxylase (ACCase) inhibitors; or oxynil (i. e. bromoxynil or ioxynil) herbicides as a result of conventional methods of breeding or genetic engineering; furthermore, plants have been made resistant to multiple classes of herbicides through multiple genetic modifications, such as resistance to both glyphosate and glufosinate or to both glyphosate and a herbicide from another class such as ALS inhibitors, HPPD inhibitors, auxin herbicides, or ACCase inhibitors. These herbicide resistance technologies are, for example, described in Pest Management Science 61, 2005, 246; 61, 2005, 258; 61, 2005, 277; 61, 2005, 269; 61, 2005, 286; 64, 2008, 326; 64, 2008, 332; Weed Science 57, 2009, 108; Australian Journal of Agricultural Research 58, 2007, 708; Science 316, 2007, 1185; and references quoted therein. Several cultivated plants have been rendered tolerant to herbicides by mutagenesis and conventional methods of breeding, e.g., Clearfield® summer rape (Canola, BASF SE, Germany) being tolerant to imidazolinones, e.g., imazamox, or ExpressSun® sunflowers (DuPont, USA) being tolerant to sulfonyl ureas, e.g., tribenuron. Genetic engineering methods have been used to render cultivated plants such as soybean, cotton, corn, beets and rape, tolerant to herbicides such as glyphosate, imidazolinones and glufosinate, some of which are under development or commercially available under the brands or trade names RoundupReady® (glyphosate tolerant, Monsanto, USA), Cultivance® (imidazolinone tolerant, BASF SE, Germany) and LibertyLink® (glufosinate tolerant, Bayer CropScience, Germany).

Furthermore, plants are also covered that are by the use of recombinant DNA techniques capable to synthesize one or more insecticidal proteins, especially those known from the bacterial genus *Bacillus*, particularly from *Bacillus thuringiensis*, such as delta-endotoxins, e.g., CryIA(b), CryIA(c), CryIF, CryIF(a2), CryIIA(b), CryIIIA, CryIIIB(b1) or Cry9c; vegetative insecticidal proteins (VIP), e.g., VIP1, VIP2, VIP3 or VIP3A; insecticidal proteins of bacteria colonizing nematodes, e.g., *Photorhabdus* spp. or *Xenorhabdus* spp.; toxins produced by animals, such as scorpion toxins, arachnid toxins, wasp toxins, or other insect-specific neurotoxins; toxins produced by fungi, such as Streptomycetes toxins, plant lectins, such as pea or barley lectins; agglutinins; proteinase inhibitors, such as trypsin inhibitors, serine protease inhibitors, patatin, cystatin or papain inhibitors; ribosome-inactivating proteins (RIP), such as ricin, maize-RIP, abrin, luffin, saporin or bryodin; steroid metabolism enzymes, such as 3-hydroxy-steroid oxidase, ecdysteroid-IDP-glycosyl-transferase, cholesterol oxidases, ecdysone inhibitors or HMG-CoAreductase; ion channel blockers, such as blockers of sodium or calcium channels; juvenile hormone esterase; diuretic hormone receptors (helicokinin receptors); stilbene synthase, bibenzyl synthase, chitinases or glucanases. In the context of the present invention these insecticidal proteins or toxins are to be understood expressly also as including pre-toxins, hybrid proteins, truncated or otherwise modified proteins. Hybrid proteins are characterized by a new combination of protein domains, (see, e.g., WO 02/015701). Further examples of such toxins or genetically modified plants capable of synthesizing such toxins are disclosed, e.g., in EP-A 374 753, WO 93/007278, WO 95/34656, EP-A 427 529, EP-A 451 878, WO 03/18810 and WO 03/52073.

The methods for producing such genetically modified plants are generally known to the person skilled in the art and are described, e.g., in the publications mentioned above. These insecticidal proteins contained in the genetically modified plants impart to the plants producing these proteins tolerance to harmful pests from all taxonomic groups of arthropods, especially to beetles (Coeloptera), two-winged insects (Diptera), and moths (Lepidoptera) and to nematodes (Nematoda). Genetically modified plants capable to synthesize one or more insecticidal proteins are, e.g., described in the publications mentioned above, and some of which are commercially available such as YieldGard® (corn cultivars producing the CryIAb toxin), YieldGard® Plus (corn cultivars producing CryIAb and Cry3Bb1 toxins), Starlink® (corn cultivars producing the Cry9c toxin), Herculex® RW (corn cultivars producing Cry34Ab1, Cry35Ab1 and the enzyme Phosphinothricin-N-Acetyltransferase [PAT]); NuCOTN® 33B (cotton cultivars producing the Cry1Ac toxin), Bollgard®1 (cotton cultivars producing the Cry1Ac toxin), Bollgard®11 (cotton cultivars producing Cry1Ac and Cry2Ab2 toxins); VIPCOT® (cotton cultivars producing a VIP-toxin); NewLeaf® (potato cultivars producing the Cry3A toxin); Bt-Xtra®, NatureGard®, Knock-Out®, BiteGard®, Protecta®, Bt11 (e.g., Agrisure® CB) and Bt176 from Syngenta Seeds SAS, France, (corn cultivars producing the Cry1Ab toxin and PAT enzyme), MIR604 from Syngenta Seeds SAS, France (corn cultivars producing a modified version of the Cry3A toxin, c.f. WO 03/018810), MON 863 from Monsanto Europe S.A., Belgium (corn cultivars producing the Cry3Bb1 toxin), IPC 531 from Monsanto Europe S.A., Belgium (cotton cultivars producing a modified version of the Cry1Ac toxin) and 1507 from Pioneer Overseas Corporation, Belgium (corn cultivars producing the Cry1F toxin and PAT enzyme).

Furthermore, plants are also covered that are by the use of recombinant DNA techniques capable to synthesize one or more proteins to increase the resistance or tolerance of those plants to bacterial, viral or fungal pathogens. Examples of such proteins are the so-called "pathogenesis-related proteins" (PR proteins, see, e.g., EP-A 392 225), plant disease resistance genes (e.g., potato cultivars, which express resistance genes acting against *Phytophthora infestans* derived from the Mexican wild potato, *Solanum bulbocastanum*) or T4-lyso-zym (e.g., potato cultivars capable of synthesizing these proteins with increased resistance against bacteria such as *Erwinia amylovora*). The methods for producing such genetically modified plants are generally known to the person skilled in the art and are described, e.g., in the publications mentioned above.

Furthermore, plants are also covered that are by the use of recombinant DNA techniques capable to synthesize one or more proteins to increase the productivity (e.g., bio-mass production, grain yield, starch content, oil content or protein content), tolerance to drought, salinity or other growth-limiting environmental factors or tolerance to pests and fungal, bacterial or viral pathogens of those plants.

Furthermore, plants are also covered that contain by the use of recombinant DNA techniques a modified amount of ingredients or new ingredients, specifically to improve human or animal nutrition, e.g., oil crops that produce health-promoting long-chain omega-3 fatty acids or unsaturated omega-9 fatty acids (e.g., Nexera® rape, Dow AgroSciences, Canada).

Furthermore, plants are also covered that contain by the use of recombinant DNA techniques a modified amount of ingredients or new ingredients, specifically to improve raw material production, e.g., potatoes that produce increased amounts of amylopectin (e.g. Amflora® potato, BASF SE, Germany).

The preparation of the azines of formula (I) is illustrated by examples; however, the subject matter of the present invention is not limited to the examples given.

PREPARATION EXAMPLES

Example 1

6-(1-Fluoro-1-methyl-ethyl)-N4-(2,3,5,6-tetrafluoro-4-pyridyl)-1,3,5-triazine-2,4-diamine

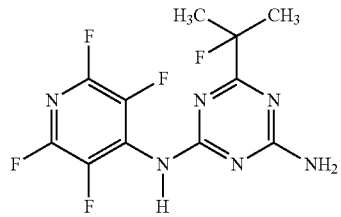 [SMILES: CC(C)(F)c1nc(N)nc(Nc2c(F)c(F)nc(F)c2F)n1]

1.1: 4-(1-fluoro-1-methyl-ethyl)-6-methylsulfanyl-1,3,5-triazin-2-amine

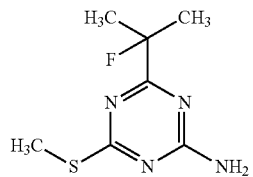

2-Fluoro-2-methyl-propanoyl chloride (23.0 g, 0.18 mol) and triethylamine (93.4 g, 0.92 mol) were added to a solution of 1-carbamimidoyl-2-methyl-isothiourea hydroiodide (48.0 g, 0.18 mol) in THF via two addition funnels. After the initial weak exothermic reaction was finished, the mixture was stirred for 3 h at 50° C. The reaction mixture was cooled to ambient temperature, diluted with water and ethyl acetate and the phases were separated. The organic phase was dried over anhydrous Na$_2$SO$_4$, filtered and concentrated under reduced pressure yielding the title compound as a colorless solid (33.3 g, 89.2% yield).

MS (ESI) m/z 203.3 [M+H+H$^+$]

$^1$H NMR (400 MHz, CDCl$_3$): δ=6.82 (brs, 1H), 5.64 (brs, 1H), 1.63 (d, J=21.0 Hz, 6H) ppm.

1.2: 4-chloro-6-(1-fluoro-1-methyl-ethyl)-1,3,5-triazin-2-amine

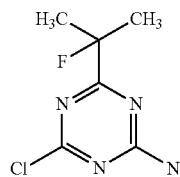

4-(1-fluoro-1-methyl-ethyl)-6-methylsulfanyl-1,3,5-triazin-2-amine (65.0 g, 0.32 mol) was dissolved in acetic acid and Cl$_2$ gas was bubbled through the solution for 30 min. The reaction mixture was stirred for an additional hour at ambient temperature and was then carefully added to a cold solution of NaOH (130 g) in water (1 L). Ethyl acetate was added and the phases were separated. The organic phase was dried over anhydrous Na$_2$SO$_4$, filtered and concentrated under reduced pressure yielding the title compound as a colorless solid (41.3 g, 67.4% yield).

MS (ESI) m/z 191.3 [M+H$^+$]

$^1$H NMR (400 MHz, CDCl$_3$): δ=7.12 (brs, 1H), 6.32 (brs, 1H), 1.69 (d, J=21.8 Hz, 6H) ppm.

1.3: 6-(1-fluoro-1-methyl-ethyl)-N4-(2,3,5,6-tetrafluorophenyl)-1,3,5-triazine-2,4-diamine

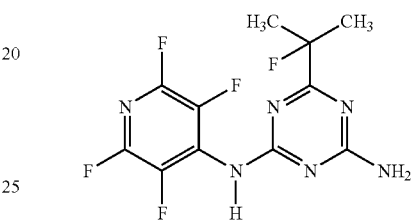

A solution of 4-chloro-6-(1-fluoro-1-methyl-ethyl)-1,3,5-triazin-2-amin (25.0 g, 131.2 mmol), 2,3,5,6-tetrafluoropyridin-4-amine (24.0 g 144 mmol), Pd(dppf)Cl$_2$ (9.62 g, 13.1 mmol) and KOtBu (44.2 g, 393.5 mmol) in dioxane was heated to 100° C. for 16 h. The reaction mixture was cooled to ambient temperature, diluted with water and ethyl acetate and the phases were separated. The organic phase was dried over anhydrous Na$_2$SO$_4$, filtered and concentrated under reduced pressure. Column chromatography of the resulting crude product (ISCO-CombiFlash Rf, cyclohexane/ethyl acetate) yielded the title compound as colorless solid (11.2 g, 26.7% yield).

MS (ESI) m/z 321.3 [M+H$^+$].

$^1$H NMR (400 MHz, H$_3$COD): δ=1.62 (d, J=21.5 Hz, 6H) ppm.

The compounds listed below in table 3 (examples 2 to 47) have been prepared similarly to the examples mentioned above:

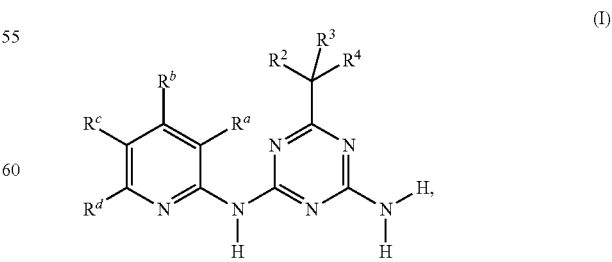

(I)

wherein A is (A.1) and
R$^1$ and R$^5$ are H

TABLE 3

| ex. no. | $R^2$ | $R^3$ | $R^4$ | $R^a$ | $R^b$ | $R^c$ | $R^d$ | MS |
|---|---|---|---|---|---|---|---|---|
| 2 | $CH_3$ | $CH_3$ | F | F | H | H | H | 267.1 |
| 3 | $CH_3$ | $CH_3$ | F | F | H | H | Cl | 301.1 |
| 4 | $CH_3$ | $CH_3$ | F | F | H | F | F | 303 |
| 5 | $CH_3$ | $CH_3$ | F | F | Cl | F | F | 337.1 |
| 6 | $CH_3$ | $CH_3$ | F | F | Br | F | F | 381 |
| 7 | H | F | F | F | H | F | F | 293 |
| 8 | H | F | F | F | H | Cl | H | 291 |
| 9 | F | F | F | F | H | F | F | 311.1 |
| 10 | H | —$(CH_2)_5$— | | F | Cl | F | F | 359.1 |
| 11 | Cl | —$(CH_2)_4$— | | F | Cl | F | F | 379.5 |
| 12 | F | —$(CH_2)_4$— | | F | Cl | F | F | 362.7 |
| 13 | $CH_3$ | $C_2H_5$ | F | F | Cl | F | F | 351.5 |
| 14 | $CH_3$ | $C_2H_5$ | F | F | H | F | F | 317.5 |
| 15 | $CH_3$ | H | F | F | H | F | F | 289.4 |
| 16 | $CH_3$ | $CH_3$ | F | F | Cl | H | H | 300.8 |
| 17 | H | —$(CH_2)_4$— | | F | Cl | F | F | 345.5 |
| 18 | $CH_3$ | $C_2H_5$ | F | F | Cl | F | F | 332.8 |
| 19 | $CH_3$ | $C_2H_5$ | F | F | Cl | F | F | 332.8 |
| 20 | $CH_3$ | $CH_3$ | F | F | F | H | F | 303.5 |
| 21 | F | —$(CH_2)_3$— | | F | Cl | F | F | 349.5 |
| 22 | $CH_3$ | $CH_3$ | $OCH_3$ | F | Cl | F | F | 348.7 |
| 23 | $CH_3$ | $CH_3$ | F | Cl | H | Cl | F | 335 |
| 24 | $CH_3$ | $CH_3$ | F | Cl | H | H | Cl | 316 |
| 25 | $CH_3$ | $CH_3$ | F | F | $SCH_3$ | F | F | 349.1 |
| 26 | $CH_3$ | $CH_3$ | F | F | $SOCH_3$ | F | F | 365.0 |
| 27 | $CH_3$ | $CH_3$ | F | F | $SO_2CH_3$ | F | F | 381.0 |
| 28 | $CH_3$ | $CH_3$ | F | H | H | Cl | Cl | 317 |
| 29 | F | $CH_3$ | $CH_3$ | F | $CH_3$ | F | F | 316.3 |
| 30 | $C_2H_5$ | F | $C_2H_5$ | F | Cl | F | F | 364.7 |
| 31 | F | $CH_3$ | $CH_3$ | F | $OCH_3$ | F | F | 333.1 |
| 32 | $CH(CH_3)_2$ | H | F | F | Cl | F | F | 351.3 |
| 33 | $CH_3$ | $CH_3$ | $OC_2H_5$ | F | Cl | F | F | 363.3 |
| 34 | F | F | F | $CH_3$ | H | H | H | 271.4 |
| 35 | F | F | F | F | H | H | H | 275.3 |
| 36 | F | F | F | $OCH(CH_3)_2$ | H | H | H | 315.3 |
| 37 | F | $CH_3$ | $CH_3$ | F | $OSO_2CH_3$ | F | F | 397.0 |
| 38 | $CH_3$ | Br | $CH_3$ | F | $OCH_3$ | F | F | 393.0 |
| 39 | $CH_3$ | Br | $CH_2Br$ | F | $OCH_3$ | F | F | 473.0 |
| 40 | $CH_3$ | F | $CH_3$ | F | OH | F | F | 319.1 |
| 41 | F | F | F | H | H | Cl | H | 290.8 |
| 42 | $CH_3$ | $CH_3$ | F | I | H | H | H | 375.3 |
| 43 | $CH_3$ | $CH_3$ | F | I | Cl | H | H | 409.1 |
| 44 | $CH_3$ | $CH_3$ | F | $OCH_3$ | H | H | H | 279.4 |
| 45 | $CH_3$ | $CH_3$ | F | $OCH_2cPr$ | H | H | H | 318.9 |
| 46 | $CH_3$ | $CH_3$ | F | Br | H | H | H | 329.3 |
| 47 | F | —$(CH_2)_5$— | | F | Cl | F | F | 377.4 |

The compounds listed below in table 4 (example 48) have been prepared similarly to the examples mentioned above:

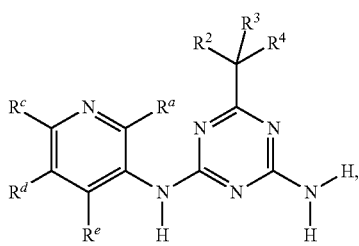

(I)

wherein A is (A.2) and
$R^1$ and $R^5$ are H

TABLE 4

| ex. no. | $R^2$ | $R^3$ | $R^4$ | $R^a$ | $R^c$ | $R^d$ | $R^e$ | MS |
|---|---|---|---|---|---|---|---|---|
| 48 | $CH_3$ | $CH_3$ | F | F | H | H | F | 285.1 |

The compounds listed below in table 5 (examples 49 to 75) have been prepared similarly to the examples mentioned above:

(I)

wherein A is (A.3) and
$R^1$ and $R^5$ are H

TABLE 5

| ex. no. | $R^2$ | $R^3$ | $R^4$ | $R^a$ | $R^b$ | $R^d$ | $R^e$ | MS |
|---|---|---|---|---|---|---|---|---|
| 49 | F | F | F | F | H | H | F | 293 |
| 50 | F | F | F | F | F | F | F | 329.1 |
| 51 | H | H | F | F | F | F | F | 293 |

TABLE 5-continued

| ex. no. | $R^2$ | $R^3$ | $R^4$ | $R^a$ | $R^b$ | $R^d$ | $R^e$ | MS |
|---|---|---|---|---|---|---|---|---|
| 52 | $C_2H_5$ | $CH_3$ | F | F | F | F | F | 335 |
| 53 | $CH_3$ | $CH_3$ | F | F | F | F | Cl | 335.1/337.1 |
| 54 | $CH_3$ | $CH_3$ | F | F | H | H | F | 285.2 |
| 55 | $CH_3$ | $CH_3$ | H | F | F | F | F | 303.1 |
| 56 | $CH_3$ | $CH_3$ | Cl | F | F | F | F | 337.1 |
| 57 | $CH_3$ | $CH_3$ | CN | F | F | F | F | 328 |
| 58 | Cl | —$(CH_2)_4$— | | F | F | F | F | 363 |
| 59 | H | —$(CH_2)_5$— | | F | F | F | F | 343.2 |
| 60 | $CH_3$ | cPr | H | F | F | F | F | 329.1 |
| 61 | $CH_3$ | $OCH_3$ | H | F | F | F | F | 318.8 |
| 62 | $CH_3$ | $CH_3$ | $CH_3$ | F | F | F | F | 317 |
| 63 | H | $C_2H_5$ | F | F | F | F | F | 321 |
| 64 | H | $C_6$-Alk | | F | F | F | F | 357.5 |
| 65 | Cl | —$(CH_2)_3$— | | F | F | F | F | 349.5 |
| 66 | F | —$(CH_2)_4$— | | F | F | F | F | 347.6 |
| 67 | $CH_3$ | —$(CH_2)_4$— | | F | F | F | F | 343.6 |
| 68 | $CH_3$ | —$(CH_2)_5$— | | F | F | F | F | 357.6 |
| 69 | $C_2H_5$ | $CH_3$ | H | F | F | F | F | 316.8 |
| 70 | F | —$(CH_2)_3$— | | F | F | F | F | 332.1 |
| 71 | $C_2H_5$ | F | $C_2H_5$ | F | F | F | F | 348.8 |
| 72 | H | —$(CH_2)_3$— | | F | F | F | F | 314.8 |
| 73 | $CH_3$ | —$(CH_2)_3$— | | F | F | F | F | 328.8 |
| 74 | F | —$(CH_2)_5$— | | F | F | F | F | 361.4 |
| 75 | $CH_3$ | $CH_3$ | F | H | F | H | H | 303.1 | cPr: cyclopropyl
C6-Alk: —$CH_2$—$CH_2$—$CH(CH_3)$—$CH_2$—$CH_2$

The compounds listed below in table 6 (examples 76 to 79) have been prepared similarly to the examples mentioned above:

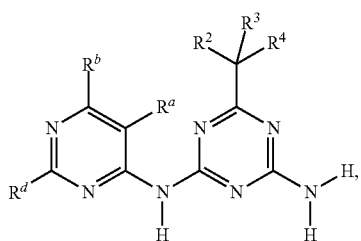

(I)

wherein A is (A 4) and
$R^1$ and $R^5$ are H

TABLE 6

| ex. no. | $R^2$ | $R^3$ | $R^4$ | $R^a$ | $R^b$ | $R^d$ | MS |
|---|---|---|---|---|---|---|---|
| 76 | $CH_3$ | $CH_3$ | F | H | H | Cl | 284 |
| 77 | $CH_3$ | $CH_3$ | F | H | $CH_3$ | F | 282 |
| 78 | $CH_3$ | $CH_3$ | F | F | H | Cl | 301 |
| 79 | $CH_3$ | $CH_3$ | F | H | F | H | 268 |

B USE EXAMPLES

The herbicidal activity of the azines of formula (I) was demonstrated by the following greenhouse experiments:

The culture containers used were plastic flowerpots containing loamy sand with approximately 3.0% of humus as the substrate. The seeds of the test plants were sown separately for each species.

For the pre-emergence treatment, the active ingredients, which had been suspended or emulsified in water, were applied directly after sowing by means of finely distributing nozzles. The containers were irrigated gently to promote germination and growth and subsequently covered with transparent plastic hoods until the plants had rooted. This cover caused uniform germination of the test plants, unless this had been impaired by the active ingredients. For the post-emergence treatment, the test plants were first grown to a height of 3 to 15 cm, depending on the plant habit, and only then treated with the active ingredients which had been suspended or emulsified in water. For this purpose, the test plants were either sown directly and grown in the same containers, or they were first grown separately as seedlings and transplanted into the test containers a few days prior to treatment.

Depending on the species, the plants were kept at 10-25° C. or 20-35° C., respectively. The test period extended over 2 to 4 weeks. During this time, the plants were tended, and their response to the individual treatments was evaluated.

Evaluation was carried out using a scale from 0 to 100. 100 means no emergence of the plants, or complete destruction of at least the aerial moieties, and 0 means no damage, or normal course of growth. A moderate herbicidal activity is given at values of at least 60, a good herbicidal activity is given at values of at least 70, and a very good herbicidal activity is given at values of at least 85.

The plants used in the greenhouse experiments were of the following species:

| Bayer code | Scientific name |
|---|---|
| ABUTH | Abutilon theophrasti |
| AMARE | Amaranthus retroflexus |
| APESV | Apera spica-venti |
| ECHCG | Echinocloa crus-galli |
| POAAN | Poa annua |
| POLCO | Polygonum convolvulus |
| SETFA | Setaria faberi |
| SETVI | Setaria viridis |
| STEME | Stellaria media |

Example 1 applied by pre-emergence method at an application rate of 62.5 g/ha, showed very good herbicidal activity against Echinocloa crus-galli, Polygonum convolvulus and Setaria viridis.

Examples 4 and 55 applied by pre-emergence method at an application rate of 125 g/ha, showed very good herbicidal activity against Amaranthus retroflexus, Polygonum convolvulus and Stellaria media.

Example 5 applied by pre-emergence method at an application rate of 125 g/ha, showed very good herbicidal activity against Amaranthus retroflexus, Setaria viridis and Echinocloa crus-galli.

Example 11 applied by pre-emergence method at an application rate of 500 g/ha, showed very good herbicidal activity against Abutilon theophrasti, Amaranthus retroflexus and Setaria faberi.

Example 12 applied by pre-emergence method at an application rate of 125 g/ha, showed very good herbicidal activity against Amaranthus retroflexus, Echinocloa crus-galli and Setaria faberi.

Example 13 applied by pre-emergence method at an application rate of 62.5 g/ha, showed very good herbicidal activity against Amaranthus retroflexus, Echinocloa crus-galli and Setaria faberi.

Example 14 applied by pre-emergence method at an application rate of 62.5 g/ha, showed very good herbicidal activity against Amaranthus retroflexus, Abutilon theophrasti and Setaria faberi.

Example 17 applied by pre-emergence method at an application rate of 250 g/ha, showed good herbicidal activity against Amaranthus retroflexus.

Example 20 applied by pre-emergence method at an application rate of 250 g/ha, showed very good herbicidal activity against *Amaranthus retroflexus, Abutilon theophrasti* and *Setaria faberi*.

Example 22 applied by pre-emergence method at an application rate of 250 g/ha, showed very good herbicidal activity against *Amaranthus retroflexus*.

Example 29 applied by pre-emergence method at an application rate of 125 g/ha, showed very good herbicidal activity against *Amaranthus retroflexus, Setaria faberi* and *Abutilon theophrasti*.

Example 30 applied by pre-emergence method at an application rate of 250 g/ha, showed very good herbicidal activity against *Amaranthus retroflexus, Echinocloa crusgalli* and *Setaria faberi*.

Example 31 applied by pre-emergence method at an application rate of 250 g/ha, showed very good herbicidal activity against *Amaranthus retroflexus, Setaria faberi* and *Abutilon theophrasti*.

Example 32 applied by pre-emergence method at an application rate of 125 g/ha, showed very good herbicidal activity against *Amaranthus retroflexus, Echinocloa crusgalli* and *Setaria faberi*.

Example 34 applied by post-emergence method at an application rate of 2000 g/ha, showed very good herbicidal activity against *Amaranthus retroflexus, Abutilon theophrasti* and *Setaria viridis*.

Example 36 applied by post-emergence method at an application rate of 1104 g/ha, showed very good herbicidal activity against *Setaria viridis*.

Example 37 applied by pre-emergence method at an application rate of 250 g/ha, showed very good herbicidal activity against *Amaranthus retroflexus* and good herbicidal activity against *Apera spica-venti*.

Example 48 applied by pre-emergence method at an application rate of 125 g/ha, showed very good herbicidal activity against *Amaranthus retroflexus*.

Example 50 applied by pre-emergence method at an application rate of 500 g/ha, showed very good herbicidal activity against *Amaranthus retroflexus* and good herbicidal activity against *Apera spica-venti*.

Example 52 applied by pre-emergence method at an application rate of 250 g/ha, showed very good herbicidal activity against *Amaranthus retroflexus, Abutilon theophrasti* and Echinocloa *crus-galli*.

Example 54 applied by pre-emergence method at an application rate of 62 g/ha, showed very good herbicidal activity against *Amaranthus retroflexus* and *Apera spica-venti*.

Example 56 applied by pre-emergence method at an application rate of 125 g/ha, showed very good herbicidal activity against *Poa annua* and *Stellaria media*.

Example 57 applied by pre-emergence method at an application rate of 250 g/ha, showed very good herbicidal activity against *Amaranthus retroflexus* and *Abutilon theophrasti*.

Example 58 applied by pre-emergence method at an application rate of 250 g/ha, showed very good herbicidal activity against *Amaranthus retroflexus, Setaria faberi* and *Echinocloa crus-galli*.

Example 59 applied by pre-emergence method at an application rate of 250 g/ha, showed very good herbicidal activity against *Poa annua* and *Stellaria media*.

Example 60 applied by post-emergence method at an application rate of 500 g/ha, showed very good herbicidal activity against *Amaranthus retroflexus, Abutilon theophrasti* and *Setaria faberi*.

Example 61 applied by pre-emergence method at an application rate of 500 g/ha, showed very good herbicidal activity against *Amaranthus retroflexus* and *Abutilon theophrasti*.

Example 62 applied by pre-emergence method at an application rate of 250 g/ha, showed very good herbicidal activity against *Amaranthus retroflexus, Abutilon theophrasti* and *Setaria faberi*.

Example 63 applied by pre-emergence method at an application rate of 125 g/ha, showed very good herbicidal activity against *Amaranthus retroflexus, Abutilon theophrasti* and *Setaria faberi*.

Example 64 applied by pre-emergence method at an application rate of 250 g/ha, showed very good herbicidal activity against *Amaranthus retroflexus, Abutilon theophrasti* and *Setaria faberi*.

Example 65 applied by pre-emergence method at an application rate of 250 g/ha, showed very good herbicidal activity against *Amaranthus retroflexus, Abutilon theophrasti* and *Echinocloa crus-galli*.

Example 66 applied by pre-emergence method at an application rate of 250 g/ha, showed very good herbicidal activity against *Amaranthus retroflexus, Abutilon theophrasti* and *Setaria faberi*.

Example 67 applied by pre-emergence method at an application rate of 250 g/ha, showed very good herbicidal activity against *Amaranthus retroflexus*.

Example 68 applied by pre-emergence method at an application rate of 250 g/ha, showed very good herbicidal activity against *Amaranthus retroflexus*.

Example 69 applied by pre-emergence method at an application rate of 125 g/ha, showed very good herbicidal activity against *Amaranthus retroflexus* and *Abutilon theophrasti*.

Example 70 applied by pre-emergence method at an application rate of 1000 g/ha, showed very good herbicidal activity against *Amaranthus retroflexus* and good herbicidal activity against *Apera spica-venti*.

Example 71 applied by pre-emergence method at an application rate of 250 g/ha, showed very good herbicidal activity against *Amaranthus retroflexus, Abutilon theophrasti* and *Setaria faberi*.

The invention claimed is:
1. An azine compound of formula (I)

(I)

wherein
A is a 6-membered heteroaryl having 1 to 3 nitrogen atoms,
which is substituted by one to four substituents $R^A$, selected from the group consisting of halogen, CN, $NO_2$, $C_1$-$C_6$-alkyl, $C_1$-$C_6$-haloalkyl, OH, $C_1$-$C_6$-alkoxy, $C_1$-$C_6$-alkylthio, ($C_1$-$C_6$-alkyl)sulfinyl, ($C_1$-

$C_6$-alkyl)sulfonyl, amino, ($C_1$-$C_6$-alkyl)amino, di($C_1$-$C_6$-alkyl)amino, ($C_1$-$C_6$-alkyl)¬carbonyl, ($C_1$-$C_6$-alkoxy)carbonyl;

$R^1$ is selected from the group consisting of H, OH, $S(O)_2NH_2$, CN, $C_1$-$C_6$-alkyl, $C_2$-$C_6$-alkenyl, $C_2$-$C_6$-alkynyl, ($C_3$-$C_6$-cycloalkyl)-$C_1$-$C_4$-alkyl, $C_1$-$C_6$-alkoxy, ($C_1$-$C_6$-alkoxy)-$C_1$-$C_6$-alkyl, ($C_1$-$C_6$-alkyl)carbonyl, ($C_1$-$C_6$-alkoxy) carbonyl, ($C_1$-$C_6$-alkyl)sulfonyl, ($C_1$-$C_6$-alkylamino)carbonyl, di($C_1$-$C_6$-alkyl)aminocarbonyl, ($C_1$-$C_6$-alkylamino)sulfonyl, di($C_1$-$C_6$-alkyl)aminosulfonyl and ($C_1$-$C_6$-alkoxy) sulfonyl, where the aliphatic and cycloaliphatic parts of the 14 aforementioned radicals are unsubstituted, partly or completely halogenated, phenyl, phenyl-$C_1$-$C_6$-alkyl, phenylsulfonyl, phenylaminosulfonyl, phenylcarbonyl and phenoxycarbonyl,
  wherein phenyl in the last 6 mentioned radicals are unsubstituted or substituted by 1, 2, 3, 4 or 5 identical or different substituents selected from the group consisting of halogen, CN, $NO_2$, $C_1$-$C_6$-alkyl, $C_1$-$C_6$-haloalkyl, $C_1$-$C_6$-alkoxy and $C_1$-$C_6$-haloalkoxy;

$R^2$ is H, halogen, OH, CN, $C_1$-$C_6$-alkyl, $C_2$-$C_6$-alkenyl, $C_3$-$C_6$-alkynyl, ($C_1$-$C_6$-alkoxy)-$C_1$-$C_6$-alkyl, $C_3$-$C_6$-cycloalkyl, $C_3$-$C_6$-cycloalkenyl, ($C_3$-$C_6$-cycloalkyl)-$C_1$-$C_4$-alkyl, $C_1$-$C_6$-alkoxy, $C_2$-$C_6$-alkenyloxy, $C_2$-$C_6$-alkynyloxy, $C_3$-$C_6$-cycloalkoxy or ($C_3$-$C_6$-cycloalkyl)-$C_1$-$C_4$-alkoxy, where the aliphatic and cycloaliphatic parts of the 9 aforementioned radicals are unsubstituted, partly or completely halogenated,
phenyl, phenyl-$C_1$-$C_6$-alkyl,
  wherein phenyl in the last 2 mentioned radicals are unsubstituted or substituted by 1, 2, 3, 4 or 5 identical or different substituents selected from the group consisting of halogen, CN, $NO_2$, $C_1$-$C_6$-alkyl, $C_1$-$C_6$-haloalkyl, $C_1$-$C_6$-alkoxy and $C_1$-$C_6$-haloalkoxy, $R^3$ is selected from the group consisting of H, halogen, CN, $C_1$-$C_6$-alkyl, $C_1$-$C_6$-haloalkyl, $C_1$-$C_6$-alkoxy and $C_1$-$C_6$-haloalkoxy;

$R^4$ is selected from the group consisting of H, halogen, CN, $C_1$-$C_6$-alkyl, $C_2$-$C_6$-alkenyl, $C_3$-$C_6$-alkynyl, $C_3$-$C_6$-cycloalkyl, ($C_3$-$C_6$-cycloalkyl)-$C_1$-$C_4$-alkyl, $C_3$-$C_6$-cycloalkenyl and $C_1$-$C_6$-alkoxy-$C_1$-$C_6$-alkyl, where the aliphatic and cycloaliphatic parts of the 7 aforementioned radicals are unsubstituted, partly or completely halogenated; or $R^3$ and $R^4$ together with the carbon atom to which they are attached form a moiety selected from the group consisting of carbonyl, $C_2$-$C_6$-alkenyl, $C_3$-$C_6$-cycloalkyl, $C_3$-$C_6$-cycloalkenyl and three- to six-membered heterocyclyl,
  wherein the $C_3$-$C_6$-cycloalkyl, $C_3$-$C_6$-cycloalkenyl, or three- to six-membered heterocyclyl is unsubstituted or substituted by one to six substituents selected from halogen, CN, $C_1$-$C_6$-alkyl and $C_1$-$C_6$-alkoxy, and wherein the heterocyclyl is a monocyclic saturated or partially unsaturated hydrocarbon having three to six ring members, which contains in addition to the carbon atoms one or two heteroatoms selected from O, S and N; and $R^5$ is selected from the group consisting of H, OH, $S(O)_2NH_2$, CN, $C_1$-$C_6$-alkyl, $C_2$-$C_6$-alkenyl, $C_2$-$C_6$-alkynyl, ($C_3$-$C_6$-cycloalkyl)-$C_1$-$C_4$-alkyl, $C_1$-$C_6$-alkoxy, ($C_1$-$C_6$-alkoxy)-$C_1$-$C_6$-alkyl, ($C_1$-$C_6$-alkyl)carbonyl, ($C_1$-$C_6$-alkoxy)carbonyl, ($C_1$-$C_6$-alkyl)sulfonyl, ($C_1$-$C_6$-alkylamino)carbonyl, di($C_1$-$C_6$-alkyl)aminocarbonyl, ($C_1$-$C_6$-alkylamino)sulfonyl, di($C_1$-$C_6$-alkyl)aminosulfonyl and ($C_1$-$C_6$-alkoxy)sulfonyl, where the aliphatic and cycloaliphatic parts of the 14 aforementioned radicals are unsubstituted, partly or completely halogenated, phenyl, phenyl-$C_1$-$C_6$-alkyl, phenyl sulfonyl, phenylaminosulfonyl, phenylcarbonyl and phenoxycarbonyl,
  wherein phenyl in the last 6 mentioned radicals are unsubstituted or substituted by 1, 2, 3, 4 or 5 identical or different substituents selected from the group consisting of halogen, CN, $NO_2$, $C_1$-$C_6$-alkyl, $C_1$-$C_6$-haloalkyl, $C_1$-$C_6$-alkoxy and $C_1$-$C_6$-haloalkoxy;
including their agriculturally acceptable salts or N-oxides, with the proviso that the following compounds are excluded:
  4-amino-6-[(2-methyl-1H-benzimidazol-5-yl)amino]-1,3,5-triazine-2-carboxylic acid,
  Methyl-4-amino-6-[(2-methyl-1H-benzimidazol-5-yl)amino]-1,3,5-triazine-2-carboxylate,
  Ethyl-4-amino-6-[(2-methyl-1H-benzimidazol-5-yl)amino]-1,3,5-triazine-2-carboxylate,
  N2-(4-methylthiazol-2-yl)-6-pentyl-1,3,5-triazine-2,4-diamine,
  N2-[(5-ethylthio)-1,3,4-thiadiazol-2-yl)]-6-methyl-N4-(2,4,6-trimethylphenyl)-1,3,5-triazine-2,4-diamine,
  6-methyl-N2-(4-methyl-1,3-benzothiazol-2-yl)-N4-(2,4,6-trimethylphenyl)-1,3,5-triazine-2,4-diamine,
  2-amino-4-(5-chloro-8-isoquinolylamino)-6-(p-isobutylbenzyl)1,3,5-triazine.

2. The compound of claim 1, wherein $R^A$ is selected from the group consisting of halogen, CN, $NO_2$, $C_1$-$C_6$-alkyl, $C_1$-$C_6$-haloalkyl, OH, $C_1$-$C_6$-alkoxy, $C_3$-$C_6$-cycloalkyl, $C_3$-$C_6$-cycloalkoxy, ($C_3$-$C_6$-cycloalkyl)methoxy, $C_2$-$C_6$-alkynyl, $C_2$-$C_6$-alkenyl, $C_2$-$C_6$-alkynyloxy, $C_2$-$C_6$-alkenyloxy, $C_1$-$C_6$-alkylthio, ($C_1$-$C_6$-alkyl)sulfinyl, ($C_1$-$C_6$-alkyl)sulfonyl, amino, ($C_1$-$C_6$-alkyl)amino, di($C_1$-$C_6$-alkyl)amino, ($C_1$-$C_6$-alkyl)carbonyl, ($C_1$-$C_6$-alkoxy)carbonyl and $C_1$-$C_6$-haloalkoxy.

3. The compound of claim 1, wherein $R^A$ is halogen, $C_1$-$C_4$-haloalkyl, $C_1$-$C_4$-alkoxy, $C_1$-$C_4$-haloalkoxy and CN.

4. The compound of claim 1, wherein A is a 6-membered heteroaryl having 1 to 3 nitrogen atoms,
  which is substituted by one to four substituents $R^A$, selected from the group consisting of halogen, CN, $C_1$-$C_6$-alkyl and $C_1$-$C_6$-alkoxy.

5. The compound of claim 1, wherein A is pyridyl, which is substituted by 1, 2, 3 or 4 identical or different radicals $R^A$.

6. The compound of claim 5, wherein A is 2,3,5,6-tetraflouro-4-pyridyl or 4-chloro-3,5,6-trifluoro-2-pyridyl.

7. The compound of claim 1, wherein $R^1$ and $R^5$ independently of one another are selected from the group consisting of H, CN, $C_1$-$C_6$-alkyl, $C_1$-$C_6$-alkoxy-$C_1$-$C_6$-alkyl, $C_1$-$C_6$-alkoxy, ($C_1$-$C_6$-alkyl)carbonyl and ($C_1$-$C_6$-alkyl)sulfonyl.

8. The compound of claim 7, wherein $R^1$ and $R^5$ are H.

9. The compound of claim 1, wherein $R^2$ is selected from the group consisting of H, halogen, $C_1$-$C_6$-alkyl, $C_1$-$C_6$-haloalkyl, $C_1$-$C_4$-alkoxy and, $C_1$-$C_6$-haloalkoxy.

10. The compound of claim 1, wherein
  $R^3$ is selected from the group consisting of hydrogen, fluorine, $C_1$-$C_4$-alkyl, $C_1$-$C_4$-haloalkyl, $C_1$-$C_4$-alkoxy and $C_1$-$C_6$-haloalkoxy;
  $R^4$ is selected from the group consisting of $C_1$-$C_6$-alkyl, $C_1$-$C_6$-haloalkyl, $C_2$-$C_6$-alkenyl, $C_3$-$C_6$-alkynyl, $C_3$-$C_6$-cycloalkyl, $C_3$-$C_6$-cycloalkenyl, and $C_1$-$C_6$-alkoxy-$C_1$-$C_6$-alkyl;
or
  $R^3$ and $R^4$ together with the carbon atom to which they are attached form a moiety selected from the group consisting of $C_3$-$C_6$-cycloalkyl, $C_3$-$C_6$-cycloalkenyl and three- to six-membered saturated or partially unsaturated heterocyclyl.

11. A process for preparing an azine of claim 1, wherein $R^1$ and $R^5$ independently of one another are H, $C_1$-$C_6$-alkyl, $C_1$-$C_6$-alkoxy-$C_1$-$C_6$-alkyl or $C_1$-$C_6$-alkoxy; and A, $R^2$, $R^3$ and $R^4$ are as defined in claim 1;
comprising reacting a halotriazine of formula (II),

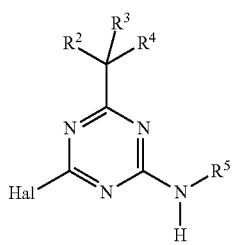
(II)

wherein $R^5$ is H, $C_1$-$C_6$-alkyl, $C_1$-$C_6$-alkoxy-$C_1$-$C_6$-alkyl or $C_1$-$C_6$-alkoxy; and
Hal is halogen;
with an amine of formula (III),

A-NHR$^1$ (III), wherein $R^1$ is H, $C_1$-$C_6$-alkyl, $C_1$-$C_6$-alkoxy-$C_1$-$C_6$-alkyl or $C_1$-$C_6$-alkoxy;
in the presence of a base and a catalyst.

12. A process for preparing an azine of claim 1, wherein $R^5$ is CN, ($C_1$-$C_6$-alkyl)carbonyl, ($C_1$-$C_6$-alkoxy)carbonyl, ($C_1$-$C_6$-alkyl)sulfonyl or phenylsulfonyl,
wherein the phenyl is unsubstituted or substituted by one to five substituents selected from the group consisting of halogen, CN, NO$_2$, $C_1$-$C_6$-alkyl, $C_1$-$C_6$-haloalkyl and $C_1$-$C_6$-alkoxy;
comprising reacting an azine of formula (I), wherein $R^5$ is hydrogen,
with a compound of formula (VII)

R$^5$—X (VII)

wherein
$R^5$ is CN, ($C_1$-$C_6$-alkyl)carbonyl, ($C_1$-$C_6$-alkoxy)carbonyl, ($C_1$-$C_6$-alkyl)sulfonyl or phenylsulfonyl,
wherein the phenyl is unsubstituted or substituted by one to five substituents selected from the group consisting of halogen, CN, NO$_2$, $C_1$-$C_6$-alkyl, $C_1$-$C_6$-haloalkyl and $C_1$-$C_6$-alkoxy; and
X is halogen or oxycarbonyl-$C_1$-$C_6$-alkyl.

13. A process for preparing an azine of claim 1, wherein $R^1$ is CN, ($C_1$-$C_6$-alkyl)carbonyl, ($C_1$-$C_6$-alkoxy)carbonyl, ($C_1$-$C_6$-alkyl)sulfonyl or phenyl sulfonyl,
wherein the phenyl is unsubstituted or substituted by one to five substituents selected from the group consisting of halogen, CN, NO$_2$, $C_1$-$C_6$-alkyl, $C_1$-$C_6$-haloalkyl and $C_1$-$C_6$-alkoxy;
comprising reacting an azine of formula (I), wherein $R^1$ is hydrogen, with a compound of formula (VIII)

R$^1$—X (VIII), wherein
$R^1$ is CN, ($C_1$-$C_6$-alkyl)carbonyl, ($C_1$-$C_6$-alkoxy)carbonyl, ($C_1$-$C_6$-alkyl)sulfonyl or phenylsulfonyl,
wherein the phenyl is unsubstituted or substituted by one to five substituents selected from the group consisting of halogen, CN, NO$_2$, $C_1$-$C_6$-alkyl, $C_1$-$C_6$-haloalkyl and $C_1$-$C_6$-alkoxy; and
X is halogen or oxycarbonyl-$C_1$-$C_6$-alkyl.

14. An agrochemical composition comprising a herbicidally active amount of at least one azine of claim 1 and at least one inert liquid and/or solid carrier and, if appropriate, at least one surface-active substance.

15. A process for the preparation of herbicidal active agrochemical compositions, which comprises mixing an herbicidally active amount of at least one azine of claim 1 and at least one inert liquid and/or solid carrier and, if desired, at least one surface-active substance.

16. A method of controlling undesired vegetation, which comprises allowing an herbicidally active amount of at least one azine of claim 1 to act on plants, their environment or on seed.

17. A method for desiccating/defoliating a plant comprising allowing an azine of claim 1 to act on plants, their environment or on seed.

18. The method of claim 16, wherein, in the azine of formula (I), $R^4$ is selected from the group consisting of halogen, CN, NO$_2$, $C_1$-$C_6$-alkyl, $C_1$-$C_6$-haloalkyl, OH, $C_1$-$C_6$-alkoxy, $C_3$-$C_6$-cycloalkyl, $C_3$-$C_6$-cycloalkoxy, ($C_3$-$C_6$-cycloalkyl)methoxy, $C_2$-$C_6$-alkynyl, $C_2$-$C_6$-alkenyl, $C_2$-$C_6$-alkynyloxy, $C_2$-$C_6$-alkenyloxy, $C_1$-$C_6$-alkylthio, ($C_1$-$C_6$-alkyl)sulfinyl, ($C_1$-$C_6$-alkyl)sulfonyl, amino, ($C_1$-$C_6$-alkyl)amino, di($C_1$-$C_6$-alkyl)amino, ($C_1$-$C_6$-alkyl)carbonyl, ($C_1$-$C_6$-alkoxy)carbonyl and $C_1$-$C_6$-haloalkoxy.

19. The method of claim 16, wherein, in the azine of formula (I), $R^4$ is halogen, $C_1$-$C_4$-haloalkyl, $C_1$-$C_4$-alkoxy, $C_1$-$C_4$-haloalkoxy and CN.

20. The method of claim 16, wherein, in the azine of formula (I), A is a 6-membered heteroaryl having 1 to 3 nitrogen atoms,
which is substituted by one to four substituents $R^4$, selected from the group consisting of halogen, CN, $C_1$-$C_6$-alkyl and $C_1$-$C_6$-alkoxy.

21. The method of claim 16, wherein, in the azine of formula (I), A is pyridyl, which is substituted by 1, 2, 3 or 4 identical or different radicals $R^4$.

22. The method of claim 21, wherein A is 2,3,5,6-tetraflouro-4-pyridyl or 4-chloro-3,5,6-trifluoro-2-pyridyl.

23. The method of claim 16, wherein, in the azine of formula (I), $R^1$ and $R^5$ independently of one another are selected from the group consisting of H, CN, $C_1$-$C_6$-alkyl, $C_1$-$C_6$-alkoxy-$C_1$-$C_6$-alkyl, $C_1$-$C_6$-alkoxy, ($C_1$-$C_6$-alkyl)carbonyl and ($C_1$-$C_6$-alkyl)sulfonyl.

24. The method of claim 16, wherein, in the azine of formula (I), $R^2$ is selected from the group consisting of H, halogen, $C_1$-$C_6$-alkyl, $C_1$-$C_6$-haloalkyl, $C_1$-$C_4$-alkoxy and, $C_1$-$C_6$-haloalkoxy.

25. The method of claim 16, wherein
$R^3$ is selected from the group consisting of hydrogen, fluorine, $C_1$-$C_4$-alkyl, $C_1$-$C_4$-haloalkyl, $C_1$-$C_4$-alkoxy and $C_1$-$C_6$-haloalkoxy;
$R^4$ is selected from the group consisting of $C_1$-$C_6$-alkyl, $C_1$-$C_6$-haloalkyl, $C_2$-$C_6$-alkenyl, $C_3$-$C_6$-alkynyl, $C_3$-$C_6$-cycloalkyl, $C_3$-$C_6$-cycloalkenyl, and $C_1$-$C_6$-alkoxy-$C_1$-$C_6$-alkyl;
or
$R^3$ and $R^4$ together with the carbon atom to which they are attached form a moiety selected from the group consisting of $C_3$-$C_6$-cycloalkyl, $C_3$-$C_6$-cycloalkenyl and three- to six-membered saturated or partially unsaturated heterocyclyl.

26. The method of claim 23, wherein $R^1$ and $R^5$ are H.

* * * * *